United States Patent
McWhirter et al.

(10) Patent No.: US 9,301,510 B2
(45) Date of Patent: Apr. 5, 2016

(54) MICE THAT PRODUCE ANTIGEN-BINDING PROTEINS WITH PH-DEPENDENT BINDING CHARACTERISTICS

(71) Applicant: Regeneron Pharmaceuticals, Inc., Tarrytown, NY (US)

(72) Inventors: John McWhirter, Tarrytown, NY (US); Lynn MacDonald, White Plains, NY (US); Andrew J. Murphy, Croton-on-Hudson, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

(21) Appl. No.: 13/832,309

(22) Filed: Mar. 15, 2013

(65) Prior Publication Data

US 2013/0247235 A1    Sep. 19, 2013

Related U.S. Application Data

(60) Provisional application No. 61/611,950, filed on Mar. 16, 2012, provisional application No. 61/613,352, filed on Mar. 20, 2012, provisional application No. 61/736,930, filed on Dec. 13, 2012.

(51) Int. Cl.
| | |
|---|---|
| *A01K 67/027* | (2006.01) |
| *C07K 16/00* | (2006.01) |
| *C12N 15/85* | (2006.01) |

(52) U.S. Cl.
CPC ......... *A01K 67/0275* (2013.01); *A01K 67/0278* (2013.01); *C07K 16/00* (2013.01); *C12N 15/8509* (2013.01); *A01K 2217/072* (2013.01); *A01K 2217/075* (2013.01); *A01K 2217/15* (2013.01); *A01K 2227/105* (2013.01); *A01K 2267/01* (2013.01); *C07K 2317/21* (2013.01); *C07K 2317/565* (2013.01); *C12N 2800/204* (2013.01)

(58) Field of Classification Search
CPC ................. A01K 2267/01; A01K 67/0275
See application file for complete search history.

(56) References Cited

U.S. PATENT DOCUMENTS

| | | | |
|---|---|---|---|
| 5,545,806 A | 8/1996 | Lonberg et al. | |
| 5,545,807 A | 8/1996 | Surani et al. | |
| 5,603,931 A | 2/1997 | Raso | |
| 5,667,988 A | 9/1997 | Barbas et al. | |
| 5,999,908 A | 12/1999 | Abelow | |
| 6,096,551 A | 8/2000 | Barbas et al. | |
| 6,162,963 A | 12/2000 | Kucherlapati et al. | |
| 6,586,251 B2 | 7/2003 | Economides et al. | |
| 6,596,541 B2 | 7/2003 | Murphy et al. | |
| 6,673,986 B1 | 1/2004 | Kucherlapati et al. | |
| 6,774,279 B2 | 8/2004 | Dymecki | |
| 6,946,548 B2 | 9/2005 | Sarkar et al. | |
| 7,052,873 B2 | 5/2006 | Tsuchiya | |
| 7,067,284 B1 | 6/2006 | Barbas et al. | |
| 7,105,348 B2 | 9/2006 | Murphy et al. | |
| 7,183,076 B2 | 2/2007 | Arathoon et al. | |
| 7,262,028 B2 | 8/2007 | Van Berkel et al. | |
| 7,276,585 B2 | 10/2007 | Lazar et al. | |
| 7,294,754 B2 | 11/2007 | Poueymirou et al. | |
| 7,435,871 B2 | 10/2008 | Green et al. | |
| 7,501,552 B2 * | 3/2009 | Lonberg et al. | 800/6 |
| 7,576,259 B2 | 8/2009 | Poueymirou et al. | |
| 7,659,442 B2 | 2/2010 | Poueymirou et al. | |
| 7,910,798 B2 | 3/2011 | Tanamachi et al. | |
| 8,062,640 B2 | 11/2011 | Sleeman et al. | |
| 8,080,243 B2 | 12/2011 | Liang et al. | |
| 8,158,419 B2 | 4/2012 | Lonberg et al. | |
| 8,502,018 B2 | 8/2013 | Murphy et al. | |
| 2002/0088016 A1 | 7/2002 | Bruggemann | |
| 2003/0078385 A1 | 4/2003 | Arathoon et al. | |
| 2003/0108925 A1 | 6/2003 | Dix et al. | |
| 2004/0018626 A1 | 1/2004 | Murphy et al. | |
| 2006/0015949 A1 | 1/2006 | Lonberg et al. | |
| 2006/0015957 A1 | 1/2006 | Lonberg et al. | |
| 2006/0099207 A1 | 5/2006 | Wu et al. | |
| 2006/0141456 A1 | 6/2006 | Edwards et al. | |
| 2006/0199204 A1 | 9/2006 | Dix et al. | |
| 2007/0061900 A1 * | 3/2007 | Murphy et al. | 800/6 |

(Continued)

FOREIGN PATENT DOCUMENTS

| | | |
|---|---|---|
| CN | 1277632 A | 12/2000 |
| CN | 1484 707 A | 3/2004 |

(Continued)

OTHER PUBLICATIONS

Corbett et al. (J. Mol. Biol. 1997; 270: 587-597).*
Ippolito et al. (Journal of Experimental Medicine. Jun. 12, 2006; 203(6): 1567-1578).*
Arnold, L. et al., "Development of B-1 cells: Segregation of Phosphatidyl Choline-specific B Cells to the B-1 Population Occurs after Immunoglobulin Gene Expression," *J. Exp. Med.*, 179:1585-1595 (1994).
Aucouturier, P.et al., "Monoclonal Ig L chain and L chain V domain fragment crystallization in myeloma-associated Fanconi's syndrome," *J. Immunol.*, 150(8):3561-3568 (1993).
Auerbach, et al., "Establishment and Chimera Analysis of 129/SvEv- and C57BL/6-Derived Mouse Embryonic Stem Cell Lines", *BioTechniques*, 29:1024-1032 (2000).

(Continued)

*Primary Examiner* — Scott Long
(74) *Attorney, Agent, or Firm* — Brownstein Hyatt Farber Schneck, LLP; Rita S. Wu; Yong-Jin Choi

(57) ABSTRACT

Genetically modified non-human animals are provided that comprise an immunoglobulin heavy chain locus comprising an unrearranged human heavy chain variable region nucleotide sequence comprising an addition of at least one histidine codon or a substitution of at least one endogenous non-histidine codon with a histidine codon. Compositions and methods for making the genetically modified non-human animals as described herein are provided. Non-human animals capable of expressing an antigen-binding protein characterized by pH-dependent antigen binding, enhanced recyclability and/or enhanced serum half-life are also provided.

35 Claims, 19 Drawing Sheets

(56) References Cited

U.S. PATENT DOCUMENTS

| | | |
|---|---|---|
| 2007/0280945 A1 | 12/2007 | Stevens et al. |
| 2008/0069822 A1 | 3/2008 | Jensen et al. |
| 2008/0078000 A1 | 3/2008 | Poueymirou et al. |
| 2009/0035836 A1 | 2/2009 | Datta et al. |
| 2009/0181855 A1 | 7/2009 | Vasquez et al. |
| 2010/0069614 A1 | 3/2010 | Houtzager et al. |
| 2010/0146647 A1 | 6/2010 | Logtenberg et al. |
| 2010/0310586 A1 | 12/2010 | Dolcetti et al. |
| 2010/0331527 A1 | 12/2010 | Davis et al. |
| 2011/0076275 A1 | 3/2011 | Igawa et al. |
| 2011/0098450 A1 | 4/2011 | Igawa et al. |
| 2011/0111406 A1* | 5/2011 | Igawa et al. ............ 435/6 |
| 2011/0195454 A1 | 8/2011 | McWhirter et al. |
| 2011/0229489 A1* | 9/2011 | Pons et al. ............ 424/158.1 |
| 2012/0021409 A1 | 1/2012 | Mcwhirter et al. |
| 2012/0167237 A1 | 6/2012 | Bradley et al. |
| 2012/0192300 A1 | 7/2012 | Babb et al. |
| 2012/0204278 A1 | 8/2012 | Bradley et al. |
| 2012/0322108 A1 | 12/2012 | MacDonald et al. |
| 2013/0011866 A1 | 1/2013 | Igawa et al. |
| 2013/0045492 A1 | 2/2013 | Babb et al. |
| 2013/0145484 A1 | 6/2013 | Logtenberg et al. |
| 2013/0185821 A1 | 7/2013 | Babb et al. |
| 2013/0247236 A1* | 9/2013 | McWhirter et al. ............ 800/18 |
| 2014/0013456 A1* | 1/2014 | McWhirter et al. ............ 800/6 |

FOREIGN PATENT DOCUMENTS

| | | |
|---|---|---|
| CN | 1560081 A | 1/2005 |
| EP | 1 317 537 A2 | 6/2003 |
| EP | 1 439 234 A1 | 7/2004 |
| EP | 1 605 058 B1 | 5/2009 |
| EP | 2 147 594 A1 | 1/2010 |
| EP | 2 275 443 A1 | 1/2011 |
| EP | 2 427 357 A | 3/2012 |
| EP | 2 501 817 A | 9/2012 |
| EP | 2 505 654 A1 | 10/2012 |
| EP | 2 517 556 A2 | 10/2012 |
| EP | 2 517 557 A2 | 10/2012 |
| EP | 2 556 747 A2 | 2/2013 |
| EP | 2 564 695 A1 | 3/2013 |
| EP | 2 582 230 A | 4/2013 |
| EP | 2762564 A1 | 8/2014 |
| WO | 92/03918 A1 | 3/1992 |
| WO | 94/02602 A1 | 2/1994 |
| WO | 96/34096 A1 | 10/1996 |
| WO | 98/46645 A2 | 10/1998 |
| WO | 98/50431 A2 | 11/1998 |
| WO | 02/20767 A2 | 3/2002 |
| WO | 02/36789 A2 | 5/2002 |
| WO | 2004/009618 A2 | 1/2004 |
| WO | 2004/106375 A1 | 12/2004 |
| WO | 2006/117699 A2 | 11/2006 |
| WO | 2007/117410 A2 | 10/2007 |
| WO | 2008/043822 A2 | 4/2008 |
| WO | 2008/054606 A2 | 5/2008 |
| WO | 2008/076379 A2 | 6/2008 |
| WO | 2008/112922 A2 | 9/2008 |
| WO | WO2009/125825 * | 10/2009 ............ C07K 16/28 |
| WO | 2009/157771 A2 | 12/2009 |
| WO | 2010/039900 A2 | 4/2010 |
| WO | 2010/070263 A1 | 6/2010 |
| WO | 2010/128897 A1 | 11/2010 |
| WO | 2011/004192 A1 | 1/2011 |
| WO | 2011/072204 AI | 6/2011 |
| WO | 2011/097603 A1 | 8/2011 |
| WO | 2011097603 A1 | 8/2011 |
| WO | 2011/111007 A2 | 9/2011 |
| WO | 2011/122011 A2 | 10/2011 |
| WO | 2011/158009 A1 | 12/2011 |
| WO | 2011/163314 A1 | 12/2011 |
| WO | 2012/141798 A1 | 10/2012 |
| WO | 2012/148873 A2 | 11/2012 |
| WO | 2013/022782 A1 | 2/2013 |
| WO | 2013022782 A1 | 2/2013 |
| WO | 2013/046722 A1 | 4/2013 |
| WO | 2013/079953 A1 | 6/2013 |
| WO | 2013/134263 A1 | 9/2013 |
| WO | 2013/184761 A1 | 12/2013 |
| WO | 2014/130690 A1 | 8/2014 |

OTHER PUBLICATIONS

Basu, S.K., "Receptor-mediated endocytosis: An overview of a dynamic process," *J. Biosci.*, 6(4):535-542 (Aug. 6, 1984).

Bauer, S. et al., "Structure and pre-B lymphocyte restricted expression of the VpreB gene in humans and conservation of its structure in other mammalian species," *The EMBO Journal*, 7(1):111-116 (1988).

Beguinot, L. et al. "Down-regulation of the epidermal growth factor receptor in KB cells is due to receptor internalization and subsequent degradation in lysosomes," *Proc. Natl. Acad Sci. USA*, 81:2384-2388 (1984).

Brezinschek, H. et al., "Pairing of Variable Heavy and Variable κ Chains in Individual Naïve and Memory B Cells," *J. Immunol.*, 160(10):4762-4767 (1998).

Brown, M.S. et al., "Recycling Receptors: The Round-Trip Itinerary of Migrant Membrane Proteins," *Cell*, 22:663-667 (1983).

Carmack, C. et al., "Influence of a V kappa 8 L chain transgene on endogenous rearrangements and the immune response to the HA(Sb) determinant of influenza virus," *J. Immunol.*, 147(6):2024-2033 (1991).

Carter, P., "Bispecific human IgG by design," *Journal of Immunological Methods*, 248(1-2):7-15 (2001).

Cascalho, M. et al., "A Quasi-Monoclonal Mouse," *Science*, 272(5268):1649-1652 (1996).

Chaparro-Riggers, J. et al. "Increasing Serum Half-life and Extending Cholesterol Lowering in Vivo by Engineering Antibody with pH-sensitive Binding to PCSK9," *J. Biol. Chem.* 287(14):11090-11097 (2012).

Chinese Search Report for related Chinese Application No. 201180013714.0, mailed May 15, 2013.

Corbett, S.J. et al., "Sequence of the Human Immunoglobulin Diversity (D) Segment Locus: A Systematic Analysis Provides No Evidence for the Use of DIR Segments, Inverted D Segments, 'Minor' D Segments or D-D Recombination," *J. Mol. Biol.* 270:587-597 (1997).

Dall'Acqua W. F. et al., "Properties of Human IgG1s Engineered for Enhanced Binding to the Neonatal Fc Receptor (FcRn)," *J. Biol. Chem.*, 281:23514-23524 (2006).

Davies, et al., "Creation of Mice Expressing Human Antibody Light Chains by Introduction of a Yeast Artificial Chromosome Containing the Core Region of the Human Immunoglobulin κ Locus", *Nature Biotechnology*, 11:911-914, (1993).

de Kruif, J. et al., "Human Immunoglobulin Repertoires against Tetanus Toxoid Contain a Large and Diverse Fraction of High-Affinity Promiscuous VH Genes," *Journal of Molecular Biology*, 387:548-558 (2009).

de Wildt, R. et al., "Analysis of heavy and light chain pairings indicates that receptor editing shapes the human antibody repertoire," *J. Mol. Biol.*, 285(3):895-901 (1999).

Deng, R. et al. "Pharmacokinetics of Humanized Monoclonal Anti-Tumor Necrosis Factor-α Antibody and Its Neonatal Fc Receptor Variants in Mice and Cynomolgus Monkeys," *Drug Metabolism and Disposition*, 38(4):600-605 (2010).

Desienhofer, J., "Crystallographic Refinement and Atomic Models of a Human Fc Fragment and Its Complex with Fragment B of Protein A from *Staphylococcus aureus* at 2.9- and 2.8-Å Resolution," *Biochemistry*, 20(9):2361-2370 (1981).

Donohoe, M. et al., "Transgenic Human λ5 Rescues the Murine Lambda5 Nullizygous Phenotype," *Journal of Immunology*, 164:5269-5276 (2000).

Dunn, K.W. et al., "Iterative Fractionation of Recycling Receptors from Lysosomally Destined Ligands in an Early Sorting Endosome," *J. Cell. Biol.*, 109(6/2):3303-3314 (1989).

Edwards, D.R., et al., "The ADAM Metalloproteinases", *Molecular Aspects of Medicine*, 29(5): 258-289 (2008).

European Examination for Application No. 11 703 799.4 mailed Oct. 9, 2012.

(56) References Cited

OTHER PUBLICATIONS

European Communication for Application No. 12 173 456.0 mailed Dec. 5, 2012.
European Search Report for Application No. 12 173 456.0 dated Aug. 10, 2012.
Fallon, E.M. et al., "Increased Endosomal Sorting of Ligand to Recycling Enhances Potency of an Interleukin-2 Analog," *J. Biol. Chem.* 275(10):6790-6797 (2000).
Featherstone, K., et al., "The Mouse Immunoglobulin Heavy Chain V-D Intergenic Sequence Contains Insulators That May Regulate Ordered V(D)J Recombination", *The Journal of Biological Chemistry*, 285(13):9327-9338 (2010).
Festing, et al., "Revised nomenclature for strain 129 mice," *Mammalian Genome*, 10:836 (1999).
Fraenkel, S. et al., "Allelic 'choice' governs somatic hypermutation in vivo at the immunoglobulin kappa-chain locus," *Nat. Immunol.*, 8(7):715-722 (2007).
Gan, Z. et al.,"Analyses of the recycling receptor, FcRn, in live cells reveal novel pathways for lysosomal delivery," *Traffic*, 10(5):600. (2009).
Gay, D. et al., "Receptor editing: an approach by autoreactive B cells to escape tolerance," *J. Exp. Med.*, 177(4):999-1008 (1993).
Giallourakis, C.C., et al., "Elements between the IgH variable (V) and diversity (D) clusters influence antisense transcription and lineage-specific V(D)K recombination," *PNAS*, 107(51):22207-22212 (2010).
Goldstein, J.L. et al., "The LDL Receptor," *Arterioscler. Thromb. Vasc. Biol.*, 29:431-438 (2009).
Goletz et al., "Selection of Large Diversities of Antiidiotypic Antibody Fragments by Phage Display", *J. Mol. Biol.*, 315:1087-97, (2002).
Gonnet, et al., "Exhaustive Matching of the Entire Protein Sequence Database," *Science*, 256:1443-1445 (1992).
Gonzalez-Fernandez, A. et al., "Analysis of somatic hypermutation in mouse Peyer's patches using immunoglobulin κ light-chain transgenes," *PNAS USA*, 90:9862-9866 (1993).
Goyenechea, B. et al., "Modifying the sequence of an immunoglobulin V-gene alters the resulting pattern of hypermutation," *PNAS USA*, 93:13979-13984 (1996).
Green, L. et al., "Antigen-specific human monoclonal antibodies from mice engineered with human Ig heavy and light chain YACs," *Nat. Genetics.*, 7(1):13-21 (1994).
Green, L. et al., "Regulation of B cell development by variable gene complexity in mice reconstituted with human immunoglobulin yeast artificial chromosomes," *J. Exp. Med.*, 188(3):483-495 (1998).
Han, C., et al., "Comprehensive Analysis of Reproductive ADAMs: Relationship of ADAM4 and ADAM6; with an ADAM Complex Required for Fertilization in Mice", *Biology of Reproduction*, 80(5): 1001-1008 (2009).
Hengstschlager, M. et al., "A λ1 transgene under the control of a heavy chain promoter and enhancer does not undergo somatic hypermutation," *Eur. J Immunol.*, 24:1649-1656 (1994).
Hendricks, J., et al., "Organization of the variable region of the immunoglobin heavy-chain gene locus of the rat," *Immunogenetics*, 62:479-486 (2010).
Hochedlinger, et al., "Monoclonal Mice Generated by Nuclear Transfer from Mature B and T Donor Cells", *Nature* 415(6875):1035-1038, (2002).
Igawa, T. et al., "Reduced elimination of IgG antibodies by engineering the variable region," *Protein Engineering, Design & Selection*, 23(5):385-392 (2010).
Igawa, T. et al., "Antibody recycling by engineered pH-dependent antigen binding improves the duration of antigen neutralization," *Nature Biotechnology*, 28(11):1203-1208 and supplement (2010).
Igawa T. et al, "Engineering the variable region of therapeutic IgG antibodies," mAbs, 3(3):243-52. (2011).
International Search Report and Written Opinion for International Patent Application No. PCT/US2011/023971 dated Apr. 11, 2011.
International Search Report and Written Opinion for International Patent Application No. PCT/US2012/034737 mailed Dec. 6, 2012.
International Search Report and Written Opinion for International Patent Application No. PCT/US2012/049600 mailed Nov. 23, 2012.
International Search Report and Written Opinion for International Patent Application No. PCT/US2013/029125 mailed Jun. 20, 2013.
International Search Report and Written Opinion for International Patent Application No. PCT/US2013/031834 mailed Jul. 2, 2013.
International Search Report and Written Opinion for International Patent Application No. PCT/US2013/032036 mailed Jul. 1, 2013.
International Search Report and Written Opinion for International Patent Application No. PCT/US2013/031823 mailed Jul. 8, 2013.
Ippolito, G.C., "Forced usage of positively charged amino acids in immunoglobulin CDR-H3 impairs B cell development and antibody production," *J. Exp. Med.*, 203(6):1567-1578 (2006).
Ito, W. et al., The His-probe method: effects of histidine residues introduced into the complementary-determining regions of antibodies on antigen-antibody interactions at different pH values, *FEBS Lett.*, 309(1):85-88. (1992).
Jakobovits, A. et al., "From XenoMouse technology to panitumumab, the first fully human antibody product from transgenic mice," *Nature Biotechnology*, vol. 25, No. 10, pp. 1134-1143 (2007).
Jolly, C. et al., "Rapid methods for the analysis of immunoglobulin gene hypermutation: application to transgenic and gene targeted mice," *Nucleic Acids Research*, 25(10):1913-1919 (1997).
Kim, T., et al., "Expression and relationship of mail reproductive ADAMs in mouse," *Biology of Reproduction*, 74:744-750 (2006).
Klotz, E. et al., "Somatic Hypermutation of a λ2 Transgene Under the Control of the λ Enhancer or the Heavy Chain Intron Enhancer," *J. Immunol.*, 157:4458-4463 (1996).
Klotz, E. et al., "Somatic Hypermutation of an Artificial Test Substrate Within an Igκ Transgene," *J. Immunol.*, 161:782-790 (1998).
Kong, Q. et al., "A λ 3' enhancer drives active and untemplated somatic hypermutation of a $\lambda_1$ transgene," *J. Immunol.*, 161:294-301 (1998).
Kufer, P. et al., "A revival of bispecific antibodies," *Trends Biotechnol.*, 22(5):238-244 (May 2004).
Lee, E-C., et al., "The application of transgenic mice for therapeutic antibody discovery," *Methods in Molecular Biology*, 901:137-148 (2012).
Lencer, W. I. et al., "A passionate kiss, then run: exocytosis and recycling of IgG by FcRn," *Trends in Cell Biol.*, 15(1):5-9 (2005).
Lefranc, M., "Nomenclature of the Human Immunoglobulin Genes," *Current Protocols in Immunology*, Supplement 40, pp. A.1P.1-A.1P. 37 (2001).
Lefranc, et al. "IMGT unique numbering for immunoglobulin and T cell receptor variable domains and Ig superfamily V-like domains," *Dev. Comp. Immunol.*, 27:55-77 (2003).
Leitzgen, K. et al., "Assembly of immunoglobulin Light Chains as a Prerequisite for Secretion," *Journal of Biological Chemistry*, 272(5): 3117-3123 (1997).
Lindhofer, H. et al., "Preferential Species-Restricted Heavy/Light Chain Pairing in Rat/Mouse Quadromas," *The Journal of Immunology*, 155:219-225 (1995).
Lonberg et al., "Antigen-specific Human Antibodies from Mice Comprising Four Distinct Genetic Modifications", *Nature*, 368:856-859, (1994).
Lonberg, N., "Human antibodies from transgenic animals," *Nature Biotechnology*, 23(9):1117-1125 (2005).
Maeda, K. et al., "pH-dependent receptor/ligand dissociation as a determining factor for intracellular sorting of ligands for epidermal growth factor receptors in rat hepatocytes," *J. Controlled Release*, 82:71-82. (2002).
Marvin, J. et al., "Recombinant approaches to IgG-like bispecific antibodies," *Acta Pharmacologica Sinica*, 26(6):649-658 (2005).
Mellman, I., "The Importance of Being Acidic: The Role of Acidfication in Intracellular Membrane Traffic," *J. Exp. Biol.*, 172:39-45 (1992).
Mendez, M. J. et al., "Functional Transplant of Megabase Human Immunoglobulin Loci Recapitulates Human Antibody Response in Mice," *Nat. Genetics*, 15(2):146-156 (1997).
Merchant, A. et al., "An efficient route to human bispecific IgG," *Nature Biotechnology*, 16(7):677-681 (1998).
Moran, Nuala "Mouse Platforms Jostle for Slice of Humanized Antibody Market", *Nature Biotech*, 3:267-268, (2013).

(56) References Cited

OTHER PUBLICATIONS

Murtaugh, M.L. et al., "A combinatorial histidine scanning library approach to engineer highly pH-dependent protein switches," *Protein Sci.*, 20(9):1619-1631 (2011).

Nakasako, M. et al., "The pH-dependent Structural Variation of Complementarity-determining Region H3 in the Crystal Structures of the Fv Fragment from an Anti-dansyl Monoclonal Antibody," *J. Mol. Biol.*, 291:117-134 (1999).

Nicholson, I. et al., "Antibody Repertoires of Four- and Five-Feature Translocus Mice Carrying Human Immunoglobulin Heavy Chain and κ and λ Light Chain Yeast Artificial Chromosomes," *Journal of Immunology*, 163:6898-6906 (1999).

O'Brien, R. et al., "Somatic hypermutation of an immunoglobulin transgene in κ mice," *Nature*, 326(6111):405-409 (1987).

Pelanda, R. et al., "A prematurely Expressed Igκ Transgene, but Not VκJκ Gene Aegment Targeted into the Igκ Locus, Can Rescue B Cell Development in λ5-Deficient Mice," *Immunity*, 5(3):229-239 (1996).

Petkova, S.B. et al., "Enhanced half-life of genetically engineered human IgG1 antibodies in a humanized FcRn mouse model: potential application in humorally mediated autoimmune disease," *Intl. Immunol.*, 18(12):1759-1769 (2006).

Poueymirou, W. et al. F0 generation mice that are essentially fully derived from the donor gene-targeted ES cells allowing immediate phenotypic analyses, *Nature Biotech.*, 25(1):91-99 (2007).

Prak, E. et al., "Light chain replacement: a new model for antibody gene rearrangement," *J. Exp. Med.*, 182(2):541-548 (1995).

Presta, L.G., "Molecular engineering and design of therapeutic antibodies," *Curr. Opin. Immunol.*, 20(4):460-470 (2008).

Raso, V. et al., "Intracellular Targeting with Low pH-triggered Bispecific Antibodies," *J Biol. Chem.*, 272(44):27623-27628 (1997).

Roberts, D.M. et al., "Isolation and Characterization of the Fc Receptor from Fetal Yolk Sac of the Rat," *J Cell. Biol.*, 111:1867-1876 (1990).

Rojas, G. et al., "Phage antibody fragments library combining a single human light chain variable region with immune mouse heavy chain variable regions," *Journal of Biotechnology*, 94:287-298 (2002).

Roopenian, D.C, et al., "FcRn: the neonatal Fc receptor comes of age," *Nature Rev. Immunol.*, 7:715-725 (Sep. 2007).

Roopenian, D.C., et al., "Clinical Ramifications of the MHC Family Fc Receptor FcRn," *J. Clin. Immunol.*, 30(6):790-797 (2010).

Sarkar, C.A. et al. "Rational cytokine design for increased lifetime and enhanced potency using pH-activated 'histidine switching'," *Nature Biotech.*, 20:908-913 (2002).

Schroeder, H.W., et al., "Similarity and divergence in the development and expression of the mouse and human antibody repertoires," *Developmental and Comparative Immunol.*, 30(1-2):119-135 (2006).

Seals, D.F., et al., "the ADAMs family of metalloproteases: multidomain; proteins with multiple functions," *Genes and Development*, 17(1):7-30 (2003).

Simister, Neil E., et al. An Fc receptor structurally related to MHC class I antigens, *Nature* 337:184-187 (Jan. 12, 1989).

Sirac, C. et al., "Role of the monoclonal kappa chain V domain and reversibility of renal damage in a transgenic model of acquired Fanconi syndrome," *Blood*, 108(2):536-543 (2006).

Smith, B. et al., "The unique and immunoglobulin-like regions of surrogate light chain component lambda5 differentially interrogate immunoglobulin heavy-chain structure," *Molecular Immunology*, 47:1195-1206 (2010).

Storb, et al., "Transgenic Mice with μ and κ Genes Encoding Antiphosphorycholine Antibodies", *J. Exp Med*, 164:627-641 (1986).

Suzuki, T. et al., "Importance of Neonatal FcR in REgulation the Serum Half-Life of Therapeutic Proteins Containing the Fc Domain of Human IgG1: A Comparative Study of the Affinity of Monoclonal Antibodies and Fc-Fusion Proteins to Human Neonatal FcR," *J. Immunol.*, 184:1968-1976 (2010).

Reply to Third Party Observations on European patent application 11 703 799.04 (Publication No. EP 2 501 817) filed in EPO on May 20, 2013.

Request to provoke an interference U.S. Appl. No. 13/750,753 Jan. 25, 2013.

Summons to attend oral proceedings arranged in connection with European patent application 09075279.1 (Publication No. EP 2 147 594 A1) mailed Mar. 6, 2013.

Tabrizi, M. A. et al. "Elimination mechanisms of therapeutic monoclonal antibodies," *Drugs Discovery Today*, 11(1/2):81-88 (2006).

Taylor et al., "A Transgenic Mouse that Expresses a Diversity of Human Sequence Heavy and Light Chain Immunoglobulins," *Nucleic Acid Research*, 20(23):6287-6295 (1992).

Taylor et al., "Human immunoglobulin transgenes undergo rearrangement, somatic mutation and class switching in mice that lack endogenous 1gM", *Int. Immunol.*, 6:579-591 (1994).

Third Party Observations Under Article 115 EPC against European Parent Application No. 09075279.1 filed in EPO on Oct. 25, 2012.

Third Party Observations on European patent application 11 703 799.4-2405 (Publication No. EP 2 501 817) mailed on Feb. 28, 2013.

Tsubata, T. et al., "The Products of the Pre-B Cell-specific Genes(Lambda5 and VpreB) and the Immunoglobulin mu Chain Form a Comples that is Transported onto the Cell Surface," *Journal of Experimental Medicine*, 172:973-976 (1990).

Tuaillon, et al., "Analysis of direct and inverted DJH rearrangements in a human Ig heavy chain transgenic minilocus," *Journal of Immunology.*, 154(12):6453-6465 (1995).

Tutt, A. et al., "Trispecific F(ab')3 Derivatives That Use Cooperative Signaling Via the TCR/CD3 Complex and CD2 to Activate and Redirect Resting Cytotoxic T Cells," *Journal of Immunology*, 147(1):60-69 (Jul. 1, 1991).

Tzaban, S. et al., "The recycling and transcytotic pathways for IgG transport by FeRn are distinct and display an inherent polarity," *J. Cell Biol.*, 185(4):673-684 (2009).

Valenzuela, D. M. et al., "High-throughput engineering of the mouse genome coupled with high-resolution expression analysis," *Nature Biotech.*, 21(6):652-659 (2003).

Vaughn, D.E., et al., "Structural basis of pH-dependent antibody binding by the neonatal receptor," *Structure*, 6:63-73(1997).

Wang, W. et al. "Monoclonal Antibody Pharmacokinetics and Pharmacodynamics," *Clinical Pharmacology & Therapeutics*, 84(5):548-558 (2008).

Watanabe, H. et al. "Optimizing pH Response of Affinity between Protein G and IgG Fc: How Electrostatic Modulations Affect Protein-Protein Interactions," *J. Biol. Chem.*, 284(18):12373-12383 (2009).

Xu, L. et al., "Combinatorial surrobody libraries," *Proceedings of the National Academy of Sciences (USA)*, 105(31):10756-10761 (2008).

Yeung, Y.A. et al. "Engineering Human IgG1 Affinity to Human Neonatal Fc Receptor: Impact of Affinity Improvement on Pharmacokinetics in Primates," *J. Immunol.*, 182(12):7663-7671 (2009).

U.S. Non-Final Office Action for U.S. Appl. No. 13/022,759 mailed Sep. 7, 2012.

U.S. Non-Final Office Action for U.S. Appl. No. 13/093,156 mailed Sep. 6, 2012.

U.S. Non-Final Office Action for U.S. Appl. No. 13/412,936 mailed Sep. 6, 2012.

International Search Report and Written Opinion mailed Sep. 4, 2013, from related International Patent Application No. PCT/US2013/044257 filed Jun. 5, 2013.

Aucouturier et al., (1992) "Human rearranged IgK mRNA VJC region," GenBank Accession No. M87478 1 page, first referenced Mar. 3, 1992, first seen at NCBI Apr. 27, 1993.

Choi et al., (2004) "Characterization and comparative genomic analysis of intronless Adams with testicular gene expression," Genomics 83(4): 636-646.

Dechiara et al., (2009) Chapter 16: VelociMouse: Fully ES Cell-Derived F0 Generation Mice Obtained from the Injection of ES Cells into 8-Cell Stage Embryos, Gene Knockout Protocols: Second Edition, vol. 530, Humana Press.

(56) References Cited

OTHER PUBLICATIONS

Fishwild et al., (1996) "High-avidity human IgGk monoclonal antibodies from a novel train of mililocus transgenic mice," Nature Biotechnology, 14(7):845-851.
Goodhardt et al., (1987), "Rearrangement and Expression of rabbit immunoglobulin K light chain gene in transgenic mice," PNAS, 84:4229-4233.
Goyenechea et al., (1997) "Cells strongly expressing Ig(kappa) transgenes show clonal recruitment of hypermutation: a role for both MAR and the enhancers," EMBO J., 16(13):3987-94.
Green et al., (1999) "Antibody engineering via geneitc engineering of the mouse: XenoMouse strains are a vehicle for the facile generation of therapeutic human monoclonal antibodies," J. Immunol. Methods, 231:11-23.
Hardy and Hayakawa, (2001) "B cell development pathways," Annu. Rev. Immunol., 19:595-621.
Hömig-Hölzel et al., (2008) "Constitutive CD40 signaling in B cells selectively activates the noncanonical NF-kappaB pathway and promotes lymphomagenesis," J. Exp. Med., 205(6):1317-1329.
Inlay et al., (2002) "Essential roles of the kappa light chain intronic enhancer and 3' enhancer in kappa rearrangement and demethylation," Nat. Immunol., 3(5):463-468.
Jakobovits, (1995) "Production of fully human antibodies by transgenic mice," Curr. Opin. Biotechnol., 6 (5):561-566.
Janeway's Immunobiology, (2008) Seventh Edition, Murphy, Travers and Walpot, eds., Garland Science, New York and London, Ch. 4, pp. 145-155.
Kabat and Wu, (1991) "Identical V region amino acid sequences and segments of sequences in antibodies of different specificities. Relative contributions of VH and VL genes, minigenes, and complementarity-determining regions to binding of antibody-combining sites," J. Immunol., 147(5):1709-1719.
Kaushik, (1990) "Stochastic pairing of heavy-chain and x light-chain variable gene families occurs in polyclonally activated B cells," Proc. Natl. Acad. Sci. USA, 87: 4932-4936.
Klöhn et al., (2013) "Ibc's 23rd Annual Antibody Engineering, 10th Annual Antibody Therapeutics international conferences and the 2012 Annual Meeting of The Antibody Society: Dec. 3-6, 2012," San Diego, CA, Mabs, 5 (2):178-201.
Logtenberg, (2007) "Antibody cocktails: next-generation biopharmaceuticals with improved potency," Trends Biotechnol., 25(9):390-394.
Nagle, (2007) "Regeneron helps make Sanofi Veloclmmune to its "weak pipeline,"" <http://www.outsourcing-pharma.com> —Published Dec. 3, 2007.
Nemazee, (2006) "Receptor editing in lymphocyte development and central tolerance," Nat. Rev. Immunol., 6 (10):728-740.
News in Brief Article (2007) "Big Pharma vies for mice," Nature Biotechnology, 25(6):613—Published Jun. 2007.
No Author Listed, Additional post-filing data and letter filed by the Applicant/Patentee for corresponding European application 09075279.1, now opposed patent EP 2147594 B1, 4 pages (Jun. 13, 2013).
No Author Listed, "Next generation transgenic mice for therapeutic human antibodies, Description of MeMoTM," filed by the Applicant/Patentee in prosecution for corresponding European application 09075279.1, now opposed patent EP 2147594 B1, 2 pages (Dec. 22, 2011).
No Author Listed, (2011) Chapter 8: The Development and Survival of Lymphocytes, Janeway's Immunobiology, 8th Edition, Eds. Kenneth Murphy et al, Garland Science (ISBN: 9780815342434), whole document, in particular p. 279 and Figure 8.4.
Orban et al., (1992) "Tissue- and site-specific DNA recombination in transgenic mice," Proc. Natl. Acad. Sci. U S A., 89(15):6861-6865.
Panka et al., (May 1988) "Variable region framework differences result in decreased or increased affinity of variant anti-digoxin antibodies," Proc. Natl. Acad. Sci. USA, 85:3080-3084.
Paul, (1993) Fundamental Immunology, 3rd ed., Raven Press, NY, Chapter 9, pp. 292-295.
Popov et al., (1999) "A human immunoglobulin lambda locus is similarly well expressed in mice and humans," J. Exp. Med., 189(10):1611-1620.
Rabquer et al., (2005) "Immunoglobulin light chain variable region, partial [Homo sapiens]," GenBank Accession No. ABA26122, 2 pages, first reference Dec. 31, 1995.
Rickert et al., (1997) "B lymphocyte-specific, Cre-mediated mutagenesis in mice," Nucleic Acids Res., 25 (6):1317-1318.
Rudikoff et al., (1982) "Single amino acid substitution altering antigen-binding specificity," Proc. Natl. Acad. Sci. USA, 79:1979-1983.
Sasaki et al., (2006) "Canonical NF-x13 Activity, Dispensable for B Cell Development, Replaces BAFF-Receptor Signals and Promotes B Cell Proliferation upon Activation," Immunity, 24:729-739.
Scott, (2007) "Mice with a human touch," Nature Biotechnology, 25(10): 1075-1077.
Sharpe et al., (1991) "Somatic hypermutation of immunoglobulin kappa may depend on sequences 3' of C kappa and occurs on passenger transgenes," EMBO J., 10(8):2139-2145.
Simon and Rajewsky, (1990), "Antibody domain mutants demonstrate autonomy of the antigen binding site," EMBO J., 9(4):1051-1056.
Soriano, (1999) "Generalized lacZ expression with the ROSA26 Cre reporter strain," Nat. Genet., 21(1):70-71.
Stevens et al., (2008) "Human Antibody Discovery, Veloclmmune—A novel platform, Pharma Focus Asia," Issue 8:72-74.
Torres and Kuhn, (1997) "Laboratory Protocols for Conditional Gene Targeting," Oxford University Press, 978-0-19-963677-8, 42-53.
Vaughan et al., (1996) "Human antibodies with sub-nanomolar affinities isolated from a large non-immunized phage display library," Nat. Biotechnol., 14(3):309-314.
Winter et al., (1997) "Insertion of 2 kb of bacteriophage DNA between an immunoglobulin promoter and leader exon stops somatic hypermutaion in a kappa transgene," Mol. Immunol., 34(5):359-366.
International Search Report and Written Opinion for PCT Application No. PCT/US2013/044257 mailed Sep. 4, 2014 (9 pages).
International Search Report and Written Opinion for PCT Application No. PCT/US2014/025982 mailed Jul. 22, 2014 (13 pages).
International Search Report and Written Opinion for PCT Application No. PCT/US2014/026040 mailed Jul. 29, 2014, (14 pages).
International Search Report and Written Opinion for PCT Application No. PCT/US2014/056285 mailed Feb. 2, 2015, (12 pages).
Sirac et al. (2011) "Toward Understanding Renal Fanconi Syndrome: Step by Step Advances through Experimental ModeLs," Exp. Models for Renal Diseases: Pathogenesis and Diagnosis, Contrib. Nephrol. Basel, Karger, 169:247-261.
Statement of Relatedness under MPEP 2001.06 dated Oct. 14, 2015.

* cited by examiner

| | Stop | SEQ ID NO. | Hydrophilic | SEQ ID NO. | Hydrophobic | SEQ ID NO. |
|---|---|---|---|---|---|---|
| D1-1 | VQLER | 8 | YNWND | 45 | GTTGT | 88 |
| HD1-1 | VPLAR | 9 | YHWHD | 46 | GTTGT | 88 |
| D1-7 | V*LEL | - | YNWNY | 47 | GITGT | 89 |
| HD1-7 | VSLAL | 10 | YHWHY | 48 | GITGT | 89 |
| D1-20 | V*LER | - | YNWND | 45 | GITGT | 89 |
| HD1-20 | VSLAR | 11 | YHWHD | 46 | GITGT | 89 |
| D1-26 | V*WELL | 12 | YSGSYY | 49 | GIVGAT | 90 |
| HD1-26 | VSWEPL | 13 | YHGSHY | 50 | GIMGAT | 91 |
| D2-2*02 | RIL*YQLLY | 14 | GYCSSTSCYT | 51 | DIVVPAAI | 92 |
| HD2-2*02 | RTL*SYQLPY | 15 | GHCSHTSCHT | 52 | DIVVIPAAI | 93 |
| D2-8*01 | RILYWCMLY | 16, 17 | GYCTNGVCYT | 53 | DIVLMVYAI | 94 |
| HD2-8*01 | RTLYSWCMPY | 18 | GHCTHGVCHT | 54 | DIVLMVYAI | 94 |
| D2-15 | RIL*WW*LLL | - | GYCSGGSCYS | 55 | DIVVVAAT | 95 |
| HD2-15 | RTL*SW*LPL | - | GHCSHGSCHS | 56 | DIVVMVAAT | 96 |
| D2-21*02 | SILWW*LLF | 19 | AYCGGDCYS | 57 | HVVVTAI | 97 |
| HD2-21*02 | STLWWSLPF | 20 | AHCGGHCHS | 58 | HVVVTAI | 97 |
| D3-3*01 | VLRFLEWLLY | 21 | YDFNSGYYT | 59 | ITIFGVII | 98 |
| HD3-3*01 | VSPFLEWSLY | 22 | YHHFWSGHYT | 60 | ITIFGVII | 98 |
| D3-9 | VLRYFDWLL* | 23 | YDILTGYYN | 61 | ITIF*LVII | 99, 100 |
| HD3-9 | VSPYFDWSL* | 24 | YHHILTGHYN | 62 | ITIF*LVII | 99, 100 |
| D3-10*01 | VLLWFGELL* | 25 | YYYGSGSYYN | 63 | ITMVRGVII | 101 |
| HD3-10*01 | VSPWFGESL* | 26 | YHHGSGSHYN | 64 | ITMVRGVII | 101 |
| D3-16*02 | VL*LRLGELSLY | 27 | YDYVWGSYRYT | 65 | IMITFGGVIVI | 102 |
| HD3-16*02 | VS*SRLGESSLY | 28 | YHDHVWGSHRYT | 66 | IMITFGGVIVI | 102 |
| D3-22 | VLL***WLLL | 29 | YYYDSSGYYY | 67 | ITMIVVVIT | 103 |
| HD3-22 | VSLS*WSLL | 30, 31 | YHYHSSGHYY | 68 | ITVVVIT | 104 |
| D4-4 | *LQ*L | - | DYSNY | 69 | TTVT | 105 |
| HD4-4 | *PQSL | 32 | DHSHY | 70 | TTVT | 105 |
| D4-11p | *LQ*L | - | DYSNY | 69 | TTVT | 105 |

FIG. 1A

| | Stop | SEQ ID NO. | Hydrophilic | SEQ ID NO. | Hydrophobic | SEQ ID NO. |
|---|---|---|---|---|---|---|
| HD4-11p | *PQSL | 32 | DHSHY | 70 | TTVT | 105 |
| D4-17 | *LR*L | - | DYGDY | 71 | TTVT | 105 |
| HD4-17 | *PRSL | 33 | DHGHY | 72 | TTVT | 105 |
| D4-23p | *LRW*L | - | DYGGNS | 73 | TTVVT | 106 |
| HD4-23p | *PRWSL | 34 | DHGGHS | 74 | TTVVT | 106 |
| D5-5 | W|QLWL | 35 | GYSYGY | 75 | VDTAMV | 107 |
| HD5-5 | WTQPWL | 36 | GHSHGY | 76 | VDTAMV | 107 |
| D5-12 | W|*WLRL | 37 | GYSGYDY | 77 | VDIVATI | 108 |
| HD5-12 | WT*WPPL | 38 | GHSGHHY | 78 | VDIVATI | 108 |
| D5-18 | WIQLWL | 35 | GYSYGY | 75 | VDTAMV | 107 |
| HD5-18 | WTQPWL | 36 | GHSHGY | 76 | VDTAMV | 107 |
| D5-24p | *RWLQL | 39 | RDGYNY | 79 | VEMATI | 109 |
| HD5-24p | *TWPPL | 40 | RHGHHY | 80 | VDMATI | 110 |
| D6-6 | V*QLV | - | EYSSSS | 81 | SIAAR | 111 |
| HD6-6 | A*PLV | 41 | EHSHSS | 82 | SIATR | 112 |
| D6-13 | V*QQLV | 42 | GYSSSWY | 83 | GIAAAG | 113 |
| HD6-13 | A*PQLV | 43 | GHSHSWY | 84 | GIATAG | 114 |
| D6-19 | V*QMLV | 44 | GYSSGWY | 85 | GIAVAG | 115 |
| HD6-19 | A*PWLV | - | GHSHGWY | 86 | GIAMAG | 116 |
| D6-25 | V*QRL | - | GYSSGY | 87 | GIAAA | 117 |
| HD6-25 | A*PRL | - | GHSHGY | 76 | GIATA | 118 |

FIG. 1B

Probes for MAID 6011 (deletion of higH DH segments in MAID1460 )

| Name | Forward Primer | Probe | Reverse Primer | Type | Label | Location |
|---|---|---|---|---|---|---|
| higH DH-1 | CGGGTCACTGCCATTTCTG (SEQ ID NO: 119) | TCTGCCATTCGCTCCAGCGC (SEQ ID NO: 120) | TCTGCGGGCATGAACCCAAT (SEQ ID NO: 121) | LOA | FAM-BHQ-1 | higH D segments |
| higH DH-2 | GTGCAGGGAGGACTTCT G (SEQ ID NO: 122) | AGTCACCAAGCACAGAGCCTGAC (SEQ ID NO: 123) | GCCAGGGAGTTGCCTAGTG (SEQ ID NO: 124) | LOA | FAM-BHQ-1 | higH D segments |
| higH DH-3 | GTGGCCACTTCCCTTCCT (SEQ ID NO: 125) | CAGCTGGAACCCACCATGACCT (SEQ ID NO: 126) | GACCTGCCTCGGATGACA (SEQ ID NO: 127) | LOA | FAM-BHQ-1 | higH D segments |
| higH DH-4 | TGGCCAGAACTGACCCTAC (SEQ ID NO: 128) | ACCGACAAGAGTCCCTCAGG (SEQ ID NO: 129) | GGAGTCGGCTCTGGATGTG (SEQ ID NO: 130) | LOA | BHQ-plus | higH D segments |
| hyg | TGCGGCCGATCTTAGCC (SEQ ID NO: 131) | ACGAGCGGGTTCGGCCATTC (SEQ ID NO: 132) | TTGACCGATTCCTTGCGG (SEQ ID NO: 133) | GOA | FA-BHQ-1 |  |
| higH1 | CAGTCCGTTGATCCAGCC (SEQ ID NO: 134) | CCCATCAGGGATTTTGTATCTCTGT GGACG (SEQ ID NO: 135) | GGATATGCAGCACTGCGAC (SEQ ID NO: 136) | AR |  | higH |
| higH9 | TCCTCCAACGACAGGTCC (SEQ ID NO: 137) | TCCCTGGAACTGCCCGACACA (SEQ ID NO: 138) | GATGAACTGACGGGCACAGG (SEQ ID NO: 139) | AR |  | higH |
| higH31 | ATCAACTCATCCCATCCC (SEQ ID NO: 140) | CCCTTCCTAAGTACCACAGAGTGG GCTC (SEQ ID NO: 141) | CACAGGGAAGCAGGAACTGC (SEQ ID NO: 142) | AR |  | higH |

FIG. 6

Probes for MAID 6012 (insertion of HD, His-substituted hIgH DH segments)

| Name | Forward Primer | Probe | Reverse Primer | Type | Label | Location |
|---|---|---|---|---|---|---|
| hyg | TGCGGCCGATCTTAGCC (SEQ ID NO: 131) | ACGAGAGCGGGTTCGGCCCATTC (SEQ ID NO: 132) | TTGACCGATTCCTTGACGG (SEQ ID NO: 133) | LOA | FAM-BHQ1 | |
| HD jxn-1 | GGAAGCCAGGCAGGACACA (SEQ ID NO: 143) | TGGGCTCGTAGTTTGACGT (SEQ ID NO: 144) | GGGACTTCTTACCCACA CTTCA (SEQ ID NO: 145) | GOA | MGB | Synthetic linker-1 in HD segments |
| HD jxn-2 | GGTCCGAGCACTCTTAATTAAA C (SEQ ID NO: 146) | CCTCGAATGGAACTAC (SEQ ID NO: 147) | GGGAGAGCAACATTCG TTGT (SEQ ID NO: 148) | GOA | MGB | Synthetic linker-2 in HD segments |
| HD jxn-3 | CCGAGGACACCGATGCATCTA (SEQ ID NO: 149) | CGGCAGTCATGTAATGC (SEQ ID NO: 150) | GGGAGGCGAACTGACTG TCA (SEQ ID NO: 151) | GOA | MGB | Synthetic linker-3 in HD segments |
| hIgH DH-1 | CGGGTCACTGCCATTTCTG (SEQ ID NO: 119) | TCTGCATTCGCTCCCAGCGC (SEQ ID NO: 120) | TCTGCGGCATGAACCCAA T (SEQ ID NO: 121) | GOA | FAM-BHQ1 | hIgH D segments |
| hIgH DH-2 | GTGCAGGGAGGACCTTCTG (SEQ ID NO: 122) | AGTACCAAGCACAGAGCCCTGA C (SEQ ID NO: 123) | GCCAGGGAGTTGCCTAG TG (SEQ ID NO: 124) | GOA | FAM-BHQ1 | hIgH D segments |
| hIgH DH-3 | GTGGCCCACTTCCCTTCCT (SEQ ID NO: 125) | CAGCTGGAACCCACCATGACCT (SEQ ID NO: 126) | GACCTGCCTCGGATGACA (SEQ ID NO: 127) | GOA | FAM-BHQ1 | hIgH D segments |
| hIgH DH-4 | TGGCCAGAACTGACCCTAC (SEQ ID NO: 128) | ACCGACAAGAGTCCTCTCAGG (SEQ ID NO: 129) | GGAGTCGGCTCTGGATGTG (SEQ ID NO: 130) | GOA | BHQ-plus | hIgH D segments |
| neo | GGTGGAGAGGCTATTCGGC (SEQ ID NO: 152) | TGGGCAACACAGACAATCGGCTG (SEQ ID NO: 153) | GAACACGGCGGCATCAG (SEQ ID NO: 154) | GOA | FAM-BHQ1 | |
| hIgH1 | CAGTCCGTTGATCCAGCC (SEQ ID NO: 134) | CCCATACAGGAGGATTTGTATCTC TGTGGACG (SEQ ID NO: 135) | GGATATGCAGCACTGTGCC AC (SEQ ID NO: 136) | AR | | hIgH |
| hIgH9 | TCCTCAACGACAGGTCC (SEQ ID NO: 137) | TCCCTGGAACTCTGCCCGGACACA (SEQ ID NO: 138) | GATGAACTGACGGGCACA GG (SEQ ID NO: 139) | AR | | hIgH |
| hIgH31 | ATCACACTCATCCATCCCC (SEQ ID NO: 140) | CCCTTCCCTAAGTACCACAGAGTG GGCTC (SEQ ID NO: 141) | CACAGGGAAGCAGGAACT GC (SEQ ID NO: 142) | AR | | hIgH |

FIG. 8

| Human D Gene Segment | | Direct 5'-3' Orientation | SEQ ID NO. | Inverted Orientation | SEQ ID NO. |
|---|---|---|---|---|---|
| IGHD1-1 | X97051, IGHD1-1*01 | ggtacaactggaacgac<br>G T T G T<br>V Q L E R<br>Y N W N D | 155<br>88<br>8<br>45 | gtcgttccagttgtacc<br>V V P V V<br>S F Q L Y<br>R S S C T | 206<br>207<br>208<br>209 |
| IGHD1-7 | X13972, IGHD1-7*01 | ggtataactggaactac<br>G I T G T<br>V * L E L<br>Y N W N Y | 156<br>89<br>-<br>47 | gtagttccagttatacc<br>V V P V I<br>* F Q L Y<br>S S S Y T | 210<br>211<br>212<br>213 |
| IGHD 1-20 | X13972, IGHD1-14*01 | ggtataacaggaacacc<br>G I T G T<br>V * P E P<br>Y N R N H | 157<br>89<br>-<br>158 | gtggttccggttatacc<br>V V P V I<br>W F R L Y<br>G S G Y T | 214<br>211<br>215<br>216 |
| IGHD 1-20 | X97501, IGHD1-20*01 | ggtataactggaacgac<br>G I T G T<br>V * L E R<br>Y N W N D | 159<br>89<br>-<br>45 | gtcgttccagttatacc<br>V V P V I<br>S F Q L Y<br>R S S Y T | 217<br>211<br>208<br>218 |
| IGHD1-26 | X97501, IGHD1-26*01 | ggtatagtgggagctactac<br>G I V G A T<br>V * W E L L<br>Y S G S Y Y | 160<br>90<br>12<br>49 | gtagtagtcccactatacc<br>V V A P T I<br>* * L P L Y<br>S S S H Y T | 219<br>220<br>221<br>222 |
| IGHD2-2 | J00232, IGHD2-2*01 | aggatattgtagtagtaccagctgctatgcc<br>R I L * Y Q L L C<br>G Y C S S T S C Y A<br>D I V V V P A A M | 161<br>162<br>163<br>164 | ggcatagcagctggtactacaatatcct<br>G I A G T T T I S<br>A * Q L V L L Q Y P<br>H S S W Y Y Y N I | 223<br>224<br>225<br>226 |

FIG. 10A

| Human D Gene Segment | | Direct 5'-3' Orientation | SEQ ID NO. | Inverted Orientation | SEQ ID NO. |
|---|---|---|---|---|---|
| | X97051, IGHD2-2*02 | aggatattgtagtagtaccagctgctatacc<br>R I L * Y Q L L Y<br>G Y C S S T S C Y T<br>D I V V V P A A I | 165<br>14<br>51<br>92 | ggtatagcagctggtactactacaatatcct<br>G I A A G T T T I S<br>V * Q L V L L Q Y P<br>Y S S W Y Y Y N I | 227<br>224<br>225<br>226 |
| IGHD2-8 | M35648, IGHD2-2*03 | tggatattgtagtagtaccagctgctatgcc<br>W I L * Y Q L L C<br>G Y C S S T S C Y A<br>D I V V V P A A M | 166<br>167<br>168<br>169 | ggcatagcagctggtactactacaatatcca<br>G I A A G T T T I S<br>A * Q L V L L Q Y P<br>H S S W Y Y Y N I | 228<br>224<br>225<br>226 |
| | X13972, IGHD2-8*01 | aggatattgtactaatggtgtgtgctataac<br>R I L Y * W C M L Y<br>G Y C T N G V C Y T<br>D I V L M V Y A I | 170<br>16, 17<br>53<br>94 | ggtatagcatacaccattagtacaatatcct<br>G I A Y T I S T I S<br>V * H T P L V Q Y P<br>Y S I H H * Y N I | 229<br>230<br>231<br>232 |
| | J00233, IGHD2-8*02 | aagatattgtactgtgtgtgtgtgtgctataac<br>R I L Y W W C M L Y<br>G Y C T G G V C Y T<br>D I V L V V Y A I | 171<br>172<br>173<br>174 | ggtatagcatacaccagtacaatatctt<br>G I A Y T T S T I S<br>V * H T P P V Q Y L<br>Y S I H H Q Y N I | 233<br>234<br>235<br>236 |
| IGHD2-15 | J00234, IGHD2-15*01 | aggatattgtagtggtgtagctgctactcc<br>R I L * W W * L L L<br>G Y C S G G S C Y S<br>D I V V V A A T | 175<br>-<br>55<br>95 | gggaatagcagctaccaccaatatcct<br>G V A A T T T I S<br>E * Q L P P L Q Y P<br>S S S Y H H Y N I | 237<br>238<br>239<br>240 |
| IGHD2-21 | J00235, IGHD2-21*01 | agcatattgtggtggtgttgactgctattcc<br>S I L W W * L L F<br>A Y C G G D C Y S<br>H I V V V I A I | 176<br>19<br>57<br>177 | ggaatagcaatatccaccacaatatgct<br>G I A I T T T I C<br>E * Q S P P Q Y A<br>N S N H H H N M | 241<br>242<br>243<br>244 |
| | X97051, IGHD2-21*02 | agcatattgtggtggtgttgactgctattcc<br>S I L W W * L L F<br>A Y C G G D C Y S<br>H I V V V T A I | 178<br>19<br>57<br>97 | ggaatagcagtaccaccacaatatgct<br>G I A V T T T I C<br>E * Q S P P Q Y A<br>N S S H H H N M | 245<br>246<br>247<br>248 |

FIG. 10B

| Human D Gene Segment | | Direct 5'-3' Orientation | SEQ ID NO. | Inverted Orientation | SEQ ID NO. |
|---|---|---|---|---|---|
| IGHD3-3 | X13972, IGHD3-3*01 | gtattacgatttggagtggttattatacc<br>V L R F E W L L Y<br>Y Y D F W S G Y Y T<br>* T I F G V V I I | 179<br>21<br>59<br>98 | ggtataataaccactccaaaaatcgtaatac<br>G I * T T P K I V I<br>V * * P L Q K S * Y<br>Y N N H S K N R N | 249<br>250<br>251<br>252 |
| | X93618, IGHD3-3*02 | gtattagcatttggagtggttattatacc<br>V L A F L E W L L Y<br>Y * H F W S G Y Y T<br>* S I F G V V I I | 180<br>181<br>182<br>183 | ggtataataaccactccaaaaatgctaatac<br>G I * T T P K M L I<br>V * * P L Q K C * Y<br>Y N N H S K N A N | 253<br>254<br>255<br>256 |
| IGHD3-9 | X13972, IGHD3-9*01 | gtattacgatatttgactcgttattataac<br>V L R Y F D W L L *<br>Y Y D I L T G Y Y N<br>* T I F * L V I I | 184<br>23<br>61<br>99, 100 | gttataataacagtcaaatatcgtaatac<br>V I I T S Q N I V I<br>L * * P V K I S * Y<br>Y N N Q S K Y R N | 257<br>258<br>259<br>260 |
| IGHD3-10 | K13972, IGHD3-10*01 | gtattactatgttcggggagttattataac<br>V L L W F G E L L *<br>Y Y Y G S G S Y Y N<br>* T M V R G V I I | 185<br>25<br>63<br>101 | gttataatactcccgaaccatagtaatac<br>V I T P R T I V I<br>L * * L P E P * * Y<br>Y N N S P N H S N | 261<br>262<br>263<br>264 |
| | X93615, IGHD3-10*02 | gtattactatgttcggggagttattactac<br>V L L C S G S Y Y N<br>Y Y Y V R G V I I<br>* T M F G R L L * | 186<br>187<br>188<br>189 | gttataatactcccgaacatagtaatac<br>V I I T P R T * * Y<br>L * * L P E H S N<br>Y N N S P N I V I | 265<br>266<br>267<br>268 |
| IGHD3-16 | X93614, IGHD3-16*01 | gtattattgattacgtttggggagtatgctatacc<br>V L * L R L G E L C L Y<br>Y Y D Y V W G S Y A Y T<br>* M I T F G G V M L I | 190<br>191<br>192<br>193 | ggtataagcataactccccaaacgtaatcataatac<br>G I S I T P P N V I I I<br>V * A * L P Q T * S * Y<br>Y K H N S P K R N H N | 269<br>270<br>271<br>272 |
| IGHD3-22 | X93616, IGHD3-22*01 | gtattactatgatagtagtggttattactac<br>V L L * * W L L L<br>Y Y Y D S S G Y Y Y<br>* T M I V V V I T | 194<br>29<br>67<br>103 | gtagtaataaccactactatcatagtaatac<br>V * I T T I I V I<br>* * * P L L S * * Y<br>S N N H Y Y H S N | 273<br>274<br>275<br>276 |

FIG. 10C

| Human D Gene Segment | | Direct 5'-3' Orientation | SEQ ID NO. | Inverted Orientation | SEQ ID NO. |
|---|---|---|---|---|---|
| IGHD4-4 | X13972, IGHD4-4*01 | tgactacagtaactac<br>* L Q * L<br>D Y S N Y<br>T T V T | 195<br>-<br>69<br>105 | gtagttactgtagtca<br>V V T V V<br>* L L * S<br>S Y C S | 277<br>278<br>-<br>279 |
| IGHD4-11 | X13972, IGHD4-11*01 | tgactacagtaactac<br>* L Q * L<br>D Y S N Y<br>T T V T | 195<br>-<br>69<br>105 | gtagttactgtagtca<br>V V T V V<br>* L L * S<br>S Y C S | 277<br>278<br>-<br>279 |
| IGHD4-17 | X97501, IGHD4-17*01 | tgactacggtgactac<br>* L R * L<br>D Y G D Y<br>T T V T | 196<br>-<br>71<br>105 | gtagtcaccgtagtca<br>V V T V V<br>* S P * S<br>S H R S | 280<br>278<br>-<br>281 |
| IGHD4-23 | X97051, IGHD4-23*01 | tgactacggtggtaactcc<br>* L R W * L<br>D Y G G N S<br>T T V V T | 197<br>-<br>73<br>106 | ggagttaccaccgtagtca<br>G V T T V V<br>E L P P * S<br>S Y H R S | 282<br>283<br>284<br>285 |
| IGHD5-5 | X13972, IGHD5-5*01 | gtggatacagctaggttac<br>V D T A M V<br>W I Q L W L<br>G Y S Y G Y | 198<br>107<br>35<br>75 | gtaaccatagctgtatccac<br>V T I A V S<br>* P * L Y P<br>N H S C I H | 286<br>287<br>-<br>288 |
| IGHD5-12 | X13972, IGHD5-12*01 | gtggatatagtggctacgattac<br>V D I V A T I<br>W I * W L R L<br>G Y S G Y D Y | 199<br>108<br>37<br>77 | gtaatcgtagccactatatccac<br>V I V A T I S<br>* S * P L Y P<br>N R S H Y I H | 289<br>290<br>291<br>292 |
| IGHD5-18 | X97051, IGHD5-18*01 | gtggatacagctaggttac<br>V D T A M V<br>W I Q L W L<br>G Y S Y G Y | 198<br>107<br>35<br>75 | gtaaccatagctgtatccac<br>V T I A V S<br>* P * L Y P<br>N H S C I H | 286<br>287<br>-<br>288 |

FIG. 10D

| Human D Gene Segment | | Direct 5'- 3' Orientation | SEQ ID NO. | Inverted Orientation | SEQ ID NO. |
|---|---|---|---|---|---|
| IGHD5-24 | X97051, IGHD5-24*01 | gtagagatggctacaattac<br>V E M A T I<br>* R W L Q L<br>R D G Y N Y | 200<br>110<br>39<br>79 | gtaattgtagccatctctac<br>V I V A I S<br>* L * P S L<br>N C S H L Y | 293<br>294<br>-<br>295 |
| IGHD6-6 | X13972, IGHD6-6*01 | gagtatagcagcagctgtac<br>E Y S S S S<br>S I A A R<br>V * Q L V | 201<br>81<br>112<br>- | ggacgagctgctgctatactc<br>G R A A I L<br>D E L L Y<br>T S C Y T | 296<br>297<br>298<br>299 |
| IGHD6-13 | X13972, IGHD6-13*01 | gggtatagcagcagctggtac<br>G Y S S S W Y<br>G I A A A G<br>V * Q Q L V | 202<br>83<br>114<br>41 | gtaccagctgctgctatactc<br>V P A A A I P<br>Y Q L L L Y<br>T S C C Y T | 300<br>301<br>302<br>303 |
| IGHD6-19 | X97051, IGHD6-19*01 | gggtatagcagtggctggtac<br>G Y S S G W Y<br>G I A V A G<br>V * Q W L V | 203<br>85<br>116<br>44 | gtaccagccactgctatactc<br>V P A T A I P<br>Y Q P L L Y<br>T S H C Y T | 304<br>305<br>306<br>307 |
| IGHD6-25 | X97051, IGHD6-25*01 | gggtatagcagcggctac<br>G Y S S G Y<br>G I A A A<br>V * Q R L | 204<br>87<br>118<br>- | gtagccgctgctataccc<br>V A A A I P<br>* P L L Y<br>S R C Y T | 308<br>309<br>310<br>311 |
| IGHD7-27 | J00256, IGHD7-27*01 | ctaactgggga<br>L T G<br>* L G<br>N W G | 205<br>-<br>-<br>- | tccccagttag<br>S P V<br>P Q L<br>P S * | 312<br>-<br>-<br>- |

| D gene segment | Hydrophilic | SEQ ID NO. |
|---|---|---|
| D4-17 | DYGDY | 71 |
| HD4-17 | DHGHY | 72 |

MICE THAT PRODUCE ANTIGEN-BINDING PROTEINS WITH PH-DEPENDENT BINDING CHARACTERISTICS

CROSS REFERENCE TO RELATED APPLICATIONS

This application claims the benefit of priority to U.S. Provisional Application No. 61/611,950, filed 16 Mar. 2012, U.S. Provisional Application No. 61/613,352, filed Mar. 20, 2012, and U.S. Provisional Application No. 61/736,930, filed 13 Dec. 2012, the entire contents of each of the applications are incorporated herein by reference.

FIELD OF THE INVENTION

Genetically modified immunoglobulin loci of non-human animals comprising an unrearranged human heavy chain variable region nucleotide sequence, wherein the unrearranged human heavy chain variable region nucleotide sequence comprises an addition of least one histidine codon or a substitution of at least one non-histidine codon with a histidine codon. Non-human animals, including rodents, e.g., mice and rats, comprising in their germline an unrearranged human immunoglobulin heavy chain variable region nucleotide sequence, wherein the unrearranged human immunoglobulin heavy chain variable region nucleotide sequence comprises an addition of least one histidine codon or a substitution of at least one non-histidine codon with a histidine codon. Genetically engineered non-human animals capable of expressing an antigen-binding protein that is characterized by pH-dependent antigen binding, improved recyclability, and/or enhanced serum half-life.

BACKGROUND OF THE INVENTION

Drugs administered into the body, including therapeutic monoclonal antibodies, can be affected via various elimination mechanisms, including glomerular filtration (e.g., into urine), secretion (e.g., into the bile), and catabolism by cells. While small molecules are cleared from the body via renal filtration, the majority of secreted antibodies (e.g., IgG, which are too big to be filtered through glomeruli) are primarily removed from the body via cell-mediated catabolism, e.g., fluid-phase endocytosis (phagocytosis) or receptor-mediated endocytosis. For example, soluble molecules with several repeated epitopes are bound by a plurality of circulating antibodies, and the resulting large antigen-antibody complexes are phagocytosed rapidly into cells for degradation. On the other hand, cell surface target receptors, which are bound by antibodies (i.e., receptor-antibody complexes), undergo target-mediated endocytosis in a dose-dependent manner, which leads to formation of endosomes destined for lysosomal degradation inside cells. In some cases, the endocytosed receptor-antibody complexes bind neonatal Fc receptors (FcRn) inside the endosomes in a pH-dependent manner and are routed back to the cell surface for release into plasma or interstitial fluids upon exposure to a neutral extracellular pH (e.g., pH 7.0-7.4).

There is a need in the art for systems, e.g., non-human animals, cells, and genomic loci that generate antigen-binding proteins with titratable residues, e.g., genetically modified loci that rearrange immunoglobulin gene segments to generate heavy chain variable domains that respond to changes in pH, e.g., that donate or accept protons and, e.g., whose binding characteristics differ according to protonation state.

There is also a need in the art for methods and compositions that can further increase recycling efficiency of endocytosed antigen-binding proteins by promoting dissociation of antigen-binding proteins from receptor-antigen-binding protein complexes or by increasing the affinity of antigen-binding proteins toward FcRn in an acidic endosomal compartment without compromising the specificity and affinity of the antigen-binding protein toward an antigen of interest.

SUMMARY OF THE INVENTION

Genetically modified immunoglobulin heavy chain loci in the germline genome of non-human animals are provided, wherein the immunoglobulin heavy chain loci comprise a genetically modified unrearranged heavy chain variable region nucleotide sequence (e.g., one or more genetically modified human $V_H$, D, and/or $J_H$ gene segment), wherein the unrearranged heavy chain variable region nucleotide sequence comprises an addition of at least one histidine codon or a substitution of at least one endogenous non-histidine codon with a histidine codon. In various embodiments, the genetically modified unrearranged heavy chain variable region nucleotide sequence comprises at least one histidine codon in at least one reading frame that encodes an immunoglobulin heavy chain variable domain. In various embodiments, the unrearranged heavy chain variable region nucleotide sequence comprising the at least one histidine codon is operably linked to a human or non-human heavy chain constant region nucleotide sequence (e.g., a heavy chain constant region nucleotide sequence that encodes an immunoglobulin isotype selected from IgM, IgD, IgA, IgE, and IgG).

Non-human animals (mammals, e.g., rodents such as mice, rats, or hamsters) are provided that are genetically engineered to contain immunoglobulin heavy chain genomic loci in their germline genome, wherein the genomic loci comprise an unrearranged heavy chain variable region nucleotide sequence (e.g., one or more genetically modified human $V_H$, D, and/or $J_H$ gene segments), wherein the unrearranged heavy chain variable region nucleotide sequence comprises an addition of at least one histidine codon or a substitution of at least one endogenous non-histidine codon with a histidine codon. In various embodiments, the genome of the non-human animals comprises a modification (i) that deletes or renders nonfunctional all, or substantially all, endogenous immunoglobulin $V_H$, D, and/or $J_H$ gene segments (e.g., via insertion of a nucleotide sequence, e.g., an exogenous nucleotide sequence, in the immunoglobulin locus or via non-functional rearrangement or inversion of endogenous $V_H$, D, and/or $J_H$ gene segments); and (ii) that introduces an unrearranged human heavy chain variable region nucleotide sequence (e.g., genetically modified human $V_H$, D, or $J_H$ gene segments), wherein the unrearranged heavy chain variable region nucleotide sequence comprises an addition of at least one histidine codon or a substitution of at least one endogenous non-histidine codon with a histidine codon. In various embodiments, the unrearranged heavy chain variable region nucleotide sequence is present at an endogenous locus (i.e., where the unrearranged heavy chain variable region nucleotide sequence is located in a wild-type non-human animal) or present ectopically (e.g., at a locus different from the endogenous immunoglobulin heavy chain locus in its genome), or within its endogenous locus (e.g., within an immunoglobulin variable locus, wherein the endogenous locus is placed or moved to a different location in the genome). In various embodiments, the immunoglobulin heavy chain variable region nucleotide sequence is operably linked to a human or non-human heavy chain constant region nucleotide sequence (e.g., a heavy chain constant region nucleotide sequence that encodes an immunoglobulin isotype selected from IgM, IgD, IgA, IgE, and IgG).

Genetically modified non-human animals are provided that are capable of expressing a genetically modified immunoglobulin heavy variable domain comprising one or more histidines, wherein the one or more histidines are not encoded by a germline gene segment of a corresponding wild-type non-human animal.

Genetically modified non-human animals are provided that comprise a B cell population that is characterized by rearranged immunoglobulin heavy chain variable genes that encode an immunoglobulin heavy chain variable domain with one or more histidines that are not encoded by a germline gene segment of a corresponding wild-type non-human animal.

Methods and compositions are provided for making non-human animals that comprise a genetically modified immunoglobulin heavy chain variable locus comprising an unrearranged human heavy chain variable region nucleotide sequence containing one or more histidine codons in at least one reading frame that encodes a heavy chain variable domain.

Methods and compositions are provided for non-human animals that make antigen-binding proteins that exhibit a pH-dependent binding of an antigen. Methods and compositions are provided for making non-human animals that have B cell populations, or antibody populations, that are enriched (as compared with corresponding wild-type animals) with antigen-binding proteins that are pH-dependent, e.g., in particular, heavy chain variable domains, and/or antigen-binding fragments thereof.

In one aspect, a genetically modified immunoglobulin locus in a germline genome of a non-human animal is provided comprising an unrearranged human heavy chain variable region nucleotide sequence, wherein the unrearranged heavy chain variable region nucleotide sequence comprises an addition of least one histidine codon or a substitution of at least one endogenous non-histidine codon with a histidine codon.

In one embodiment, the non-human animal is a mammal, including a rodent, e.g., a mouse, a rat, or a hamster.

In one embodiment, the added or substituted histidine codon is present in an immunoglobulin heavy chain gene segment selected from a human $V_H$ gene segment, a human D gene segment, a human $J_H$ gene segment, and a combination thereof. In one embodiment, the immunoglobulin heavy chain gene segment is selected from a human germline $V_H$ gene segment, a human germline D gene segment, a human germline $J_H$ gene segment, and a combination thereof.

In one embodiment, the human V gene segment ($V_H$) is selected from the group consisting of $V_H$1-2, $V_H$1-3, $V_H$1-8, $V_H$1-18, $V_H$1-24, $V_H$1-45, $V_H$1-46, $V_H$1-58, $V_H$1-69, $V_H$2-5, $V_H$2-26, $V_H$2-70, $V_H$3-7, $V_H$3-9, $V_H$3-11, $V_H$3-13, $V_H$3-15, $V_H$3-16, $V_H$3-20, $V_H$3-21, $V_H$3-23, $V_H$3-30, $V_H$3-30-3, $V_H$3-30-5, $V_H$3-33, $V_H$3-35, $V_H$3-38, $V_H$3-43, $V_H$3-48, $V_H$3-49, $V_H$3-53, $V_H$3-64, $V_H$3-66, $V_H$3-72, $V_H$3-73, $V_H$3-74, $V_H$4-4, $V_H$4-28, $V_H$4-30-1, $V_H$4-30-2, $V_H$4-30-4, $V_H$4-31, $V_H$4-34, $V_H$4-39, $V_H$4-59, $V_H$4-61, $V_H$5-51, $V_H$6-1, $V_H$7-4-1, $V_H$7-81, and a combination thereof.

In one embodiment, the human D gene segment is selected from the group consisting of D1-1, D1-7, D1-14, D1-20, D1-26, D2-2, D2-8, D2-15, D2-21, D3-3, D3-9, D3-10, D3-16, D3-22, D4-4, D4-11, D4-17, D4-23, D5-12, D5-5, D5-18, D5-24, D6-6, D6-13, D6-19, D6-25, D7-27, and a combination thereof.

In one embodiment, the human J gene segment is selected from the group consisting of $J_H$1, $J_H$2, $J_H$3, $J_H$4, $J_H$5, $J_H$6, and a combination thereof.

In one embodiment, the added or substituted histidine codon is present in the unrearranged heavy chain variable region nucleotide sequence that encodes an N-terminal region, a loop 4 region, a CDR1, a CDR2, a CDR3, or a combination thereof.

In one embodiment, the unrearranged heavy chain variable region nucleotide sequence comprises 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, 20 or more, 21 or more, 22 or more, 23 or more, 24 or more, or 25 or more, 26 or more, 27 or more, 28 or more, 29 or more, 30 or more, 31 or more, 32 or more, 33 or more, 34 or more 35 or more, 36 or more, 37 or more, 38 or more, 39 or more, 40 or more, 41 or more, 42 or more, 43 or more, 44 or more, 45 or more, 46 or more, 47 or more, 48 or more, 49 or more, 50 or more, 51 or more, 52 or more, 53 or more, 54 or more, 55 or more, 56 or more, 57 or more, 58 or more, 59 or more, 60 or more, or 61 or more of histidine codons.

In one embodiment, the unrearranged heavy chain variable region nucleotide sequence is operably linked to a human or non-human heavy chain constant region nucleotide sequence that encodes an immunoglobulin isotype selected from IgM, IgD, IgG, IgE, and IgA.

In one embodiment, the human unrearranged immunoglobulin heavy chain variable region nucleotide sequence is operably linked to a human or non-human heavy chain constant region nucleotide sequence selected from a $C_H$1, a hinge, a $C_H$2, a $C_H$3, and a combination thereof. In one embodiment, the heavy chain constant region nucleotide sequence comprises a $C_H$1, a hinge, a $C_H$2, and a $C_H$3 (i.e., $C_H$1-hinge-$C_H$2-$C_H$3).

In one embodiment, a heavy chain constant region nucleotide sequence is present at an endogenous locus (i.e., where the nucleotide sequence is located in a wild-type non-human animal) or present ectopically (e.g., at a locus different from the endogenous immunoglobulin chain locus in its genome, or within its endogenous locus, e.g., within an immunoglobulin variable locus, wherein the endogenous locus is placed or moved to a different location in the genome).

In one embodiment, the heavy chain constant region nucleotide sequence comprises a modification in a $C_H$2 or a $C_H$3, wherein the modification increases the affinity of the heavy chain constant region amino acid sequence to FcRn in an acidic environment (e.g., in an endosome where pH ranges from about 5.5 to about 6.0).

In one embodiment, the heavy chain constant region nucleotide sequence encodes a human heavy chain constant region amino acid sequence comprising a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., L/R/S/P/Q or K) and/or 434 (e.g., H/F or Y); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 259I (e.g., V259I), and 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P), wherein the modification increases the affinity of the heavy chain constant region amino acid sequence to FcRn in an acidic environment (e.g., in an endosome where pH ranges from about 5.5 to about 6.0).

In one embodiment, the heavy chain constant region nucleotide sequence encodes a human $C_H2$ amino acid sequence comprising at least one modification between amino acid residues at positions 252 and 257, wherein the modification increases the affinity of the human $C_H2$ amino acid sequence to FcRn in an acidic environment (e.g., in an endosome where pH ranges from about 5.5 to about 6.0).

In one embodiment, the heavy chain constant region nucleotide sequence encodes a human $C_H2$ amino acid sequence comprising at least one modification between amino acid residues at positions 307 and 311, wherein the modification increases the affinity of the $C_H2$ amino acid sequence to FcRn in an acidic environment (e.g., in an endosome where pH ranges from about 5.5 to about 6.0).

In one embodiment, the heavy chain constant region nucleotide sequence encodes a human $C_H3$ amino acid sequence, wherein the $C_H3$ amino acid sequence comprises at least one modification between amino acid residues at positions 433 and 436, wherein the modification increases the affinity of the $C_H3$ amino acid sequence to FcRn in an acidic environment (e.g., in an endosome where pH ranges from about 5.5 to about 6.0).

In one embodiment, the heavy chain constant region nucleotide sequence encodes a human heavy chain constant region amino acid sequence comprising a mutation selected from the group consisting of M428L, N434S, and a combination thereof.

In one embodiment, the heavy chain constant region nucleotide sequence encodes a human heavy chain constant region amino acid sequence comprising a mutation selected from the group consisting of M428L, V259I, V308F, and a combination thereof.

In one embodiment, the heavy chain constant region nucleotide sequence encodes a human heavy chain constant region amino acid sequence comprising an N434A mutation.

In one embodiment, the heavy chain constant region nucleotide sequence encodes a human heavy chain constant region amino acid sequence comprising a mutation selected from the group consisting of M252Y, S254T, T256E, and a combination thereof.

In one embodiment, the heavy chain constant region nucleotide sequence encodes a human heavy chain constant region amino acid sequence comprising a mutation selected from the group consisting of T250Q, M248L, or both.

In one embodiment, the heavy chain constant region nucleotide sequence encodes a human heavy chain constant region amino acid sequence comprising a mutation selected from the group consisting of H433K, N434Y, or both.

In one embodiment, the genetically modified immunoglobulin locus comprises: (1) a first allele, wherein the unrearranged human immunoglobulin heavy chain variable region nucleotide sequence as described herein is operably linked to a first heavy chain constant region nucleotide sequence encoding a first $CH_3$ amino acid sequence of a human IgG selected from IgG1, IgG2, IgG4, and a combination thereof; and (2) a second allele, wherein the unrearranged human immunoglobulin heavy chain variable region nucleotide sequence as described herein is operably linked to a second heavy chain constant region nucleotide sequence encoding a second $C_H3$ amino acid sequence of the human IgG selected from IgG1, IgG2, IgG4, and a combination thereof, and wherein the second $CH_3$ amino acid sequence comprises a modification that reduces or eliminates binding for the second $CH_3$ amino acid sequence to Protein A (see, for example, US 2010/0331527A1, which is incorporated by reference herein in its entirety).

In one embodiment, the second $CH_3$ amino acid sequence comprises an H95R modification (by IMGT exon numbering; H435R by EU numbering). In one embodiment the second $CH_3$ amino acid sequence further comprises an Y96F modification (by IMGT exon numbering; H436F by EU). In another embodiment, the second $CH_3$ amino acid sequence comprises both an H95R modification (by IMGT exon numbering; H435R by EU numbering) and an Y96F modification (by IMGT exon numbering; H436F by EU).

In one embodiment, the second $CH_3$ amino acid sequence is from a modified human IgG1 and further comprises a mutation selected from the group consisting of D16E, L18M, N44S, K52N, V57M, and V82I (IMGT; D356E, L38M, N384S, K392N, V397M, and V422I by EU).

In one embodiment, the second $CH_3$ amino acid sequence is from a modified human IgG2 and further comprises a mutation selected from the group consisting of N44S, K52N, and V82I (IMGT: N384S, K392N, and V422I by EU).

In one embodiment, the second $CH_3$ amino acid sequence is from a modified human IgG4 and further comprises a mutation selected from the group consisting of Q15R, N44S, K52N, V57M, R69K, E79Q, and V82I (IMGT: Q355R, N384S, K392N, V397M, R409K, E419Q, and V422I by EU).

In one embodiment, the heavy chain constant region amino acid sequence is a non-human constant region amino acid sequence, and the heavy chain constant region amino acid sequence comprises one or more of any of the types of modifications described above.

In one embodiment, all or substantially all endogenous $V_H$, D, and $J_H$ gene segments are deleted from an immunoglobulin heavy chain locus or rendered non-functional (e.g., via insertion of a nucleotide sequence (e.g., an exogenous nucleotide sequence) in the immunoglobulin locus or via non-functional rearrangement, or inversion, of the endogenous $V_H$, D, $J_H$ segments). In one embodiment, e.g., about 80% or more, about 85% or more, about 90% or more, about 95% or more, about 96% or more, about 97% or more, about 98% or more, or about 99% or more of all endogenous $V_H$, D, or $J_H$ gene segments are deleted or rendered non-functional. In one embodiment, e.g., at least 95%, 96%, 97%, 98%, or 99% of endogenous functional V, D, or J gene segments are deleted or rendered non-functional.

In one embodiment, the genetically modified immunoglobulin heavy chain locus comprises a modification that deletes or renders non-functional all, or substantially all, endogenous $V_H$, D, and $J_H$ gene segments; and the genetically modified locus comprises an unrearranged heavy chain variable region nucleotide sequence comprising one or more human $V_H$, D, and/or $J_H$ gene segments having one or more histidine codons, wherein the unrearranged heavy chain variable region nucleotide sequence is present at an endogenous location (i.e., where the nucleotide sequence is located in a wild-type non-human animal) or present ectopically (e.g., at a locus different from the endogenous immunoglobulin chain locus in its genome), or within its endogenous locus (e.g., within an immunoglobulin variable locus, wherein the endogenous locus is placed or moved to a different location in the genome).

In one embodiment, the genetically modified immunoglobulin locus comprises an endogenous Adam6a gene, Adam6b gene, or both, and the genetic modification does not affect the expression and/or function of the endogenous Adam6a gene, Adam6b gene, or both.

In one embodiment, the genetically modified immunoglobulin locus comprises an ectopically present Adam6a gene, Adam6b gene, or both. In one embodiment, the Adam6a gene is a non-human Adam6a gene. In one embodiment, the Adam6a gene is a human Adam6a gene. In one embodiment, the Adam6b gene is a non-human Adam6b gene. In one embodiment, the Adam6b gene is a human Adam6b gene.

In one embodiment, the genetically modified immunoglobulin locus further comprises a humanized, unrearranged λ and/or κ light chain variable gene sequence. In one embodiment, the humanized, unrearranged λ and/or κ light chain variable gene sequence is operably linked to an immunoglobulin light chain constant region nucleotide sequence selected from a λ light chain constant region nucleotide sequence and a κ light chain constant region nucleotide sequence. In one embodiment, the humanized, unrearranged λ light chain variable region nucleotide sequence is operably linked to a λ light chain constant region nucleotide sequence. In one embodiment, the λ light chain constant region nucleotide sequence is a mouse, rat, or human sequence. In one embodiment, the humanized, unrearranged κ light chain variable region nucleotide sequence is operably linked to a κ light chain constant region nucleotide sequence. In one embodiment, the κ light chain constant region nucleotide sequence is a mouse, rat, or human sequence.

In one embodiment, the genetically modified immunoglobulin locus comprises an unrearranged light chain variable gene sequence that contains at least one modification that introduces at least one histidine codon in at least one reading frame encoding a light chain variable domain. In one embodiment, the genetically modified immunoglobulin locus comprises a rearranged (e.g., rearranged λ or κ V/J sequence) sequence that comprises one, two, three, or four codons for histidine in a light chain CDR. In one embodiment, the CDR is a selected from a CDR1, CDR2, CDR3, and a combination thereof. In one embodiment, the unrearranged or rearranged light chain variable region nucleotide sequence is an unrearranged or rearranged human λ or κ light chain variable region nucleotide sequence. In one embodiment, the unrearranged or rearranged human λ or κ light chain variable region nucleotide sequence is present at an endogenous mouse immunoglobulin light chain locus. In one embodiment, the mouse immunoglobulin light chain locus is a mouse κ locus. In one embodiment, the mouse immunoglobulin light chain locus is a mouse λ locus.

In one embodiment, the genetically modified immunoglobulin locus as described herein is present in an immunoglobulin heavy chain locus of a mouse. In one embodiment, the genetically modified immunoglobulin locus is present in a humanized immunoglobulin heavy chain locus in a VELOCIMMUNE® mouse.

In one embodiment, an antigen-binding protein comprising a heavy chain variable domain expressed by the genetically modified immunoglobulin heavy chain locus as described herein exhibits a weaker antigen binding at an acidic environment (e.g., at a pH of about 5.5 to about 6.0) than a corresponding wild-type heavy chain variable domain without the genetic modification.

In one embodiment, an antigen-binding protein comprising a heavy chain variable domain expressed by the genetically modified immunoglobulin heavy chain locus as described herein has a dissociative half-life ($t_{1/2}$) of less than 2 min at an acidic pH (e.g., pH of about 5.5 to about 6.0) at 25° C. In one embodiment, an antigen-binding protein comprising a heavy chain variable domain expressed by the genetically modified immunoglobulin heavy chain locus as described herein has a dissociative half-life ($t_{1/2}$) of less than 2 min at an acidic pH (e.g., pH of about 5.5 to about 6.0) at 37° C. In one embodiment, an antigen-binding protein comprising a heavy chain variable domain expressed by the genetically modified immunoglobulin heavy chain locus as described herein has a dissociative half-life ($t_{1/2}$) of less than 1 min at an acidic pH (e.g., pH of about 5.5 to about 6.0) at 25° C. In one embodiment, an antigen-binding protein comprising a heavy chain variable domain expressed by the genetically modified immunoglobulin heavy chain locus as described herein has a dissociative half-life ($t_{1/2}$) of less than 1 min at an acidic pH (e.g., pH of about 5.5 to about 6.0) at 37° C. In one embodiment, an antigen-binding protein comprising a heavy chain variable domain expressed by the genetically modified immunoglobulin locus as described herein has at least about 2-fold, at least about 3-fold, at least about 4-fold, at least about 5-fold, at least about 10-fold, at least about 15-fold, at least about 20-fold, at least about 25-fold, or at least about 30-fold decrease in dissociative half-life ($t_{1/2}$) at an acidic pH (e.g., pH of about 5.5 to about 6.0) as compared to the dissociative half-life ($t_{1/2}$) of the antigen-binding protein at a neutral pH (e.g., pH of about 7.0 to about 7.4).

In one embodiment, the genetically modified immunoglobulin locus described herein comprises a B cell population that, upon stimulation with an antigen of interest, is capable of producing antigen-binding proteins, e.g., antibodies, comprising a heavy chain variable domain with one or more histidine residues. The antigen-binding proteins as described herein, when administered into a subject, exhibits an increased serum half-life over a corresponding wild-type antigen-binding protein, which possesses a similar or sufficiently similar amino acid sequence that encodes the heavy chain variable domain but does not comprise a histidine residue in the heavy chain variable domain. In some embodiments, the antigen-binding protein described herein exhibits an increased serum half-life that is at least about 2-fold, at least about 5-fold, at least about 10-fold, at least about 15-fold, at least about 20-fold higher than the corresponding wild-type antigen-binding protein, which possesses a similar or sufficiently similar amino acid sequence that encodes the heavy chain variable domain but does not comprise a histidine residue in the heavy chain variable domain.

In one embodiment, an antigen-binding protein comprising a heavy chain variable domain expressed by the genetically modified immunoglobulin locus as described herein is characterized by improved pH-dependent recyclability, enhanced serum half-life, or both as compared with a wild-type antigen-binding protein without the genetic modification as described herein.

In one aspect, a genetically modified immunoglobulin locus in a germline genome of a non-human animal is provided comprising an unrearranged human heavy chain variable region nucleotide sequence, wherein the human unrearranged heavy chain variable region nucleotide sequence comprises a substitution of at least one endogenous non-histidine codon with a histidine codon.

In one embodiment, the non-human animal is a mammal, including a rodent, e.g., a mouse, a rat, or a hamster.

In one embodiment, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, 20 or more, 21 or more, 22 or more, 23 or more, 24 or more, 25 or more, 26 or more, 27 or more, 28 or more, 29 or more, 30 or more, 31 or more, 32 or more, 33 or more, 34 or more, 35 or more, 36 or more, 37 or more, 38 or more, 39 or more, 40 or more, 41 or more, 42 or more, 43 or more, 44 or more, 45 or more, 46 or more, 47 or more, 48 or more, 49 or more, 50 or more, 51 or more, 52 or more, 53 or more, 54 or more, 55 or more, 56 or more, 57 or more, 58 or more, 59 or more, 60 or more, or 61 or more of the endogenous non-histidine codons are replaced with histidine codons.

In one embodiment, the endogenous non-histone codon encodes the amino acid selected from Y, N, D, Q, S, W, and R.

In one embodiment, the substituted histidine codon is present in an unrearranged heavy chain variable region nucleotide sequence that encodes an immunoglobulin variable domain selected from an N-terminal region, a loop 4 region, a CDR1, a CDR2, a CDR3, a combination thereof.

In one embodiment, the substituted histidine codon is present in an unrearranged heavy chain variable region nucleotide sequence that encodes a complementary determining region (CDR) selected from a CDR1, a CDR2, a CDR3, and a combination thereof.

In one embodiment, the substituted histidine codon is present in an unrearranged heavy chain variable region nucleotide sequence that encodes a frame region (FR) selected from FR1, FR2, FR3, FR4, and a combination thereof.

In one embodiment, the unrearranged heavy chain variable region nucleotide sequence comprises a genetically modified human $V_H$ gene segment, wherein one or more endogenous non-histidine codon in at least one reading frame of the human $V_H$ gene segment has been replaced with a histidine codon.

In one embodiment, the human unrearranged heavy chain variable region nucleotide sequence comprises a modification that replaces at least one endogenous non-histidine codon of a human $V_H$ gene segment with a histidine codon, wherein the human $V_H$ gene segment is selected from the group consisting of $V_H$1-2, $V_H$1-3, $V_H$1-8, $V_H$1-18, $V_H$1-24, $V_H$1-45, $V_H$1-46, $V_H$1-58, $V_H$1-69, $V_H$2-5, $V_H$2-26, $V_H$2-70, $V_H$3-7, $V_H$3-9, $V_H$3-11, $V_H$3-13, $V_H$3-15, $V_H$3-16, $V_H$3-20, $V_H$3-21, $V_H$3-23, $V_H$3-30, $V_H$3-30-3, $V_H$3-30-5, $V_H$3-33, $V_H$3-35, $V_H$3-38, $V_H$3-43, $V_H$3-48, $V_H$3-49, $V_H$3-53, $V_H$3-64, $V_H$3-66, $V_H$3-72, $V_H$3-73, $V_H$3-74, $V_H$4-4, $V_H$4-28, $V_H$4-30-1, $V_H$4-30-2, $V_H$4-30-4, $V_H$4-31, $V_H$4-34, $V_H$4-39, $V_H$4-59, $V_H$4-61, $V_H$5-51, $V_H$6-1, $V_H$7-4-1, $V_H$7-81, and a combination thereof.

In one embodiment, the human unrearranged heavy chain variable region nucleotide sequence comprises a genetically modified human $J_H$ gene segment, wherein one or more endogenous non-histidine codon in at least one reading frame of the human $J_H$ gene segment has been replaced with a histidine codon.

In one embodiment, the human unrearranged heavy chain variable region nucleotide sequence comprises a modification that replaces at least one endogenous non-histidine codon of a human $J_H$ segment with a histidine codon, wherein the human $J_H$ gene segment is selected from the group consisting of $J_H$1, $J_H$2, $J_H$3, $J_H$4, $J_H$S, $J_H$6, and a combination thereof.

In one embodiment, the substituted histidine codon is present in a heavy chain variable region nucleotide sequence that encodes part of a CDR3. In one embodiment, the part of CDR3 comprises an amino acid sequence derived from a reading frame of a genetically modified human D gene segment comprising a modification that replaces at least one endogenous non-histidine codon in the reading frame with a histidine codon.

In one embodiment, the endogenous non-histidine codon that is substituted with a histidine codon encodes the amino acid selected from Y, N, D, Q, S, W, and R.

In one embodiment, the substituted histidine codon is present in at least one reading frame of the human D gene segment that is most frequently observed in VELOCIM-MUNE® humanized immunoglobulin mice.

In one embodiment, the reading frame of the genetically modified human D gene segment that encodes part of CDR3 is selected from a hydrophobic frame, a stop frame, and a hydrophilic frame.

In one embodiment, the reading frame is a hydrophobic frame of a human D gene segment.

In one embodiment, the hydrophobic frame of the human D gene segment comprises a nucleotide sequence that encodes the amino acid sequence selected from the group consisting of D1-1 (GTTGT; SEQ ID NO: 88), D1-7 (GITGT; SEQ ID NO: 89), D1-20 (GITGT; SEQ ID NO: 89), and D1-26 (GIVGAT; SEQ ID NO: 90), and the human D gene segment further comprises a modification that replaces at least one endogenous non-histidine codon in the nucleotide sequence with a histidine codon.

In one embodiment, the hydrophobic frame of the human D gene segment comprises a nucleotide sequence that encodes the amino acid sequence selected from the group consisting of D2-2 (DIVVVPAAI; SEQ ID NO: 92), D2-8 (DIVLMVYAI; SEQ ID NO: 94), D2-15 (DIVVVVAAT; SEQ ID NO: 95), and D2-21 (HIVVVTAI; SEQ ID NO: 97), and the human D gene segment further comprises a modification that replaces at least one endogenous non-histidine codon in the nucleotide sequence with a histidine codon.

In one embodiment, the hydrophobic frame of the human D gene segment comprises a nucleotide sequence that encodes the amino acid sequence selected from the group consisting of D3-3 (ITIFGVVII; SEQ ID NO: 98), D3-9 (ITIF*LVII; SEQ ID NO: 99, SEQ ID NO:100), D3-10 (ITMVRGVII; SEQ ID NO:101), D3-16 (IMITFGGVIVI; SEQ ID NO:102), and D3-22 (ITMIVVVIT; SEQ ID NO:103), and the human D gene segment further comprises a modification that replaces at least one endogenous codon in the nucleotide sequence with a histidine codon.

In one embodiment, the hydrophobic frame of the human D gene segment comprises a nucleotide sequence that encodes the amino acid sequence selected from the group consisting of D4-4 (TTVT; SEQ ID NO: 105), D4-11 (TTVT; SEQ ID NO:105), D4-17 (TTVT; SEQ ID NO:105), D4-23 (TTVVT; SEQ ID NO: 106) and the human D gene segment further comprises a modification that replaces at least one endogenous non-histidine codon in the nucleotide sequence with a histidine codon.

In one embodiment, the hydrophobic frame of the human D gene segment comprises a nucleotide sequence that encodes the amino acid sequence selected from the group consisting of D5-5 (VDTAMV; SEQ ID NO: 107), D5-12 (VDIVATI; SEQ ID NO: 108), D5-18 (VDTAMV; SEQ ID NO:107), and D5-24 (VEMATI; SEQ ID NO:109), and the human D gene segment further comprises a modification that replaces at least one endogenous non-histidine codon in the nucleotide sequence with a histidine codon.

In one embodiment, the hydrophobic frame of the human D gene segment comprises a nucleotide sequence that encodes the amino acid sequence selected from the group consisting of D6-6 (SIAAR; SEQ ID NO: 111), D6-13 (GIAAAG; SEQ ID NO: 113), and D6-19 (GIAVAG; SEQ ID NO:115), and the human D gene segment further comprises a modification that replaces at least one endogenous non-histidine codon in the nucleotide sequence with a histidine codon.

In one embodiment, the hydrophobic frame comprises a nucleotide sequence that encodes human D7-27 (LTG), and the human D gene segment further comprises a modification that replaces at least one endogenous non-histidine codon in the nucleotide sequence with a histidine codon.

In one embodiment, the reading frame is a stop reading frame of a human D gene segment.

In one embodiment, the stop reading frame of the human D gene segment comprises a nucleotide sequence that encodes the amino acid sequence selected from the group consisting of D1-1 (VQLER; SEQ ID NO:8), D1-7 (V*LEL), D1-20 (V*LER), D1-26 (V*WELL; SEQ ID NO: 12), and the human D gene segment further comprises a modification that replaces at least one endogenous non-histidine codon in the nucleotide sequence with a histidine codon.

In one embodiment, the stop reading frame of the human D gene segment comprises a nucleotide sequence that encodes the amino acid sequence selected from the group consisting of D2-2 (RIL**YQLLY; SEQ ID NO:14), D2-8 (RILY*WCMLY; SEQ ID NO:16 and SEQ ID NO: 17), D2-15 (RIL*WW*LLL), and D2-21 (SILWW*LLF; SEQ ID NO:19), and the human D gene segment further comprises a modification that replaces at least one endogenous non-histidine codon in the nucleotide sequence with a histidine codon.

In one embodiment, the stop reading frame of the human D gene segment comprises a nucleotide sequence that encodes the amino acid sequence selected from the group consisting of D3-3 (VLRFLEWLLY; SEQ ID NO:21), D3-9 (VLRYFD-WLL*; SEQ ID NO:23), D3-10 (VLLWFGELL*; SEQ ID NO:25), D3-16 (VL*LRLGELSLY; SEQ ID NO:27), and D3-22 (VLL***WLLL; SEQ ID NO:29), and the human D gene segment comprises a modification that replaces at least one endogenous non-histidine codon in the nucleotide sequence with a histidine codon.

In one embodiment, the stop reading frame of the human D gene segment comprises a nucleotide sequence that encodes the amino acid sequence selected from the group consisting of D4-4 (*LQ*L), D4-11 (*LQ*L), D4-17 (*LR*L), and D4-23 (*LRW*L), and the human D gene segment comprises a modification that replaces at least one endogenous non-histidine codon in the nucleotide sequence with a histidine codon.

In one embodiment, the stop reading frame of the human D gene segment comprises a nucleotide sequence that encodes the amino acid sequence selected from the group consisting of D5-5 (WIQLWL; SEQ ID NO:35); D5-12 (WI*WLRL; SEQ ID NO:37), D5-18 (WIQLWL; SEQ ID NO:35), and D5-24 (*RWLQL; SEQ ID NO:39), and the human D gene segment comprises a modification that replaces at least one endogenous non-histidine codon in the nucleotide sequence with a histidine codon.

In one embodiment, the stop reading frame of the human D gene segment comprises a nucleotide sequence that encodes the amino acid sequence selected from the group consisting of D6-6 (V*QLV), D6-13 (V*QQLV; SEQ ID NO:41), and D6-19 (V*QWLV; SEQ ID NO:43), and the human D gene segment further comprises a modification that replaces at least one endogenous non-histidine codon in the nucleotide sequence with a histidine codon.

In one embodiment, the stop reading frame of the human D gene segment comprises a nucleotide sequence that encodes D7-27 (*LG), and the human D gene segment further comprises a modification that replaces at least one endogenous codon of the human D gene segment in the nucleotide sequence with a histidine codon.

In one embodiment, the reading frame is a hydrophilic frame of a human D gene segment.

In one embodiment, the hydrophilic frame of the human D gene segment comprises a nucleotide sequence that encodes the amino acid sequence selected from the group consisting of D1-1 (YNWND; SEQ ID NO: 45), D1-7 (YNWNY; SEQ ID NO: 47), D1-20 (YNWND; SEQ ID NO: 45), and D1-26 (YSGSYY; SEQ ID NO:49), and the human D gene segment further comprises a modification that replaces at least one endogenous codon in the nucleotide sequence with a histidine codon. In one embodiment, the hydrophilic frame comprises a nucleotide sequence that encodes the amino acid sequence selected from the group consisting of SEQ ID NO: 46, SEQ ID NO: 48, SEQ ID NO: 50, and a combination thereof.

In one embodiment, the hydrophilic frame of the human D gene segment comprises a nucleotide sequence that encodes the amino acid sequence selected from the group consisting of D2-2 (GYCSSTSCYT; SEQ ID NO:51), D2-8 (GYCT-NGVCYT; SEQ ID NO: 53), D2-15 (GYCSGGSCYS; SEQ ID NO:55), and D2-21 (AYCGGDCYS; SEQ ID NO:57), and the human D gene segment further comprises a modification that replaces at least one endogenous codon in the nucleotide sequence with a histidine codon. In one embodiment, the hydrophilic frame comprises a nucleotide sequence that encodes the amino acid sequence selected from the group consisting of SEQ ID NO: 52, SEQ ID NO: 54, SEQ ID NO: 56, SEQ ID NO: 58, and a combination thereof.

In one embodiment, the hydrophilic frame of the human D gene segment comprises a nucleotide sequence that encodes the amino acid sequence selected from the group consisting of D3-3 (YYDFWSGYYT; SEQ ID NO:59), D3-9 (YYDILT-GYYN; SEQ ID NO:61), D3-10 (YYYGSGSYYN; SEQ ID NO:63), D3-16 (YYDYVWGSYRYT; SEQ ID NO:65), and D3-22 (YYYDSSGYYY; SEQ ID NO:67), and the human D gene segment further comprises a modification that replaces at least one endogenous codon in the nucleotide sequence with a histidine codon. In one embodiment, the hydrophilic frame comprises a nucleotide sequence encodes the amino acid sequence selected from the group consisting of SEQ ID NO: 60, SEQ ID NO: 62, SEQ ID NO: 64, SEQ ID NO: 66, SEQ ID NO: 68, and a combination thereof.

In one embodiment, the hydrophilic frame of the human D gene segment comprises a nucleotide sequence that encodes the amino acid sequence selected from the group consisting of D4-4 (DYSNY; SEQ ID NO:69), D4-11 (DYSNY; SEQ ID NO:69), D4-17 (DYGDY; SEQ ID NO:71), and D4-23 (DYGGNS; SEQ ID NO:73), and the human D gene segment comprises a modification that replaces at least one endogenous codon in the nucleotide sequence with a histidine codon. In one embodiment, the hydrophilic frame comprises a nucleotide sequence that encodes the amino acid sequence selected from the group consisting of SEQ ID NO: 70, SEQ ID NO: 72, SEQ ID NO: 74, and a combination thereof.

In one embodiment, the hydrophilic frame of the human D gene segment comprises a nucleotide sequence that encodes the amino acid sequence selected from the group consisting of D5-5 (GYSYGY; SEQ ID NO:75), D5-12 (GYSGYDY; SEQ ID NO:77), D5-18 (GYSYGY; SEQ ID NO:75), and D5-24 (RDGYNY; SEQ ID NO:79), and the human D gene segment further comprises a modification that replaces at least one endogenous codon in the nucleotide sequence with a histidine codon. In one embodiment, the hydrophilic frame comprises a nucleotide sequence that encodes the amino acid sequence selected from the group consisting of SEQ ID NO: 76, SEQ ID NO: 78, SEQ ID NO: 80, and a combination thereof.

In one embodiment, the hydrophilic frame of the human D gene segment comprises a nucleotide sequence that encodes the amino acid sequence selected from the group consisting of D6-6 (EYSSSS; SEQ ID NO: 81), D6-13 (GYSSSWY; SEQ ID NO:83), and D6-19 (GYSSGWY; SEQ ID NO:85), and the human D gene segment further comprises a modification that replaces at least one endogenous codon in the nucleotide sequence with a histidine codon. In one embodiment, the hydrophilic frame comprises a nucleotide sequence that encodes the amino acid sequence selected from the group consisting of SEQ ID NO: 82, SEQ ID NO: 84, SEQ ID NO: 86, SEQ ID NO: 76, and a combination thereof.

In one embodiment, the hydrophilic frame of the human D gene segment comprises a nucleotide sequence that encodes D7-27 (NWG), and the human D gene segment further comprises a modification that replaces at least one endogenous codon in the nucleotide sequence a histidine codon.

In one embodiment, the hydrophilic frame of the human D gene segment comprises a nucleotide sequence that encodes the amino acid sequence selected from the group consisting of SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, and a combination thereof.

In one embodiment, the human unrearranged immunoglobulin heavy chain variable region nucleotide sequence is operably linked to a human or non-human heavy chain constant region nucleotide sequence selected from a $C_H1$, a hinge, a $C_H2$, a $C_H3$, and a combination thereof. In one embodiment, the heavy chain constant region nucleotide sequence comprises a $C_H1$, a hinge, a $C_H2$, and a $C_H3$ (i.e., $C_H1$-hinge-$C_H2$-$C_H3$).

In one embodiment, a heavy chain constant region nucleotide sequence is present at an endogenous locus (i.e., where the nucleotide sequence is located in a wild-type non-human animal) or present ectopically (e.g., at a locus different from the endogenous immunoglobulin chain locus in its genome), or within its endogenous locus, e.g., within an immunoglobulin variable locus, wherein the endogenous locus is placed or moved to a different location in the genome.

In one embodiment, the heavy chain constant region nucleotide sequence comprises a modification in a $C_H2$ or a $C_H3$, wherein the modification increases the affinity of the heavy chain constant region amino acid sequence to FcRn in an acidic environment (e.g., in an endosome where pH ranges from about 5.5 to about 6.0).

In one embodiment, the heavy chain constant region nucleotide sequence encodes a human heavy chain constant region amino acid sequence comprising a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., L/R/S/P/Q or K) and/or 434 (e.g., H/F or Y); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 259I (e.g., V259I), and 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P), wherein the modification increases the affinity of the heavy chain constant region amino acid sequence to FcRn in an acidic environment (e.g., in an endosome where pH ranges from about 5.5 to about 6.0).

In one embodiment, the heavy chain constant region nucleotide sequence encodes a human $C_H2$ amino acid sequence comprising at least one modification between amino acid residues at positions 252 and 257, wherein the modification increases the affinity of the human $C_H2$ amino acid sequence to FcRn in an acidic environment (e.g., in an endosome where pH ranges from about 5.5 to about 6.0).

In one embodiment, the heavy chain constant region nucleotide sequence encodes a human $C_H2$ amino acid sequence comprising at least one modification between amino acid residues at positions 307 and 311, wherein the modification increases the affinity of the $C_H2$ amino acid sequence to FcRn in an acidic environment (e.g., in an endosome where pH ranges from about 5.5 to about 6.0).

In one embodiment, the heavy chain constant region nucleotide sequence encodes a human $C_H3$ amino acid sequence, wherein the $C_H3$ amino acid sequence comprises at least one modification between amino acid residues at positions 433 and 436, wherein the modification increases the affinity of the $C_H3$ amino acid sequence to FcRn in an acidic environment (e.g., in an endosome where pH ranges from about 5.5 to about 6.0).

In one embodiment, the heavy chain constant region nucleotide sequence encodes a human heavy chain constant region amino acid sequence comprising a mutation selected from the group consisting of M428L, N434S, and a combination thereof.

In one embodiment, the heavy chain constant region nucleotide sequence encodes a human heavy chain constant region amino acid sequence comprising a mutation selected from the group consisting of M428L, V259I, V308F, and a combination thereof.

In one embodiment, the heavy chain constant region nucleotide sequence encodes a human heavy chain constant region amino acid sequence comprising an N434A mutation.

In one embodiment, the heavy chain constant region nucleotide sequence encodes a human heavy chain constant region amino acid sequence comprising a mutation selected from the group consisting of M252Y, S254T, T256E, and a combination thereof.

In one embodiment, the heavy chain constant region nucleotide sequence encodes a human heavy chain constant region amino acid sequence comprising a mutation selected from the group consisting of T250Q, M248L, or both.

In one embodiment, the heavy chain constant region nucleotide sequence encodes a human heavy chain constant region amino acid sequence comprising a mutation selected from the group consisting of H433K, N434Y, or both.

In one embodiment, the genetically modified immunoglobulin locus comprises: (1) a first allele, wherein the unrearranged human immunoglobulin heavy chain variable region nucleotide sequence as described herein is operably linked to a first heavy chain constant region nucleotide sequence encoding a first $CH_3$ amino acid sequence of a human IgG selected from IgG1, IgG2, IgG4, and a combination thereof; and (2) a second allele, wherein the unrearranged human immunoglobulin heavy chain variable region nucleotide sequence as described herein is operably linked to a second heavy chain constant region nucleotide sequence encoding a second $C_H3$ amino acid sequence of the human IgG selected from IgG1, IgG2, IgG4, and a combination thereof, and wherein the second $CH_3$ amino acid sequence comprises a modification that reduces or eliminates binding for the second $CH_3$ amino acid sequence to Protein A (see, for example, US 2010/0331527A1, which is incorporated by reference herein in its entirety).

In one embodiment, the second $CH_3$ amino acid sequence comprises an H95R modification (by IMGT exon numbering; H435R by EU numbering). In one embodiment the second $CH_3$ amino acid sequence further comprises an Y96F modification (by IMGT exon numbering; H436F by EU). In another embodiment, the second $CH_3$ amino acid sequence comprises both an H95R modification (by IMGT exon numbering; H435R by EU numbering) and an Y96F modification (by IMGT exon numbering; H436F by EU).

In one embodiment, the second CH₃ amino acid sequence is from a modified human IgG1 and further comprises a mutation selected from the group consisting of D16E, L18M, N44S, K52N, V57M, and V82I (IMGT; D356E, L38M, N384S, K392N, V397M, and V422I by EU).

In one embodiment, the second CH₃ amino acid sequence is from a modified human IgG2 and further comprises a mutation selected from the group consisting of N44S, K52N, and V82I (IMGT: N384S, K392N, and V422I by EU).

In one embodiment, the second CH₃ amino acid sequence is from a modified human IgG4 and further comprises a mutation selected from the group consisting of Q15R, N44S, K52N, V57M, R69K, E79Q, and V82I (IMGT: Q355R, N384S, K392N, V397M, R409K, E419Q, and V422I by EU).

In one embodiment, the heavy chain constant region amino acid sequence is a non-human constant region amino acid sequence, and the heavy chain constant region amino acid sequence comprises one or more of any of the types of modifications described above.

In one embodiment, the heavy chain constant region nucleotide sequence is a human heavy chain constant region amino acid sequence, and the human heavy chain constant region amino acid sequence comprises one or more of any of the types of modifications described above.

In one embodiment, all or substantially all endogenous $V_H$, D, and $J_H$ gene segments are deleted from an immunoglobulin heavy chain locus or rendered non-functional (e.g., via insertion of a nucleotide sequence, e.g., an exogenous nucleotide sequence, in the immunoglobulin locus or via non-functional rearrangement, or inversion, of the endogenous $V_H$, D, $J_H$ segments). In one embodiment, e.g., about 80% or more, about 85% or more, about 90% or more, about 95% or more, about 96% or more, about 97% or more, about 98% or more, or about 99% or more of all endogenous $V_H$, D, or $J_H$ gene segments are deleted or rendered non-functional. In one embodiment, e.g., at least 95%, 96%, 97%, 98%, or 99% of endogenous functional V, D, or J gene segments are deleted or rendered non-functional.

In one embodiment, the genetically modified locus comprises a modification that deletes or renders non-functional all or substantially all endogenous $V_H$, D, and $J_H$ gene segments; and the genomic locus comprises a genetically modified, unrearranged human heavy chain variable region nucleotide sequence comprising a substitution of at least one endogenous non-histidine codon with a histidine codon in at least one reading frame. In one embodiment, the genetically modified, unrearranged immunoglobulin heavy chain variable gene sequence is present at an endogenous location (i.e., where the nucleotide sequence is located in a wild-type non-human animal) or present ectopically (e.g., at a locus different from the endogenous immunoglobulin chain locus in its genome), or within its endogenous locus, e.g., within an immunoglobulin variable locus, wherein the endogenous locus is placed or moved to a different location in the genome.

In one embodiment, the genetically modified locus comprises an endogenous Adam6a gene, Adam6b gene, or both, and the genetic modification does not affect the expression and/or function of the endogenous Adam6a gene, Adam6b gene, or both.

In one embodiment, the genetically modified locus comprises an ectopically present Adam6a gene, Adam6b gene, or both. In one embodiment, the Adam6a gene is a non-human Adam6a gene. In one embodiment, the Adam6a gene is a mouse Adam6a gene. In one embodiment, the Adam6a gene is a human Adam6a gene. In one embodiment, the Adam6b gene is a non-human Adam6b gene. In one embodiment, the Adam6b gene is a mouse Adam6b gene. In one embodiment, the Adam6b gene is a human Adam6b gene.

In one embodiment, the genetically modified immunoglobulin locus further comprises a humanized, unrearranged λ and/or κ light chain variable gene sequence. In one embodiment, the humanized, unrearranged λ and/or κ light chain variable gene sequence is operably linked to an immunoglobulin light chain constant region nucleotide sequence selected from a λ light chain constant region nucleotide sequence and a κ light chain constant region nucleotide sequence. In one embodiment, the humanized, unrearranged λ light chain variable region nucleotide sequence is operably linked to a λ light chain constant region nucleotide sequence. In one embodiment, the λ light chain constant region nucleotide sequence is a mouse, rat, or human sequence. In one embodiment, the humanized, unrearranged κ light chain variable region nucleotide sequence is operably linked to a κ light chain constant region nucleotide sequence. In one embodiment, the κ light chain constant region nucleotide sequence is a mouse, rat, or human sequence.

In one embodiment, the genetically modified immunoglobulin locus comprises an unrearranged light chain variable gene sequence that contains at least one modification that introduces at least one histidine codon in at least one reading frame encoding a light chain variable domain. In one embodiment, the genetically modified immunoglobulin locus comprises a rearranged (e.g., a rearranged λ or κ V/J sequence) sequence that comprises one, two, three, or four codons for histidine in a light chain CDR. In one embodiment, the CDR is a selected from a CDR1, CDR2, CDR3, and a combination thereof. In one embodiment, the unrearranged or rearranged light chain variable region nucleotide sequence is an unrearranged or rearranged human λ or κ light chain variable region nucleotide sequence. In one embodiment, the unrearranged or rearranged human λ or κ light chain variable region nucleotide sequence is present at an endogenous mouse immunoglobulin light chain locus. In one embodiment, the mouse immunoglobulin light chain locus is a mouse κ locus. In one embodiment the mouse immunoglobulin light chain locus is a mouse λ locus.

In one embodiment, the genetically modified immunoglobulin locus as described herein is present in an immunoglobulin heavy chain locus of a mouse. In one embodiment, the genetically modified immunoglobulin locus is present in a humanized immunoglobulin heavy chain locus in a VELOCIMMUNE® mouse.

In one embodiment, an antigen-binding protein comprising a heavy chain variable domain expressed by the genetically modified immunoglobulin heavy chain locus as described herein exhibits a weaker antigen binding at an acidic environment (e.g., at a pH of about 5.5 to about 6.0) than a corresponding wild-type heavy chain variable domain without the genetic modification described herein.

In one embodiment, an antigen-binding protein comprising a heavy chain variable domain expressed by the genetically modified immunoglobulin heavy chain locus as described herein has a dissociative half-life ($t_{1/2}$) of less than 2 min at an acidic pH (e.g., pH of about 5.5 to about 6.0) at 25° C. In one embodiment, an antigen-binding protein comprising a heavy chain variable domain expressed by the genetically modified immunoglobulin heavy chain locus as described herein has a dissociative half-life ($t_{1/2}$) of less than 2 min at an acidic pH (e.g., pH of about 5.5 to about 6.0) at 37° C. In one embodiment, an antigen-binding protein comprising a heavy chain variable domain expressed by the genetically modified immunoglobulin heavy chain locus as described herein has a dissociative half-life ($t_{1/2}$) of less than 1 min at an acidic pH (e.g., pH of about 5.5 to about 6.0) at 25° C. In one embodiment, an antigen-binding protein comprising a heavy chain variable domain expressed by the genetically modified immunoglobulin heavy chain locus as described herein has a dissociative half-life ($t_{1/2}$) of less than 1 min at an acidic pH (e.g., pH of about 5.5 to about 6.0) at 37° C. In one embodiment, an antigen-binding protein comprising a heavy chain variable domain expressed by the genetically modified immunoglobulin locus as described herein has at least about 2-fold, at least about 3-fold, at least about 4-fold, at least about 5-fold, at least about 10-fold, at least about 15-fold, at least about 20-fold, at least about 25-fold, or at least about 30-fold decrease in dissociative half-life ($t_{1/2}$) at an acidic pH (e.g., pH of about 5.5 to about 6.0) as compared to the dissociative half-life ($t_{1/2}$) of the antigen-binding protein at a neutral pH (e.g., pH of about 7.0 to about 7.4).

In one embodiment, an antigen-binding protein comprising a heavy chain variable domain expressed by the genetically modified immunoglobulin locus as described herein is characterized by improved pH-dependent recyclability, enhanced serum half-life, or both as compared with a wild-type antigen-binding protein without the genetic modification.

In one embodiment, the genetically modified immunoglobulin locus described herein comprises a B cell population that, upon stimulation with an antigen of interest, is capable of producing antigen-binding proteins, e.g., antibodies, comprising a heavy chain variable domain comprising one or more histidine residues. The antigen-binding proteins, which are produced by the genetically modified immunoglobulin locus described herein, when administered into a subject, exhibits an increased serum half-life over a corresponding wild-type antigen-binding protein, which possesses a similar or sufficiently similar amino acid sequence that encodes the heavy chain variable domain but does not comprise a histidine residue in the heavy chain variable domain. In some embodiments, the antigen-binding protein described herein exhibits an increased serum half-life that is at least about 2-fold, at least about 5-fold, at least about 10-fold, at least about 15-fold, at least about 20-fold higher than the corresponding wild-type antigen-binding protein, which possesses a similar or sufficiently similar amino acid sequence that encodes the heavy chain variable domain but does not comprise a histidine residue in the heavy chain variable domain.

In one aspect, a genetically modified immunoglobulin locus of a non-human animal comprising a human $V_H$, D, and $J_H$ gene segment is provided, wherein at least one human D gene segment has been inverted 5' to 3' with respect to a corresponding wild-type sequence, and wherein at least one reading frame of the inverted human D gene segment comprises one ore more histidine codon.

In one embodiment, the non-human animal is a mammal, including a rodent, e.g., a mouse, a rat, or a hamster In one embodiment, the genetically modified immunoglobulin locus is present in a germline genome.

In one embodiment, the genetically modified immunoglobulin locus encodes an immunoglobulin heavy chain variable domain comprising one or more, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, 20 or more, 21 or more, 22 or more, 23 or more, 24 or more, 25 or more, 26 or more, 27 or more, 28 or more, 29 or more, 30 or more, 31 or more, 32 or more, 33 or more, or 34 or more of histidine residues.

In one embodiment, at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, at least twenty, at least twenty one, at least twenty two, at least twenty three, at least twenty four, or all or substantially all of functional human D gene segments have inverted orientation with respect to corresponding wild type sequences.

In one embodiment, all or substantially all of endogenous immunoglobulin $V_H$, D, $J_H$ gene segments are deleted from the immunoglobulin heavy chain locus or rendered non-functional (e.g., via insertion of a nucleotide sequence, e.g., exogenous nucleotide sequence, in the immunoglobulin locus or via non-functional rearrangement or inversion of all, or substantially all, endogenous immunoglobulin $V_H$, D, $J_H$ segments), and the genetically modified immunoglobulin locus comprises a human $V_H$, D, and $J_H$ gene segments, wherein at least one human D gene segment is present in an inverted orientation with respect to a corresponding wild type sequence, and wherein at least one reading frame in the inverted human D gene segment comprises at least one histidine codon.

In one embodiment, the inverted human D gene segment is operably linked to a human $V_H$ gene segment, and/or human $J_H$ gene segment In one embodiment, the human D gene segment that is present in the inverted orientation relative to a corresponding wild type sequence is selected from the group consisting of D1-1, D1-7, D1-20, D1-26, D2-2, D2-8, D2-15, D2-21, D3-3, D3-9, D3-10, D3-16, D3-22, D4-4, D4-11, D4-17, D4-23, D5-5, D5-12, D5-18, D5-24, D6-6, D6-13, D6-19, D7-27, and a combination thereof.

In one embodiment, the human D gene segment that is present in the inverted orientation relative to a corresponding wild type sequence is a D1 gene segment selected from the group consisting of D1-1, D1-7, D1-20, D1-26, and a combination thereof.

In one embodiment, the human D gene segment that is present in the inverted orientation relative a corresponding wild type sequence is a D2 gene segment selected from the group consisting of D2-2, D2-8, D2-15, D2-21, and a combination thereof.

In one embodiment, the human D gene segment that is present in the inverted orientation relative to a corresponding wild type sequence is a D3 gene segment selected from the group consisting of D3-3, D3-9, D3-10, D3-16, D3-22, and a combination thereof.

In one embodiment, the human D gene segment that is present in the inverted orientation relative to a corresponding wild type sequence is a D4 gene segment selected from the group consisting of D4-4, D4-11, D4-17, D4-23, and a combination thereof.

In one embodiment, the human D gene segment that is present in the inverted orientation relative to a corresponding wild type sequence is a D5 gene segment selected from the group consisting of D5-5, D5-12, D5-18, D5-24, and a combination thereof.

In one embodiment, the human D gene segment that is present in the inverted orientation relative to a corresponding wild type sequence is a D6 gene segment selected from the group consisting of D6-6, D6-13, D6-19, and a combination thereof.

In one embodiment, the human D gene segment that is present in the inverted orientation relative to a corresponding wild type sequence is D7-27.

In one embodiment, the reading frame of the human D gene segment is selected from a stop reading frame, a hydrophilic reading frame, and a hydrophobic reading frame, and at least one reading frame of the inverted human D gene segment comprises one or more histidine codon.

In one embodiment, the unrearranged heavy chain variable region nucleotide sequence comprising the inverted human D gene segment is operably linked to a human or non-human heavy chain constant region nucleotide sequence that encodes an immunoglobulin isotype selected from IgM, IgD, IgG, IgE, and IgA.

In one embodiment, the unrearranged heavy chain variable region nucleotide sequence comprising the inverted human D gene segment is operably linked to a human or non-human heavy chain constant region nucleotide sequence that encodes an immunoglobulin isotype selected from IgM, IgD, IgG, IgE, and IgA.

In one embodiment, the human unrearranged immunoglobulin heavy chain variable region nucleotide sequence is operably linked to a human or non-human heavy chain constant region nucleotide sequence selected from a $C_H1$, a hinge, a $C_H2$, a $C_H3$, and a combination thereof. In one embodiment, the heavy chain constant region nucleotide sequence comprises a $C_H1$, a hinge, a $C_H2$, and a $C_H3$ (i.e., $C_H1$-hinge-$C_H2$-$C_H3$).

In one embodiment, a heavy chain constant region nucleotide sequence is present at an endogenous locus (i.e., where the nucleotide sequence is located in a wild-type non-human animal) or present ectopically (e.g., at a locus different from the endogenous immunoglobulin chain locus in its genome), or within its endogenous locus, e.g., within an immunoglobulin variable locus, wherein the endogenous locus is placed or moved to a different location in the genome.

In one embodiment, the heavy chain constant region nucleotide sequence comprises a modification in a $C_H2$ or a $C_H3$, wherein the modification increases the affinity of the heavy chain constant region amino acid sequence to FcRn in an acidic environment (e.g., in an endosome where pH ranges from about 5.5 to about 6.0).

In one embodiment, the heavy chain constant region nucleotide sequence encodes a human heavy chain constant region amino acid sequence comprising a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., L/R/S/P/Q or K) and/or 434 (e.g., H/F or Y); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 259I (e.g., V259I), and 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P), wherein the modification increases the affinity of the heavy chain constant region amino acid sequence to FcRn in an acidic environment (e.g., in an endosome where pH ranges from about 5.5 to about 6.0).

In one embodiment, the heavy chain constant region nucleotide sequence encodes a human $C_H2$ amino acid sequence comprising at least one modification between amino acid residues at positions 252 and 257, wherein the modification increases the affinity of the human $C_H2$ amino acid sequence to FcRn in an acidic environment (e.g., in an endosome where pH ranges from about 5.5 to about 6.0).

In one embodiment, the heavy chain constant region nucleotide sequence encodes a human $C_H2$ amino acid sequence comprising at least one modification between amino acid residues at positions 307 and 311, wherein the modification increases the affinity of the $C_H2$ amino acid sequence to FcRn in an acidic environment (e.g., in an endosome where pH ranges from about 5.5 to about 6.0).

In one embodiment, the heavy chain constant region nucleotide sequence encodes a human $C_H3$ amino acid sequence, wherein the $C_H3$ amino acid sequence comprises at least one modification between amino acid residues at positions 433 and 436, wherein the modification increases the affinity of the $C_H3$ amino acid sequence to FcRn in an acidic environment (e.g., in an endosome where pH ranges from about 5.5 to about 6.0).

In one embodiment, the heavy chain constant region nucleotide sequence encodes a human heavy chain constant region amino acid sequence comprising a mutation selected from the group consisting of M428L, N434S, and a combination thereof.

In one embodiment, the heavy chain constant region nucleotide sequence encodes a human heavy chain constant region amino acid sequence comprising a mutation selected from the group consisting of M428L, V259I, V308F, and a combination thereof.

In one embodiment, the heavy chain constant region nucleotide sequence encodes a human heavy chain constant region amino acid sequence comprising an N434A mutation.

In one embodiment, the heavy chain constant region nucleotide sequence encodes a human heavy chain constant region amino acid sequence comprising a mutation selected from the group consisting of M252Y, S254T, T256E, and a combination thereof.

In one embodiment, the heavy chain constant region nucleotide sequence encodes a human heavy chain constant region amino acid sequence comprising a mutation selected from the group consisting of T250Q, M248L, or both.

In one embodiment, the heavy chain constant region nucleotide sequence encodes a human heavy chain constant region amino acid sequence comprising a mutation selected from the group consisting of H433K, N434Y, or both.

In one embodiment, the genetically modified immunoglobulin locus comprises: (1) a first allele, wherein the unrearranged human immunoglobulin heavy chain variable region nucleotide sequence as described herein is operably linked to a first heavy chain constant region nucleotide sequence encoding a first $CH_3$ amino acid sequence of a human IgG selected from IgG1, IgG2, IgG4, and a combination thereof; and (2) a second allele, wherein the unrearranged human immunoglobulin heavy chain variable region nucleotide sequence as described herein is operably linked to a second heavy chain constant region nucleotide sequence encoding a second $C_H3$ amino acid sequence of the human IgG selected from IgG1, IgG2, IgG4, and a combination thereof, and wherein the second $CH_3$ amino acid sequence comprises a modification that reduces or eliminates binding for the second $CH_3$ amino acid sequence to Protein A (see, for example, US 2010/0331527A1, incorporated by reference herein in its entirety).

In one embodiment, the second $CH_3$ amino acid sequence comprises an H95R modification (by IMGT exon numbering; H435R by EU numbering). In one embodiment the second $CH_3$ amino acid sequence further comprises an Y96F modification (by IMGT exon numbering; H436F by EU). In another embodiment, the second $CH_3$ amino acid sequence comprises both an H95R modification (by IMGT exon numbering; H435R by EU numbering) and an Y96F modification (by IMGT exon numbering; H436F by EU).

In one embodiment, the second CH₃ amino acid sequence is from a modified human IgG1 and further comprises a mutation selected from the group consisting of D16E, L18M, N44S, K52N, V57M, and V82I (IMGT; D356E, L38M, N384S, K392N, V397M, and V422I by EU).

In one embodiment, the second CH₃ amino acid sequence is from a modified human IgG2 and further comprises a mutation selected from the group consisting of N44S, K52N, and V82I (IMGT: N384S, K392N, and V422I by EU).

In one embodiment, the second CH₃ amino acid sequence is from a modified human IgG4 and further comprises a mutation selected from the group consisting of Q15R, N44S, K52N, V57M, R69K, E79Q, and V82I (IMGT: Q355R, N384S, K392N, V397M, R409K, E419Q, and V422I by EU).

In one embodiment, the heavy chain constant region amino acid sequence is a non-human constant region amino acid sequence, and the heavy chain constant region amino acid sequence comprises one or more of any of the types of modifications described above.

In one embodiment, the heavy chain constant region nucleotide sequence is a human heavy chain constant region amino acid sequence, and the human heavy chain constant region amino acid sequence comprises one or more of any of the types of modifications described above.

In one embodiment, all, or substantially all, endogenous $V_H$, D, and $J_H$ gene segments are deleted from an immunoglobulin heavy chain locus or rendered non-functional (e.g., via insertion of a nucleotide sequence (e.g., an exogenous nucleotide sequence) in the immunoglobulin locus or via non-functional rearrangement, or inversion, of the endogenous $V_H$, D, $J_H$ segments). In one embodiment, e.g., about 80% or more, about 85% or more, about 90% or more, about 95% or more, about 96% or more, about 97% or more, about 98% or more, or about 99% or more of all endogenous $V_H$, D, or $J_H$ gene segments are deleted or rendered non-functional. In one embodiment, e.g., at least 95%, 96%, 97%, 98%, or 99% of endogenous functional V, D, or J gene segments are deleted or rendered non-functional.

In one embodiment, the genetically modified immunoglobulin heavy chain locus comprises a modification that deletes or renders non-functional, all or substantially all, endogenous $V_H$, D, and $J_H$ gene segments; and the genetically modified locus comprises an unrearranged heavy chain variable region nucleotide sequence comprising at least one inverted human D gene segment as described herein wherein the unrearranged heavy chain variable region nucleotide sequence is present at an endogenous location (i.e., where the nucleotide sequence is located in a wild-type non-human animal) or present ectopically (e.g., at a locus different from the endogenous immunoglobulin chain locus in its genome, or within its endogenous locus, e.g., within an immunoglobulin variable locus, wherein the endogenous locus is placed or moved to a different location in the genome).

In one embodiment, the genetically modified immunoglobulin locus comprises an endogenous Adam6a gene, Adam6b gene, or both, and the genetic modification does not affect the expression and/or function of the endogenous Adam6a gene, Adam6b gene, or both.

In one embodiment, the genetically modified immunoglobulin locus comprises an ectopically present Adam6a gene, Adam6b gene, or both. In one embodiment, the Adam6a gene is a non-human Adam6a gene. In one embodiment, the Adam6a gene is a mouse Adam6a gene. In one embodiment, the Adam6a gene is a human Adam6a gene. In one embodiment, the Adam6b gene is a non-human Adam6b gene. In one embodiment, the Adam6b gene is a mouse Adam6b gene. In one embodiment, the Adam6b gene is a human Adam6b gene.

In one embodiment, the genetically modified immunoglobulin locus further comprises a humanized, unrearranged λ and/or κ light chain variable gene sequence. In one embodiment, the humanized, unrearranged λ and/or κ light chain variable gene sequence is operably linked to an immunoglobulin light chain constant region nucleotide sequence selected from a λ light chain constant region nucleotide sequence and a κ light chain constant region nucleotide sequence. In one embodiment, the humanized, unrearranged λ light chain variable region nucleotide sequence is operably linked to a λ light chain constant region nucleotide sequence. In one embodiment, the λ light chain constant region nucleotide sequence is a mouse, rat, or human sequence. In one embodiment, the humanized, unrearranged κ light chain variable region nucleotide sequence is operably linked to a κ light chain constant region nucleotide sequence. In one embodiment, the κ light chain constant region nucleotide sequence is a mouse, rat, or human sequence.

In one embodiment, the genetically modified immunoglobulin locus comprises an unrearranged light chain variable gene sequence that contains at least one modification that introduces at least one histidine codon in at least one reading frame encoding a light chain variable domain. In one embodiment, the genetically modified immunoglobulin locus comprises a rearranged (e.g., a rearranged λ or κ V/J sequence) sequence that comprises one, two, three, or four codons for histidine in a light chain CDR. In one embodiment, the CDR is a selected from a CDR1, CDR2, CDR3, and a combination thereof. In one embodiment, the unrearranged or rearranged light chain variable region nucleotide sequence is an unrearranged or rearranged human λ or κ light chain variable region nucleotide sequence. In one embodiment, the unrearranged or rearranged human λ or κ light chain variable region nucleotide sequence is present at an endogenous mouse immunoglobulin light chain locus. In one embodiment, the mouse immunoglobulin light chain locus is a mouse κ locus. In one embodiment, the mouse immunoglobulin light chain locus is a mouse immunoglobulin light chain locus is a mouse λ locus.

In one embodiment, the genetically modified immunoglobulin locus as described herein is present in an immunoglobulin heavy chain locus of a mouse. In one embodiment, the genetically modified immunoglobulin locus is present in a humanized immunoglobulin heavy chain locus in a VELOCIMMUNE® mouse.

In one embodiment, an antigen-binding protein comprising a heavy chain variable domain expressed by the genetically modified immunoglobulin heavy chain locus as described herein exhibits a weaker antigen binding at an acidic environment (e.g., at a pH of about 5.5 to about 6.0) than a corresponding wild-type heavy chain variable domain without the genetic modification.

In one embodiment, an antigen-binding protein comprising a heavy chain variable domain expressed by the genetically modified immunoglobulin heavy chain locus as described herein has a dissociative half-life ($t_{1/2}$) of less than 2 min at an acidic pH (e.g., pH of about 5.5 to about 6.0) at 25° C. In one embodiment, an antigen-binding protein comprising a heavy chain variable domain expressed by the genetically modified immunoglobulin heavy chain locus as described herein has a dissociative half-life ($t_{1/2}$) of less than 2 min at an acidic pH (e.g., pH of about 5.5 to about 6.0) at 37° C. In one embodiment, an antigen-binding protein comprising a heavy chain variable domain expressed by the genetically modified immunoglobulin heavy chain locus as described herein has a dissociative half-life ($t_{1/2}$) of less than 1 min at an acidic pH (e.g., pH of about 5.5 to about 6.0) at 25° C. In one embodiment, an antigen-binding protein comprising a heavy chain variable domain expressed by the genetically modified immunoglobulin heavy chain locus as described herein has a dissociative half-life ($t_{1/2}$) of less than 1 min at an acidic pH (e.g., pH of about 5.5 to about 6.0) at 37° C. In one embodiment, an antigen-binding protein comprising a heavy chain variable domain expressed by the genetically modified immunoglobulin locus as described herein has at least about 2-fold, at least about 3-fold, at least about 4-fold, at least about 5-fold, at least about 10-fold, at least about 15-fold, at least about 20-fold, at least about 25-fold, or at least about 30-fold decrease in dissociative half-life ($t_{1/2}$) at an acidic pH (e.g., pH of about 5.5 to about 6.0) as compared to the dissociative half-life ($t_{1/2}$) of the antigen-binding protein at a neutral pH (e.g., pH of about 7.0 to about 7.4).

In one embodiment, an antigen-binding protein comprising a heavy chain variable domain expressed by the genetically modified immunoglobulin locus as described herein is characterized by improved pH-dependent recyclability, enhanced serum half-life, or both as compared with a wild-type antigen-binding protein without the genetic modification.

In one embodiment, the genetically modified immunoglobulin locus described herein comprises a B cell population that, upon stimulation with an antigen of interest, is capable of producing antigen-binding proteins, e.g., antibodies, comprising a heavy chain variable domain comprising one or more histidine residues. The antigen-binding proteins as described herein when administered into a subject, exhibits an increased serum half-life over a corresponding wild-type antigen-binding protein, which possesses a similar or sufficiently similar amino acid sequence that encodes the heavy chain variable domain but does not comprise a histidine residue in the heavy chain variable domain. In some embodiments, the antigen-binding protein described herein exhibits an increased serum half-life that is at least about 2-fold, at least about 5-fold, at least about 10-fold, at least about 15-fold, at least about 20-fold higher than the corresponding wild-type antigen-binding protein, which possesses a similar or sufficiently similar amino acid sequence that encodes the heavy chain variable domain but does not comprise a histidine residue in the heavy chain variable domain.

In one aspect, a non-human animal is provided comprising in its germline genome a genetically modified immunoglobulin locus comprising an unrearranged human heavy chain variable region nucleotide sequence, wherein the unrearranged heavy chain variable region nucleotide sequence comprises an addition of least one histidine codon or a substitution of at least one endogenous non-histidine codon with a histidine codon.

In one embodiment, the non-human animal is a mammal, including a rodent, e.g., a mouse, a rat, or a hamster.

In one embodiment, the added or substituted histidine codon is present in an immunoglobulin heavy chain gene segment selected from a human $V_H$ gene segment, a human D gene segment, a human $J_H$ gene segment, and a combination thereof. In one embodiment, the immunoglobulin heavy chain gene segment is selected from a human germline $V_H$ gene segment, a human germline D gene segment, a human germline $J_H$ gene segment, and a combination thereof.

In one embodiment, the human $V_H$ gene segment is selected from the group consisting of $V_H$1-2, $V_H$1-3, $V_H$1-8, $V_H$1-18, $V_H$1-24, $V_H$1-45, $V_H$1-46, $V_H$1-58, $V_H$1-69, $V_H$2-5, $V_H$2-26, $V_H$2-70, $V_H$3-7, $V_H$3-9, $V_H$3-11, $V_H$3-13, $V_H$3-15, $V_H$3-16, $V_H$3-20, $V_H$3-21, $V_H$3-23, $V_H$3-30, $V_H$3-30-3, $V_H$3-30-5, $V_H$3-33, $V_H$3-35, $V_H$3-38, $V_H$3-43, $V_H$3-48, $V_H$3-49, $V_H$3-53, $V_H$3-64, $V_H$3-66, $V_H$3-72, $V_H$3-73, $V_H$3-74, $V_H$4-4, $V_H$4-28, $V_H$4-30-1, $V_H$4-30-2, $V_H$4-30-4, $V_H$4-31, $V_H$4-34, $V_H$4-39, $V_H$4-59, $V_H$4-61, $V_H$5-51, $V_H$6-1, $V_H$7-4-1, $V_H$7-81, and a combination thereof.

In one embodiment, the human D gene segment is selected from the group consisting of D1-1, D1-7, D1-14, D1-20, D1-26, D2-2, D2-8, D2-15, D2-21, D3-3, D3-9, D3-10, D3-16, D3-22, D4-4, D4-11, D4-17, D4-23, D5-12, D5-5, D5-18, D5-24, D6-6, D6-13, D6-19, D6-25, D7-27, and a combination thereof.

In one embodiment, the human $J_H$ gene segment is selected from the group consisting of $J_H$1, $J_H$2, $J_H$3, $J_H$4, $J_H$5, $J_H$6, and a combination thereof.

In one embodiment, the added or substituted histidine codon is present in the unrearranged heavy chain variable region nucleotide sequence encoding an N-terminal region, a loop 4 region, a CDR1, a CDR2, a CDR3, or a combination thereof.

In one embodiment, the unrearranged heavy chain variable region nucleotide sequence comprises 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, 20 or more, 21 or more, 22 or more, 23 or more, 24 or more, or 25 or more, 26 or more, 27 or more, 28 or more, 29 or more, 30 or more, 31 or more, 32 or more, 33 or more, 34 or more 35 or more, 36 or more, 37 or more, 38 or more, 39 or more, 40 or more, 41 or more, 42 or more, 43 or more, 44 or more, 45 or more, 46 or more, 47 or more, 48 or more, 49 or more, 50 or more, 51 or more, 52 or more, 53 or more, 54 or more, 55 or more, 56 or more, 57 or more, 58 or more, 59 or more, 60 or more, or 61 or more of histidine codons.

In one embodiment, the unrearranged heavy chain variable region nucleotide sequence comprising the inverted human D gene segment is operably linked to a human or non-human heavy chain constant region nucleotide sequence that encodes an immunoglobulin isotype selected from IgM, IgD, IgG, IgE, and IgA.

In one embodiment, the human unrearranged immunoglobulin heavy chain variable region nucleotide sequence is operably linked to a human or non-human heavy chain constant region nucleotide sequence selected from a $C_H1$, a hinge, a $C_H2$, a $C_H3$, and a combination thereof. In one embodiment, the heavy chain constant region nucleotide sequence comprises a $C_H1$, a hinge, a $C_H2$, and a $C_H3$ (i.e., $C_H1$-hinge-$C_H2$-$C_H3$).

In one embodiment, a heavy chain constant region nucleotide sequence is present at an endogenous locus (i.e., where the nucleotide sequence is located in a wild-type non-human animal) or present ectopically (e.g., at a locus different from the endogenous immunoglobulin chain locus in its genome), or within its endogenous locus, e.g., within an immunoglobulin variable locus, wherein the endogenous locus is placed or moved to a different location in the genome.

In one embodiment, the heavy chain constant region nucleotide sequence comprises a modification in a $C_H2$ or a $C_H3$, wherein the modification increases the affinity of the heavy chain constant region amino acid sequence to FcRn in an acidic environment (e.g., in an endosome where pH ranges from about 5.5 to about 6.0).

In one embodiment, the heavy chain constant region nucleotide sequence encodes a human heavy chain constant region amino acid sequence comprising a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., L/R/S/P/Q or K) and/or 434 (e.g., H/F or Y); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 259I (e.g., V259I), and 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P), wherein the modification increases the affinity of the heavy chain constant region amino acid sequence to FcRn in an acidic environment (e.g., in an endosome where pH ranges from about 5.5 to about 6.0).

In one embodiment, the heavy chain constant region nucleotide sequence encodes a human $C_H2$ amino acid sequence comprising at least one modification between amino acid residues at positions 252 and 257, wherein the modification increases the affinity of the human $C_H2$ amino acid sequence to FcRn in an acidic environment (e.g., in an endosome where pH ranges from about 5.5 to about 6.0).

In one embodiment, the heavy chain constant region nucleotide sequence encodes a human $C_H2$ amino acid sequence comprising at least one modification between amino acid residues at positions 307 and 311, wherein the modification increases the affinity of the $C_H2$ amino acid sequence to FcRn in an acidic environment (e.g., in an endosome where pH ranges from about 5.5 to about 6.0).

In one embodiment, the heavy chain constant region nucleotide sequence encodes a human $C_H3$ amino acid sequence, wherein the $C_H3$ amino acid sequence comprises at least one modification between amino acid residues at positions 433 and 436, wherein the modification increases the affinity of the $C_H3$ amino acid sequence to FcRn in an acidic environment (e.g., in an endosome where pH ranges from about 5.5 to about 6.0).

In one embodiment, the heavy chain constant region nucleotide sequence encodes a human heavy chain constant region amino acid sequence comprising a mutation selected from the group consisting of M428L, N434S, and a combination thereof.

In one embodiment, the heavy chain constant region nucleotide sequence encodes a human heavy chain constant region amino acid sequence comprising a mutation selected from the group consisting of M428L, V259I, V308F, and a combination thereof.

In one embodiment, the heavy chain constant region nucleotide sequence encodes a human heavy chain constant region amino acid sequence comprising an N434A mutation.

In one embodiment, the heavy chain constant region nucleotide sequence encodes a human heavy chain constant region amino acid sequence comprising a mutation selected from the group consisting of M252Y, S254T, T256E, and a combination thereof.

In one embodiment, the heavy chain constant region nucleotide sequence encodes a human heavy chain constant region amino acid sequence comprising a mutation selected from the group consisting of T250Q, M248L, or both.

In one embodiment, the heavy chain constant region nucleotide sequence encodes a human heavy chain constant region amino acid sequence comprising a mutation selected from the group consisting of H433K, N434Y, or both.

In one embodiment, the genetically modified immunoglobulin locus comprises: (1) a first allele, wherein the unrearranged human immunoglobulin heavy chain variable region nucleotide sequence as described herein is operably linked to a first heavy chain constant region nucleotide sequence encoding a first $CH_3$ amino acid sequence of a human IgG selected from IgG1, IgG2, IgG4, and a combination thereof; and (2) a second allele, wherein the unrearranged human immunoglobulin heavy chain variable region nucleotide sequence as described herein is operably linked to a second heavy chain constant region nucleotide sequence encoding a second $C_H3$ amino acid sequence of the human IgG selected from IgG1, IgG2, IgG4, and a combination thereof, and wherein the second $CH_3$ amino acid sequence comprises a modification that reduces or eliminates binding for the second $CH_3$ amino acid sequence to Protein A (see, for example, US 2010/0331527A1, which is incorporated by reference herein in its entirety).

In one embodiment, the second $CH_3$ amino acid sequence comprises an H95R modification (by IMGT exon numbering; H435R by EU numbering). In one embodiment the second $CH_3$ amino acid sequence further comprises an Y96F modification (by IMGT exon numbering; H436F by EU). In another embodiment, the second $CH_3$ amino acid sequence comprises both an H95R modification (by IMGT exon numbering; H435R by EU numbering) and an Y96F modification (by IMGT exon numbering; H436F by EU).

In one embodiment, the second $CH_3$ amino acid sequence is from a modified human IgG1 and further comprises a mutation selected from the group consisting of D16E, L18M, N44S, K52N, V57M, and V82I (IMGT; D356E, L38M, N384S, K392N, V397M, and V422I by EU).

In one embodiment, the second $CH_3$ amino acid sequence is from a modified human IgG2 and further comprises a mutation selected from the group consisting of N44S, K52N, and V82I (IMGT: N384S, K392N, and V422I by EU).

In one embodiment, the second $CH_3$ amino acid sequence is from a modified human IgG4 and further comprises a mutation selected from the group consisting of Q15R, N44S, K52N, V57M, R69K, E79Q, and V82I (IMGT: Q355R, N384S, K392N, V397M, R409K, E419Q, and V422I by EU).

In one embodiment, the heavy chain constant region amino acid sequence is a non-human constant region amino acid sequence, and the heavy chain constant region amino acid sequence comprises one or more of any of the types of modifications described above.

In one embodiment, the heavy chain constant region nucleotide sequence is a human heavy chain constant region amino acid sequence, and the human heavy chain constant region amino acid sequence comprises one or more of any of the types of modifications described above.

In one embodiment, all or substantially all endogenous $V_H$, D, and $J_H$ gene segments are deleted from an immunoglobulin heavy chain locus or rendered non-functional (e.g., via insertion of a nucleotide sequence (e.g., an exogenous nucleotide sequence) in the immunoglobulin locus or via non-functional rearrangement, or inversion, of the endogenous $V_H$, D, $J_H$ segments). In one embodiment, e.g., about 80% or more, about 85% or more, about 90% or more, about 95% or more, about 96% or more, about 97% or more, about 98% or more, or about 99% or more of all endogenous $V_H$, D, or $J_H$ gene segments are deleted or rendered non-functional. In one embodiment, e.g., at least 95%, 96%, 97%, 98%, or 99% of endogenous functional V, D, or J gene segments are deleted or rendered non-functional.

In one embodiment, the genetically modified immunoglobulin heavy chain locus comprises a modification that deletes or renders, all or substantially all, non-functional endogenous $V_H$, D, and $J_H$ gene segments; and the genetically modified locus comprises an unrearranged heavy chain variable region nucleotide sequence comprising one or more human $V_H$, D, and/or $J_H$ gene segments having one or more histidine codons, wherein the unrearranged heavy chain variable region nucleotide sequence is present at an endogenous location (i.e., where the nucleotide sequence is located in a wild-type non-human animal) or present ectopically (e.g., at a locus different from the endogenous immunoglobulin chain locus in its genome, or within its endogenous locus, e.g., within an immunoglobulin variable locus, wherein the endogenous locus is placed or moved to a different location in the genome).

In one embodiment, the genetically modified immunoglobulin locus comprises an endogenous Adam6a gene, Adam6b gene, or both, and the genetic modification does not affect the expression and/or function of the endogenous Adam6a gene, Adam6b gene, or both.

In one embodiment, the genetically modified immunoglobulin locus comprises an ectopically present Adam6a gene, Adam6b gene, or both. In one embodiment, the Adam6a gene is a non-human Adam6a gene. In one embodiment, the Adam6a gene is a human Adam6a gene. In one embodiment, the Adam6b gene is a non-human Adam6b gene. In one embodiment, the Adam6b gene is a human Adam6b gene.

In one embodiment, the genetically modified immunoglobulin locus further comprises a humanized, unrearranged λ and/or κ light chain variable gene sequence. In one embodiment, the humanized, unrearranged λ and/or κ light chain variable gene sequence is operably linked to an immunoglobulin light chain constant region nucleotide sequence selected from a λ light chain constant region nucleotide sequence and a κ light chain constant region nucleotide sequence. In one embodiment, the humanized, unrearranged λ light chain variable region nucleotide sequence is operably linked to a λ light chain constant region nucleotide sequence. In one embodiment, the λ light chain constant region nucleotide sequence is a mouse, rat, or human sequence. In one embodiment, the humanized, unrearranged κ light chain variable region nucleotide sequence is operably linked to a κ light chain constant region nucleotide sequence. In one embodiment, the κ light chain constant region nucleotide sequence is a mouse, rat, or human sequence.

In one embodiment, the genetically modified immunoglobulin locus comprises an unrearranged light chain variable gene sequence that contains at least one modification that introduces at least one histidine codon in at least one reading frame encoding a light chain variable domain. In one embodiment, the genetically modified immunoglobulin locus comprises a rearranged (e.g., a rearranged λ or κ V/J sequence) sequence that comprises one, two, three, or four codons for histidine in a light chain CDR. In one embodiment, the CDR is a selected from a CDR1, CDR2, CDR3, and a combination thereof. In one embodiment, the unrearranged or rearranged light chain variable region nucleotide sequence is an unrearranged or rearranged human λ or κ light chain variable region nucleotide sequence. In one embodiment, the unrearranged or rearranged human λ or κ light chain variable region nucleotide sequence is present at an endogenous mouse immunoglobulin light chain locus. In one embodiment, the mouse immunoglobulin light chain locus is a mouse κ locus. In one embodiment, the mouse immunoglobulin light chain locus is a mouse λ locus.

In one embodiment, the genetically modified immunoglobulin locus as described herein is present in an immunoglobulin heavy chain locus of a mouse. In one embodiment, the genetically modified immunoglobulin locus is present in a humanized immunoglobulin heavy chain locus in a VELOCIMMUNE® mouse.

In one embodiment, the non-human animal is heterozygous for the genetically modified immunoglobulin heavy chain locus, and the non-human animal is capable of expressing a human immunoglobulin heavy chain variable domain comprising at least one histidine residue derived predominantly from the genetically modified immunoglobulin heavy chain locus as described herein.

In one embodiment, an antigen-binding protein comprising a heavy chain variable domain expressed by the genetically modified immunoglobulin heavy chain locus as described herein exhibits a weaker antigen binding at an acidic environment (e.g., at a pH of about 5.5 to about 6.0) than a corresponding wild-type heavy chain variable domain without the genetic modification.

In one embodiment, an antigen-binding protein comprising a heavy chain variable domain expressed by the genetically modified immunoglobulin heavy chain locus as described herein has a dissociative half-life ($t_{1/2}$) of less than 2 min at an acidic pH (e.g., pH of about 5.5 to about 6.0) at 25° C. In one embodiment, an antigen-binding protein comprising a heavy chain variable domain expressed by the genetically modified immunoglobulin heavy chain locus as described herein has a dissociative half-life ($t_{1/2}$) of less than 2 min at an acidic pH (e.g., pH of about 5.5 to about 6.0) at 37° C. In one embodiment, an antigen-binding protein comprising a heavy chain variable domain expressed by the genetically modified immunoglobulin heavy chain locus as described herein has a dissociative half-life ($t_{1/2}$) of less than 1 min at an acidic pH (e.g., pH of about 5.5 to about 6.0) at 25° C. In one embodiment, an antigen-binding protein comprising a heavy chain variable domain expressed by the genetically modified immunoglobulin heavy chain locus as described herein has a dissociative half-life ($t_{1/2}$) of less than 1 min at an acidic pH (e.g., pH of about 5.5 to about 6.0) at 37° C. In one embodiment, an antigen-binding protein comprising a heavy chain variable domain expressed by the genetically modified immunoglobulin locus as described herein has at least about 2-fold, at least about 3-fold, at least about 4-fold, at least about 5-fold, at least about 10-fold, at least about 15-fold, at least about 20-fold, at least about 25-fold, or at least about 30-fold decrease in dissociative half-life ($t_{1/2}$) at an acidic pH (e.g., pH of about 5.5 to about 6.0) as compared to the dissociative half-life ($t_{1/2}$) of the antigen-binding protein at a neutral pH (e.g., pH of about 7.0 to about 7.4).

In one embodiment, an antigen-binding protein comprising a heavy chain variable domain expressed by the genetically modified immunoglobulin locus as described herein is characterized by improved pH-dependent recyclability, enhanced serum half-life, or both as compared with a wild-type antigen-binding protein without the genetic modification.

In one embodiment, the genetically modified immunoglobulin locus described herein comprises a B cell population that, upon stimulation with an antigen of interest, is capable of producing antigen-binding proteins, e.g., antibodies, comprising a heavy chain variable domain comprising one or more histidine residues. The antigen-binding proteins as described herein when administered into a subject, exhibits an increased serum half-life over a corresponding wild-type antigen-binding protein, which possesses a similar or sufficiently similar amino acid sequence that encodes the heavy chain variable domain but does not comprise a histidine residue in the heavy chain variable domain. In some embodiments, the antigen-binding protein described herein exhibits an increased serum half-life that is at least about 2-fold, at least about 5-fold, at least about 10-fold, at least about 15-fold, at least about 20-fold higher than the corresponding wild-type antigen-binding protein, which possesses a similar or sufficiently similar amino acid sequence that encodes the heavy chain variable domain but does not comprise a histidine residue in the heavy chain variable domain.

In one aspect, a non-human animal comprising a genetically modified immunoglobulin locus is provided, wherein the genetically modified immunoglobulin locus comprises an unrearranged human heavy chain variable region nucleotide sequence, and wherein the human unrearranged heavy chain variable region nucleotide sequence comprises a substitution of at least one endogenous non-histidine codon with a histidine codon.

In one embodiment, the non-human animal is a mammal, including a rodent, e.g., a mouse, a rat, or a hamster.

In one embodiment, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, 20 or more, 21 or more, 22 or more, 23 or more, 24 or more, 25 or more, 26 or more, 27 or more, 28 or more, 29 or more, 30 or more, 31 or more, 32 or more, 33 or more, 34 or more, 35 or more, 36 or more, 37 or more, 38 or more, 39 or more, 40 or more, 41 or more, 42 or more, 43 or more, 44 or more, 45 or more, 46 or more, 47 or more, 48 or more, 49 or more, 50 or more, 51 or more, 52 or more, 53 or more, 54 or more, 55 or more, 56 or more, 57 or more, 58 or more, 59 or more, 60 or more, or 61 or more of the endogenous non-histidine codons are replaced with histidine codons.

In one embodiment, the endogenous non-histone codon encodes the amino acid selected from Y, N, D, Q, S, W, and R.

In one embodiment, the substituted histidine codon is present in an unrearranged heavy chain variable region nucleotide sequence that encodes an immunoglobulin variable domain selected from an N-terminal region, a loop 4 region, a CDR1, a CDR2, a CDR3, a combination thereof.

In one embodiment, the substituted histidine codon is present in an unrearranged heavy chain variable region nucleotide sequence that encodes a complementary determining region (CDR) selected from a CDR1, a CDR2, a CDR3, and a combination thereof.

In one embodiment, the substituted histidine codon is present in an unrearranged heavy chain variable region nucleotide sequence that encodes a frame region (FR) selected from FR1, FR2, FR3, FR4, and a combination thereof.

In one embodiment, the unrearranged heavy chain variable region nucleotide sequence comprises a genetically modified human $V_H$ gene segment, wherein one or more endogenous non-histidine codon in at least one reading frame of the human $V_H$ gene segment has been replaced with a histidine codon.

In one embodiment, the human unrearranged heavy chain variable region nucleotide sequence comprises a modification that replaces at least one endogenous non-histidine codon of a human $V_H$ gene segment with a histidine codon, wherein the human $V_H$ gene segment is selected from the group consisting of $V_H$1-2, $V_H$1-3, $V_H$1-8, $V_H$1-18, $V_H$1-24, $V_H$1-45, $V_H$1-46, $V_H$1-58, $V_H$1-69, $V_H$2-5, $V_H$2-26, $V_H$2-70, $V_H$3-7, $V_H$3-9, $V_H$3-11, $V_H$3-13, $V_H$3-15, $V_H$3-16, $V_H$3-20, $V_H$3-21, $V_H$3-23, $V_H$3-30, $V_H$3-30-3, $V_H$3-30-5, $V_H$3-33, $V_H$3-35, $V_H$3-38, $V_H$3-43, $V_H$3-48, $V_H$3-49, $V_H$3-53, $V_H$3-64, $V_H$3-66, $V_H$3-72, $V_H$3-73, $V_H$3-74, $V_H$4-4, $V_H$4-28, $V_H$4-30-1, $V_H$4-30-2, $V_H$4-30-4, $V_H$4-31, $V_H$4-34, $V_H$4-39, $V_H$4-59, $V_H$4-61, $V_H$5-51, $V_H$6-1, $V_H$7-4-1, $V_H$7-81, and a combination thereof.

In one embodiment, the human unrearranged heavy chain variable region nucleotide sequence comprises a genetically modified human $J_H$ gene segment, wherein one or more endogenous non-histidine codon in at least one reading frame of the human $J_H$ gene segment has been replaced with a histidine codon.

In one embodiment, the human unrearranged heavy chain variable region nucleotide sequence comprises a modification that replaces at least one endogenous non-histidine codon of a human $J_H$ segment with a histidine codon, wherein the human $J_H$ gene segment is selected from the group consisting of $J_H$1, $J_H$2, $J_H$3, $J_H$4, $J_H$5, $J_H$6, and a combination thereof.

In one embodiment, the substituted histidine codon is present in a heavy chain variable region nucleotide sequence that encodes part of a CDR3. In one embodiment, the part of CDR3 comprises an amino acid sequence derived from a reading frame of a genetically modified human D gene segment comprising a modification that replaces at least one endogenous non-histidine codon in the reading frame with a histidine codon.

In one embodiment, the endogenous non-histidine codon that is substituted with a histidine codon encodes the amino acid selected from Y, N, D, Q, S, W, and R.

In one embodiment, the substituted histidine codon is present in at least one reading frame of the human D gene segment that is most frequently observed in VELOCIMMUNE® humanized immunoglobulin mice.

In one embodiment, the reading frame of the genetically modified human D gene segment that encodes part of CDR3 is selected from a hydrophobic frame, a stop frame, and a hydrophilic frame.

In one embodiment, the reading frame is a hydrophobic frame of a human D gene segment.

In one embodiment, the hydrophobic frame of the human D gene segment comprises a nucleotide sequence that encodes the amino acid sequence selected from the group consisting of D1-1 (GTTGT; SEQ ID NO: 88), D1-7 (GITGT; SEQ ID NO: 89), D1-20 (GITGT; SEQ ID NO: 89), and D1-26 (GIVGAT; SEQ ID NO:90), and the human D gene segment further comprises a modification that replaces at least one endogenous non-histidine codon in the nucleotide sequence with a histidine codon.

In one embodiment, the hydrophobic frame of the human D gene segment comprises a nucleotide sequence that encodes the amino acid sequence selected from the group consisting of D2-2 (DIVVVPAAI; SEQ ID NO:92), D2-8 (DIVLMVYAI; SEQ ID NO: 94), D2-15 (DIVVVAAT; SEQ ID NO:95), and D2-21 (HIVVVTAI; SEQ ID NO: 97), and the human D gene segment further comprises a modification that replaces at least one endogenous non-histidine codon in the nucleotide sequence with a histidine codon.

In one embodiment, the hydrophobic frame of the human D gene segment comprises a nucleotide sequence that encodes the amino acid sequence selected from the group consisting of D3-3 (ITIFGVVII; SEQ ID NO:98), D3-9 (ITIF*LVII; SEQ ID NO:99, SEQ ID NO:100), D3-10 (ITMVRGVII; SEQ ID NO:101), D3-16 (IMITFGGVIVI; SEQ ID NO:102), and D3-22 (ITMIVVVIT; SEQ ID NO:103), and the human D gene segment further comprises a modification that replaces at least one endogenous codon in the nucleotide sequence with a histidine codon.

In one embodiment, the hydrophobic frame of the human D gene segment comprises a nucleotide sequence that encodes the amino acid sequence selected from the group consisting of D4-4 (TTVT; SEQ ID NO:105), D4-11 (TTVT; SEQ ID NO:105), D4-17 (TTVT; SEQ ID NO:105), D4-23 (TTVVT; SEQ ID NO: 106) and the human D gene segment further comprises a modification that replaces at least one endogenous non-histidine codon in the nucleotide sequence with a histidine codon.

In one embodiment, the hydrophobic frame of the human D gene segment comprises a nucleotide sequence that encodes the amino acid sequence selected from the group consisting of D5-5 (VDTAMV; SEQ ID NO: 107), D5-12 (VDIVATI; SEQ ID NO:108), D5-18 (VDTAMV; SEQ ID NO:107), and D5-24 (VEMATI; SEQ ID NO:109), and the human D gene segment further comprises a modification that replaces at least one endogenous non-histidine codon in the nucleotide sequence with a histidine codon.

In one embodiment, the hydrophobic frame of the human D gene segment comprises a nucleotide sequence that encodes the amino acid sequence selected from the group consisting of D6-6 (SIAAR; SEQ ID NO:111), D6-13 (GIAAAG; SEQ ID NO:113), and D6-19 (GIAVAG; SEQ ID NO:115), and the human D gene segment further comprises a modification that replaces at least one endogenous non-histidine codon in the nucleotide sequence with a histidine codon.

In one embodiment, the hydrophobic frame comprises a nucleotide sequence that encodes human D7-27 (LTG), and the human D gene segment further comprises a modification that replaces at least one endogenous non-histidine codon in the nucleotide sequence with a histidine codon.

In one embodiment, the reading frame is a stop reading frame of a human D gene segment.

In one embodiment, the stop reading frame of the human D gene segment comprises a nucleotide sequence that encodes the amino acid sequence selected from the group consisting of D1-1 (VQLER; SEQ ID NO:8), D1-7 (V*LEL), D1-20 (V*LER), D1-26 (V*WELL; SEQ ID NO:12), and the human D gene segment further comprises a modification that replaces at least one endogenous non-histidine codon in the nucleotide sequence with a histidine codon.

In one embodiment, the stop reading frame of the human D gene segment comprises a nucleotide sequence that encodes the amino acid sequence selected from the group consisting of D2-2 (RIL**YQLLY; SEQ ID NO:14), D2-8 (RILY*WCMLY; SEQ ID NO:16 and SEQ ID NO: 17), D2-15 (RIL*WW*LLL), and D2-21 (SILWW*LLF; SEQ ID NO:19), and the human D gene segment further comprises a modification that replaces at least one endogenous non-histidine codon in the nucleotide sequence with a histidine codon.

In one embodiment, the stop reading frame of the human D gene segment comprises a nucleotide sequence that encodes the amino acid sequence selected from the group consisting of D3-3 (VLRFLEWLLY; SEQ ID NO:21), D3-9 (VLRYFD-WLL*; SEQ ID NO:23), D3-10 (VLLWFGELL*; SEQ ID NO:25), D3-16 (VL*LRLGELSLY; SEQ ID NO:27), and D3-22 (VLL***WLLL; SEQ ID NO:29), and the human D gene segment comprises a modification that replaces at least one endogenous non-histidine codon in the nucleotide sequence with a histidine codon.

In one embodiment, the stop reading frame of the human D gene segment comprises a nucleotide sequence that encodes the amino acid sequence selected from the group consisting of D4-4 (*LQ*L), D4-11 (*LQ*L), D4-17 (*LR*L), and D4-23 (*LRW*L), and the human D gene segment comprises a modification that replaces at least one endogenous non-histidine codon in the nucleotide sequence with a histidine codon.

In one embodiment, the stop reading frame of the human D gene segment comprises a nucleotide sequence that encodes the amino acid sequence selected from the group consisting of D5-5 (WIQLWL; SEQ ID NO:35); D5-12 (Wl*WLRL; SEQ ID NO:37), D5-18 (WIQLWL; SEQ ID NO:35), and D5-24 (*RWLQL; SEQ ID NO:39), and the human D gene segment comprises a modification that replaces at least one endogenous non-histidine codon in the nucleotide sequence with a histidine codon.

In one embodiment, the stop reading frame of the human D gene segment comprises a nucleotide sequence that encodes the amino acid sequence selected from the group consisting of D6-6 (V*QLV), D6-13 (V*QQLV; SEQ ID NO:41), and D6-19 (V*QWLV; SEQ ID NO:43), and the human D gene segment further comprises a modification that replaces at least one endogenous non-histidine codon in the nucleotide sequence with a histidine codon.

In one embodiment, the stop reading frame of the human D gene segment comprises a nucleotide sequence that encodes D7-27 (*LG), and the human D gene segment further comprises a modification that replaces at least one endogenous codon of the human D gene segment in the nucleotide sequence with a histidine codon.

In one embodiment, the reading frame is a hydrophilic frame of a human D gene segment.

In one embodiment, the hydrophilic frame of the human D gene segment comprises a nucleotide sequence that encodes the amino acid sequence selected from the group consisting of D1-1 (YNWND; SEQ ID NO: 45), D1-7 (YNWNY; SEQ ID NO: 47), D1-20 (YNWND; SEQ ID NO: 45), and D1-26 (YSGSYY; SEQ ID NO:49), and the human D gene segment further comprises a modification that replaces at least one endogenous codon in the nucleotide sequence with a histidine codon. In one embodiment, the hydrophilic frame comprises a nucleotide sequence that encodes the amino acid sequence selected from the group consisting of SEQ ID NO: 46, SEQ ID NO: 48, SEQ ID NO: 50, and a combination thereof.

In one embodiment, the hydrophilic frame of the human D gene segment comprises a nucleotide sequence that encodes the amino acid sequence selected from the group consisting of D2-2 (GYCSSTSCYT; SEQ ID NO:51), D2-8 (GYCT-NGVCYT; SEQ ID NO: 53), D2-15 (GYCSGGSCYS; SEQ ID NO:55), and D2-21 (AYCGGDCYS; SEQ ID NO:57), and the human D gene segment further comprises a modification that replaces at least one endogenous codon in the nucleotide sequence with a histidine codon. In one embodiment, the hydrophilic frame comprises a nucleotide sequence that encodes the amino acid sequence selected from the group consisting of SEQ ID NO: 52, SEQ ID NO: 54, SEQ ID NO: 56, SEQ ID NO: 58, and a combination thereof.

In one embodiment, the hydrophilic frame of the human D gene segment comprises a nucleotide sequence that encodes the amino acid sequence selected from the group consisting of D3-3 (YYDFWSGYYT; SEQ ID NO:59), D3-9 (YYDILT-GYYN; SEQ ID NO:61), D3-10 (YYYGSGSYYN; SEQ ID NO:63), D3-16 (YYDYVWGSYRYT; SEQ ID NO:65), and D3-22 (YYYDSSGYYY; SEQ ID NO:67), and the human D gene segment further comprises a modification that replaces at least one endogenous codon in the nucleotide sequence with a histidine codon. In one embodiment, the hydrophilic frame comprises a nucleotide sequence encodes the amino acid sequence selected from the group consisting of SEQ ID NO: 60, SEQ ID NO: 62, SEQ ID NO: 64, SEQ ID NO: 66, SEQ ID NO: 68, and a combination thereof.

In one embodiment, the hydrophilic frame of the human D gene segment comprises a nucleotide sequence that encodes the amino acid sequence selected from the group consisting of D4-4 (DYSNY; SEQ ID NO:69), D4-11 (DYSNY; SEQ ID NO:69), D4-17 (DYGDY; SEQ ID NO:71), and D4-23 (DYGGNS; SEQ ID NO:73), and the human D gene segment comprises a modification that replaces at least one endogenous codon in the nucleotide sequence with a histidine codon. In one embodiment, the hydrophilic frame comprises a nucleotide sequence that encodes the amino acid sequence selected from the group consisting of SEQ ID NO: 70, SEQ ID NO: 72, SEQ ID NO: 74, and a combination thereof.

In one embodiment, the hydrophilic frame of the human D gene segment comprises a nucleotide sequence that encodes the amino acid sequence selected from the group consisting of D5-5 (GYSYGY; SEQ ID NO:75), D5-12 (GYSGYDY; SEQ ID NO:77), D5-18 (GYSYGY; SEQ ID NO:75), and D5-24 (RDGYNY; SEQ ID NO:79), and the human D gene segment further comprises a modification that replaces at least one endogenous codon in the nucleotide sequence with a histidine codon. In one embodiment, the hydrophilic frame comprises a nucleotide sequence that encodes the amino acid sequence selected from the group consisting of SEQ ID NO: 76, SEQ ID NO: 78, SEQ ID NO: 80, and a combination thereof.

In one embodiment, the hydrophilic frame of the human D gene segment comprises a nucleotide sequence that encodes the amino acid sequence selected from the group consisting of D6-6 (EYSSSS; SEQ ID NO: 81), D6-13 (GYSSSWY; SEQ ID NO:83), and D6-19 (GYSSGWY; SEQ ID NO:85), and the human D gene segment further comprises a modification that replaces at least one endogenous codon in the nucleotide sequence with a histidine codon. In one embodiment, the hydrophilic frame comprises a nucleotide sequence that encodes the amino acid sequence selected from the group consisting of SEQ ID NO: 82, SEQ ID NO: 84, SEQ ID NO: 86, SEQ ID NO: 76, and a combination thereof.

In one embodiment, the hydrophilic frame of the human D gene segment comprises a nucleotide sequence that encodes D7-27 (NWG), and the human D gene segment further comprises a modification that replaces at least one endogenous codon in the nucleotide sequence a histidine codon.

In one embodiment, the hydrophilic frame of the human D gene segment comprises a nucleotide sequence that encodes the amino acid sequence selected from the group consisting of SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, and a combination thereof.

In one embodiment, the unrearranged heavy chain variable region nucleotide sequence comprising the inverted human D gene segment is operably linked to a human or non-human heavy chain constant region nucleotide sequence that encodes an immunoglobulin isotype selected from IgM, IgD, IgG, IgE, and IgA.

In one embodiment, the human unrearranged immunoglobulin heavy chain variable region nucleotide sequence is operably linked to a human or non-human heavy chain constant region nucleotide sequence selected from a $C_H1$, a hinge, a $C_H2$, a $C_H3$, and a combination thereof. In one embodiment, the heavy chain constant region nucleotide sequence comprises a $C_H1$, a hinge, a $C_H2$, and a $C_H3$ (i.e., $C_H1$-hinge-$C_H2$-$C_H3$).

In one embodiment, a heavy chain constant region nucleotide sequence is present at an endogenous locus (i.e., where the nucleotide sequence is located in a wild-type non-human animal) or present ectopically (e.g., at a locus different from the endogenous immunoglobulin chain locus in its genome, or within its endogenous locus, e.g., within an immunoglobulin variable locus, wherein the endogenous locus is placed or moved to a different location in the genome).

In one embodiment, the heavy chain constant region nucleotide sequence comprises a modification in a $C_H2$ or a $C_H3$, wherein the modification increases the affinity of the heavy chain constant region amino acid sequence to FcRn in an acidic environment (e.g., in an endosome where pH ranges from about 5.5 to about 6.0).

In one embodiment, the heavy chain constant region nucleotide sequence encodes a human heavy chain constant region amino acid sequence comprising a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., L/R/S/P/Q or K) and/or 434 (e.g., H/F or Y); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 259I (e.g., V259I), and 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P), wherein the modification increases the affinity of the heavy chain constant region amino acid sequence to FcRn in an acidic environment (e.g., in an endosome where pH ranges from about 5.5 to about 6.0).

In one embodiment, the heavy chain constant region nucleotide sequence encodes a human $C_H2$ amino acid sequence comprising at least one modification between amino acid residues at positions 252 and 257, wherein the modification increases the affinity of the human $C_H2$ amino acid sequence to FcRn in an acidic environment (e.g., in an endosome where pH ranges from about 5.5 to about 6.0).

In one embodiment, the heavy chain constant region nucleotide sequence encodes a human $C_H2$ amino acid sequence comprising at least one modification between amino acid residues at positions 307 and 311, wherein the modification increases the affinity of the $C_H2$ amino acid sequence to FcRn in an acidic environment (e.g., in an endosome where pH ranges from about 5.5 to about 6.0).

In one embodiment, the heavy chain constant region nucleotide sequence encodes a human $C_H3$ amino acid sequence, wherein the $C_H3$ amino acid sequence comprises at least one modification between amino acid residues at positions 433 and 436, wherein the modification increases the affinity of the $C_H3$ amino acid sequence to FcRn in an acidic environment (e.g., in an endosome where pH ranges from about 5.5 to about 6.0).

In one embodiment, the heavy chain constant region nucleotide sequence encodes a human heavy chain constant region amino acid sequence comprising a mutation selected from the group consisting of M428L, N434S, and a combination thereof.

In one embodiment, the heavy chain constant region nucleotide sequence encodes a human heavy chain constant region amino acid sequence comprising a mutation selected from the group consisting of M428L, V259I, V308F, and a combination thereof.

In one embodiment, the heavy chain constant region nucleotide sequence encodes a human heavy chain constant region amino acid sequence comprising an N434A mutation.

In one embodiment, the heavy chain constant region nucleotide sequence encodes a human heavy chain constant region amino acid sequence comprising a mutation selected from the group consisting of M252Y, S254T, T256E, and a combination thereof.

In one embodiment, the heavy chain constant region nucleotide sequence encodes a human heavy chain constant region amino acid sequence comprising a mutation selected from the group consisting of T250Q, M248L, or both.

In one embodiment, the heavy chain constant region nucleotide sequence encodes a human heavy chain constant region amino acid sequence comprising a mutation selected from the group consisting of H433K, N434Y, or both.

In one embodiment, the genetically modified immunoglobulin locus comprises: (1) a first allele, wherein the unrearranged human immunoglobulin heavy chain variable region nucleotide sequence as described herein is operably linked to a first heavy chain constant region nucleotide sequence encoding a first $CH_3$ amino acid sequence of a human IgG selected from IgG1, IgG2, IgG4, and a combination thereof; and (2) a second allele, wherein the unrearranged human immunoglobulin heavy chain variable region nucleotide sequence as described herein is operably linked to a second heavy chain constant region nucleotide sequence encoding a second $C_H3$ amino acid sequence of the human IgG selected from IgG1, IgG2, IgG4, and a combination thereof, and wherein the second $CH_3$ amino acid sequence comprises a modification that reduces or eliminates binding for the second $CH_3$ amino acid sequence to Protein A (see, for example, US 2010/0331527A1, which is incorporated by reference herein in its entirety).

In one embodiment, the second $CH_3$ amino acid sequence comprises an H95R modification (by IMGT exon numbering; H435R by EU numbering). In one embodiment the second $CH_3$ amino acid sequence further comprises an Y96F modification (by IMGT exon numbering; H436F by EU). In another embodiment, the second $CH_3$ amino acid sequence comprises both an H95R modification (by IMGT exon numbering; H435R by EU numbering) and an Y96F modification (by IMGT exon numbering; H436F by EU).

In one embodiment, the second $CH_3$ amino acid sequence is from a modified human IgG1 and further comprises a mutation selected from the group consisting of D16E, L18M, N44S, K52N, V57M, and V82I (IMGT; D356E, L38M, N384S, K392N, V397M, and V422I by EU).

In one embodiment, the second $CH_3$ amino acid sequence is from a modified human IgG2 and further comprises a mutation selected from the group consisting of N44S, K52N, and V82I (IMGT: N384S, K392N, and V422I by EU).

In one embodiment, the second $CH_3$ amino acid sequence is from a modified human IgG4 and further comprises a mutation selected from the group consisting of Q15R, N44S, K52N, V57M, R69K, E79Q, and V82I (IMGT: Q355R, N384S, K392N, V397M, R409K, E419Q, and V422I by EU).

In one embodiment, the heavy chain constant region amino acid sequence is a non-human constant region amino acid sequence, and the heavy chain constant region amino acid sequence comprises one or more of any of the types of modifications described above.

In one embodiment, the heavy chain constant region nucleotide sequence is a human heavy chain constant region amino acid sequence, and the human heavy chain constant region amino acid sequence comprises one or more of any of the types of modifications described above.

In one embodiment, all, or substantially all, endogenous $V_H$, D, and $J_H$ gene segments are deleted from an immunoglobulin heavy chain locus or rendered non-functional (e.g., via insertion of a nucleotide sequence (e.g., an exogenous nucleotide sequence) in the immunoglobulin locus or via non-functional rearrangement, or inversion, of the endogenous $V_H$, D, $J_H$ segments). In one embodiment, e.g., about 80% or more, about 85% or more, about 90% or more, about 95% or more, about 96% or more, about 97% or more, about 98% or more, or about 99% or more of all endogenous $V_H$, D, or $J_H$ gene segments are deleted or rendered non-functional. In one embodiment, e.g., at least 95%, 96%, 97%, 98%, or 99% of endogenous functional V, D, or J gene segments are deleted or rendered non-functional.

In one embodiment, the genetically modified locus comprises a modification that deletes or renders non-functional all or substantially all endogenous $V_H$, D, and $J_H$ gene segments; and the genomic locus comprises the genetically modified, unrearranged human heavy chain variable region nucleotide sequence comprising a substitution of at least one endogenous non-histidine codon with a histidine codon in at least one reading frame. In one embodiment, the genetically modified, unrearranged immunoglobulin heavy chain variable gene sequence is present at an endogenous location (i.e., where the nucleotide sequence is located in a wild-type non-human animal) or present ectopically (e.g., at a locus different from the endogenous immunoglobulin chain locus in its genome), or within its endogenous locus, e.g., within an immunoglobulin variable locus, wherein the endogenous locus is placed or moved to a different location in the genome.

In one embodiment, the genetically modified locus comprises an endogenous Adam6a gene, Adam6b gene, or both, and the genetic modification does not affect the expression and/or function of the endogenous Adam6a gene, Adam6b gene, or both.

In one embodiment, the genetically modified locus comprises an ectopically present Adam6a gene, Adam6b gene, or both. In one embodiment, the Adam6a gene is a non-human Adam6a gene. In one embodiment, the Adam6a gene is a mouse Adam6a gene. In one embodiment, the Adam6a gene is a human Adam6a gene. In one embodiment, the Adam6b gene is a non-human Adam6b gene. In one embodiment, the Adam6b gene is a mouse Adam6b gene. In one embodiment, the Adam6b gene is a human Adam6b gene.

In one embodiment, the genetically modified immunoglobulin locus further comprises a humanized, unrearranged λ and/or κ light chain variable gene sequence. In one embodiment, the humanized, unrearranged λ and/or κ light chain variable gene sequence is operably linked to an immunoglobulin light chain constant region nucleotide sequence selected from a λ light chain constant region nucleotide sequence and a κ light chain constant region nucleotide sequence. In one embodiment, the humanized, unrearranged λ light chain variable region nucleotide sequence is operably linked to a λ light chain constant region nucleotide sequence. In one embodiment, the λ light chain constant region nucleotide sequence is a mouse, rat, or human sequence. In one embodiment, the humanized, unrearranged κ light chain variable region nucleotide sequence is operably linked to a κ light chain constant region nucleotide sequence. In one embodiment, the κ light chain constant region nucleotide sequence is a mouse, rat, or human sequence.

In one embodiment, the genetically modified immunoglobulin locus comprises an unrearranged light chain variable gene sequence that contains at least one modification that introduces at least one histidine codon in at least one reading frame encoding a light chain variable domain. In one embodiment, the genetically modified immunoglobulin locus comprises a rearranged (e.g., rearranged λ or κ V/J sequence) sequence that comprises one, two, three, or four codons for histidine in a light chain CDR. In one embodiment, the CDR is a selected from a CDR1, CDR2, CDR3, and a combination thereof. In one embodiment, the unrearranged or rearranged light chain variable region nucleotide sequence is an unrearranged or rearranged human λ or κ light chain variable region nucleotide sequence. In one embodiment, the unrearranged or rearranged human λ or κ light chain variable region nucleotide sequence is present at an endogenous mouse immunoglobulin light chain locus. In one embodiment, the mouse immunoglobulin light chain locus is a mouse κ locus. In one embodiment the mouse immunoglobulin light chain locus is a mouse λ locus.

In one embodiment, the genetically modified immunoglobulin locus as described herein is present in an immunoglobulin heavy chain locus of a mouse. In one embodiment, the genetically modified immunoglobulin locus is present in a humanized immunoglobulin heavy chain locus in a VELOCI-MMUNE® mouse.

In one embodiment, an antigen-binding protein comprising a heavy chain variable domain expressed by the genetically modified immunoglobulin heavy chain locus as described herein exhibits a weaker antigen binding at an acidic environment (e.g., at a pH of about 5.5 to about 6.0) than a corresponding wild-type heavy chain variable domain without the genetic modification.

In one embodiment, an antigen-binding protein comprising a heavy chain variable domain expressed by the genetically modified immunoglobulin heavy chain locus as described herein has a dissociative half-life ($t_{1/2}$) of less than 2 min at an acidic pH (e.g., pH of about 5.5 to about 6.0) at 25° C. In one embodiment, an antigen-binding protein comprising a heavy chain variable domain expressed by the genetically modified immunoglobulin heavy chain locus as described herein has a dissociative half-life ($t_{1/2}$) of less than 2 min at an acidic pH (e.g., pH of about 5.5 to about 6.0) at 37° C. In one embodiment, an antigen-binding protein comprising a heavy chain variable domain expressed by the genetically modified immunoglobulin heavy chain locus as described herein has a dissociative half-life ($t_{1/2}$) of less than 1 min at an acidic pH (e.g., pH of about 5.5 to about 6.0) at 25° C. In one embodiment, an antigen-binding protein comprising a heavy chain variable domain expressed by the genetically modified immunoglobulin heavy chain locus as described herein has a dissociative half-life ($t_{1/2}$) of less than 1 min at an acidic pH (e.g., pH of about 5.5 to about 6.0) at 37° C. In one embodiment, an antigen-binding protein comprising a heavy chain variable domain expressed by the genetically modified immunoglobulin locus as described herein has at least about 2-fold, at least about 3-fold, at least about 4-fold, at least about 5-fold, at least about 10-fold, at least about 15-fold, at least about 20-fold, at least about 25-fold, or at least about 30-fold decrease in dissociative half-life ($t_{1/2}$) at an acidic pH (e.g., pH of about 5.5 to about 6.0) as compared to the dissociative half-life ($t_{1/2}$) of the antigen-binding protein at a neutral pH (e.g., pH of about 7.0 to about 7.4).

In one embodiment, an antigen-binding protein comprising a heavy chain variable domain expressed by the genetically modified immunoglobulin locus as described herein is characterized by improved pH-dependent recyclability, enhanced serum half-life, or both as compared with a wild-type antigen-binding protein without the genetic modification.

In one embodiment, the genetically modified immunoglobulin locus as described herein comprises a B cell population that, upon stimulation with an antigen of interest, is capable of producing antigen-binding proteins, e.g., antibodies, comprising a heavy chain variable domain comprising one or more histidine residues. The antigen-binding proteins as described herein, when administered into a subject, exhibits an increased serum half-life over a corresponding wild-type antigen-binding protein, which possesses a similar or sufficiently similar amino acid sequence that encodes the heavy chain variable domain but does not comprise a histidine residue in the heavy chain variable domain. In some embodiments, the antigen-binding protein described herein exhibits an increased serum half-life that is at least about 2-fold, at least about 5-fold, at least about 10-fold, at least about 15-fold, at least about 20-fold higher than the corresponding wild-type antigen-binding protein, which possesses a similar or sufficiently similar amino acid sequence that encodes the heavy chain variable domain but does not comprise a histidine residue in the heavy chain variable domain.

In one embodiment, the non-human animal is heterozygous for the genetically modified immunoglobulin heavy chain locus, and the non-human animal is capable of expressing the human immunoglobulin heavy chain variable domain comprising at least one histidine residue derived predominantly from the genetically modified immunoglobulin heavy chain locus as described herein.

In one aspect, a non-human animal comprising a genetically modified immunoglobulin locus comprising a human $V_H$, D, and $J_H$ gene segment is provided, wherein at least one of the human D gene segment has been inverted 5' to 3' with respect to a corresponding wild-type sequence, and wherein at least one reading frame of the inverted human D gene segment comprises a histidine codon.

In one embodiment, the non-human animal is a mammal, including a rodent, e.g., a mouse, a rat, or a hamster In one embodiment, the genetically modified immunoglobulin locus is present in a germline genome.

In one embodiment, wherein the reading frame of the inverted human D gene segment comprises one or more, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, 20 or more, 21 or more, 22 or more, 23 or more, 24 or more, 25 or more, 26 or more, 27 or more, 28 or more, 29 or more, 30 or more, 31 or more, 32 or more, 33 or more, or 34 or more of histidine codons.

In one embodiment, at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, at least twenty, at least twenty one, at least twenty two, at least twenty three, at least twenty four, or all or substantially all of functional human D gene segments have inverted orientation with respect to corresponding wild type sequences.

In one embodiment, all or substantially all of endogenous immunoglobulin $V_H$, D, $J_H$ gene segments are deleted from the immunoglobulin heavy chain locus or rendered non-functional (e.g., via insertion of a nucleotide sequence, e.g., exogenous nucleotide sequence, in the immunoglobulin locus or via non-functional rearrangement or inversion of all, or substantially all, endogenous immunoglobulin $V_H$, D, $J_H$ segments), and the genetically modified immunoglobulin locus comprises a human $V_H$, D, and $J_H$ gene segments, wherein at least one of the human D gene segment is present in an inverted orientation with respect to corresponding wild type sequences, and wherein at least one reading frame of the inverted human D gene segment comprises at least one histidine codon.

In one embodiment, the inverted human D gene segment is operably linked to a human $V_H$ gene segment, and/or human $J_H$ gene segment In one embodiment, the human D gene segment that is present in the inverted orientation relative to a corresponding wild type sequence is selected from the group consisting of D1-1, D1-7, D1-20, D1-26, D2-2, D2-8, D2-15, D2-21, D3-3, D3-9, D3-10, D3-16, D3-22, D4-4, D4-11, D4-17, D4-23, D5-5, D5-12, D5-18, D5-24, D6-6, D6-13, D6-19, D7-27, and a combination thereof.

In one embodiment, the human D gene segment that is present in the inverted orientation relative to a corresponding wild type sequence is a D1 gene segment selected from the group consisting of D1-1, D1-7, D1-20, D1-26, and a combination thereof.

In one embodiment, the human D gene segment that is present in the inverted orientation relative to a corresponding wild type sequences is a D2 gene segment selected from the group consisting of D2-2, D2-8, D2-15, D2-21, and a combination thereof.

In one embodiment, the human D gene segment that is present in the inverted orientation relative to a corresponding wild type sequence is a D3 gene segment selected from the group consisting of D3-3, D3-9, D3-10, D3-16, D3-22, and a combination thereof.

In one embodiment, the human D gene segment that is present in the inverted orientation relative to a corresponding wild type sequence is a D4 gene segment selected from the group consisting of D4-4, D4-11, D4-17, D4-23, and a combination thereof.

In one embodiment, the human D gene segment that is present in the inverted orientation relative to a corresponding wild type sequence is a D5 gene segment selected from the group consisting of D5-5, D5-12, D5-18, D5-24, and a combination thereof.

In one embodiment, the human D gene segment that is present in the inverted orientation relative to a corresponding wild type sequence is a D6 gene segment selected from the group consisting of D6-6, D6-13, D6-19, and a combination thereof.

In one embodiment, the human D gene segment that is present in the inverted orientation relative to a corresponding wild type sequence is $D_7$-27.

In one embodiment, the reading frame of the human D gene segment is selected from a stop reading frame, a hydrophilic reading frame, a hydrophobic reading frame, and a combination thereof, wherein at least one reading frame of the inverted human D gene segment comprises a histidine codon.

In one embodiment, the unrearranged heavy chain variable region nucleotide sequence comprising the inverted human D gene segment is operably linked to a human or non-human heavy chain constant region nucleotide sequence that encodes an immunoglobulin isotype selected from IgM, IgD, IgG, IgE, and IgA.

In one embodiment, the human unrearranged immunoglobulin heavy chain variable region nucleotide sequence is operably linked to a human or non-human heavy chain constant region nucleotide sequence selected from a $C_H1$, a hinge, a $C_H2$, a $C_H3$, and a combination thereof. In one embodiment, the heavy chain constant region nucleotide sequence comprises a $C_H1$, a hinge, a $C_H2$, and a $C_H3$ (i.e., $C_H1$-hinge-$C_H2$-$C_H3$).

In one embodiment, a heavy chain constant region nucleotide sequence is present at an endogenous locus (i.e., where the nucleotide sequence is located in a wild-type non-human animal) or present ectopically (e.g., at a locus different from the endogenous immunoglobulin chain locus in its genome, or within its endogenous locus, e.g., within an immunoglobulin variable locus, wherein the endogenous locus is placed or moved to a different location in the genome).

In one embodiment, the heavy chain constant region nucleotide sequence comprises a modification in a $C_H2$ or a $C_H3$, wherein the modification increases the affinity of the heavy chain constant region amino acid sequence to FcRn in an acidic environment (e.g., in an endosome where pH ranges from about 5.5 to about 6.0).

In one embodiment, the heavy chain constant region nucleotide sequence encodes a human heavy chain constant region amino acid sequence comprising a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., L/R/S/P/Q or K) and/or 434 (e.g., H/F or Y); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 259I (e.g., V259I), and 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P), wherein the modification increases the affinity of the heavy chain constant region amino acid sequence to FcRn in an acidic environment (e.g., in an endosome where pH ranges from about 5.5 to about 6.0).

In one embodiment, the heavy chain constant region nucleotide sequence encodes a human $C_H2$ amino acid sequence comprising at least one modification between amino acid residues at positions 252 and 257, wherein the modification increases the affinity of the human $C_H2$ amino acid sequence to FcRn in an acidic environment (e.g., in an endosome where pH ranges from about 5.5 to about 6.0).

In one embodiment, the heavy chain constant region nucleotide sequence encodes a human $C_H2$ amino acid sequence comprising at least one modification between amino acid residues at positions 307 and 311, wherein the modification increases the affinity of the $C_H2$ amino acid sequence to FcRn in an acidic environment (e.g., in an endosome where pH ranges from about 5.5 to about 6.0).

In one embodiment, the heavy chain constant region nucleotide sequence encodes a human $C_H3$ amino acid sequence, wherein the $C_H3$ amino acid sequence comprises at least one modification between amino acid residues at positions 433 and 436, wherein the modification increases the affinity of the $C_H3$ amino acid sequence to FcRn in an acidic environment (e.g., in an endosome where pH ranges from about 5.5 to about 6.0).

In one embodiment, the heavy chain constant region nucleotide sequence encodes a human heavy chain constant region amino acid sequence comprising a mutation selected from the group consisting of M428L, N434S, and a combination thereof.

In one embodiment, the heavy chain constant region nucleotide sequence encodes a human heavy chain constant region amino acid sequence comprising a mutation selected from the group consisting of M428L, V259I, V308F, and a combination thereof.

In one embodiment, the heavy chain constant region nucleotide sequence encodes a human heavy chain constant region amino acid sequence comprising an N434A mutation.

In one embodiment, the heavy chain constant region nucleotide sequence encodes a human heavy chain constant region amino acid sequence comprising a mutation selected from the group consisting of M252Y, S254T, T256E, and a combination thereof.

In one embodiment, the heavy chain constant region nucleotide sequence encodes a human heavy chain constant region amino acid sequence comprising a mutation selected from the group consisting of T250Q, M248L, or both.

In one embodiment, the heavy chain constant region nucleotide sequence encodes a human heavy chain constant region amino acid sequence comprising a mutation selected from the group consisting of H433K, N434Y, or both.

In one embodiment, the genetically modified immunoglobulin locus comprises: (1) a first allele, wherein the unrearranged human immunoglobulin heavy chain variable region nucleotide sequence as described herein is operably linked to a first heavy chain constant region nucleotide sequence encoding a first $C_{H}3$ amino acid sequence of a human IgG selected from IgG1, IgG2, IgG4, and a combination thereof; and (2) a second allele, wherein the unrearranged human immunoglobulin heavy chain variable region nucleotide sequence as described herein is operably linked to a second heavy chain constant region nucleotide sequence encoding a second $C_{H}3$ amino acid sequence of the human IgG selected from IgG1, IgG2, IgG4, and a combination thereof, and wherein the second $CH_3$ amino acid sequence comprises a modification that reduces or eliminates binding for the second $CH_3$ amino acid sequence to Protein A (see, for example, US 2010/0331527A1, incorporated by reference herein in its entirety).

In one embodiment, the second $CH_3$ amino acid sequence comprises an H95R modification (by IMGT exon numbering; H435R by EU numbering). In one embodiment the second $CH_3$ amino acid sequence further comprises an Y96F modification (by IMGT exon numbering; H436F by EU). In another embodiment, the second $CH_3$ amino acid sequence comprises both an H95R modification (by IMGT exon numbering; H435R by EU numbering) and an Y96F modification (by IMGT exon numbering; H436F by EU).

In one embodiment, the second $CH_3$ amino acid sequence is from a modified human IgG1 and further comprises a mutation selected from the group consisting of D16E, L18M, N44S, K52N, V57M, and V82I (IMGT; D356E, L38M, N384S, K392N, V397M, and V422I by EU).

In one embodiment, the second $CH_3$ amino acid sequence is from a modified human IgG2 and further comprises a mutation selected from the group consisting of N44S, K52N, and V82I (IMGT: N384S, K392N, and V422I by EU).

In one embodiment, the second $CH_3$ amino acid sequence is from a modified human IgG4 and further comprises a mutation selected from the group consisting of Q15R, N44S, K52N, V57M, R69K, E79Q, and V82I (IMGT: Q355R, N384S, K392N, V397M, R409K, E419Q, and V422I by EU).

In one embodiment, the heavy chain constant region amino acid sequence is a non-human constant region amino acid sequence, and the heavy chain constant region amino acid sequence comprises one or more of any of the types of modifications described above.

In one embodiment, the heavy chain constant region nucleotide sequence is a human heavy chain constant region amino acid sequence, and the human heavy chain constant region amino acid sequence comprises one or more of any of the types of modifications described above.

In one embodiment, all or substantially all endogenous $V_H$, D, and $J_H$ gene segments are deleted from an immunoglobulin heavy chain locus or rendered non-functional (e.g., via insertion of a nucleotide sequence (e.g., an exogenous nucleotide sequence) in the immunoglobulin locus or via non-functional rearrangement, or inversion, of the endogenous $V_H$, D, $J_H$ segments). In one embodiment, e.g., about 80% or more, about 85% or more, about 90% or more, about 95% or more, about 96% or more, about 97% or more, about 98% or more, or about 99% or more of all endogenous $V_H$, D, or $J_H$ gene segments are deleted or rendered non-functional. In one embodiment, e.g., at least 95%, 96%, 97%, 98%, or 99% of endogenous functional V, D, or J gene segments are deleted or rendered non-functional.

In one embodiment, the genetically modified immunoglobulin heavy chain locus comprises a modification that deletes or renders, all or substantially all, non-functional endogenous $V_H$, D, and $J_H$ gene segments; and the genetically modified locus comprises an unrearranged heavy chain variable region nucleotide sequence comprising at least one inverted human D gene segment as described herein wherein the unrearranged heavy chain variable region nucleotide sequence is present at an endogenous location (i.e., where the nucleotide sequence is located in a wild-type non-human animal) or present ectopically (e.g., at a locus different from the endogenous immunoglobulin chain locus in its genome, or within its endogenous locus, e.g., within an immunoglobulin variable locus, wherein the endogenous locus is placed or moved to a different location in the genome).

In one embodiment, the genetically modified immunoglobulin locus comprises an endogenous Adam6a gene, Adam6b gene, or both, and the genetic modification does not affect the expression and/or function of the endogenous Adam6a gene, Adam6b gene, or both.

In one embodiment, the genetically modified immunoglobulin locus comprises an ectopically present Adam6a gene, Adam6b gene, or both. In one embodiment, the Adam6a gene is a non-human Adam6a gene. In one embodiment, the Adam6a gene is a mouse Adam6a gene. In one embodiment, the Adam6a gene is a human Adam6a gene. In one embodiment, the Adam6b gene is a non-human Adam6b gene. In one embodiment, the Adam6b gene is a mouse Adam6b gene. In one embodiment, the Adam6b gene is a human Adam6b gene.

In one embodiment, the genetically modified immunoglobulin locus further comprises a humanized, unrearranged λ and/or κ light chain variable gene sequence. In one embodiment, the humanized, unrearranged λ and/or κ light chain variable gene sequence is operably linked to an immunoglobulin light chain constant region nucleotide sequence selected from a λ light chain constant region nucleotide sequence and a κ light chain constant region nucleotide sequence. In one embodiment, the humanized, unrearranged λ light chain variable region nucleotide sequence is operably linked to a λ light chain constant region nucleotide sequence. In one embodiment, the λ light chain constant region nucleotide sequence is a mouse, rat, or human sequence. In one embodiment, the humanized, unrearranged κ light chain variable region nucleotide sequence is operably linked to a κ light chain constant region nucleotide sequence. In one embodiment, the κ light chain constant region nucleotide sequence is a mouse, rat, or human sequence.

In one embodiment, the genetically modified immunoglobulin locus comprises an unrearranged light chain variable gene sequence that contains at least one modification that introduces at least one histidine codon in at least one reading frame encoding a light chain variable domain. In one embodiment, the genetically modified immunoglobulin locus comprises a rearranged (e.g., a rearranged λ or κ V/J sequence) sequence that comprises one, two, three, or four codons for histidine in a light chain CDR. In one embodiment, the CDR is a selected from a CDR1, CDR2, CDR3, and a combination thereof. In one embodiment, the unrearranged or rearranged light chain variable region nucleotide sequence is an unrearranged or rearranged human λ or κ light chain variable region nucleotide sequence. In one embodiment, the unrearranged or rearranged human λ or κ light chain variable region nucleotide sequence is present at an endogenous mouse immunoglobulin light chain locus. In one embodiment, the mouse immunoglobulin light chain locus is a mouse κ locus. In one embodiment, the mouse immunoglobulin light chain locus is a mouse immunoglobulin light chain locus is a mouse λ locus.

In one embodiment, the genetically modified immunoglobulin locus as described herein is present in an immunoglobulin heavy chain locus of a mouse. In one embodiment, the genetically modified immunoglobulin locus is present in a humanized immunoglobulin heavy chain locus in a VELOCIMMUNE® mouse.

In one embodiment, the non-human animal is heterozygous for the genetically modified immunoglobulin heavy chain locus, and the non-human animal is capable of expressing the human immunoglobulin heavy chain variable domain comprising at least one histidine residue derived predominantly from the genetically modified immunoglobulin heavy chain locus as described herein.

In one embodiment, an antigen-binding protein comprising a heavy chain variable domain expressed by the genetically modified immunoglobulin heavy chain locus as described herein exhibits a weaker antigen binding at an acidic environment (e.g., at a pH of about 5.5 to about 6.0) than a corresponding wild-type heavy chain variable domain without the genetic modification.

In one embodiment, an antigen-binding protein comprising a heavy chain variable domain expressed by the genetically modified immunoglobulin heavy chain locus as described herein has a dissociative half-life ($t_{1/2}$) of less than 2 min at an acidic pH (e.g., pH of about 5.5 to about 6.0) at 25° C. In one embodiment, an antigen-binding protein comprising a heavy chain variable domain expressed by the genetically modified immunoglobulin heavy chain locus as described herein has a dissociative half-life ($t_{1/2}$) of less than 2 min at an acidic pH (e.g., pH of about 5.5 to about 6.0) at 37° C. In one embodiment, an antigen-binding protein comprising a heavy chain variable domain expressed by the genetically modified immunoglobulin heavy chain locus as described herein has a dissociative half-life ($t_{1/2}$) of less than 1 min at an acidic pH (e.g., pH of about 5.5 to about 6.0) at 25° C. In one embodiment, an antigen-binding protein comprising a heavy chain variable domain expressed by the genetically modified immunoglobulin heavy chain locus as described herein has a dissociative half-life ($t_{1/2}$) of less than 1 min at an acidic pH (e.g., pH of about 5.5 to about 6.0) at 37° C. In one embodiment, an antigen-binding protein comprising a heavy chain variable domain expressed by the genetically modified immunoglobulin locus as described herein has at least about 2-fold, at least about 3-fold, at least about 4-fold, at least about 5-fold, at least about 10-fold, at least about 15-fold, at least about 20-fold, at least about 25-fold, or at least about 30-fold decrease in dissociative half-life ($t_{1/2}$) at an acidic pH (e.g., pH of about 5.5 to about 6.0) as compared to the dissociative half-life ($t_{1/2}$) of the antigen-binding protein at a neutral pH (e.g., pH of about 7.0 to about 7.4).

In one embodiment, an antigen-binding protein comprising a heavy chain variable domain expressed by the genetically modified immunoglobulin locus as described herein is characterized by improved pH-dependent recyclability, enhanced serum half-life, or both as compared with a wild-type antigen-binding protein without the genetic modification.

In one embodiment, the genetically modified immunoglobulin locus described herein comprises a B cell population that, upon stimulation with an antigen of interest, is capable of producing antigen-binding proteins, e.g., antibodies, comprising a heavy chain variable domain comprising one or more histidine residues. The antigen-binding proteins as described herein when administered into a subject, exhibits an increased serum half-life over a corresponding wild-type antigen-binding protein, which possesses a similar or sufficiently similar amino acid sequence that encodes the heavy chain variable domain but does not comprise a histidine residue in the heavy chain variable domain. In some embodiments, the antigen-binding protein described herein exhibits an increased serum half-life that is at least about 2-fold, at least about 5-fold, at least about 10-fold, at least about 15-fold, at least about 20-fold higher than the corresponding wild-type antigen-binding protein, which possesses a similar or sufficiently similar amino acid sequence that encodes the heavy chain variable domain but does not comprise a histidine residue in the heavy chain variable domain.

In one aspect, a non-human animal that is capable of expressing an antigen-binding protein with enhanced pH-dependent recyclability and/or enhanced serum half-life are provided, wherein the non-human animal comprises in its germline genome an unrearranged human immunoglobulin heavy chain variable region nucleotide sequence, wherein the unrearranged heavy chain variable region nucleotide sequence comprises an addition of least one histidine codon or a substitution of at least one endogenous non-histidine codon with a histidine codon as described herein.

In one embodiment, the antigen-binding protein comprising a heavy chain variable domain expressed by the genetically modified immunoglobulin heavy chain locus as described herein exhibits a weaker antigen binding at an acidic environment (e.g., at a pH of about 5.5 to about 6.0) than a corresponding wild-type heavy chain variable domain without the genetic modification.

In one embodiment, an antigen-binding protein comprising a heavy chain variable domain expressed by the genetically modified immunoglobulin heavy chain locus as described herein has a dissociative half-life ($t_{1/2}$) of less than 2 min at an acidic pH (e.g., pH of about 5.5 to about 6.0) at 25° C. In one embodiment, an antigen-binding protein comprising a heavy chain variable domain expressed by the genetically modified immunoglobulin heavy chain locus as described herein has a dissociative half-life ($t_{1/2}$) of less than 2 min at an acidic pH (e.g., pH of about 5.5 to about 6.0) at 37° C. In one embodiment, an antigen-binding protein comprising a heavy chain variable domain expressed by the genetically modified immunoglobulin heavy chain locus as described herein has a dissociative half-life ($t_{1/2}$) of less than 1 min at an acidic pH (e.g., pH of about 5.5 to about 6.0) at 25° C. In one embodiment, an antigen-binding protein comprising a heavy chain variable domain expressed by the genetically modified immunoglobulin heavy chain locus as described herein has a dissociative half-life ($t_{1/2}$) of less than 1 min at an acidic pH (e.g., pH of about 5.5 to about 6.0) at 37° C. In one embodiment, an antigen-binding protein comprising a heavy chain variable domain expressed by the genetically modified immunoglobulin locus as described herein has at least about 2-fold, at least about 3-fold, at least about 4-fold, at least about 5-fold, at least about 10-fold, at least about 15-fold, at least about 20-fold, at least about 25-fold, or at least about 30-fold decrease in dissociative half-life ($t_{1/2}$) at an acidic pH (e.g., pH of about 5.5 to about 6.0) as compared to the dissociative half-life ($t_{1/2}$) of the antigen-binding protein at a neutral pH (e.g., pH of about 7.0 to about 7.4).

In one embodiment, the antigen-binding protein comprising a heavy chain variable domain expressed by the genetically modified immunoglobulin locus as described herein is characterized by improved pH-dependent recyclability, enhanced serum half-life, or both as compared with a wild-type antigen-binding protein without the genetic modification.

In one embodiment, the genetically modified immunoglobulin locus described herein comprises a B cell population that, upon stimulation with an antigen of interest, is capable of producing antigen-binding proteins, e.g., antibodies, comprising a heavy chain variable domain comprising one or more histidine residues. The antigen-binding proteins as described herein when administered into a subject, exhibits an increased serum half-life over a corresponding wild-type antigen-binding protein, which possesses a similar or sufficiently similar amino acid sequence that encodes the heavy chain variable domain but does not comprise a histidine residue in the heavy chain variable domain. In some embodiments, the antigen-binding protein described herein exhibits an increased serum half-life that is at least about 2-fold, at least about 5-fold, at least about 10-fold, at least about 15-fold, at least about 20-fold higher than the corresponding wild-type antigen-binding protein, which possesses a similar or sufficiently similar amino acid sequence that encodes the heavy chain variable domain but does not comprise a histidine residue in the heavy chain variable domain.

In one aspect, a targeting construct is provided, comprising 5' and 3' targeting arms homologous to a genomic D region or genomic V and J region of a non-human animal, wherein at least one $V_H$, D, or $J_H$ gene segment comprises any of the modifications as described herein, e.g., an addition of at least one histidine codon, a substitution of at least one endogenous non-histidine codon into a histidine codon, and/or inversion of at least one functional D gene segment with respect to a corresponding wild type sequence.

In one aspect, a hybridoma or quadroma is provided that is derived from a cell of any of the non-human animal as described herein. In one embodiment, the non-human animal is a rodent, e.g., a mouse, a rat, or a hamster.

In one aspect, pluripotent, induced pluripotent, or totipotent stem cells derived form a non-human animal comprising the various genomic modifications of the described invention are provided. In a specific embodiment, the pluripotent, induced pluripotent, or totipotent stem cells are mouse or rat embryonic stem (ES) cells. In one embodiment, the pluripotent, induced pluripotent, or totipotent stem cells have an XX karyotype or an XY karyotype. In one embodiment, the pluripotent or induced pluripotent stem cells are hematopoietic stem cells.

In one aspect, cells that comprise a nucleus containing a genetic modification as described herein are also provided, e.g., a modification introduced into a cell by pronuclear injection. In one embodiment, the pluripotent, induced pluripotent, or totipotent stem cells comprise a genetically modified immunoglobulin genomic locus, wherein the genomic locus comprises, from 5' to 3', (1) an FRT recombination site, (2) human $V_H$ gene segments, (3) a mouse adam6 gene, (4) a loxP recombination site, (5) histidine-substituted human D gene segments, (6) human $J_H$ gene segments, followed by (7) a mouse $E_i$ (intronic enhancer), and (8) a mouse IgM constant region nucleotide sequence.

In one aspect, a lymphocyte isolated from a genetically modified non-human animal as described herein is provided. In one embodiment, the lymphocyte is a B cell, wherein the B cell comprises an immunoglobulin genomic locus comprising an unrearranged heavy chain variable region nucleotide sequence wherein the unrearranged heavy chain variable gene sequence comprises an addition of least one histidine codon or a substitution of at least one endogenous non-histidine codon with a histidine codon.

In one aspect, a lymphocyte isolated from a genetically modified non-human animal as described herein is provided. In one embodiment, the lymphocyte is a B cell, wherein the B cell comprises an immunoglobulin locus that comprises a human V, D, and J gene segment, wherein at least one of the human D gene segment has been inverted 5' to 3' with respect to wild-type sequences, and wherein at least one reading frame of the inverted human D gene segment encodes at least one histidine residue. In one embodiment, the B cell is capable of producing an antigen-binding protein comprising the genetically modified heavy chain variable domain as described herein. In one embodiment, the genetically modified heavy chain variable domain as described herein is operably linked to a heavy chain constant region amino acid sequence.

In one aspect, a B cell population is provided that are capable of expressing an antigen-binding protein comprising at least one histidine residue in a heavy chain variable domain, wherein the B cell population comprises any genetic modifications as described herein. In one embodiment, the at least one histidine residue is present in a heavy chain CDR. In one embodiment, the CDR is a selected from a CDR1, CDR2, CDR3, and a combination thereof. In one embodiment, the at least one histidine residue is present in CDR3.

In one aspect, a B cell population is provided that are capable of expressing an antigen-binding protein with enhanced serum half-life and/or enhanced pH-dependent recyclability, wherein the B cell population comprises any genetic modifications as described herein.

In one aspect, a method for making a non-human animal comprising a genetically modified immunoglobulin heavy chain variable locus is provided, comprising:

(a) modifying a genome of a non-human animal to delete or render non-functional endogenous immunoglobulin heavy chain V, D, and J gene segments (e.g., via insertion of a nucleotide sequence, e.g., an exogenous nucleotide sequence, in the immunoglobulin locus or via non-functional rearrangement or inversion of endogenous $V_H$, D, $J_H$ segments); and (b) placing in the genome an unrearranged heavy chain variable region nucleotide sequence, wherein the unrearranged heavy chain variable region nucleotide sequence comprises an addition of least one histidine codon or a substitution of at least one endogenous non-histidine codon with a histidine codon as described herein.

In one embodiment, the non-human animal is a mammal, including a rodent, e.g., a mouse, a rat, or a hamster.

In one embodiment, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, 20 or more, 21 or more, 22 or more, 23 or more, 24 or more, 25 or more, 26 or more, 27 or more, 28 or more, 29 or more, 30 or more, 31 or more, 32 or more, 33 or more, 34 or more, 35 or more, 36 or more, 37 or more, 38 or more, 39 or more, 40 or more, 41 or more, 42 or more, 43 or more, 44 or more, 45 or more, 46 or more, 47 or more, 48 or more, 49 or more, 50 or more, 51 or more, 52 or more, 53 or more, 54 or more, 55 or more, 56 or more, 57 or more, 58 or more, 59 or more, 60 or more, or 61 or more of the endogenous non-histidine codons are replaced with histidine codons.

In one embodiment, the endogenous non-histone codon encodes the amino acid selected from Y, N, D, Q, S, W, and R.

In one embodiment, the added or substituted histidine codon is present in an unrearranged heavy chain variable region nucleotide sequence that encodes an immunoglobulin variable domain selected from an N-terminal region, a loop 4 region, a CDR1, a CDR2, a CDR3, a combination thereof.

In one embodiment, the added substituted histidine codon histidine codon is present in an unrearranged heavy chain variable region nucleotide sequence that encodes a complementary determining region (CDR) selected from a CDR1, a CDR2, a CDR3, and a combination thereof.

In one embodiment, the added or substituted histidine codon is present in an unrearranged heavy chain variable region nucleotide sequence that encodes a frame region (FR) selected from FR1, FR2, FR3, FR4, and a combination thereof.

In one embodiment, the unrearranged heavy chain variable region nucleotide sequence comprises a genetically modified human $V_H$ gene segment, wherein one or more endogenous non-histidine codon in at least one reading frame of the human $V_H$ gene segment has been replaced with a histidine codon.

In one embodiment, the human unrearranged heavy chain variable region nucleotide sequence comprises a modification that replaces at least one endogenous non-histidine codon of a human $V_H$ gene segment with a histidine codon, wherein the human $V_H$ gene segment is selected from the group consisting of $V_H1$-2, $V_H1$-3, $V_H1$-8, $V_H1$-18, $V_H1$-24, $V_H1$-45, $V_H1$-46, $V_H1$-58, $V_H1$-69, $V_H2$-5, $V_H2$-26, $V_H2$-70, $V_H3$-7, $V_H3$-9, $V_H3$-11, $V_H3$-13, $V_H3$-15, $V_H3$-16, $V_H3$-20, $V_H3$-21, $V_H3$-23, $V_H3$-30, $V_H3$-30-3, $V_H3$-30-5, $V_H3$-33, $V_H3$-35, $V_H3$-38, $V_H3$-43, $V_H3$-48, $V_H3$-49, $V_H3$-53, $V_H3$-64, $V_H3$-66, $V_H3$-72, $V_H3$-73, $V_H3$-74, $V_H4$-4, $V_H4$-28, $V_H4$-30-1, $V_H4$-30-2, $V_H4$-30-4, $V_H4$-31, $V_H4$-34, $V_H4$-39, $V_H4$-59, $V_H4$-61, $V_H5$-51, $V_H6$-1, $V_H7$-4-1, $V_H7$-81, and a combination thereof.

In one embodiment, the human unrearranged heavy chain variable region nucleotide sequence comprises a genetically modified human $J_H$ gene segment, wherein one or more endogenous non-histidine codon in at least one reading frame of the human $J_H$ gene segment has been replaced with a histidine codon.

In one embodiment, the human unrearranged heavy chain variable region nucleotide sequence comprises a modification that replaces at least one endogenous non-histidine codon of a human $J_H$ segment with a histidine codon, wherein the human $J_H$ gene segment is selected from the group consisting of $J_H1$, $J_H2$, $J_H3$, $J_H4$, $J_H5$, $J_H6$, and a combination thereof.

In one embodiment, the added or substituted histidine codon is present in a heavy chain variable region nucleotide sequence that encodes part of a CDR3. In one embodiment, the part of CDR3 comprises an amino acid sequence derived from a reading frame of a genetically modified human D gene segment comprising a modification that replaces at least one endogenous non-histidine codon in the reading frame with a histidine codon.

In one embodiment, the endogenous non-histidine codon that is substituted with a histidine codon encodes the amino acid selected from Y, N, D, Q, S, W, and R.

In one embodiment, the added or substituted histidine codon is present in at least one reading frame of the human D gene segment that is most frequently observed in VELOCIMMUNE® humanized immunoglobulin mice.

In one embodiment, the reading frame of the genetically modified human D gene segment that encodes part of CDR3 is selected from a hydrophobic frame, a stop frame, and a hydrophilic frame.

In one embodiment, the reading frame is a hydrophobic frame of a human D gene segment.

In one embodiment, the hydrophobic frame of the human D gene segment comprises a nucleotide sequence that encodes the amino acid sequence selected from the group consisting of D1-1 (GTTGT; SEQ ID NO: 88), D1-7 (GITGT; SEQ ID NO: 89), D1-20 (GITGT; SEQ ID NO: 89), and D1-26 (GIVGAT; SEQ ID NO:90), and the human D gene segment further comprises a modification that replaces at least one endogenous non-histidine codon in the nucleotide sequence with a histidine codon.

In one embodiment, the hydrophobic frame of the human D gene segment comprises a nucleotide sequence that encodes the amino acid sequence selected from the group consisting of D2-2 (DIVVVPAAI; SEQ ID NO:92), D2-8 (DIVLMVYAI; SEQ ID NO: 94), D2-15 (DIVVVAAT; SEQ ID NO:95), and D2-21 (HIVVVTAI; SEQ ID NO: 97), and the human D gene segment further comprises a modification that replaces at least one endogenous non-histidine codon in the nucleotide sequence with a histidine codon.

In one embodiment, the hydrophobic frame of the human D gene segment comprises a nucleotide sequence that encodes the amino acid sequence selected from the group consisting of D3-3 (ITIFGVVII; SEQ ID NO:98), D3-9 (ITIF*LVII; SEQ ID NO:99, SEQ ID NO:100), D3-10 (ITMVRGVII; SEQ ID NO:101), D3-16 (IMITFGGVIVI; SEQ ID NO:102), and D3-22 (ITMIVVVIT; SEQ ID NO:103), and the human D gene segment further comprises a modification that replaces at least one endogenous codon in the nucleotide sequence with a histidine codon.

In one embodiment, the hydrophobic frame of the human D gene segment comprises a nucleotide sequence that encodes the amino acid sequence selected from the group consisting of D4-4 (TTVT; SEQ ID NO:105), D4-11 (TTVT; SEQ ID NO:105), D4-17 (TTVT; SEQ ID NO:105), D4-23 (TTVVT; SEQ ID NO: 106) and the human D gene segment further comprises a modification that replaces at least one endogenous non-histidine codon in the nucleotide sequence with a histidine codon.

In one embodiment, the hydrophobic frame of the human D gene segment comprises a nucleotide sequence that encodes the amino acid sequence selected from the group consisting of D5-5 (VDTAMV; SEQ ID NO: 107), D5-12 (VDIVATI; SEQ ID NO:108), D5-18 (VDTAMV; SEQ ID NO:107), and D5-24 (VEMATI; SEQ ID NO:109), and the human D gene segment further comprises a modification that replaces at least one endogenous non-histidine codon in the nucleotide sequence with a histidine codon.

In one embodiment, the hydrophobic frame of the human D gene segment comprises a nucleotide sequence that encodes the amino acid sequence selected from the group consisting of D6-6 (SIAAR; SEQ ID NO:111), D6-13 (GIAAAG; SEQ ID NO:113), and D6-19 (GIAVAG; SEQ ID NO:115), and the human D gene segment further comprises a modification that replaces at least one endogenous non-histidine codon in the nucleotide sequence with a histidine codon.

In one embodiment, the hydrophobic frame comprises a nucleotide sequence that encodes human D7-27 (LTG), and the human D gene segment further comprises a modification that replaces at least one endogenous non-histidine codon in the nucleotide sequence with a histidine codon.

In one embodiment, the reading frame is a stop reading frame of a human D gene segment.

In one embodiment, the stop reading frame of the human D gene segment comprises a nucleotide sequence that encodes the amino acid sequence selected from the group consisting of D1-1 (VQLER; SEQ ID NO:8), D1-7 (V*LEL), D1-20 (V*LER), D1-26 (V*WELL; SEQ ID NO:12), and the human D gene segment further comprises a modification that replaces at least one endogenous non-histidine codon in the nucleotide sequence with a histidine codon.

In one embodiment, the stop reading frame of the human D gene segment comprises a nucleotide sequence that encodes the amino acid sequence selected from the group consisting of D2-2 (RIL**YQLLY; SEQ ID NO:14), D2-8 (RILY*WCMLY; SEQ ID NO:16 and SEQ ID NO: 17), D2-15 (RIL*WW*LLL), and D2-21 (SILWW*LLF; SEQ ID NO:19), and the human D gene segment further comprises a modification that replaces at least one endogenous non-histidine codon in the nucleotide sequence with a histidine codon.

In one embodiment, the stop reading frame of the human D gene segment comprises a nucleotide sequence that encodes the amino acid sequence selected from the group consisting of D3-3 (VLRFLEWLLY; SEQ ID NO:21), D3-9 (VLRYFDWLL*; SEQ ID NO:23), D3-10 (VLLWFGELL*; SEQ ID NO:25), D3-16 (VL*LRLGELSLY; SEQ ID NO:27), and D3-22 (VLL***WLLL; SEQ ID NO:29), and the human D gene segment comprises a modification that replaces at least one endogenous non-histidine codon in the nucleotide sequence with a histidine codon.

In one embodiment, the stop reading frame of the human D gene segment comprises a nucleotide sequence that encodes the amino acid sequence selected from the group consisting of D4-4 (*LQ*L), D4-11 (*LQ*L), D4-17 (*LR*L), and D4-23 (*LRW*L), and the human D gene segment comprises a modification that replaces at least one endogenous non-histidine codon in the nucleotide sequence with a histidine codon.

In one embodiment, the stop reading frame of the human D gene segment comprises a nucleotide sequence that encodes the amino acid sequence selected from the group consisting of D5-5 (WIQLWL; SEQ ID NO:35); D5-12 (WI*WLRL; SEQ ID NO:37), D5-18 (WIQLWL; SEQ ID NO:35), and D5-24 (*RWLQL; SEQ ID NO:39), and the human D gene segment comprises a modification that replaces at least one endogenous non-histidine codon in the nucleotide sequence with a histidine codon.

In one embodiment, the stop reading frame of the human D gene segment comprises a nucleotide sequence that encodes the amino acid sequence selected from the group consisting of D6-6 (V*QLV), D6-13 (V*QQLV; SEQ ID NO:41), and D6-19 (V*QWLV; SEQ ID NO:43), and the human D gene segment further comprises a modification that replaces at least one endogenous non-histidine codon in the nucleotide sequence with a histidine codon.

In one embodiment, the stop reading frame of the human D gene segment comprises a nucleotide sequence that encodes D7-27 (*LG), and the human D gene segment further comprises a modification that replaces at least one endogenous codon of the human D gene segment in the nucleotide sequence with a histidine codon.

In one embodiment, the reading frame is a hydrophilic frame of a human D gene segment.

In one embodiment, the hydrophilic frame of the human D gene segment comprises a nucleotide sequence that encodes the amino acid sequence selected from the group consisting of D1-1 (YNWND; SEQ ID NO: 45), D1-7 (YNWNY; SEQ ID NO: 47), D1-20 (YNWND; SEQ ID NO: 45), and D1-26 (YSGSYY; SEQ ID NO:49), and the human D gene segment further comprises a modification that replaces at least one endogenous codon in the nucleotide sequence with a histidine codon. In one embodiment, the hydrophilic frame comprises a nucleotide sequence that encodes the amino acid sequence selected from the group consisting of SEQ ID NO: 46, SEQ ID NO: 48, SEQ ID NO: 50, and a combination thereof.

In one embodiment, the hydrophilic frame of the human D gene segment comprises a nucleotide sequence that encodes the amino acid sequence selected from the group consisting of D2-2 (GYCSSTSCYT; SEQ ID NO:51), D2-8 (GYCTNGVCYT; SEQ ID NO: 53), D2-15 (GYCSGGSCYS; SEQ ID NO:55), and D2-21 (AYCGGDCYS; SEQ ID NO:57), and the human D gene segment further comprises a modification that replaces at least one endogenous codon in the nucleotide sequence with a histidine codon. In one embodiment, the hydrophilic frame comprises a nucleotide sequence that encodes the amino acid sequence selected from the group consisting of SEQ ID NO: 52, SEQ ID NO: 54, SEQ ID NO: 56, SEQ ID NO: 58, and a combination thereof.

In one embodiment, the hydrophilic frame of the human D gene segment comprises a nucleotide sequence that encodes the amino acid sequence selected from the group consisting of D3-3 (YYDFWSGYYT; SEQ ID NO:59), D3-9 (YYDILTGYYN; SEQ ID NO:61), D3-10 (YYYGSGSYYN; SEQ ID NO:63), D3-16 (YYDYVWGSYRYT; SEQ ID NO:65), and D3-22 (YYYDSSGYYY; SEQ ID NO:67), and the human D gene segment further comprises a modification that replaces at least one endogenous codon in the nucleotide sequence with a histidine codon. In one embodiment, the hydrophilic frame comprises a nucleotide sequence encodes the amino acid sequence selected from the group consisting of SEQ ID NO: 60, SEQ ID NO: 62, SEQ ID NO: 64, SEQ ID NO: 66, SEQ ID NO: 68, and a combination thereof.

In one embodiment, the hydrophilic frame of the human D gene segment comprises a nucleotide sequence that encodes the amino acid sequence selected from the group consisting of D4-4 (DYSNY; SEQ ID NO:69), D4-11 (DYSNY; SEQ ID NO:69), D4-17 (DYGDY; SEQ ID NO:71), and D4-23 (DYGGNS; SEQ ID NO:73), and the human D gene segment comprises a modification that replaces at least one endogenous codon in the nucleotide sequence with a histidine codon. In one embodiment, the hydrophilic frame comprises a nucleotide sequence that encodes the amino acid sequence selected from the group consisting of SEQ ID NO: 70, SEQ ID NO: 72, SEQ ID NO: 74, and a combination thereof.

In one embodiment, the hydrophilic frame of the human D gene segment comprises a nucleotide sequence that encodes the amino acid sequence selected from the group consisting of D5-5 (GYSYGY; SEQ ID NO:75), D5-12 (GYSGYDY; SEQ ID NO:77), D5-18 (GYSYGY; SEQ ID NO:75), and D5-24 (RDGYNY; SEQ ID NO:79), and the human D gene segment further comprises a modification that replaces at least one endogenous codon in the nucleotide sequence with a histidine codon. In one embodiment, the hydrophilic frame comprises a nucleotide sequence that encodes the amino acid sequence selected from the group consisting of SEQ ID NO: 76, SEQ ID NO: 78, SEQ ID NO: 80, and a combination thereof.

In one embodiment, the hydrophilic frame of the human D gene segment comprises a nucleotide sequence that encodes the amino acid sequence selected from the group consisting of D6-6 (EYSSSS; SEQ ID NO: 81), D6-13 (GYSSSWY; SEQ ID NO:83), and D6-19 (GYSSGWY; SEQ ID NO:85), and the human D gene segment further comprises a modification that replaces at least one endogenous codon in the nucleotide sequence with a histidine codon. In one embodiment, the hydrophilic frame comprises a nucleotide sequence that encodes the amino acid sequence selected from the group consisting of SEQ ID NO: 82, SEQ ID NO: 84, SEQ ID NO: 86, SEQ ID NO: 76, and a combination thereof.

In one embodiment, the hydrophilic frame of the human D gene segment comprises a nucleotide sequence that encodes D7-27 (NWG), and the human D gene segment further comprises a modification that replaces at least one endogenous codon in the nucleotide sequence a histidine codon.

In one embodiment, the hydrophilic frame of the human D gene segment comprises a nucleotide sequence that encodes the amino acid sequence selected from the group consisting of SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, and a combination thereof.

In one embodiment, the unrearranged heavy chain variable region nucleotide sequence comprising the inverted human D gene segment is operably linked to a human or non-human heavy chain constant region nucleotide sequence that encodes an immunoglobulin isotype selected from IgM, IgD, IgG, IgE, and IgA.

In one embodiment, the human unrearranged immunoglobulin heavy chain variable region nucleotide sequence is operably linked to a human or non-human heavy chain constant region nucleotide sequence selected from a $C_H1$, a hinge, a $C_H2$, a $C_H3$, and a combination thereof. In one embodiment, the heavy chain constant region nucleotide sequence comprises a $C_H1$, a hinge, a $C_H2$, and a $C_H3$ (i.e., $C_H1$-hinge-$C_H2$-$C_H3$).

In one embodiment, a heavy chain constant region nucleotide sequence is present at an endogenous locus (i.e., where the nucleotide sequence is located in a wild-type non-human animal) or present ectopically (e.g., at a locus different from the endogenous immunoglobulin chain locus in its genome, or within its endogenous locus, e.g., within an immunoglobulin variable locus, wherein the endogenous locus is placed or moved to a different location in the genome).

In one embodiment, the heavy chain constant region nucleotide sequence comprises a modification in a $C_H2$ or a $C_H3$, wherein the modification increases the affinity of the heavy chain constant region amino acid sequence to FcRn in an acidic environment (e.g., in an endosome where pH ranges from about 5.5 to about 6.0).

In one embodiment, the heavy chain constant region nucleotide sequence encodes a human heavy chain constant region amino acid sequence comprising a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., L/R/S/P/Q or K) and/or 434 (e.g., H/F or Y); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 259I (e.g., V259I), and 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P), wherein the modification increases the affinity of the heavy chain constant region amino acid sequence to FcRn in an acidic environment (e.g., in an endosome where pH ranges from about 5.5 to about 6.0).

In one embodiment, the heavy chain constant region nucleotide sequence encodes a human $C_H2$ amino acid sequence comprising at least one modification between amino acid residues at positions 252 and 257, wherein the modification increases the affinity of the human $C_H2$ amino acid sequence to FcRn in an acidic environment (e.g., in an endosome where pH ranges from about 5.5 to about 6.0).

In one embodiment, the heavy chain constant region nucleotide sequence encodes a human $C_H2$ amino acid sequence comprising at least one modification between amino acid residues at positions 307 and 311, wherein the modification increases the affinity of the $C_H2$ amino acid sequence to FcRn in an acidic environment (e.g., in an endosome where pH ranges from about 5.5 to about 6.0).

In one embodiment, the heavy chain constant region nucleotide sequence encodes a human $C_H3$ amino acid sequence, wherein the $C_H3$ amino acid sequence comprises at least one modification between amino acid residues at positions 433 and 436, wherein the modification increases the affinity of the $C_H3$ amino acid sequence to FcRn in an acidic environment (e.g., in an endosome where pH ranges from about 5.5 to about 6.0).

In one embodiment, the heavy chain constant region nucleotide sequence encodes a human heavy chain constant region amino acid sequence comprising a mutation selected from the group consisting of M428L, N434S, and a combination thereof.

In one embodiment, the heavy chain constant region nucleotide sequence encodes a human heavy chain constant region amino acid sequence comprising a mutation selected from the group consisting of M428L, V259I, V308F, and a combination thereof.

In one embodiment, the heavy chain constant region nucleotide sequence encodes a human heavy chain constant region amino acid sequence comprising an N434A mutation.

In one embodiment, the heavy chain constant region nucleotide sequence encodes a human heavy chain constant region amino acid sequence comprising a mutation selected from the group consisting of M252Y, S254T, T256E, and a combination thereof.

In one embodiment, the heavy chain constant region nucleotide sequence encodes a human heavy chain constant region amino acid sequence comprising a mutation selected from the group consisting of T250Q, M248L, or both.

In one embodiment, the heavy chain constant region nucleotide sequence encodes a human heavy chain constant region amino acid sequence comprising a mutation selected from the group consisting of H433K, N434Y, or both.

In one embodiment, the genetically modified immunoglobulin locus comprises: (1) a first allele, wherein the unrearranged human immunoglobulin heavy chain variable region nucleotide sequence as described herein is operably linked to a first heavy chain constant region nucleotide sequence encoding a first $CH_3$ amino acid sequence of a human IgG selected from IgG1, IgG2, IgG4, and a combination thereof; and (2) a second allele, wherein the unrearranged human immunoglobulin heavy chain variable region nucleotide sequence as described herein is operably linked to a second heavy chain constant region nucleotide sequence encoding a second $C_H3$ amino acid sequence of the human IgG selected from IgG1, IgG2, IgG4, and a combination thereof, and wherein the second $CH_3$ amino acid sequence comprises a modification that reduces or eliminates binding for the second $CH_3$ amino acid sequence to Protein A (see, for example, US 2010/0331527A1, which is incorporated by reference herein in its entirety).

In one embodiment, the second $CH_3$ amino acid sequence comprises an H95R modification (by IMGT exon numbering; H435R by EU numbering). In one embodiment the second $CH_3$ amino acid sequence further comprises an Y96F modification (by IMGT exon numbering; H436F by EU). In another embodiment, the second $CH_3$ amino acid sequence comprises both an H95R modification (by IMGT exon numbering; H435R by EU numbering) and an Y96F modification (by IMGT exon numbering; H436F by EU).

In one embodiment, the second $CH_3$ amino acid sequence is from a modified human IgG1 and further comprises a mutation selected from the group consisting of D16E, L18M, N44S, K52N, V57M, and V82I (IMGT; D356E, L38M, N384S, K392N, V397M, and V422I by EU).

In one embodiment, the second $CH_3$ amino acid sequence is from a modified human IgG2 and further comprises a mutation selected from the group consisting of N44S, K52N, and V82I (IMGT: N384S, K392N, and V422I by EU).

In one embodiment, the second CH₃ amino acid sequence is from a modified human IgG4 and further comprises a mutation selected from the group consisting of Q15R, N44S, K52N, V57M, R69K, E79Q, and V82I (IMGT: Q355R, N384S, K392N, V397M, R409K, E419Q, and V422I by EU).

In one embodiment, the heavy chain constant region amino acid sequence is a non-human constant region amino acid sequence, and the heavy chain constant region amino acid sequence comprises one or more of any of the types of modifications described above.

In one embodiment, the heavy chain constant region nucleotide sequence is a human heavy chain constant region amino acid sequence, and the human heavy chain constant region amino acid sequence comprises one or more of any of the types of modifications described above.

In one embodiment, all or substantially all endogenous $V_H$, D, and $J_H$ gene segments are deleted from an immunoglobulin heavy chain locus or rendered non-functional (e.g., via insertion of a nucleotide sequence (e.g., an exogenous nucleotide sequence) in the immunoglobulin locus or via non-functional rearrangement, or inversion, of the endogenous $V_H$, D, $J_H$ segments). In one embodiment, e.g., about 80% or more, about 85% or more, about 90% or more, about 95% or more, about 96% or more, about 97% or more, about 98% or more, or about 99% or more of all endogenous $V_H$, D, or $J_H$ gene segments are deleted or rendered non-functional. In one embodiment, e.g., at least 95%, 96%, 97%, 98%, or 99% of endogenous functional V, D, or J gene segments are deleted or rendered non-functional.

In one embodiment, the genetically modified locus comprises a modification that deletes or renders non-functional all or substantially all endogenous $V_H$, D, and $J_H$ gene segments; and the genomic locus comprises the genetically modified, unrearranged human heavy chain variable region nucleotide sequence comprising a substitution of at least one endogenous non-histidine codon with a histidine codon in at least one reading frame. In one embodiment, the genetically modified, unrearranged immunoglobulin heavy chain variable gene sequence is present at an endogenous location (i.e., where the nucleotide sequence is located in a wild-type non-human animal) or present ectopically (e.g., at a locus different from the endogenous immunoglobulin chain locus in its genome), or within its endogenous locus, e.g., within an immunoglobulin variable locus, wherein the endogenous locus is placed or moved to a different location in the genome.

In one embodiment, the genetically modified locus comprises an endogenous Adam6a gene, Adam6b gene, or both, and the genetic modification does not affect the expression and/or function of the endogenous Adam6a gene, Adam6b gene, or both.

In one embodiment, the genetically modified locus comprises an ectopically present Adam6a gene, Adam6b gene, or both. In one embodiment, the Adam6a gene is a non-human Adam6a gene. In one embodiment, the Adam6a gene is a mouse Adam6a gene. In one embodiment, the Adam6a gene is a human Adam6a gene. In one embodiment, the Adam6b gene is a non-human Adam6b gene. In one embodiment, the Adam6b gene is a mouse Adam6b gene. In one embodiment, the Adam6b gene is a human Adam6b gene.

In one embodiment, the genetically modified immunoglobulin locus further comprises a humanized, unrearranged λ and/or κ light chain variable gene sequence. In one embodiment, the humanized, unrearranged λ and/or κ light chain variable gene sequence is operably linked to an immunoglobulin light chain constant region nucleotide sequence selected from a λ light chain constant region nucleotide sequence and a κ light chain constant region nucleotide sequence. In one embodiment, the humanized, unrearranged λ light chain variable region nucleotide sequence is operably linked to a λ light chain constant region nucleotide sequence. In one embodiment, the λ light chain constant region nucleotide sequence is a mouse, rat, or human sequence. In one embodiment, the humanized, unrearranged κ light chain variable region nucleotide sequence is operably linked to a κ light chain constant region nucleotide sequence. In one embodiment, the κ light chain constant region nucleotide sequence is a mouse, rat, or human sequence.

In one embodiment, the genetically modified immunoglobulin locus comprises an unrearranged light chain variable gene sequence that contains at least one modification that introduces at least one histidine codon in at least one reading frame encoding a light chain variable domain. In one embodiment, the genetically modified immunoglobulin locus comprises a rearranged (e.g., a rearranged λ or κ V/J sequence) sequence that comprises one, two, three, or four codons for histidine in a light chain CDR. In one embodiment, the CDR is a selected from a CDR1, CDR2, CDR3, and a combination thereof. In one embodiment, the unrearranged or rearranged light chain variable region nucleotide sequence is an unrearranged or rearranged human λ or κ light chain variable region nucleotide sequence. In one embodiment, the unrearranged or rearranged human λ or κ light chain variable region nucleotide sequence is present at an endogenous mouse immunoglobulin light chain locus. In one embodiment, the mouse immunoglobulin light chain locus is a mouse κ locus. In one embodiment the mouse immunoglobulin light chain locus is a mouse λ locus.

In one embodiment, the genetically modified immunoglobulin locus as described herein is present in an immunoglobulin heavy chain locus of a mouse. In one embodiment, the genetically modified immunoglobulin locus is present in a humanized immunoglobulin heavy chain locus in a VELOCIMMUNE® mouse.

In one embodiment, an antigen-binding protein comprising a heavy chain variable domain expressed by the genetically modified immunoglobulin heavy chain locus as described herein exhibits a weaker antigen binding at an acidic environment (e.g., at a pH of about 5.5 to about 6.0) than a corresponding wild-type heavy chain variable domain without the genetic modification.

In one embodiment, an antigen-binding protein comprising a heavy chain variable domain expressed by the genetically modified immunoglobulin heavy chain locus as described herein has a dissociative half-life ($t_{1/2}$) of less than 2 min at an acidic pH (e.g., pH of about 5.5 to about 6.0) at 25° C. In one embodiment, an antigen-binding protein comprising a heavy chain variable domain expressed by the genetically modified immunoglobulin heavy chain locus as described herein has a dissociative half-life ($t_{1/2}$) of less than 2 min at an acidic pH (e.g., pH of about 5.5 to about 6.0) at 37° C. In one embodiment, an antigen-binding protein comprising a heavy chain variable domain expressed by the genetically modified immunoglobulin heavy chain locus as described herein has a dissociative half-life ($t_{1/2}$) of less than 1 min at an acidic pH (e.g., pH of about 5.5 to about 6.0) at 25° C. In one embodiment, an antigen-binding protein comprising a heavy chain variable domain expressed by the genetically modified immunoglobulin heavy chain locus as described herein has a dissociative half-life ($t_{1/2}$) of less than 1 min at an acidic pH (e.g., pH of about 5.5 to about 6.0) at 37° C. In one embodiment, an antigen-binding protein comprising a heavy chain variable domain expressed by the genetically modified immunoglobulin locus as described herein has at least about 2-fold, at least about 3-fold, at least about 4-fold, at least about 5-fold, at least about 10-fold, at least about 15-fold, at least about 20-fold, at least about 25-fold, or at least about 30-fold decrease in dissociative half-life ($t_{1/2}$) at an acidic pH (e.g., pH of about 5.5 to about 6.0) as compared to the dissociative half-life ($t_{1/2}$) of the antigen-binding protein at a neutral pH (e.g., pH of about 7.0 to about 7.4).

In one embodiment, an antigen-binding protein comprising a heavy chain variable domain expressed by the genetically modified immunoglobulin locus as described herein is characterized by improved pH-dependent recyclability, enhanced serum half-life, or both as compared with a wild-type antigen-binding protein without the genetic modification.

In one embodiment, the genetically modified immunoglobulin locus described herein comprises a B cell population that, upon stimulation with an antigen of interest, is capable of producing antigen-binding proteins, e.g., antibodies, comprising a heavy chain variable domain comprising one or more histidine residues. The antigen-binding proteins as described herein when administered into a subject, exhibits an increased serum half-life over a corresponding wild-type antigen-binding protein, which possesses a similar or sufficiently similar amino acid sequence that encodes the heavy chain variable domain but does not comprise a histidine residue in the heavy chain variable domain. In some embodiments, the antigen-binding protein described herein exhibits an increased serum half-life that is at least about 2-fold, at least about 5-fold, at least about 10-fold, at least about 15-fold, at least about 20-fold higher than the corresponding wild-type antigen-binding protein, which possesses a similar or sufficiently similar amino acid sequence that encodes the heavy chain variable domain but does not comprise a histidine residue in the heavy chain variable domain.

In one aspect, a method for making a non-human animal comprising a genetically modified immunoglobulin heavy chain variable locus is provided, comprising:

(a) modifying a genome of a non-human animal to delete or render non-functional endogenous immunoglobulin heavy chain V, D, and J gene segments (e.g., via insertion of a nucleotide sequence (e.g., an exogenous nucleotide sequence) in the immunoglobulin locus or via non-functional rearrangement or inversion of endogenous $V_H$, D, $J_H$ segments); and (b) placing in the genome a human $V_H$, D, and $J_H$ gene segment, wherein at least one of the human D gene segment has been inverted 5' to 3' with respect to a corresponding wild-type sequence, and wherein at least one reading frame of the inverted human D gene segment comprises a histidine codon.

In one embodiment, the non-human animal is a mammal, including a rodent, e.g., a mouse, a rat, or a hamster In one embodiment, the genetically modified immunoglobulin locus is present in a germline genome.

In one embodiment, the genetically modified immunoglobulin locus encodes an immunoglobulin heavy chain variable domain comprising one or more, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, 20 or more, 21 or more, 22 or more, 23 or more, 24 or more, 25 or more, 26 or more, 27 or more, 28 or more, 29 or more, 30 or more, 31 or more, 32 or more, 33 or more, or 34 or more of histidine residues.

In one embodiment, at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, at least twenty, at least twenty one, at least twenty two, at least twenty three, at least twenty four, or all or substantially all of functional human D gene segments have inverted orientation with respect to corresponding wild type sequences.

In one embodiment, all or substantially all of endogenous immunoglobulin $V_H$, D, $J_H$ gene segments are deleted from the immunoglobulin heavy chain locus or rendered non-functional (e.g., via insertion of a nucleotide sequence, e.g., exogenous nucleotide sequence, in the immunoglobulin locus or via non-functional rearrangement or inversion of all, or substantially all, endogenous immunoglobulin $V_H$, D, $J_H$ segments), and the genetically modified immunoglobulin locus comprises a human $V_H$, D, and $J_H$ gene segments, wherein at least one of the human D gene segment is present in an inverted orientation with respect to a corresponding wild type sequence, and wherein at least one reading frame in the inverted human D gene segment comprises at least one histidine codon.

In one embodiment, the inverted human D gene segment is operably linked to a human $V_H$ gene segment, and/or human $J_H$ gene segment In one embodiment, the human D gene segment that is present in the inverted orientation relative to wild type sequences is selected from the group consisting of D1-1, D1-7, D1-20, D1-26, D2-2, D2-8, D2-15, D2-21, D3-3, D3-9, D3-10, D3-16, D3-22, D4-4, D4-11, D4-17, D4-23, D5-5, D5-12, D5-18, D5-24, D6-6, D6-13, D6-19, D7-27, and a combination thereof.

In one embodiment, the human D gene segment that is present in the inverted orientation relative to a corresponding wild type sequence is a D1 gene segment selected from the group consisting of D1-1, D1-7, D1-20, D1-26, and a combination thereof.

In one embodiment, the human D gene segment that is present in the inverted orientation relative to a corresponding wild type sequence is a D2 gene segment selected from the group consisting of D2-2, D2-8, D2-15, D2-21, and a combination thereof.

In one embodiment, the human D gene segment that is present in the inverted orientation relative to a corresponding wild type sequence is a D3 gene segment selected from the group consisting of D3-3, D3-9, D3-10, D3-16, D3-22, and a combination thereof.

In one embodiment, the human D gene segment that is present in the inverted orientation relative to a corresponding wild type sequence is a D4 gene segment selected from the group consisting of D4-4, D4-11, D4-17, D4-23, and a combination thereof.

In one embodiment, the human D gene segment that is present in the inverted orientation relative to a corresponding wild type sequence is a D5 gene segment selected from the group consisting of D5-5, D5-12, D5-18, D5-24, and a combination thereof.

In one embodiment, the human D gene segment that is present in the inverted orientation relative to a corresponding wild type sequence is a D6 gene segment selected from the group consisting of D6-6, D6-13, D6-19, and a combination thereof.

In one embodiment, the human D gene segment that is present in the inverted orientation relative to a corresponding wild type sequence is D7-27.

In one embodiment, the reading frame of the human D gene segment is selected from a stop reading frame, a hydrophilic reading frame, a hydrophobic reading frame, and a combination thereof.

In one embodiment, the unrearranged heavy chain variable region nucleotide sequence comprising the inverted human D gene segment is operably linked to a human or non-human heavy chain constant region nucleotide sequence that encodes an immunoglobulin isotype selected from IgM, IgD, IgG, IgE, and IgA.

In one embodiment, the human unrearranged immunoglobulin heavy chain variable region nucleotide sequence is operably linked to a human or non-human heavy chain constant region nucleotide sequence selected from a $C_H1$, a hinge, a $C_H2$, a $C_H3$, and a combination thereof. In one embodiment, the heavy chain constant region nucleotide sequence comprises a $C_H1$, a hinge, a $C_H2$, and a $C_H3$ (i.e., $C_H1$-hinge-$C_H2$-$C_H3$).

In one embodiment, a heavy chain constant region nucleotide sequence is present at an endogenous locus (i.e., where the nucleotide sequence is located in a wild-type non-human animal) or present ectopically (e.g., at a locus different from the endogenous immunoglobulin chain locus in its genome, or within its endogenous locus, e.g., within an immunoglobulin variable locus, wherein the endogenous locus is placed or moved to a different location in the genome).

In one embodiment, the heavy chain constant region nucleotide sequence comprises a modification in a $C_H2$ or a $C_H3$, wherein the modification increases the affinity of the heavy chain constant region amino acid sequence to FcRn in an acidic environment (e.g., in an endosome where pH ranges from about 5.5 to about 6.0).

In one embodiment, the heavy chain constant region nucleotide sequence encodes a human heavy chain constant region amino acid sequence comprising a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., L/R/S/P/Q or K) and/or 434 (e.g., H/F or Y); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 259I (e.g., V259I), and 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P), wherein the modification increases the affinity of the heavy chain constant region amino acid sequence to FcRn in an acidic environment (e.g., in an endosome where pH ranges from about 5.5 to about 6.0).

In one embodiment, the heavy chain constant region nucleotide sequence encodes a human $C_H2$ amino acid sequence comprising at least one modification between amino acid residues at positions 252 and 257, wherein the modification increases the affinity of the human $C_H2$ amino acid sequence to FcRn in an acidic environment (e.g., in an endosome where pH ranges from about 5.5 to about 6.0).

In one embodiment, the heavy chain constant region nucleotide sequence encodes a human $C_H2$ amino acid sequence comprising at least one modification between amino acid residues at positions 307 and 311, wherein the modification increases the affinity of the $C_H2$ amino acid sequence to FcRn in an acidic environment (e.g., in an endosome where pH ranges from about 5.5 to about 6.0).

In one embodiment, the heavy chain constant region nucleotide sequence encodes a human $C_H3$ amino acid sequence, wherein the $C_H3$ amino acid sequence comprises at least one modification between amino acid residues at positions 433 and 436, wherein the modification increases the affinity of the $C_H3$ amino acid sequence to FcRn in an acidic environment (e.g., in an endosome where pH ranges from about 5.5 to about 6.0).

In one embodiment, the heavy chain constant region nucleotide sequence encodes a human heavy chain constant region amino acid sequence comprising a mutation selected from the group consisting of M428L, N434S, and a combination thereof.

In one embodiment, the heavy chain constant region nucleotide sequence encodes a human heavy chain constant region amino acid sequence comprising a mutation selected from the group consisting of M428L, V259I, V308F, and a combination thereof.

In one embodiment, the heavy chain constant region nucleotide sequence encodes a human heavy chain constant region amino acid sequence comprising an N434A mutation.

In one embodiment, the heavy chain constant region nucleotide sequence encodes a human heavy chain constant region amino acid sequence comprising a mutation selected from the group consisting of M252Y, S254T, T256E, and a combination thereof.

In one embodiment, the heavy chain constant region nucleotide sequence encodes a human heavy chain constant region amino acid sequence comprising a mutation selected from the group consisting of T250Q, M248L, or both.

In one embodiment, the heavy chain constant region nucleotide sequence encodes a human heavy chain constant region amino acid sequence comprising a mutation selected from the group consisting of H433K, N434Y, or both.

In one embodiment, the genetically modified immunoglobulin locus comprises: (1) a first allele, wherein the unrearranged human immunoglobulin heavy chain variable region nucleotide sequence as described herein is operably linked to a first heavy chain constant region nucleotide sequence encoding a first $CH_3$ amino acid sequence of a human IgG selected from IgG1, IgG2, IgG4, and a combination thereof; and (2) a second allele, wherein the unrearranged human immunoglobulin heavy chain variable region nucleotide sequence as described herein is operably linked to a second heavy chain constant region nucleotide sequence encoding a second $CH_3$ amino acid sequence of the human IgG selected from IgG1, IgG2, IgG4, and a combination thereof, and wherein the second $CH_3$ amino acid sequence comprises a modification that reduces or eliminates binding for the second $CH_3$ amino acid sequence to Protein A (see, for example, US 2010/0331527A1, which is incorporated by reference herein in its entirety).

In one embodiment, the second $CH_3$ amino acid sequence comprises an H95R modification (by IMGT exon numbering; H435R by EU numbering). In one embodiment the second $CH_3$ amino acid sequence further comprises an Y96F modification (by IMGT exon numbering; H436F by EU). In another embodiment, the second $CH_3$ amino acid sequence comprises both an H95R modification (by IMGT exon numbering; H435R by EU numbering) and an Y96F modification (by IMGT exon numbering; H436F by EU).

In one embodiment, the second $CH_3$ amino acid sequence is from a modified human IgG1 and further comprises a mutation selected from the group consisting of D16E, L18M, N44S, K52N, V57M, and V82I (IMGT; D356E, L38M, N384S, K392N, V397M, and V422I by EU).

In one embodiment, the second $CH_3$ amino acid sequence is from a modified human IgG2 and further comprises a mutation selected from the group consisting of N44S, K52N, and V82I (IMGT: N384S, K392N, and V422I by EU).

In one embodiment, the second $CH_3$ amino acid sequence is from a modified human IgG4 and further comprises a mutation selected from the group consisting of Q15R, N44S, K52N, V57M, R69K, E79Q, and V82I (IMGT: Q355R, N384S, K392N, V397M, R409K, E419Q, and V422I by EU).

In one embodiment, the heavy chain constant region amino acid sequence is a non-human constant region amino acid sequence, and the heavy chain constant region amino acid sequence comprises one or more of any of the types of modifications described above.

In one embodiment, the heavy chain constant region nucleotide sequence is a human heavy chain constant region amino acid sequence, and the human heavy chain constant region amino acid sequence comprises one or more of any of the types of modifications described above.

In one embodiment, all or substantially all endogenous $V_H$, D, and $J_H$ gene segments are deleted from an immunoglobulin heavy chain locus or rendered non-functional (e.g., via insertion of a nucleotide sequence (e.g., an exogenous nucleotide sequence) in the immunoglobulin locus or via non-functional rearrangement, or inversion, of the endogenous $V_H$, D, $J_H$ segments). In one embodiment, e.g., about 80% or more, about 85% or more, about 90% or more, about 95% or more, about 96% or more, about 97% or more, about 98% or more, or about 99% or more of all endogenous $V_H$, D, or $J_H$ gene segments are deleted or rendered non-functional. In one embodiment, e.g., at least 95%, 96%, 97%, 98%, or 99% of endogenous functional V, D, or J gene segments are deleted or rendered non-functional.

In one embodiment, the genetically modified immunoglobulin heavy chain locus comprises a modification that deletes or renders, all or substantially all, non-functional endogenous $V_H$, D, and $J_H$ gene segments; and the genetically modified locus comprises an unrearranged heavy chain variable region nucleotide sequence comprising at least one inverted human D gene segment as described herein wherein the unrearranged heavy chain variable region nucleotide sequence is present at an endogenous location (i.e., where the nucleotide sequence is located in a wild-type non-human animal) or present ectopically (e.g., at a locus different from the endogenous immunoglobulin chain locus in its genome, or within its endogenous locus, e.g., within an immunoglobulin variable locus, wherein the endogenous locus is placed or moved to a different location in the genome).

In one embodiment, the genetically modified immunoglobulin locus comprises an endogenous Adam6a gene, Adam6b gene, or both, and the genetic modification does not affect the expression and/or function of the endogenous Adam6a gene, Adam6b gene, or both.

In one embodiment, the genetically modified immunoglobulin locus comprises an ectopically present Adam6a gene, Adam6b gene, or both. In one embodiment, the Adam6a gene is a non-human Adam6a gene. In one embodiment, the Adam6a gene is a mouse Adam6a gene. In one embodiment, the Adam6a gene is a human Adam6a gene. In one embodiment, the Adam6b gene is a non-human Adam6b gene. In one embodiment, the Adam6b gene is a mouse Adam6b gene. In one embodiment, the Adam6b gene is a human Adam6b gene.

In one embodiment, the genetically modified immunoglobulin locus further comprises a humanized, unrearranged λ and/or κ light chain variable gene sequence. In one embodiment, the humanized, unrearranged λ and/or κ light chain variable gene sequence is operably linked to an immunoglobulin light chain constant region nucleotide sequence selected from a λ light chain constant region nucleotide sequence and a κ light chain constant region nucleotide sequence. In one embodiment, the humanized, unrearranged λ light chain variable region nucleotide sequence is operably linked to a λ light chain constant region nucleotide sequence. In one embodiment, the λ light chain constant region nucleotide sequence is a mouse, rat, or human sequence. In one embodiment, the humanized, unrearranged κ light chain variable region nucleotide sequence is operably linked to a κ light chain constant region nucleotide sequence. In one embodiment, the κ light chain constant region nucleotide sequence is a mouse, rat, or human sequence.

In one embodiment, the genetically modified immunoglobulin locus comprises an unrearranged light chain variable gene sequence that contains at least one modification that introduces at least one histidine codon in at least one reading frame encoding a light chain variable domain. In one embodiment, the genetically modified immunoglobulin locus comprises a rearranged (e.g., a rearranged λ or κ V/J sequence) sequence that comprises one, two, three, or four codons for histidine in a light chain CDR. In one embodiment, the CDR is a selected from a CDR1, CDR2, CDR3, and a combination thereof. In one embodiment, the unrearranged or rearranged light chain variable region nucleotide sequence is an unrearranged or rearranged human λ or κ light chain variable region nucleotide sequence. In one embodiment, the unrearranged or rearranged human λ or κ light chain variable region nucleotide sequence is present at an endogenous mouse immunoglobulin light chain locus. In one embodiment, the mouse immunoglobulin light chain locus is a mouse κ locus. In one embodiment, the mouse immunoglobulin light chain locus is a mouse immunoglobulin light chain locus is a mouse λ locus.

In one embodiment, the genetically modified immunoglobulin locus as described herein is present in an immunoglobulin heavy chain locus of a mouse. In one embodiment, the genetically modified immunoglobulin locus is present in a humanized immunoglobulin heavy chain locus in a VELOCIMMUNE® mouse.

In one embodiment, an antigen-binding protein comprising a heavy chain variable domain expressed by the genetically modified immunoglobulin heavy chain locus as described herein exhibits a weaker antigen binding at an acidic environment (e.g., at a pH of about 5.5 to about 6.0) than a corresponding wild-type heavy chain variable domain without the genetic modification.

In one embodiment, an antigen-binding protein comprising a heavy chain variable domain expressed by the genetically modified immunoglobulin heavy chain locus as described herein has a dissociative half-life ($t_{1/2}$) of less than 2 min at an acidic pH (e.g., pH of about 5.5 to about 6.0) at 25° C. In one embodiment, an antigen-binding protein comprising a heavy chain variable domain expressed by the genetically modified immunoglobulin heavy chain locus as described herein has a dissociative half-life ($t_{1/2}$) of less than 2 min at an acidic pH (e.g., pH of about 5.5 to about 6.0) at 37° C. In one embodiment, an antigen-binding protein comprising a heavy chain variable domain expressed by the genetically modified immunoglobulin heavy chain locus as described herein has a dissociative half-life ($t_{1/2}$) of less than 1 min at an acidic pH (e.g., pH of about 5.5 to about 6.0) at 25° C. In one embodiment, an antigen-binding protein comprising a heavy chain variable domain expressed by the genetically modified immunoglobulin heavy chain locus as described herein has a dissociative half-life ($t_{1/2}$) of less than 1 min at an acidic pH (e.g., pH of about 5.5 to about 6.0) at 37° C. In one embodiment, an antigen-binding protein comprising a heavy chain variable domain expressed by the genetically modified immunoglobulin locus as described herein has at least about 2-fold, at least about 3-fold, at least about 4-fold, at least about 5-fold, at least about 10-fold, at least about 15-fold, at least about 20-fold, at least about 25-fold, or at least about 30-fold decrease in dissociative half-life ($t_{1/2}$) at an acidic pH (e.g., pH of about 5.5 to about 6.0) as compared to the dissociative half-life ($t_{1/2}$) of the antigen-binding protein at a neutral pH (e.g., pH of about 7.0 to about 7.4).

In one embodiment, an antigen-binding protein comprising a heavy chain variable domain expressed by the genetically modified immunoglobulin locus as described herein is characterized by improved pH-dependent recyclability, enhanced serum half-life, or both as compared with a wild-type antigen-binding protein without the genetic modification.

In one embodiment, the genetically modified immunoglobulin locus described herein comprises an enriched B cell population that, upon stimulation with an antigen of interest, is capable of producing antigen-binding proteins, e.g., antibodies, comprising a heavy chain variable domain comprising one or more histidine residues. The antigen-binding proteins as described herein, when administered into a subject, exhibits an increased serum half-life over a corresponding wild-type antigen-binding protein, which possesses a similar or sufficiently similar amino acid sequence that encodes the heavy chain variable domain but does not comprise a histidine residue in the heavy chain variable domain. In some embodiments, the antigen-binding protein described herein exhibits an increased serum half-life that is at least about 2-fold, at least about 5-fold, at least about 10-fold, at least about 15-fold, at least about 20-fold higher than the corresponding wild-type antigen-binding protein, which possesses a similar or sufficiently similar amino acid sequence that encodes the heavy chain variable domain but does not comprise a histidine residue in the heavy chain variable domain.

In one aspect, a method for making a non-human animal that is capable of producing an immunoglobulin heavy chain variable domain with enhanced serum half-life and/or enhanced pH-dependent recyclability is provided, comprising (a) modifying a genome of a non-human animal to delete or render non-functional endogenous immunoglobulin heavy chain V, D, and J gene segments (e.g., via insertion of a nucleotide sequence (e.g., an exogenous nucleotide sequence) in the immunoglobulin locus or via non-functional rearrangement or inversion of endogenous $V_H$, D, $J_H$ segments); and (b) placing in the genome an unrearranged human heavy chain variable region nucleotide sequence, wherein the unrearranged heavy chain variable region nucleotide sequence comprises an addition of least one histidine codon or a substitution of at least one endogenous non-histidine codon with a histidine codon, and wherein an antigen-binding protein comprising the immunoglobulin heavy chain variable domain produced by the non-human animal exhibits enhanced serum half-life and/or enhanced pH-dependent recyclability as compared to a wild-type immunoglobulin heavy chain domain.

In one embodiment, the non-human animal, upon contact with an antigen, can produce an enriched population of B cell repertoire that expresses an antigen-binding protein with enhanced serum half-life and/or enhanced pH-dependent recyclability, wherein the enriched B cell population comprises any genetic modifications as described herein.

In one embodiment, an antigen-binding protein produced by the genetically modified non-human animal is characterized by sufficient affinity to an antigen of interest at a neutral pH (e.g., pH of about 7.0 to about 7.4) and enhanced dissociation of the antibody from an antigen-antigen-binding protein complex at a pH less than the neutral pH (e.g., at an endosomal pH, e.g. pH of about 5.5 to 6.0).

In one embodiment, an antigen-binding protein comprising a heavy chain variable domain expressed by the genetically modified immunoglobulin heavy chain locus as described herein has a dissociative half-life ($t_{1/2}$) of less than 2 min at an acidic pH (e.g., pH of about 5.5 to about 6.0) at 25° C. In one embodiment, an antigen-binding protein comprising a heavy chain variable domain expressed by the genetically modified immunoglobulin heavy chain locus as described herein has a dissociative half-life ($t_{1/2}$) of less than 2 min at an acidic pH (e.g., pH of about 5.5 to about 6.0) at 37° C. In one embodiment, an antigen-binding protein comprising a heavy chain variable domain expressed by the genetically modified immunoglobulin heavy chain locus as described herein has a dissociative half-life ($t_{1/2}$) of less than 1 min at an acidic pH (e.g., pH of about 5.5 to about 6.0) at 25° C. In one embodiment, an antigen-binding protein comprising a heavy chain variable domain expressed by the genetically modified immunoglobulin heavy chain locus as described herein has a dissociative half-life ($t_{1/2}$) of less than 1 min at an acidic pH (e.g., pH of about 5.5 to about 6.0) at 37° C. In one embodiment, an antigen-binding protein comprising a heavy chain variable domain expressed by the genetically modified immunoglobulin locus as described herein has at least about 2-fold, at least about 3-fold, at least about 4-fold, at least about 5-fold, at least about 10-fold, at least about 15-fold, at least about 20-fold, at least about 25-fold, or at least about 30-fold decrease in dissociative half-life ($t_{1/2}$) at an acidic pH (e.g., pH of about 5.5 to about 6.0) as compared to the dissociative half-life ($t_{1/2}$) of the antigen-binding protein at a neutral pH (e.g., pH of about 7.0 to about 7.4).

In one embodiment, an antigen-binding protein comprising a heavy chain variable domain expressed by the genetically modified immunoglobulin locus as described herein is characterized by improved pH-dependent recyclability, enhanced serum half-life, or both as compared with a wild-type antigen-binding protein without the genetic modification.

In one embodiment, the genetically modified immunoglobulin locus described herein comprises a an enriched B cell population that, upon stimulation with an antigen of interest, is capable of producing antigen-binding proteins, e.g., antibodies, comprising a heavy chain variable domain comprising one or more histidine residues. The antigen-binding proteins as described herein when administered into a subject, exhibits an increased serum half-life over a corresponding wild-type antigen-binding protein, which possesses a similar or sufficiently similar amino acid sequence that encodes the heavy chain variable domain but does not comprise a histidine residue in the heavy chain variable domain. In some embodiments, the antigen-binding protein described herein exhibits an increased serum half-life that is at least about 2-fold, at least about 5-fold, at least about 10-fold, at least about 15-fold, at least about 20-fold higher than the corresponding wild-type antigen-binding protein, which possesses a similar or sufficiently similar amino acid sequence that encodes the heavy chain variable domain but does not comprise a histidine residue in the heavy chain variable domain.

In one embodiment, the antigen-binding protein comprises an immunoglobulin heavy chain variable domain that is capable of specifically binding an antigen of interest with an affinity ($K_D$) lower than $10^{-6}$, $10^{-7}$, $10^{-8}$, $10^{-9}$, $10^{-10}$, $10^{-11}$, and $10^{-12}$ at a neutral pH (e.g., pH of about 7.0 to about 7.4).

In one aspect, a method for obtaining an antigen-binding protein with enhanced recyclability and/or improved serum half-life is provided, comprising:

(a) immunizing a non-human animal having a genetically modified immunoglobulin locus as described herein wherein the non-human animal comprises an unrearranged human heavy chain variable region nucleotide sequence comprising an addition of least one histidine codon or a substitution of at least one endogenous non-histidine codon with a histidine codon;

(b) allowing the non-human animal to mount an immune response;

(c) harvesting a lymphocyte (e.g., a B cell) from the immunized non-human animal;

(d) fusing the lymphocyte with a myeloma cell to form a hybridoma cell, and (e) obtaining an antigen-binding protein produced by the hybridoma cell, wherein the antigen-binding protein exhibits enhanced recyclability and/or serum stability.

In one aspect, a genetically modified immunoglobulin heavy chain locus obtainable by any of the methods as described herein is provided.

In one aspect, a genetically modified non-human animal obtainable by any of the methods as described herein is provided.

In various embodiments, the non-human animal is a mammal. In one embodiment, the mammal is a rodent, e.g., a mouse, a rat, or a hamster.

In various embodiments, the genetically modified immunoglobulin loci as described herein are present in the germline genome of a non-human animal, e.g., a mammal, e.g., a rodent, e.g., a mouse, a rat, or a hamster.

BRIEF DESCRIPTION OF THE DRAWINGS

FIGS. 1A and 1B illustrate the amino acid sequences encoded by the three reading frames (i.e., stop, hydrophilic, and hydrophobic reading frames) of human D gene segments (D) and the amino acid sequences encoded by the three reading frames of histidine-substituted human D gene segments (HD). Introduction of histidine codons (typed in bold) in the hydrophilic reading frame also changed many stop codons in the stop reading frame to Ser codons (typed in bold) but introduced few changes in the hydrophobic reading frame. The "*" symbol represents a stop codon, and the comma between the two SEQ ID NOs indicates that there are two amino acid sequences separated by the stop codon.

FIG. 6 shows a list of primers and probes used to confirm a loss of allele (LOA), a gain of allele (GOA), or a parental allele (Parental) in the screening assays for identifying MAID 6011.

FIG. 8 shows a list of primers and probes used to confirm a loss of allele (LOA), a gain of allele (GOA), or a parental allele (Parental) in the screening assay for identifying MAID 6012.

FIGS. 10A-10E illustrate human D gene segment nucleotide sequences with translations for each of the six reading frames, i.e., three reading frames for direct 5' to 3' orientation and three reading frames for inverted orientation (3' to 5' orientation). The "*" symbol represents a stop codon, and the comma between two SEQ ID NOs indicates that there are two amino acid sequences separated by the stop codon.

FIGS. 11-13 illustrate mRNA sequences and their encoded protein sequences expressed by 6013 F0 heterozygous mice, which comprise histidine-substituted human D gene segments (HD 1.1-6.6 (9586 bp; SEQ ID NO: 1), HD 1.7-6.13 (9268 bp; SEQ ID NO: 2), HD 1.14-6.19 (9441 bp; SEQ ID NO: 3), and HD 1.20-6.25, 1.26 (11592 bp; SEQ ID NO: 4)) in the immunoglobulin heavy chain locus in their 129 strain-derived chromosome. The boxed sequences in each figure indicate the presence of histidine codons in the CDR3 sequences derived from the genetically modified immunoglobulin heavy chain locus comprising the histidine-substituted human D gene segments. FWR represents frame region and CDR represents complementarity determining region. In the alignment, the dot "." indicates a sequence identical to the query sequence, and the dash "-" indicates a gap in the sequence.

DETAILED DESCRIPTION OF THE INVENTION

Figure 2:
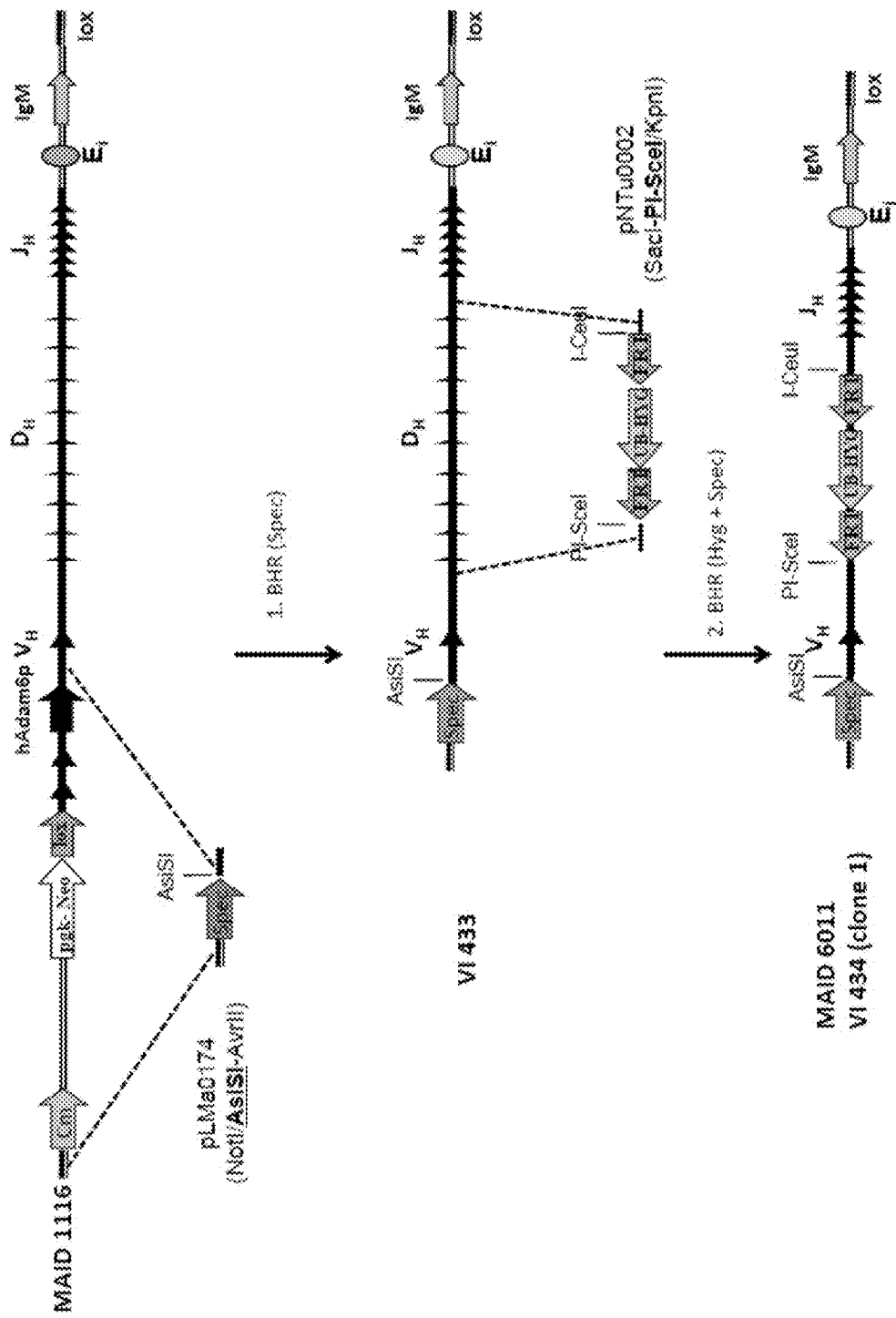
FIG. 2 illustrates schemes for targeting pLMa0174 containing a spectinomycin selection cassette into the 5' end of MAID 1116 (Step 1. BHR (Spec)). In Step 1, a chloramphenicol selection cassette, a neomycin selection cassette, a loxP site, two $V_H$ gene segments (h$V_H$1-3 and h$V_H$1-2), the human Adam6 gene, all of which are located upstream of h$V_H$6-1, were deleted from the clone and replaced by a spectinomycin cassette to yield the V1433 clone. In Step 2 (BHR (Hyg+ Spec)), pNTu0002 containing a hygromycin cassette flanked by FRT sites was targeted into a region comprising human immunoglobulin D gene segments. Via Step 2, all human D gene segments were deleted from V1433 and replaced with the hygromycin cassette to yield MAID6011 VI 434 (clone 1).

This invention is not limited to particular methods, and experimental conditions described, as such methods and conditions may vary. It is also to be understood that the terminology used herein is for the purpose of describing particular embodiments only, and is not intended to be limiting, since the scope of the present invention is defined by the claims.

Unless defined otherwise, all terms and phrases used herein include the meanings that the terms and phrases have attained in the art, unless the contrary is clearly indicated or clearly apparent from the context in which the term or phrase is used. Although any methods and materials similar or equivalent to those described herein can be used in the practice or testing of the present invention, particular methods and materials are now described. All publications mentioned are hereby incorporated by reference

DEFINITIONS

The term "complementary determining region" or "CDR," as used herein, includes an amino acid sequence encoded by a nucleic acid sequence of an organism's immunoglobulin genes that normally (i.e., in a wild type animal) appears between two framework regions in a variable region of a light or a heavy chain of an immunoglobulin molecule (e.g., an antibody or a T cell receptor). A CDR can be encoded by, for example, a germline sequence or a rearranged sequence, and, for example, by a naïve or a mature B cell or a T cell. A CDR can be somatically mutated (e.g., vary from a sequence encoded in an animal's germline), humanized, and/or modified with amino acid substitutions, additions, or deletions. In some circumstances (e.g., for a CDR3), CDRs can be encoded by two or more sequences (e.g., germline sequences) that are not contiguous (e.g., in an unrearranged nucleic acid sequence) but are contiguous in a B cell nucleic acid sequence, e.g., as a result of splicing or connecting the sequences (e.g., V-D-J recombination to form a heavy chain CDR3).

The term "dissociative half-life" or "$t_{1/2}$" as used herein refers to the value calculated by the following formula: $t_{1/2}$ (min)=(ln2/$k_d$)/60, wherein $k_d$ represents a dissociation rate constant.

The term "germline" in reference to an immunoglobulin nucleic acid sequence includes a nucleic acid sequence that can be passed to progeny.

The phrase "heavy chain," or "immunoglobulin heavy chain" includes an immunoglobulin heavy chain sequence, including immunoglobulin heavy chain constant region sequence, from any organism. Heavy chain variable domains include three heavy chain CDRs and four FR regions, unless otherwise specified. Fragments of heavy chains include CDRs, CDRs and FRs, and combinations thereof. A typical heavy chain has, following the variable domain (from N-terminal to C-terminal), a $C_H1$ domain, a hinge, a $C_H2$ domain, and a $C_H3$ domain. A functional fragment of a heavy chain includes a fragment that is capable of specifically recognizing an epitope (e.g., recognizing the epitope with a $K_D$ in the micromolar, nanomolar, or picomolar range), that is capable of expressing and secreting from a cell, and that comprises at least one CDR. Heavy chain variable domains are encoded by variable region nucleotide sequence, which generally comprises $V_H$, $D_H$, and $J_H$ segments derived from a repertoire of $V_H$, $D_H$, and $J_H$ segments present in the germline. Sequences, locations and nomenclature for V, D, and J heavy chain segments for various organisms can be found in IMGT database, which is accessible via the internet on the world wide web (www) at the URL "imgt.org."

The phrase "light chain" includes an immunoglobulin light chain sequence from any organism, and unless otherwise specified includes human kappa (κ) and lambda (λ) light chains and a VpreB, as well as surrogate light chains. Light chain variable domains typically include three light chain CDRs and four framework (FR) regions, unless otherwise specified. Generally, a full-length light chain includes, from amino terminus to carboxyl terminus, a variable domain that includes FR1-CDR1-FR2-CDR2-FR3-CDR3-FR4, and a light chain constant region amino acid sequence. Light chain variable domains are encoded by the light chain variable region nucleotide sequence, which generally comprises light chain $V_L$ and light chain $J_L$ gene segments, derived from a repertoire of light chain V and J gene segments present in the germline. Sequences, locations and nomenclature for light chain V and J gene segments for various organisms can be found in IMGT database, which is accessible via the internet on the world wide web (www) at the URL "imgt.org." Light chains include those, e.g., that do not selectively bind either a first or a second epitope selectively bound by the epitope-binding protein in which they appear. Light chains also include those that bind and recognize, or assist the heavy chain with binding and recognizing, one or more epitopes selectively bound by the epitope-binding protein in which they appear.

The phrase "operably linked" refers to a relationship wherein the components operably linked function in their intended manner. In one instance, a nucleic acid sequence encoding a protein may be operably linked to regulatory sequences (e.g., promoter, enhancer, silencer sequence, etc.) so as to retain proper transcriptional regulation. In one instance, a nucleic acid sequence of an immunoglobulin variable region (or V(D)J segments) may be operably linked to a nucleic acid sequence of an immunoglobulin constant region so as to allow proper recombination between the sequences into an immunoglobulin heavy or light chain sequence.

The phrase "somatically mutated," as used herein, includes reference to a nucleic acid sequence from a B cell that has undergone class-switching, wherein the nucleic acid sequence of an immunoglobulin variable region, e.g., a heavy chain variable region (e.g., a heavy chain variable domain or including a heavy chain CDR or FR sequence) in the class-switched B cell is not identical to the nucleic acid sequence in the B cell prior to class-switching, such as, for example a difference in a CDR or a framework nucleic acid sequence between a B cell that has not undergone class-switching and a B cell that has undergone class-switching. The phrase "somatically mutated" includes reference to nucleic acid sequences from affinity-matured B cells that are not identical to corresponding immunoglobulin variable region nucleotide sequences in B cells that are not affinity-matured (i.e., sequences in the genome of germline cells). The phrase "somatically matured" also includes reference to an immunoglobulin variable region nucleic acid sequence from a B cell after exposure of the B cell to an epitope of interest, wherein the nucleic acid sequence differs from the corresponding nucleic acid sequence prior to exposure of the B cell to the epitope of interest. The term "somatically mutated" also refers to sequences from antibodies that have been generated in an animal, e.g., a mouse having human immunoglobulin variable region nucleic acid sequences, in response to an immunogen challenge, and that result from the selection processes inherently operative in such an animal.

Non-Human Animals that Express Immunoglobulin Heavy Chain Variable Domain Comprising Histidine Residues The described invention provides genetically modified non-human animals that can produce antigen-binding proteins with pH-dependent antigen binding characteristics. In various embodiments, the antigen-binding proteins produced by the genetically modified non-human animals as described herein exhibit increased pH-dependent recycling efficiency and/or enhanced serum half-life. In particular, the described invention employs genetic modifications in the immunoglobulin heavy chain locus to introduce histidine codons into a human heavy chain variable region nucleotide sequence and, optionally, to introduce a mutation(s) in a constant region nucleotide sequence that encodes $C_H2$ and/or $C_H3$ domains that increases the binding of the antibody constant region to an FcRn receptor, which facilitates recycling of the antigen-binding protein. Antigen-binding proteins comprising the modification may more loosely bind its target in an acidic intracellular compartment (e.g., in an endosome where pH ranges from about 5.5 to about 6.0) than in an extracellular environment or at the surface of a cell (i.e., at a physiological pH, e.g., a pH ranging from about 7.0 to about 7.4) due to protonated histidine residues located in the antigen binding sites. Therefore, the antigen-biding proteins comprising the genetic modifications as described herein would be able to be recycled more rapidly or efficiently than wild-type antigen-binding proteins that do not comprise such genetic modifications following target-mediated endocytosis. Furthermore, since the modified histidine residues are protonated only in an acidic environment, but not at a neutral pH, it is expected that such modification would not affect binding affinity and/or specificity of the antigen-binding protein toward an antigen of interest at a physiological pH.

In various aspects, non-human animals are provided comprising immunoglobulin heavy chain loci that comprise an unrearranged human heavy chain variable region nucleotide sequence, wherein the unrearranged human heavy chain variable region nucleotide sequence comprises an addition of least one histidine codon or a substitution of at least one endogenous non-histidine codon with a histidine codon.

In various aspects, methods of making and using the non-human animals are also provided. When immunized with an antigen of interest, the genetically modified non-human animals are capable of generating B cell populations that produce antigen-binding proteins comprising heavy chain variable domains with histidine residues, wherein the antigen-binding proteins exhibit enhanced pH-dependent recycling and/or increased serum half-life. In various embodiments, the non-human animals generate B cell populations that express human heavy chain variable domains along with cognate human light chain variable domains. In various embodiments, the genetically modified immunoglobulin heavy chain loci are present in a germline genome of the non-human animal.

In various embodiments, the genetically modified immunoglobulin heavy chain locus comprises a modification that deletes or renders, all or substantially all, non-functional endogenous $V_H$, D, and $J_H$ gene segments; and the genetically modified locus comprises an unrearranged heavy chain variable region nucleotide sequence comprising one or more human $V_H$, D, and/or $J_H$ gene segments having one or more histidine codons, wherein the unrearranged heavy chain variable region nucleotide sequence is present at an endogenous location (i.e., where the nucleotide sequence is located in a wild-type non-human animal) or present ectopically (e.g., at a locus different from the endogenous immunoglobulin chain locus in its genome, or within its endogenous locus, e.g., within an immunoglobulin variable locus, wherein the endogenous locus is placed or moved to a different location in the genome). In one embodiment, e.g., about 80% or more, about 85% or more, about 90% or more, about 95% or more, about 96% or more, about 97% or more, about 98% or more, or about 99% or more of all endogenous heavy chain V, D, or J gene segments are deleted or rendered non-functional. In one embodiment, e.g., at least 95%, 96%, 97%, 98%, or 99% of endogenous functional heavy chain V, D, or J gene segments are deleted or rendered non-functional.

In one embodiment, the non-human animal is a mammal. Although embodiments directed to introducing histidine codons into an unrearranged human heavy chain variable gene sequence in a mouse are extensively discussed herein, other non-human animals are also provided that comprise a genetically modified immunoglobulin locus containing an unrearranged human heavy chain variable region nucleotide sequence comprising an addition of least one histidine codon or a substitution of at least one endogenous non-histidine codon with a histidine codon. Such non-human animals include any of those which can be genetically modified to express the histidine-containing heavy chain variable domain as disclosed herein, including, e.g., mouse, rat, rabbit, pig, bovine (e.g., cow, bull, buffalo), deer, sheep, goat, chicken, cat, dog, ferret, primate (e.g., marmoset, rhesus monkey), etc. For example, for those non-human animals for which suitable genetically modifiable ES cells are not readily available, other methods are employed to make a non-human animal comprising the genetic modification. Such methods include, e.g., modifying a non-ES cell genome (e.g., a fibroblast or an induced pluripotent cell) and employing somatic cell nuclear transfer (SCNT) to transfer the genetically modified genome to a suitable cell, e.g., an enucleated oocyte, and gestating the modified cell (e.g., the modified oocyte) in a non-human animal under suitable conditions to form an embryo. Methods for modifying a non-human animal genome (e.g., a pig, cow, rodent, chicken, etc. genome) include, e.g., employing a zinc finger nuclease (ZFN) or a transcription activator-like effector nuclease (TALEN) to modify a genome to include a nucleotides sequence that encodes In one embodiment, the non-human animal is a small mammal, e.g., of the superfamily Dipodoidea or Muroidea. In one embodiment, the genetically modified animal is a rodent. In one embodiment, the rodent is selected from a mouse, a rat, and a hamster. In one embodiment, the rodent is selected from the superfamily Muroidea. In one embodiment, the genetically modified animal is from a family selected from Calomyscidae (e.g., mouse-like hamsters), Cricetidae (e.g., hamster, New World rats and mice, voles), Muridae (true mice and rats, gerbils, spiny mice, crested rats), Nesomyidae (climbing mice, rock mice, with-tailed rats, Malagasy rats and mice), Platacanthomyidae (e.g., spiny dormice), and Spalacidae (e.g., mole rats, bamboo rats, and zokors). In a specific embodiment, the genetically modified rodent is selected from a true mouse or rat (family Muridae), a gerbil, a spiny mouse, and a crested rat. In one embodiment, the genetically modified mouse is from a member of the family Muridae. In one embodiment, the animal is a rodent. In a specific embodiment, the rodent is selected from a mouse and a rat. In one embodiment, the non-human animal is a mouse.

In one embodiment, the non-human animal is a rodent that is a mouse of a C57BL strain selected from C57BL/A, C57BL/An, C57BL/GrFa, C57BL/KaLwN, C57BL/6, C57BL/6J, C57BL/6ByJ, C57BL/6N, C57BL/6NJ, C57BL/10, C57BL/10ScSn, C57BL/10Cr, and C57BL/Ola. In another embodiment, the mouse is a 129 strain. In one embodiment, the 129 strain is selected from the group consisting of 129P1, 129P2, 129P3, 129X1, 129S1 (e.g., 129S1/SV, 129S1/Svlm), 129S2, 129S4, 129S5, 129S9/SvEvH, 129S6 (129/SvEvTac), 129S7, 129S8, 129T1, 129T2 (see, e.g., Festing et al. (1999) Revised nomenclature for strain 129 mice, Mammalian Genome 10:836, see also, Auerbach et al. (2000) Establishment and Chimera Analysis of 129/SvEv- and C57BL/6-Derived Mouse Embryonic Stem Cell Lines). In one embodiment, the genetically modified mouse is a mix of an aforementioned 129 strain and an aforementioned C57BL strain (e.g., a C57BL/6 strain). In another embodiment, the mouse is a mix of aforementioned 129 strains, or a mix of aforementioned C57BL/6 strains. In one embodiment, the 129 strain of the mix is a 129S6 (129/SvEvTac) strain. In another embodiment, the mouse is a mix of a 129/SvEv- and a C57BL/6-derived strain. In a specific embodiment, the mouse is a mix of a 129/SvEv- and a C57BL/6-derived strain as described in Auerbach et al. 2000 *Bio Techniques* 29:1024-1032. In another embodiment, the mouse is a BALB strain, e.g., BALB/c strain. In another embodiment, the mouse is a mix of a BALB strain (e.g., BALB/c strain) and another aforementioned strain.

In one embodiment, the non-human animal is a rat. In one embodiment, the rat is selected from a Wistar rat, an LEA strain, a Sprague Dawley strain, a Fischer strain, F344, F6, and Dark Agouti. In one embodiment, the rat strain is a mix of two or more of a strain selected from the group consisting of Wistar, LEA, Sprague Dawley, Fischer, F344, F6, and Dark Agouti.

In one embodiment, the non-human animal is a mouse. In one embodiment, the mouse is a VELOCIMMUNE® humanized mouse.

VELOCIMMUNE® humanized mice (see, e.g., U.S. Pat. No. 6,596,541, U.S. Pat. No. 7,105,348, and US20120322108A1, which are incorporated herein by reference in their entireties), which contain a precise replacement of mouse immunoglobulin variable regions with human immunoglobulin variable regions at the endogenous mouse loci, display a surprising and remarkable similarity to wild-type mice with respect to B cell development. VELOCIMMUNE® humanized mice display an essentially normal, wild-type response to immunization that differed only in one significant respect from wild-type mice—the variable regions generated in response to immunization are fully human.

VELOCIMMUNE® humanized mice contain a precise, large-scale replacement of germline variable region nucleotide sequences of mouse immunoglobulin heavy chain (IgH) and immunoglobulin light chain (e.g., κ light chain, Igκ) with corresponding human immunoglobulin variable region nucleotide sequences, at the endogenous loci (see, e.g., U.S. Pat. No. 6,596,541, U.S. Pat. No. 7,105,348, US 20120322108A1, which are incorporated herein by reference in their entireties). In total, about six megabases of mouse loci are replaced with about 1.5 megabases of human genomic sequence. This precise replacement results in a mouse with hybrid immunoglobulin loci that make heavy and light chains that have a human variable regions and a mouse constant region. The precise replacement of mouse $V_H$-D-$J_H$ and Vκ-Jκ segments leave flanking mouse sequences intact and functional at the hybrid immunoglobulin loci. The humoral immune system of the mouse functions like that of a wild-type mouse. B cell development is unhindered in any significant respect and a rich diversity of human variable regions is generated in the mouse upon antigen challenge.

VELOCIMMUNE® humanized mice are possible because immunoglobulin gene segments for heavy and κ light chains rearrange similarly in humans and mice, which is not to say that their loci are the same or even nearly so—clearly they are not. However, the loci are similar enough that humanization of the heavy chain variable gene locus can be accomplished by replacing about three million base pairs of contiguous mouse sequence that contains all the $V_H$, D, and $J_H$ gene segments with about one million bases of contiguous human genomic sequence covering basically the equivalent sequence from a human immunoglobulin locus.

In some embodiments, further replacement of certain mouse constant region nucleotide sequences with human constant region nucleotide sequences (e.g., replacement of mouse heavy chain $C_H1$ nucleotide sequence with human heavy chain $C_H1$ nucleotide sequence, and replacement of mouse light chain constant region nucleotide sequence with human light chain constant region nucleotide sequence) results in mice with hybrid immunoglobulin loci that make antibodies that have human variable regions and partly human constant regions, suitable for, e.g., making fully human antibody fragments, e.g., fully human Fab's. Mice with hybrid immunoglobulin loci exhibit normal variable gene segment rearrangement, normal somatic hypermutation frequencies, and normal class switching. These mice exhibit a humoral immune system that is indistinguishable from wild type mice, and display normal cell populations at all stages of B cell development and normal lymphoid organ structures—even where the mice lack a full repertoire of human variable region nucleotide segments. Immunizing these mice results in robust humoral responses that display a wide diversity of variable gene segment usage.

The precise replacement of the mouse germline variable region nucleotide sequence allows for making mice that have partly human immunoglobulin loci. Because the partly human immunoglobulin loci rearrange, hypermutate, and class switch normally, the partly human immunoglobulin loci generate antibodies in a mouse that comprise human variable regions. Nucleotide sequences that encode the variable regions can be identified and cloned, then fused (e.g., in an in vitro system) with any sequences of choice, e.g., any immunoglobulin isotype suitable for a particular use, resulting in an antibody or antigen-binding protein derived wholly from human sequences.

In various embodiments, at least one histidine codon is present in an unrearranged heavy chain variable region nucleotide sequence that encodes an N-terminal region, a loop 4 region, a CDR1, a CDR2, a CDR3, or a combination thereof.

In various embodiments, at least one histidine codon is present in an unrearranged heavy chain variable region nucleotide sequence that encodes a framework region (FR) selected from the group consisting of FR1, FR2, FR3, and FR4.

In various aspects, the genetically modified immunoglobulin locus comprises a nucleotide sequence wherein at least one codon has been replaced with a histidine codon.

In various aspects, the genetically modified immunoglobulin locus comprises an unrearranged human heavy chain variable region nucleotide sequence comprising a substitution of at least one endogenous non-histidine codon with a histidine codon.

In one embodiment, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, 20 or more, 21 or more, 22 or more, 23 or more, 24 or more, 25 or more, 26 or more, 27 or more, 28 or more, 29 or more, 30 or more, 31 or more, 32 or more, 33 or more, 34 or more, 35 or more, 36 or more, 37 or more, 38 or more, 39 or more, 40 or more, 41 or more, 42 or more, 43 or more, 44 or more, 45 or more, 46 or more, 47 or more, 48 or more, 49 or more, 50 or more, 51 or more, 52 or more, 53 or more, 54 or more, 55 or more, 56 or more, 57 or more, 58 or more, 59 or more, 60 or more, or 61 or more of the endogenous non-histidine codons are replaced with histidine codons.

Previous studies on reading frame usage of human immunoglobulin D gene segments have shown that, of the three reading frames (i.e., stop, hydrophobic, and hydrophilic), the stop frame is used very infrequently. Apparently, some stop frames are chewed back and result in expression. However, stop reading frames are used at such a low frequency that for the purposes of engineering histidine codons, it is more efficient not to use the stop reading frame. As between hydrophilic and hydrophobic reading frames, the hydrophilic reading frame appears to be preferred. Thus, in one embodiment, the hydrophilic reading frame of human D gene segments is engineered to contain one or more histidine codons (as compared with the stop frame or with the hydrophobic frame).

Methods of introducing a mutation in vitro, e.g., site-directed mutagenesis, are well known in the art. In some embodiments of the described invention, histidine codons are enriched by designing histidine-substituted human D gene segments in silico (e.g., mutation of Y, D, and N codons to H codons, e.g., CAT, CAC), which are synthesized (e.g., chemical synthesis) with (unique) restriction enzyme sites for ligating them back together. The synthesized D gene segments are made with the appropriate recombination signal sequences (RSS) upstream and downstream. In one embodiment, when ligated to one another, the synthesized histidine-substituted D gene segments include the intergenic sequences observed in a human between each D gene segment.

It is understood that the codons that encode the one or more histidines, upon rearrangement and/or somatic hypermutation, may change such that one or more of the histidines will be changed to another amino acid. However, this may not occur for each and every codon encoding histidine, in each and every rearrangement in the non-human animal. If such changes occur, the changes may occur in some but not all B cells or in some but not all heavy chain variable sequences.

In various aspects, the genetically modified immunoglobulin locus comprises a human heavy chain V, D, and J gene segment, wherein at least one of the human D gene segment has been inverted 5' to 3' with respect to a corresponding wild-type sequence, and wherein at least one reading frame of the inverted human D gene segment comprises a histidine codon.

In various embodiments, the nucleotide sequence comprises one or more, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, 20 or more, 21 or more, 22 or more, 23 or more, 24 or more, or 25 or more of histidine codons.

There are 25 functional human D gene segments in 6 families of 3-5 members each (one family—the D7 family—has a single member). Direct recombination of human D gene segments is much more frequent than inversion, although inverted reading frames exhibit more histidine codons. Certain D gene segments and reading frames are used more frequently than others. All three direct reading frames and all three inverted orientation reading frames for all the functional D gene segments are presented in FIGS. 10A-10E. As shown in FIGS. 10A-10E, there are many more histidine codons in inverted reading frames than in direct reading frames. More specifically, there are 34 histidines in inverted reading frames and only four in direct reading frames. In addition, of the four in direct reading frames, three histidines are encoded by pseudogenes or present in alternate alleles. Therefore, there is only a single direct reading frame of a germline human D gene segment that contains a histidine codon, with further histidine codons possibly encountered in alternate alleles (presumably in subsets of the human population).

Inverted D rearrangements are extremely rare. Tuaillon et al. (J. Immunol., 154(12): 5453-6465, incorporated by reference herein in its entirety) showed that usage of inverted reading frames (as measured by limiting dilution PCT) is very rare, i.e., that the ratio of direct to indirect rearrangements are, in most cases, 100 to 1000. To the extent that the ratio of direct to indirect rearrangement was low, it was only observed in those D segments that exhibit very low usage. It was also shown that D gene segment family 7, which is located adjacent to J1 (far down from other D family members) is mostly used in fetuses, but exhibits a low usage in adults (Schroeder et al., Immunology 30, 2006, 119-135, incorporated by reference herein in its entirety). Therefore, in one embodiment, D family 7 sequences are not inverted 5' to 3'.

In one embodiment, at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, at least twenty, at least twenty one, at least twenty two, at least twenty three, at least twenty four, or all or substantially all of the human functional D gene segments are inverted 5' to 3' with respect to corresponding wild type sequences.

In one embodiment, the human immunoglobulin heavy chain variable domain comprising at least one non-naturally occurring histidine residue exhibits pH-dependent antigen binding characteristics. For example, an antibody comprising the modified immunoglobulin heavy chain variable domain binds a target with sufficient affinity at around a neutral pH (e.g., pH of about 7.0 to about 7.4), but either does not bind or binds weaker to the same target at an acidic pH (e.g., pH of about 5.5 to about 6.0). In one embodiment, the acidic pH is selected from about 5.5, about 5.6, about 5.7, about 5.8, about 5.9, and about 6.0. In one embodiment, the neutral pH is selected from about 7.0, about 7.1, about 7.2, about 7.3, and about 7.4.

In one embodiment, an antigen-binding protein comprising a heavy chain variable domain expressed by the genetically modified immunoglobulin heavy chain locus as described herein has a dissociative half-life ($t_{1/2}$) of less than 2 min at an acidic pH (e.g., pH of about 5.5 to about 6.0) at 25° C. In one embodiment, an antigen-binding protein comprising a heavy chain variable domain expressed by the genetically modified immunoglobulin heavy chain locus as described herein has a dissociative half-life ($t_{1/2}$) of less than 2 min at an acidic pH (e.g., pH of about 5.5 to about 6.0) at 37° C. In one embodiment, an antigen-binding protein comprising a heavy chain variable domain expressed by the genetically modified immunoglobulin heavy chain locus as described herein has a dissociative half-life ($t_{1/2}$) of less than 1 min at an acidic pH (e.g., pH of about 5.5 to about 6.0) at 25° C. In one embodiment, an antigen-binding protein comprising a heavy chain variable domain expressed by the genetically modified immunoglobulin heavy chain locus as described herein has a dissociative half-life ($t_{1/2}$) of less than 1 min at an acidic pH (e.g., pH of about 5.5 to about 6.0) at 37° C. In one embodiment, an antigen-binding protein comprising a heavy chain variable domain expressed by the genetically modified immunoglobulin locus as described herein has at least about 2-fold, at least about 3-fold, at least about 4-fold, at least about 5-fold, at least about 10-fold, at least about 15-fold, at least about 20-fold, at least about 25-fold, or at least about 30-fold decrease in dissociative half-life ($t_{1/2}$) at an acidic pH (e.g., pH of about 5.5 to about 6.0) as compared to the dissociative half-life ($t_{1/2}$) of the antigen-binding protein at a neutral pH (e.g., pH of about 7.0 to about 7.4).

In one embodiment, antigen binding proteins comprising the genetically modified human immunoglobulin heavy chain variable domain is capable of specifically binding an antigen of interest with an affinity ($K_D$) lower than $10^{-6}$, $10^{-7}$, $10^{-8}$, $10^{-9}$ or $10^{-10}$, $10^{-11}$, $10^{-12}$ at a neutral or physiological pH (pH of about 7.0 to about 7.4).

The altered binding property of the immunoglobulin heavy chain variable domain at an acidic pH (e.g., pH of about 5.5 to about 6.0) would, in some circumstances, allow faster turn-over of the antibody because the therapeutic antibody will bind a target on a cell's surface, be internalized into an endosome, and more readily or more rapidly dissociate from the target in the endosome, so that the therapeutic can be recycled to bind yet another molecule of target present in another cell. This would allow one to administer a therapeutic antibody at a lower dose, or administer the therapeutic antibody less frequently. This is particularly useful in a situation where it is not desirable to administer a therapeutic antibody frequently, or administer at a level above a certain dosage for safety or toxicity reasons.

In various embodiments, the human immunoglobulin heavy chain variable region nucleotide sequence as described herein is operably linked to a human or non-human heavy chain constant region nucleotide sequence (e.g., a heavy chain constant region nucleotide sequence that encodes an immunoglobulin isotype selected from IgM, IgD, IgG, IgE, and IgA). In various embodiments, the human or non-human heavy chain constant region nucleotide sequence is selected from the group consisting of a $C_H1$, a hinge, a $C_H2$, a $C_H3$, and a combination thereof. In one embodiment, the constant region nucleotide sequence comprises a $C_H1$, a hinge, a $C_H2$, and a $C_H3$ (e.g., $C_H1$-hinge-a $C_H2$-$C_H3$).

In various embodiments, the heavy chain constant region nucleotide sequence is present at an endogenous locus (i.e., where the nucleotide sequence is located in a wild-type non-human animal) or present ectopically (e.g., at a locus different from the endogenous immunoglobulin chain locus in its genome, or within its endogenous locus, e.g., within an immunoglobulin variable locus, wherein the endogenous locus is placed or moved to a different location in the genome).

In one embodiment, the heavy chain constant region nucleotide sequence comprises a modification in a $C_H2$ or a $C_H3$, wherein the modification increases the affinity of the heavy chain constant region amino acid sequence to FcRn in an acidic environment (e.g., in an endosome where pH ranges from about 5.5 to about 6.0).

The neonatal Fc receptor for IgG (FcRn) has been well characterized in the transfer of passive humoral immunity from a mother to her fetus across the placenta and proximal small intestine (Roopenian, D. and Akilesh, S., Nat. Rev. Immun., 2007, 7:715-725, which is incorporated by reference herein in its entirety). FcRn binds to the Fc portion of IgG at a site that is distinct from the binding sites of the classical FcγRs or the C1q component of complement, which initiates the classical pathway of complement activation. More specifically, it was shown that FcRn binds the $C_H2$-$C_H3$ hinge region of IgG antibodies—a versatile region of Fc that also binds Staphylococcal protein A, Streptococcal protein G, and the rheumatoid factor. In contrast to other Fc-binding proteins, however, FcRn binds the Fc region of IgG in a strictly pH-dependent manner; at physiological pH 7.4, FcRn does not bind IgG, whereas at the acidic pH of the endosome (e.g., where the pH ranges from about 5.5 to about 6.0), FcRn exhibits a low micromolar to nanomolar affinity for the Fc region of IgG. This pH-dependent interaction has been shown to be mediated by the titration of histidine residues in the $C_H2$-$C_H3$ region of IgG and their subsequent interaction with acidic residue on the surface of FcRn (Roopenian, D. and Akilesh, S., Nat. Rev. Immun., 2007, 7:715-725, incorporated by reference in its entirety).

Various mutations in the $C_H2$-$C_H3$ region of IgG that can increase the affinity of Fc region to FcRn at an acidic pH are known in the art. These include, but are not limited to, modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at 428 and/or 433 (e.g., L/R/S/P/Q or K) and/or 434 (e.g., H/F or Y); or a modification at 250 and/or 428; or a modification at 307 or 308 (e.g., 308F, V308F), and 434. In another example, the modification can comprise a 428L (e.g., M428L) and 434S (e.g., N434S) modification; a 428L, 259I (e.g., V259I), and 308F (e.g., V308F) modification; a 433K (e.g., H433K) and a 434 (e.g., 434Y) modification; a 252, 254, and 256 (e.g., 52Y, 254T, and 256E) modification; a 250Q and 428L modification, or a combination thereof.

In one embodiment, the heavy chain constant region nucleotide sequence encodes a human $C_H2$ amino acid sequence comprising at least one modification between amino acid residues at positions 252 and 257, wherein the modification increases the affinity of the human $C_H2$ amino acid sequence to FcRn in an acidic environment (e.g., in an endosome where pH ranges from about 5.5 to about 6.0).

In one embodiment, the heavy chain constant region nucleotide sequence encodes a human $C_H2$ amino acid sequence comprising at least one modification between amino acid residues at positions 307 and 311, wherein the modification increases the affinity of the $C_H2$ amino acid sequence to FcRn in an acidic environment (e.g., in an endosome where pH ranges from about 5.5 to about 6.0).

In one embodiment, the heavy chain constant region nucleotide sequence encodes a human $C_H3$ amino acid sequence, wherein the $C_H3$ amino acid sequence comprises at least one modification between amino acid residues at positions 433 and 436, wherein the modification increases the affinity of the $C_H3$ amino acid sequence to FcRn in an acidic environment (e.g., in an endosome where pH ranges from about 5.5 to about 6.0).

In one embodiment, the human constant region amino acid sequence encoded by the heavy chain constant region nucleotide sequence described herein comprises a mutation selected from the group consisting of M428L, N434S, and a combination thereof. In one embodiment, the human constant region amino acid sequence comprises a mutation selected from the group consisting of M428L, V259I, V308F, and a combination thereof. In one embodiment, the human constant region amino acid sequence comprises an N434A mutation.

In one embodiment, the human constant region amino acid sequence comprises a mutation selected from the group consisting of M252Y, S254T, T256E, and a combination thereof. In one embodiment, the human constant region amino acid sequence comprises a mutation selected from the group consisting of T250Q, M248L, or both. In one embodiment, the human constant region amino acid sequence comprises a mutation selected from the group consisting of H433K, N434Y, or both.

In one embodiment, the heavy chain constant region amino acid sequence is a non-human constant region amino acid sequence, and the heavy chain constant region amino acid sequence comprises one or more of any of the types of modifications described above.

In one embodiment, the heavy chain constant region nucleotide sequence is a human heavy chain constant region amino acid sequence, and the human heavy chain constant region amino acid sequence comprises one or more of any of the types of modifications described above.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Construction of Humanized Immunoglobulin Heavy Chain Loci Comprising Histidine-Substituted D Gene Segments Construction of immunoglobulin heavy chain loci comprising histidine-substituted human D gene segments was carried out by series of homologous recombination reactions in bacterial cells (BHR) using Bacterial Artificial Chromosome (BAC) DNA. Several targeting constructs for creation of a genetically engineered mouse that expresses a heavy chain variable domain comprising one or more histidine residues were generated using VELOCIGENE® genetic engineering technology (see, e.g., U.S. Pat. No. 6,586,251 and Valenzuela, D. M. et al. (2003), High-throughput engineering of the mouse genome coupled with high-resolution expression analysis, *Nature Biotechnology* 21(6):652-659, which is incorporated herein by reference in their entireties).

Figure 3:
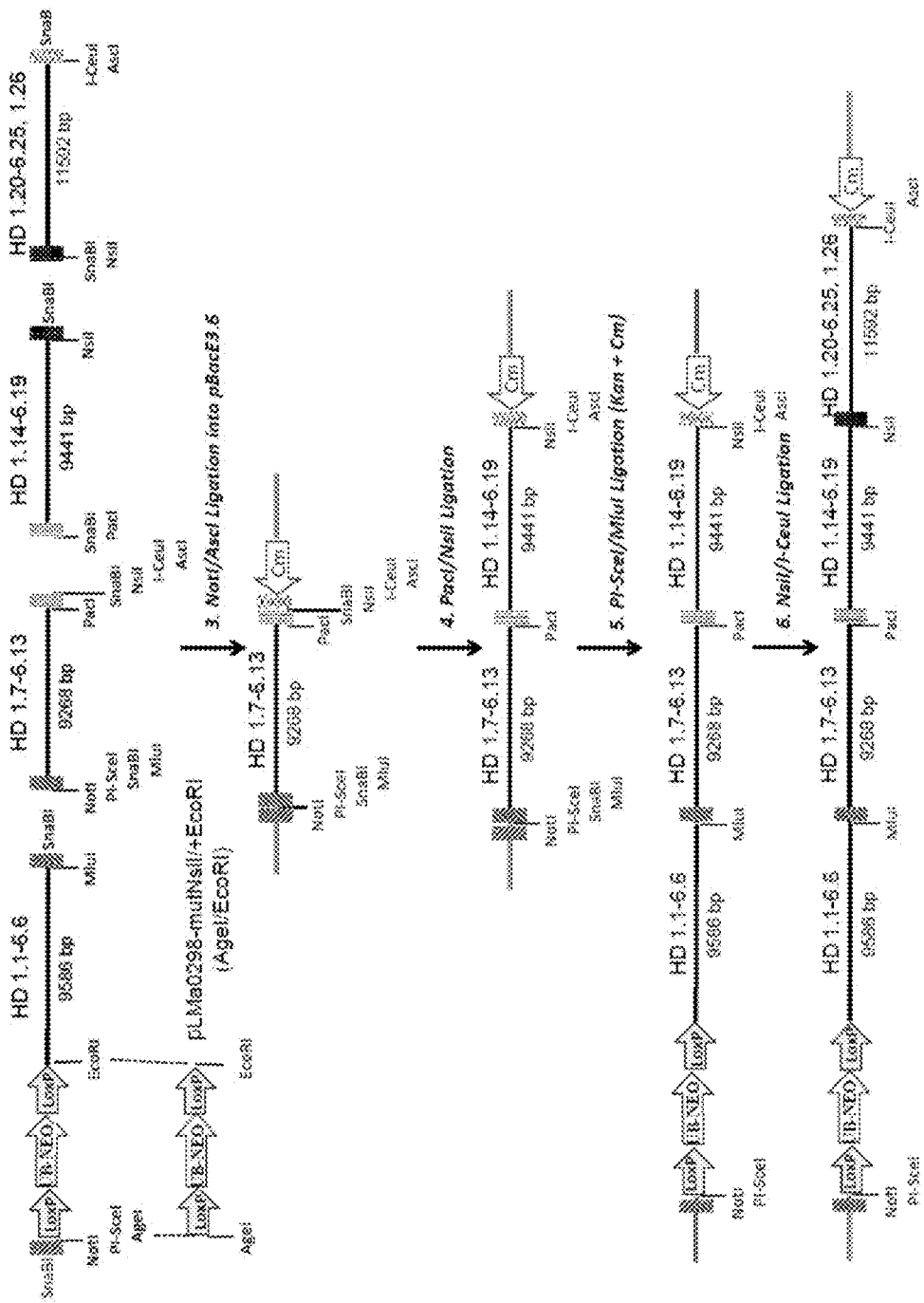
FIG. 3 illustrates schemes for assembling histidine-substituted human D gene segments via sequential ligation.

Initially, human D gene segments were synthesized in silico as four pieces (4 repeats) in which the codons encoding tyrosine (Y), asparagine (N), serine (S), glycine (G), and aspartate (D) in the hydrophilic frame were substituted with histidine codons (hereinafter "histidine-substituted human D gene segments", i.e., HD 1.1-6.6 (9586 bp; SEQ ID NO: 1), HD 1.7-6.13 (9268 bp; SEQ ID NO: 2), HD 1.14-6.19 (9441 bp; SEQ ID NO: 3), and HD 1.20-6.25, 1.26 (11592 bp; SEQ ID NO: 4) (FIG. 3). The four repeats also contained unique restriction enzyme sites at the ends for ligating them back together. The specific location of the histidine substitutions (labeled in bold type) in each human D gene segment is shown in FIGS. 1A and 1B in the column labeled "Hydrophilic." As shown in FIG. 1, while the modification introduced histidine codons in the hydrophilic reading frame, it also changed some stop codons to serine codons in the "Stop" reading frame. The modification, however, made few changes in the "Hydrophobic" reading frame. The detailed procedure for ligating the four synthesized D segment repeats is illustrated in FIG. 3 (sequential ligation). The resulting clone contained, from 5' to 3', a 5' mouse homology arm, a floxed neomycin cassette, human D gene segments comprising histidine substitutions (i.e., HD 1.1-6.6 (9586 bp; SEQ ID NO: 1), HD 1.7-6.13 (9268 bp; SEQ ID NO: 2), HD 1.14-6.19 (9441 bp; SEQ ID NO: 3), and HD 1.20-6.25, 1.26 (11592 bp; SEQ ID NO: 4)), a chloramphenicol selection cassette, and a 3' homology arm.

The following six genetic modifications were carried out in order to replace the endogenous human D gene segments in the VELOCIMMUNE® humanized mouse with the histidine-substituted human D gene segments described above.

First, pLMa0174, containing a spectinomycin selection cassette and an AsiSI restriction site, was targeted into the 5' end of the MAID 1116 clone (Step 1. BHR (Spec); FIG. 2). During Step 1, a chloramphenicol selection cassette, a neomycin selection cassette, a loxP site, two $V_H$ gene segments (hV$_H$1-3 and hV$_H$1-2), and the human Adam6p gene, all of which are located 5' upstream of hV$_H$6-1, were deleted from the MAID 1116 clone and replaced by a spectinomycin cassette to yield the V1433 clone.

Second, in Step 2 (BHR (Hyg+Spec); FIG. 2), pNTu0002 containing a hygromycin cassette flanked by FRT sites was targeted into a region comprising human immunoglobulin D$_H$ gene segments. During Step 2, all human heavy chain D gene segments were deleted from V1433 and replaced with the hygromycin cassette to yield MAID6011 VI 434 (clone 1). The modification also introduced the PI-SceI and the I-CeuI restriction sites at the 5' and 3' end of the hygromycin cassette.

Figure 4:
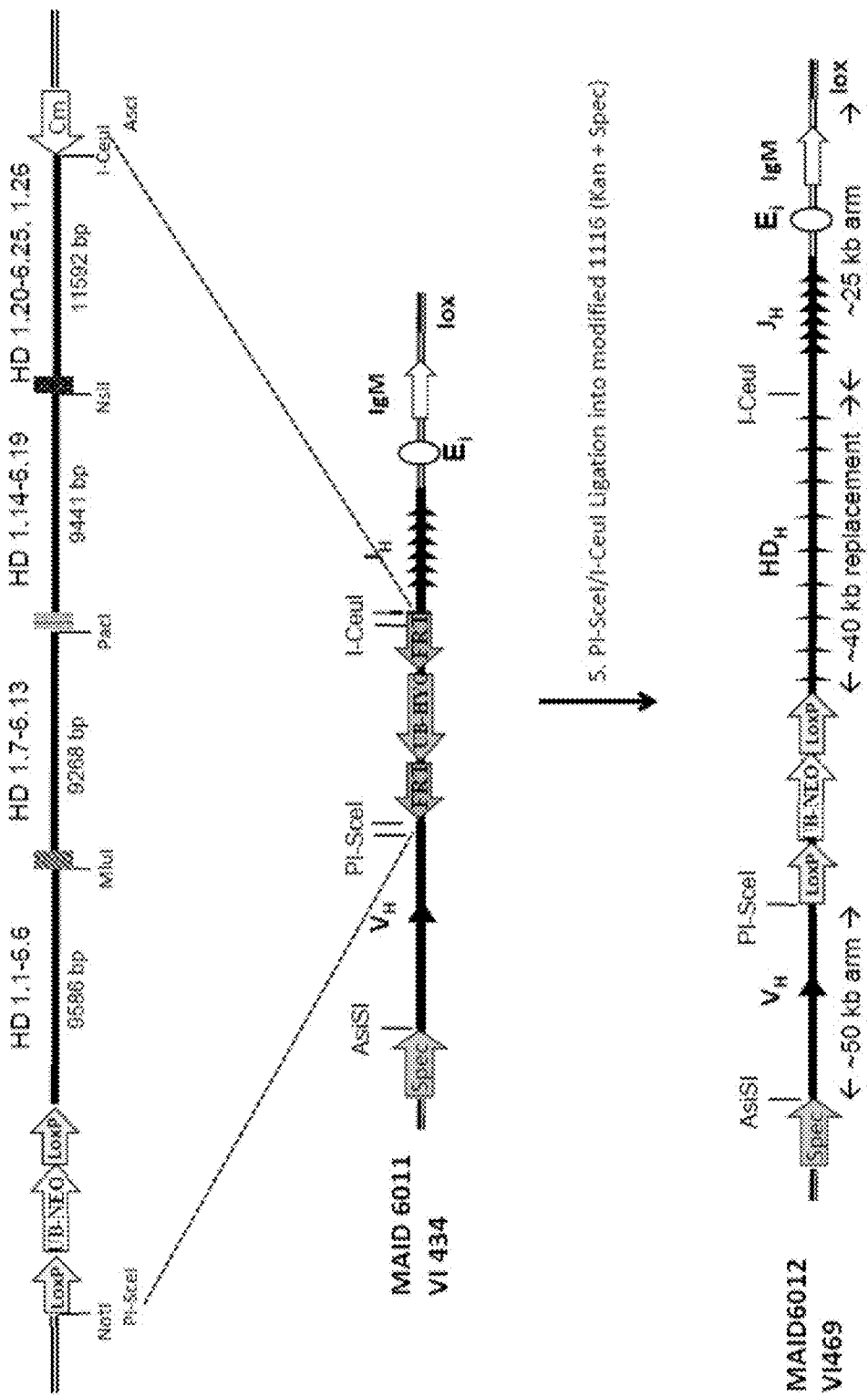
FIG. 4 illustrates the introduction of pre-assembled, histidine-substituted human D gene segments containing a neomycin cassette into a region between the most D-proximal $V_H$ gene segment ($V_H$6-1) and the most D-proximal $J_H$ gene segment ($J_H$1) via enzyme-mediated digestion (PI-SceI and I-CeuI) and ligation. This process removes the hygromycin cassette from MAID 6011 V1434 and introduces pre-assembled human histidine-substituted D gene segments into the clone. Bacterial cells comprising a successfully targeted clone are selected based on both neomycin and spectinomycin resistance. The resulting clone (MAID6012 V1469) comprises, from 5' to 3', (1) a spectinomycin selection cassette, (2) a 50 kb arm comprising a human $V_H$ gene segment ($V_H$6-1), (3) a neomycin cassette flanked by loxP sites, (4) human D gene segments containing histidine substitutions (HD 1.1-6.6 (9586 bp; SEQ ID NO: 1), HD 1.7-6.13 (9268 bp; SEQ ID NO: 2), HD 1.14-6.19 (9441 bp; SEQ ID NO: 3), and HD 1.20-6.25, 1.26 (11592 bp; SEQ ID NO: 4)), (5) about 25 kb of a genomic region containing human $J_H$ gene segments, (6) a mouse E, sequence (SEQ ID NO: 5; an intronic enhancer that promotes $V_H$ to $DJ_H$ rearrangement in developing B cells), and (7) a mouse IgM constant region nucleotide sequence (mIgM exon 1; SEQ ID NO: 7).

Third, the genomic region comprising histidine-substituted human D gene segments (HD 1.1-6.6 (9586 bp; SEQ ID NO: 1), HD 1.7-6.13 (9268 bp; SEQ ID NO: 2), HD 1.14-6.19 (9441 bp; SEQ ID NO: 3), and HD 1.20-6.25, 1.26 (11592 bp; SEQ ID NO: 4)) were introduced into a region between the PI-SceI and the I-CeuI sites of MAID 6011 V1434 via restriction digestion and ligation (PI-SceI/I-CeuI Ligation modified 1116 (Kan+Spec); FIG. 4). This yielded MAID6012 V1469 containing, from 5' to 3', a spectinomycin cassette, about 50 kb of a genomic region comprising V$_H$6-1, a floxed neomycin cassette, about 40 kb of the histidine-substituted human D gene segments (HD 1.1-6.6 (9586 bp; SEQ ID NO: 1), HD 1.7-6.13 (9268 bp; SEQ ID NO: 2), HD 1.14-6.19 (9441 bp; SEQ ID NO: 3), and HD 1.20-6.25, 1.26 (11592 bp; SEQ ID NO: 4)), and about 25 kb of a genomic region containing human J$_H$ gene segments, followed by a mouse E$_i$(mIgH intronic enhancer; SEQ ID NO: 5), a mouse switch region (SEQ ID NO: 6), and a mouse IgM constant region nucleotide sequence (mIgM exon 1; SEQ ID NO: 7). Bacterial cells containing the modification were selected based on Kanamycin and Spectinomycin selection.

Figure 5:
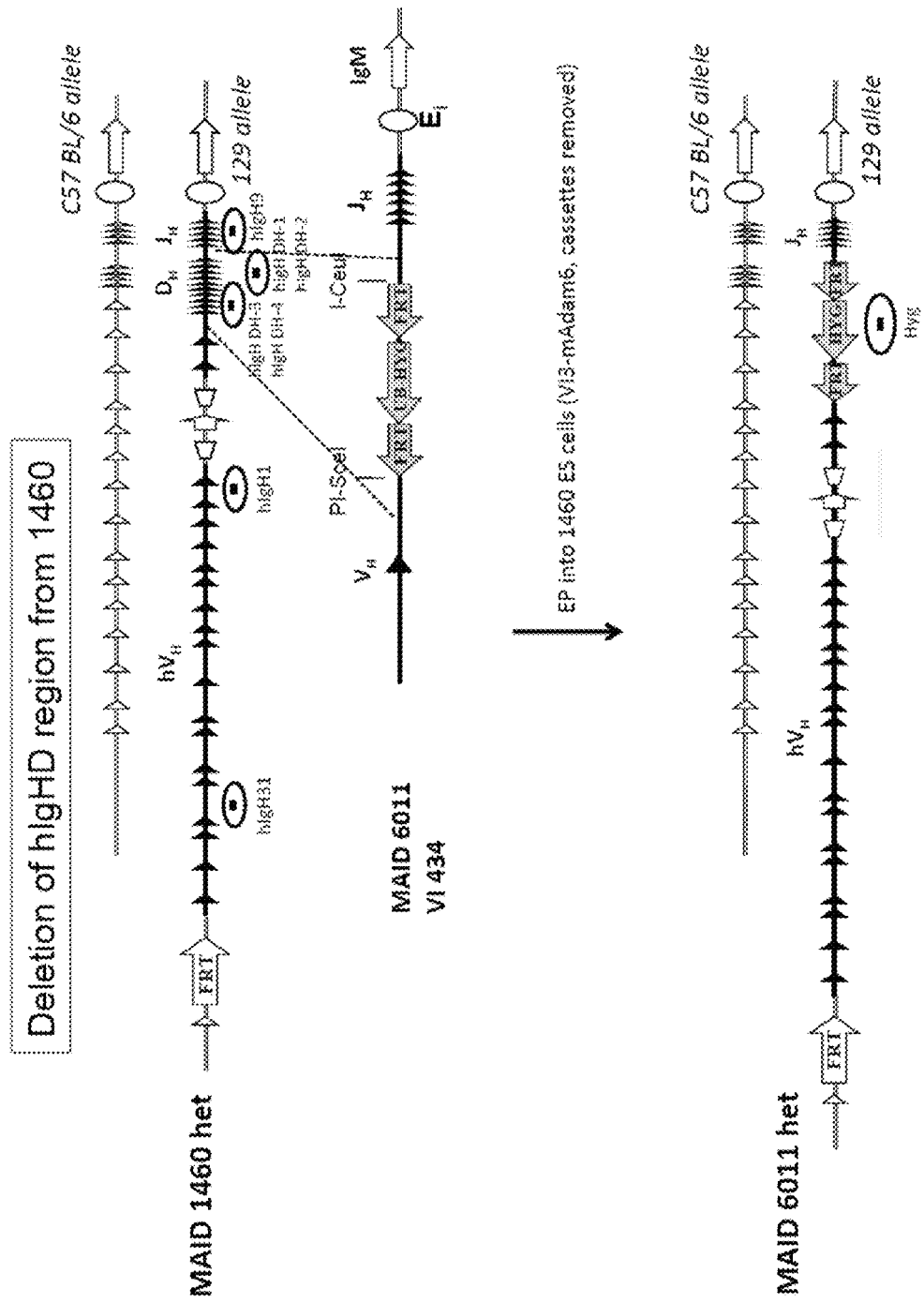
FIG. 5 illustrates schemes for deleting the human immunoglobulin heavy chain D gene region from the MAID 1460 heterozygous ES cells by targeting the 129 strain-derived chromosome of MAID 1460 het with the hygromycin selection cassette in MAID 6011 V1434.

Fourth, MAID 1460 heterozygous mouse ES cells were targeted with MAID 6011 V1434 via electroporation in order to remove all endogenous human D gene segments from the MAID 1460 clone as illustrated in FIG. 5. This yielded MAID 6011 heterozygous mouse ES cells comprising in its immunoglobulin heavy chain locus (at the 129 strain-derived chromosome), from 5' to 3', an FRT site, human V$_H$ gene segments, a mouse genomic region encompassing adam6a/b genes, a hygromycin cassette flanked by FRT sites, and human J$_H$ segments, followed by a mouse E$_i$ sequence and an IgM constant region nucleotide sequence. The genetic modification of MAID 6011 (a loss of alleles, a gain of alleles, and presence of parental alleles) was confirmed by using the probes and primers as shown in FIG. 6.

Figure 7:
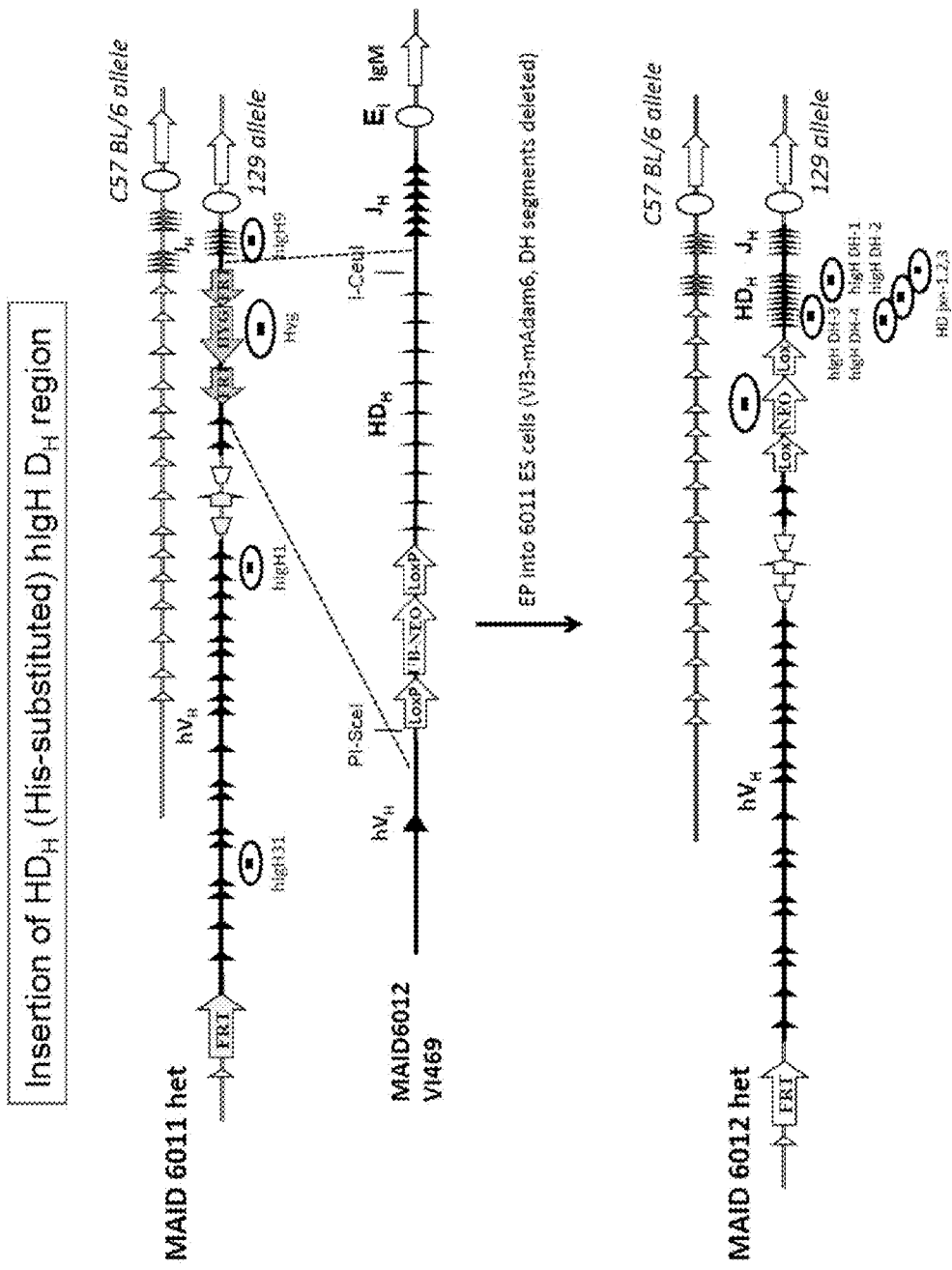
FIG. 7 illustrates schemes for constructing MAID 6012 het by targeting MAID 6011 heterozygous ES cells with MAID 6012 V1469. Electroporation of the MAID 6012 V1469 construct into the MAID 6011 heterozygous ES cells yielded MAID 6012 heterozygous ES cells in which the 129 strain-derived chromosome is modified to contain, from 5' to 3' direction, an FRT site, human $V_H$ gene segments, a mouse genomic region comprising adam6 genes, a floxed neomycin selection cassette, human D gene segments comprising histidine substitutions (HD 1.1-6.6 (9586 bp; SEQ ID NO: 1), HD 1.7-6.13 (9268 bp; SEQ ID NO: 2), HD 1.14-6.19 (9441 bp; SEQ ID NO: 3), and HD 1.20-6.25, 1.26 (11592 bp; SEQ ID NO: 4)), human $J_H$ gene segments, a mouse $E_i$ sequence (SEQ ID NO: 5; an intronic enhancer that promotes $V_H$ to $DJ_H$ rearrangement in developing B cells), and a mouse IgM constant region nucleotide sequence (mIgM exon 1; SEQ ID NO: 7).

Fifth, MAID 6011 heterozygous mouse ES cells were electroporated with MAID 6012 V1469 in order to introduce histidine-substituted human D gene segments (i.e., HD 1.1-6.6 (9586 bp; SEQ ID NO: 1), HD 1.7-6.13 (9268 bp; SEQ ID NO: 2), HD 1.14-6.19 (9441 bp; SEQ ID NO: 3), and HD 1.20-6.25, 1.26 (11592 bp; SEQ ID NO: 4)) into MAID 6011. The targeting step removed the floxed hygromycin selection cassette from MAID 6011 and replaced the sequence with the histidine-substituted human D gene segments. This lead to MAID 6012 hetrozygous ES cells comprising a wild-type C57BL/6 strain-derived chromosome and a genetically modified 129 strain-derived chromosome comprising human wild-type $V_H$ and $J_H$ gene segments and the histidine-substituted human D gene segments described herein. In addition, the ES cells contained a mouse genomic region encompassing adam6a/b genes and a floxed neomycin cassette between the $V_H$ and D segments (FIG. 7). The genetic modification of MAID 6012 (a loss of alleles, a gain of alleles, and presence of parental alleles) was confirmed by using the probes and primers as shown in FIG. 8.

Figure 9:
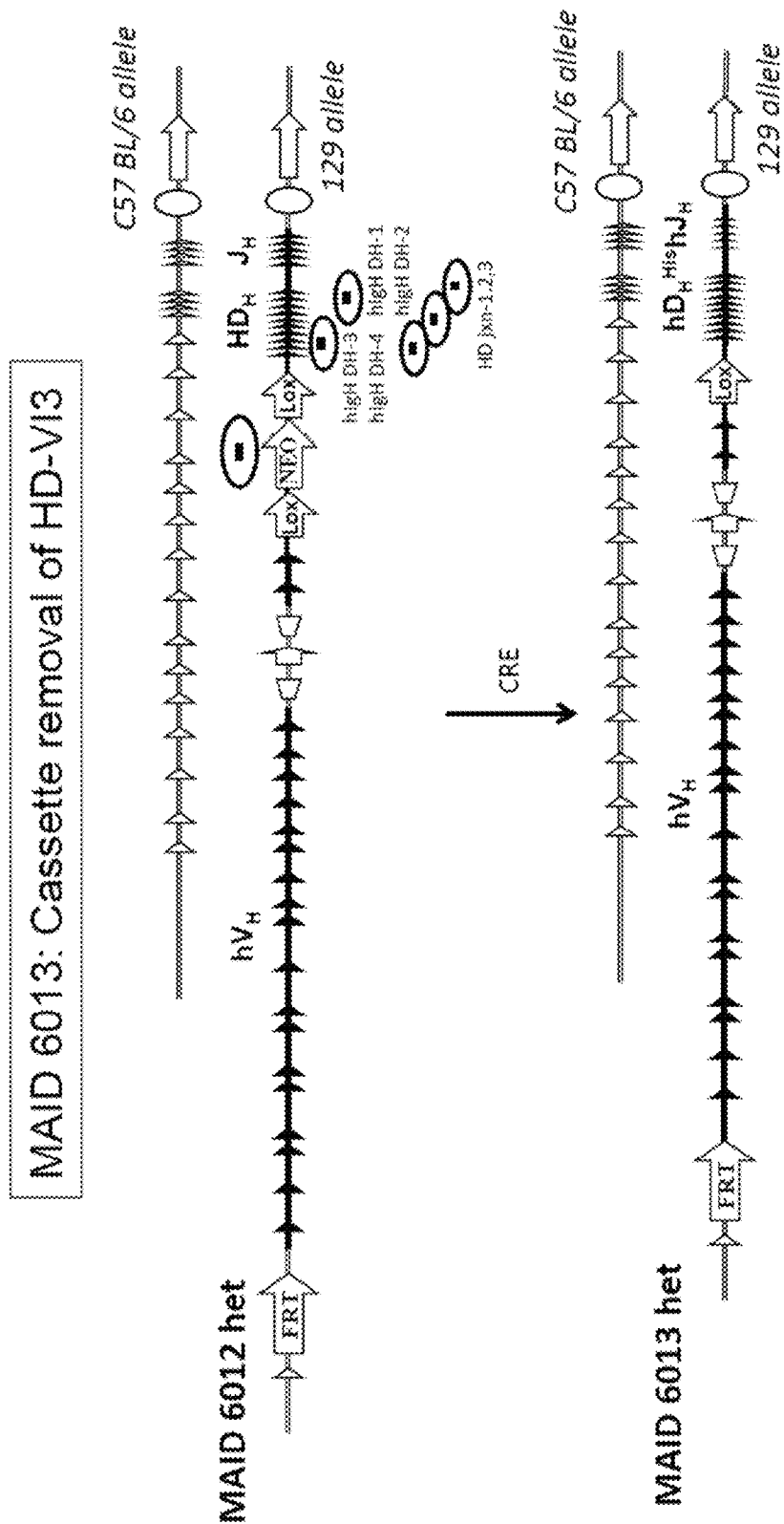
FIG. 9 illustrates schemes for removing a neomycin cassette from MAID 6012 heterozygous ES cells. Electroporation of a Cre-expressing plasmid into the MAID 6012 ES cells lead to recombination and deletion of the floxed neomycin cassette, yielding MAID 6013 heterozygous ES cells.

Lastly, MAID 6012 ES cells were electroporated with a plasmid that expresses a Cre recombinase in order to remove the neomycin selection cassette from the MAID 6012 ES cells, resulting in MAID 6013 heterozygous ES cells (FIG. 9). The final MAID 6013 heterozygous ("MAID 6013 het") ES cell contains a wild-type C57BL/6 strain-derived chromosome and a genetically modified, 129 strain-derived chromosome comprising in its immunoglobulin heavy chain locus, from 5' to 3', (1) an FRT site; (2) human $V_H$ gene segments; (3) a mouse genomic region encompassing adam6a/b genes; (4) a floxed neomycin selection cassette; (5) histidine-substituted human D gene segments (HD 1.1-6.6 (9586 bp; SEQ ID NO: 1), HD 1.7-6.13 (9268 bp; SEQ ID NO: 2), HD 1.14-6.19 (9441 bp; SEQ ID NO: 3), and HD 1.20-6.25, 1.26 (11592 bp; SEQ ID NO: 4)); (6) human $J_H$ gene segments; followed by (7) a mouse $E_\mu$ sequence (mIgH intronic enhancer; SEQ ID NO: 5), (8) a switch region (SEQ ID NO: 6); and (9) a mouse IgM constant region nucleotide sequence (mIgM exon 1; SEQ ID NO: 7) as illustrated in FIG. 9.

The targeted ES cells (MAID 6013) described above were used as donor ES cells and introduced into an 8-cell stage mouse embryo by the VELOCIMOUSE® method (see, e.g., U.S. Pat. No. 7,576,259, U.S. Pat. No. 7,659,442, U.S. Pat. No. 7,294,754, US 2008-0078000 A1, all of which are incorporated by reference herein in their entireties). Mice bearing the genetically modified immunoglobulin heavy chain locus comprising the histidine-substituted human heavy chain D gene segments described herein were identified by genotyping using the primers and probes set forth in FIG. 8. The resulting genetically modified F0 mouse was crossed to a wild-type mouse to obtain F1 offspring. F1 pups were genotyped, and the F1 pups that are heterozygous for the genetically modified immunoglobulin locus comprising histidine-substituted human heavy chain D gene segments were selected for further characterization.

Example 2

Analysis of Rearranged Heavy Chain Variable Region Nucleotide Sequences

Next, it was examined whether the genetically modified mouse comprising histidine-substituted human D gene segments described herein, i.e., 6013 F0 heterozygous mouse, which comprises in its germline a 129 strain-derived chromosome comprising human $V_H$, $J_H$ gene segments, and histidine-substituted human D gene segments (HD 1.1-6.6 (9586 bp; SEQ ID NO: 1), HD 1.7-6.13 (9268 bp; SEQ ID NO: 2), HD 1.14-6.19 (9441 bp; SEQ ID NO: 3), and HD 1.20-6.25, 1.26 (11592 bp; SEQ ID NO: 4), can express rearranged heavy chain V(D)J sequences comprising one or more histidine codons derived from the genetically modified immunoglobulin heavy chain locus.

To this end, mRNA sequences encoding IgM heavy chain variable region were analyzed for the presence of IgM CDR3 sequences derived from the histidine-substituted human D gene segments via high throughput sequencing. Briefly, spleens were harvested and homogenized in 1×PBS (Gibco) using glass slides. Cells were pelleted in a centrifuge (500×g for 5 minutes), and red blood cells were lysed in ACK Lysis buffer (Gibco) for 3 minutes. Cells were washed with 1×PBS and filtered using a 0.7 µm cell strainer. B-cells were isolated from spleen cells using MACS magnetic positive selection for CD19 (Miltenyi Biotec). Total RNA was isolated from pelleted B-cells using the RNeasy Plus kit (Qiagen). PolyA+ mRNA was isolated from total RNA using the Oligotex® Direct mRNA mini kit (Qiagen).

Double-stranded cDNA was prepared from splenic B cell mRNA by 5' RACE using the SMARTer™ Pico cDNA Synthesis Kit (Clontech). The Clontech reverse transcriptase and dNTPs were substituted with Superscript II and dNTPs from Invitrogen. Heavy chain variable region ($V_H$) antibody repertoires were amplified from the cDNA using primers specific for IgM constant regions and the SMARTer™ 5' RACE primer (Table 1). PCR products were cleaned up using a QIAquick® PCR Purification Kit (Qiagen). A second round of PCR was done using the same 5' RACE primer and a nested 3' primer specific for the IgM constant regions (Table 2). The second round PCR products were purified using a SizeSelect™ E-Gel® system (Invitrogen). A third PCR was performed with primers that added 454 adapters and barcodes. The third round PCR products were purified using Agencourt® AMPure® XP Beads. Purified PCR products were quantified by SYBR®-qPCR using a KAPA Library Quantification Kit (KAPA Biosystems). Pooled libraries were subjected to emulsion PCR (emPCR) using the 454 GS Junior Titanium Series Lib-A emPCR Kit (Roche Diagnostics) and bidirectional sequencing using Roche 454 GS Junior instrument according to the manufacturers protocols.

TABLE 1

| NAME | SEQUENCE |
|---|---|
| 3' mIgM CH1 outer | TCTTATCAGACAGGGGCTCTC (SEQ ID NO: 321) |

TABLE 2

| NAME | SEQUENCE |
|---|---|
| 3' mIgM CH1 inner | GGAAGACATTTGGGAAGGACTG (SEQ ID NO: 322) |

Bioinfomatic Analysis

The 454 sequences were sorted based on the sample barcode perfect match and trimmed for quality. Custom D database was created using histidine-substituted human D-gene segments. Sequences were annotated based on alignment of rearranged Ig sequences to human germline V and J gene segments database using local installation of igblast (NCBI, v2.2.25+). Sequences derived from the endogenous mouse immunoglobulin heavy chain locus were filtered out using similarity threshold of 90%. A sequence was marked as ambiguous and removed from analysis when multiple best hits with identical score were detected. A set of perl scripts was developed to analyze results and store data in mysql database. The CDR3 region was defined between conserved C codon and FGXG motif (SEQ ID NO: 323) for light chains and WGXG motif (SEQ ID NO: 324) for heavy chains. CDR3 length was determined using only productive antibodies. Number of histidine codons was calculated for each CDR3 region.

Figure 11:
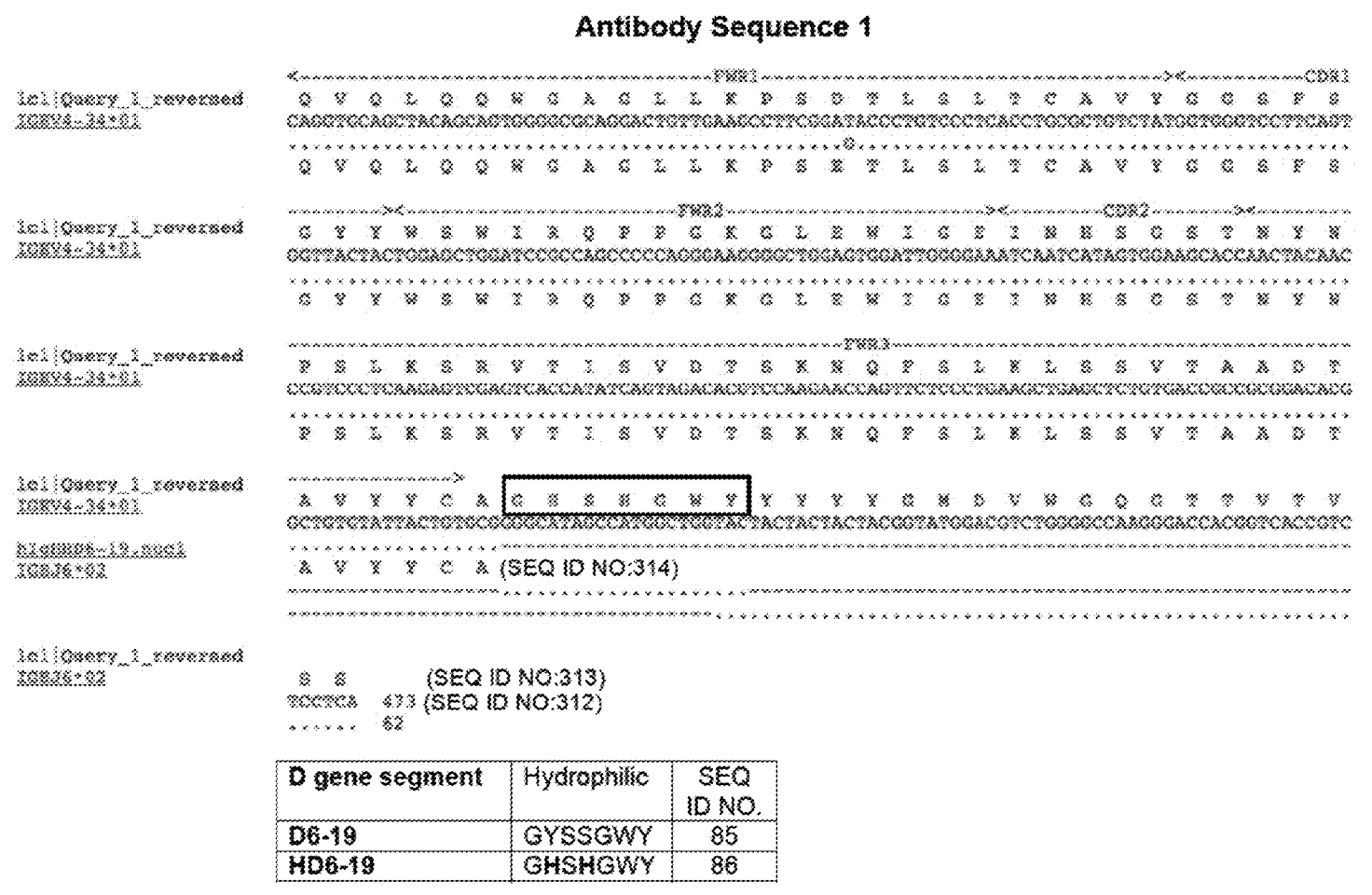
Figure 13:
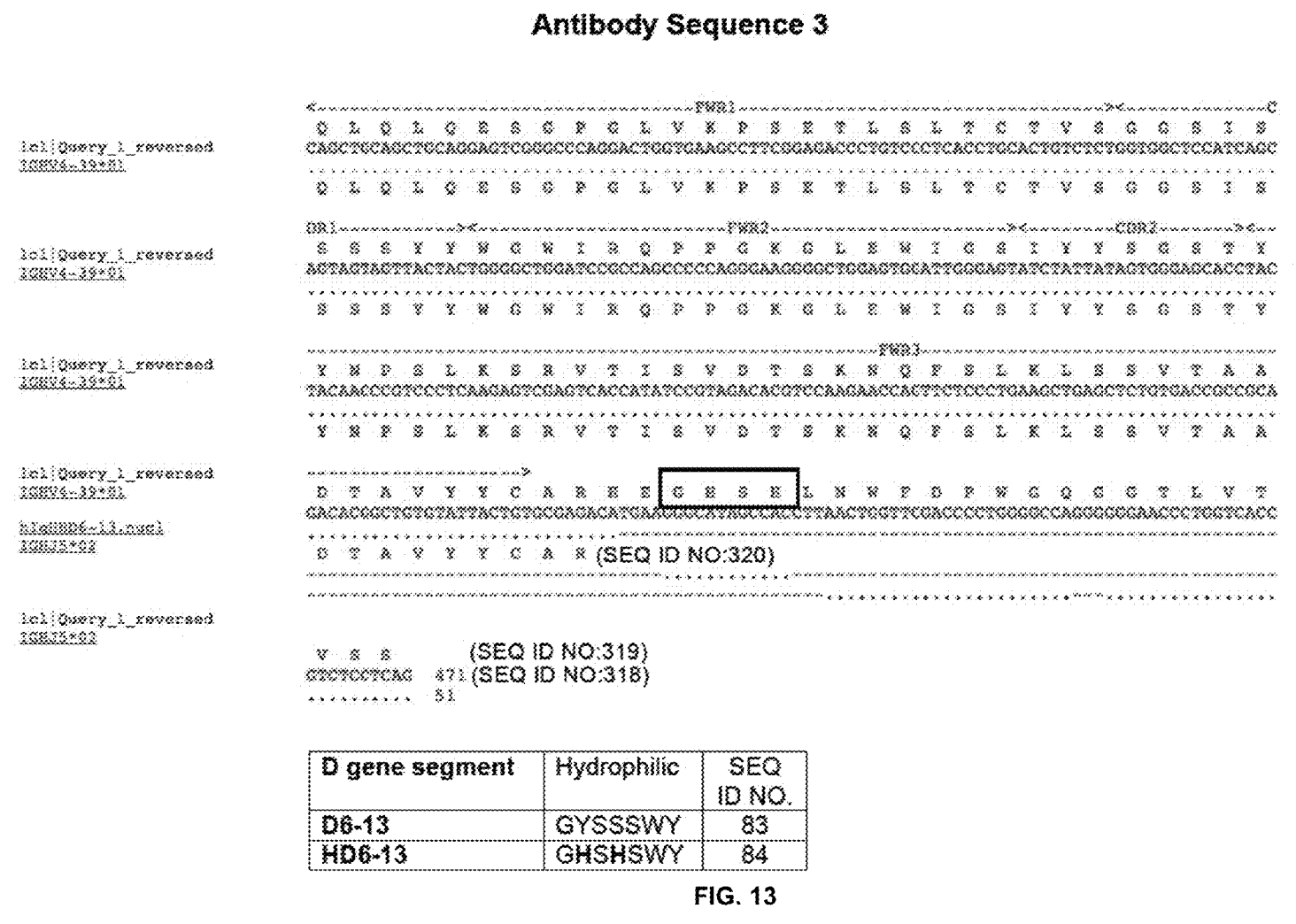
Figure 14:
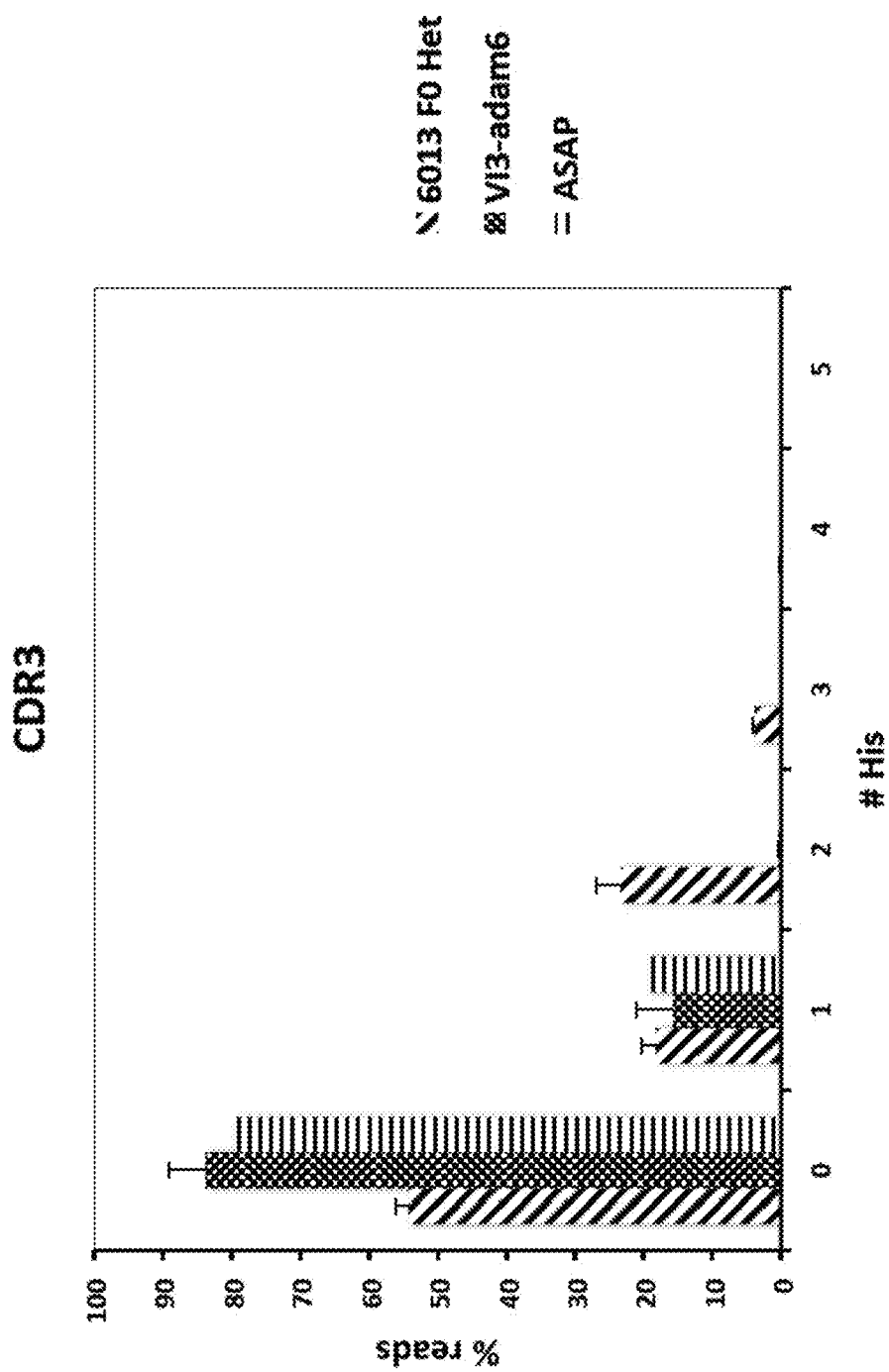
FIG. 14 illustrates histidine incorporation frequency in immunoglobulin heavy chain CDR3 sequences. The X-axis represents the number of histidine codons appeared in each CDR3 sequence, and the Y-axis represents the corresponding proportion of reads. The "6013 F0 het" indicates CDR3 sequences expressed by the 6013 heterozygous mice comprising histidine-substituted D gene segments. The "V13-Adam6" indicates CDR3 sequences obtained from control mice comprising human $V_H$, D, and $J_H$ gene segments without the histidine modification as described herein. The "ASAP" indicates CDR3 sequences obtained from the Regeneron antibody database, which was used as another control.

As shown in FIGS. 11-13, the 6013 F0 heterozygous mice expressed a diverse repertoire of rearranged heavy chain variable region mRNA sequences (rearranged V-D-J sequences) encoding one or more histidine codons in CDR3. The sequencing and alignment data suggested that the histidine codons appeared in CDR3 sequences were derived from various histidine-substituted human D gene segments present in the genetically modified immunoglobulin heavy chain locus of the 6013 mice described herein. In addition, as compared with control mice comprising human $V_H$, $D_H$, $J_H$ gene segments and mouse adam6 genes (VI3-Adam6, US Publication No. 2012/0322108A1, which is incorporated by reference in its entirety), the genetically modified 6013 F0 heterozygous mice exhibited a higher frequency of histidine occurrence in the heavy chain CDR3 sequences (FIG. 14).

While the described invention has been described with reference to the specific embodiments thereof it should be understood by those skilled in the art that various changes may be made and equivalents may be substituted without departing from the true spirit and scope of the invention. In addition, many modifications may be made to adopt a particular situation, material, composition of matter, process, process step or steps, to the objective spirit and scope of the described invention. All such modifications are intended to be within the scope of the claims appended hereto.

What is claimed is:

1. A non-human animal comprising
   (i) in its germline genome a genetically modified immunoglobulin heavy chain locus comprising an unrearranged human immunoglobulin heavy chain variable region nucleotide sequence, wherein the unrearranged heavy chain variable region nucleotide sequence comprises an addition of at least one histidine codon or a substitution of at least one non-histidine codon with a histidine codon, wherein the histidine codon is not encoded by a corresponding human germline heavy chain variable region gene segment; and
   wherein the added or substituted histidine codon is present in a complementary determining region 3 (CDR3) encoding sequence.

2. The non-human animal of claim 1, wherein the non-human animal is a mammal.

3. The non-human animal of claim 2, wherein the mammal is a rodent selected from the group consisting of a mouse, a rat, and a hamster.

4. The non-human animal of claim 1, wherein the CDR3 encoding sequence is selected from a human $V_H$ gene segment sequence, a human D gene segment sequence, a human $J_H$ gene segment sequence, and a combination thereof.

5. The non-human animal of claim 1, wherein the CDR3 encoding sequence is selected from a human germline $V_H$ gene segment sequence, a human germline D gene segment sequence, a human germline $J_H$ gene segment sequence, and a combination thereof.

6. The non-human animal of claim 5, further comprising at least a second additional or substituted histidine codon in at least one reading frame of the human immunoglobulin heavy chain gene segment that encodes a heavy chain variable domain selected from an N-terminal region, a loop 4 region, a complementary determining region 1 (CDR1), a complementary determining region 2 (CDR2), the complementary determining region 3 (CDR3), and a combination thereof.

7. The non-human animal of claim 1, wherein the endogenous non-histidine codon that is substituted with the histidine codon encodes the amino acid selected from the group consisting of Y, N, D, Q, S, W, and R.

8. The non-human animal of claim 1, wherein the added or substituted histidine codon is present in at least one reading frame of a human D gene segment.

9. The non-human animal of claim 8, wherein the reading frame is a hydrophilic frame of the human D gene segment, and the hydrophilic frame comprises a nucleotide sequence that encodes the amino acid sequence selected from the group consisting of SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, and a combination thereof.

10. The non-human animal of claim 1, wherein the unrearranged human immunoglobulin heavy chain variable region nucleotide sequence is operably linked to a human or non-human heavy chain constant region nucleotide sequence.

11. The non-human animal of claim 10, wherein the unrearranged human immunoglobulin heavy chain variable region nucleotide sequence is operably linked to an endogenous non-human heavy chain constant region nucleotide sequence selected from the group consisting of a $C_H1$, a hinge, a $C_H2$, a $C_H3$, and a combination thereof.

12. The non-human animal of claim 10, wherein the human heavy chain constant region nucleotide sequence comprises a modification that increases an affinity of a $C_H2$-$C_H3$ region of an IgG heavy chain constant region amino acid sequence to neonatal Fc receptor (FcRn) at a pH ranging from about 5.5 to about 6.0, wherein the modification is a mutation in the IgG heavy chain constant region amino acid sequence selected from the group consisting of M428L, N434S, V259I, V308F, N434A, M252Y, S254T, T256E, T250Q, H433K, N434Y, and a combination thereof.

13. The non-human animal of claim 1, wherein the non-human animal is homozygous for the genetically modified immunoglobulin heavy chain locus in the germline.

14. The non-human animal of claim 1, wherein the non-human animal further comprises an unrearranged human immunoglobulin light chain V gene segment and an unrearranged human immunoglobulin light chain J gene segment.

15. The non-human animal of claim 1, wherein the non-human animal comprises a B cell population that is capable of producing a diverse population of antigen-binding proteins that exhibit pH-dependent binding, each comprising a heavy chain variable domain having at least one histidine residue derived from the added or substituted histidine codon.

16. The non-human animal of claim 15, wherein at least one B cell of the B cell population comprises a rearranged human immunoglobulin heavy chain variable region sequence that is derived from the modified immunoglobulin heavy chain locus and that comprises at least one somatic hypermutation (SHM).

17. The non-human animal of claim 15, wherein the antigen-binding protein produced by the B cell population exhibits a decreased antigen-binding affinity at a pH ranging from about 5.5 to about 6.0 as compared with at a neutral pH ranging from about 7.0 to about 7.4.

18. The non-human animal of claim 1, wherein the non-human animal is heterozygous for the genetically modified immunoglobulin heavy chain locus in the germline.

19. The non-human animal of claim 1, wherein the non-human animal comprises an Adam6a gene, an Adam6b gene, or both.

20. A method of making a non-human animal that comprises a genetically modified immunoglobulin heavy chain locus in its germline genome, the method comprising:

(a) modifying a genome of a non-human animal to delete or render non-functional endogenous immunoglobulin heavy chain V, D, and J gene segments in an immunoglobulin heavy chain locus; and (b) placing in the genome an unrearranged human heavy chain variable region nucleotide sequence comprising an addition of at least one histidine codon or a substitution of at least one endogenous non-histidine codon with a histidine codon, wherein the histidine codon is not encoded by a corresponding human germline heavy chain variable region gene segment; and wherein the added or substituted histidine codon is present in a complementary determining region 3 (CDR3) encoding sequence.

21. The method of claim 20, wherein the CDR3 encoding sequence is selected from a human $V_H$ gene segment, a human D gene segment, a human $J_H$ gene segment, and a combination thereof.

22. The method of claim 20, wherein the CDR3 encoding sequence is selected from a human germline $V_H$ gene segment sequence, a human germline D gene segment sequence, a human germline $J_H$ gene segment sequence, and a combination thereof.

23. The method of claim 20, further comprising at least a second additional or substituted histidine codon in at least one reading frame encoding a heavy chain variable domain selected from an N-terminal region, a loop 4 region, a complementary determining region 1 (CDR1), a complementary determining region 2 (CDR2), the complementary determining region 3 (CDR3), and a combination thereof.

24. The method of claim 20, wherein the endogenous non-histidine codon that is replaced with the histidine codon encodes the amino acid selected from the group consisting of Y, N, D, Q, S, W, and R.

25. The method of claim 20, wherein the added or substituted histidine codon is present in one or more reading frame of a human D gene segment.

26. The method of claim 25, wherein the reading frame is a hydrophilic frame of the human D gene segment, and the hydrophilic frame comprises a nucleotide sequence that encodes the amino acid sequence selected from the group consisting of SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, and a combination thereof.

27. The method of claim 20, wherein the unrearranged immunoglobulin human heavy chain variable region nucleotide sequence is operably linked to a human or non-human heavy chain constant region nucleotide sequence selected from the group consisting of a $C_H1$, a hinge, a $C_H2$, a $C_H3$, and a combination thereof.

28. The method of claim 27, wherein the unrearranged immunoglobulin human heavy chain variable region nucleotide sequence is operably linked to an endogenous non-human heavy chain constant region nucleotide sequence selected from the group consisting of a $C_H1$, a hinge, a $C_H2$, a $C_H3$, and a combination thereof.

29. The method of claim 27, wherein the human heavy chain constant region nucleotide sequence comprises a modification that increases an affinity of a $C_H2$-$C_H3$ region of an IgG heavy chain constant region amino acid sequence to neonatal Fc receptor (FcRn) at a pH ranging from about 5.5 to about 6.0, wherein the modification is a mutation in the IgG heavy chain constant region amino acid sequence selected from the group consisting of M428L, N4345, V2591, V308F, N434A, M252Y, 5254T, T256E T250Q, H433K, N434Y, and a combination thereof.

30. The method of claim 20, wherein the non-human animal is homozygous for the genetically modified immunoglobulin heavy chain locus in the germline genome.

31. The method of claim 20, wherein the non-human animal comprising the genetically modified immunoglobulin heavy chain locus comprises a B cell population that is capable of producing an diverse population of antigen-binding proteins that exhibit pH-dependent binding, each comprising a heavy chain variable domain having at least one histidine residue derived from the added or substituted histidine codon.

32. The method of claim 31, wherein at least one B cell of the B cell population comprises a rearranged human immunoglobulin heavy chain variable region sequence that is derived from the modified immunoglobulin heavy chain locus and that comprises at least one somatic hypermutation (SHM).

33. The method of claim 31, wherein the antigen-binding protein produced by the B cell population exhibits a decreased antigen-binding affinity at a pH ranging from about 5.5 to about 6.0 as compared with at a neutral pH ranging from about 7.0 to about 7.4.

34. The method of claim 20, wherein the non-human animal comprises an Adam6a gene, an Adam6b gene, or both.

35. The method of claim 20, wherein the method results in a genetically modified animal that comprises a population of B cells for antibodies exhibiting enhanced pH-dependent binding to an antigen of interest.

* * * * *

SEQUENCE LISTING

```
<160> NUMBER OF SEQ ID NOS: 324

<210> SEQ ID NO 1
<211> LENGTH: 9586
<212> TYPE: DNA
<213> ORGANISM: Homo sapiens
<220> FEATURE:
<221> NAME/KEY: misc_feature
<222> LOCATION: (1)..(9586)
<223> OTHER INFORMATION: HD 1.1-6.6

<400> SEQUENCE: 1
tccccgttga agctgacctg cccagagggg cctgggccca ccccacacac cggggcggaa      60
tgtgtacagg ccccggtctc tgtgggtgtt ccgctaactg gggctcccag tgctcacccc     120
acaactaaag cgagccccag cctccagagc ccccgaagga gatgccgccc acaagcccag     180
cccccatcca ggaggcccca gagctcaggg cgccggggca gattctgaac agccccgagt     240
cacggtgggt accactggca cgaccaccgt gagaaaaact gtgtccaaaa ctgtctcctg     300
gcccctgctg gaggccgcgc cagagagggg agcagccgcc ccgaacctag gtcctgctca     360
gctcacacga cccccagcac ccagagcaca acggagtccc cattgaatgg tgaggacggg     420
gaccagggct ccaggggggtc atggaagggg ctggacccca tcctactgct atggtcccag     480
tgctcctggc cagaactgac cctaccaccg acaagagtcc ctcagggaaa cggggtcac      540 tggcacctcc cagcatcaaa cccaggcagc acaggcataa accccacatc cagagccgac     600
tccaggagca gagacacccc agtaccctgg gggacaccga ccctgatgac tccccactgg     660
aatccacccc agagtccacc aggaccaaag accccgcccc tgtctctgtc cctcactcag     720
gacctgctgc ggggcgggcc atgagaccag actcgggctt agggaacacc actgtggccc     780
caacctcgac caggccacag gcccttcctt cctgccctgc ggcagcacag actttggggt     840
ctgtgcagag aggaatcaca gaggcccag gctgaggtgg tggggtgga agaccccag       900 gaggtggccc acttcccttc ctcccagctg gaacccacca tgaccttctt aagatagggg     960
tgtcatccga ggcaggtcct ccatggagct cccttcaggc tcctccccgg tcctcactag    1020
gcctcagtcc cggctgcggg aatgcagcca ccacaggcac accaggcagc ccagaccccag    1080 ccagcctgca gtgcccaagc ccacattctg gagcagagca ggctgtgtct gggagagtct    1140
gggctcccca ccgccccccc gcacacccca cccacccctg tccaggcccct atgcaggagg    1200 gtcagagccc cccatggggt atggacttag ggtctcactc acgtggctcc cctcctgggt    1260
```

```
gaaggggtct catgcccaga tccccacagc agagctggtc aaaggtggag gcagtggccc     1320
cagggccacc ctgacctgga ccctcaggct cctctagccc tggctgccct gctgtccctg     1380
ggaggcctgg actccaccag accacaggtc cagggcaccg cccataggtg ctgcccacac     1440
tcagttcaca ggaagaagat aagctccaga cccccaagac tgggacctgc cttcctgcca     1500
ccgcttgtag ctccagacct ccgtgcctcc cccgaccact tacacacggg ccagggagct     1560
gttccacaaa gatcaaccccc aaaccgggac cgcctggcac tcgggccgct gccacttccc     1620
tctccatttg ttcccagcac ctctgtgctc cctccctcct ccctccttca ggggaacagc     1680
ctgtgcagcc cctccctgca ccccacaccc tggggaggcc caaccctgcc tcagcccctt     1740 tctccccgc tgctcttcct gcccatccag acaaccctgg ggtcccatcc ctgcagccta     1800
caccctggtc tccacccaga cccctgtctc tccctccaga caccccctccc aggccaaccc     1860 tgcacatgca ggccctcccc ttttctgctg ccagagcctc agtttctacc ctctgtgcct     1920
accccctgcc tcctcctgcc cacaactcga gctcttcctc tcctggggcc cctgagccat     1980
ggcactgacc gtgcactccc accccacac tgcccatgcc ctcaccttcc tcctggacac     2040
tctgaccccg ctccctctt ggacccagcc ctggtatttc caggacaaag gctcacccaa     2100
gtcttcccca tgcaggccct tgccctcact gcccggttac acggcagcct cctgtgcaca     2160
gaagcaggga gctcagccct tccacaggca gaaggcactg aaagaaatcg gcctccagca     2220
ccctgatgca cgtccgcctg tgtctctcac tgcccgcacc tgcagggagg ctcggcactc     2280
cctgtaaaga cgagggatcc aggcagcaac atcatgggag aatgcagggc tcccagacag     2340
cccagccctc tcgcaggcct ctcctgggaa gagacctgca gccaccactg aacagccacg     2400
gagcccgctg gatagtaact gagtcagtga ccgacctgga gggcagggga gcagtgaacc     2460
ggagcccaga ccatagggac agagaccagc cgctgacatc ccgagcccct cactggcggc     2520
cccagaacac cgcgtggaaa cagaacagac ccacattccc acctggaaca gggcagacac     2580
tgctgagccc ccagcaccag ccctgagaaa caccaggcaa cggcatcaga gggggctcct     2640 gagaagaaa ggaggggagg tctccttcac cagcaagtac ttcccttgac caaaaacagg     2700
gtccacgcaa ctcccccagg acaaaggagg agccccctgt acagcactgg gctcagagtc     2760
ctctcccaca caccctgagt ttcagacaaa aacccctgg aaatcatagt atcagcagga     2820
gaactagcca gagacagcaa gaggggactc agtgactccc gcggggacag gaggattttg     2880
tgggggctcg tgtcactgtg aggacattgt agtcatacca gctgccatac ccacagtgac     2940
acagccccat tcccaaagcc ctgctgtaaa cgcttccact tctggagctg aggggctggg     3000
gggagcgtct gggaagtagg gcctaggggt ggccatcaat gcccaaaacg caccagactc     3060
ccccccagac atcaccccac tggccagtga gcagagtaaa cagaaaatga gaagcagctg     3120
ggaagcttgc acaggcccca aggaaagagc tttggcgggt gtgcaagagg ggatgcgggc     3180
agagcctgag cagggccttt tgctgtttct gctttcctgt gcagatagtt ccataaactg     3240
gtgttcaaga tcgatggctg ggagtgagcc caggaggaca gtgtgggaag gcacaggga     3300 aggagaagca gccgctatcc tacactgtca tctttcaaga gtttgccctg tgcccacaat     3360
gctgcatcat gggatgctta acagctgatg tagacacagc taaagagaga atcagtgaaa     3420
tggatttgca gcacagatct gaataaattc tccagaatgt ggagccacac agaagcaagc     3480
acaaggaaag tgcctgatgc aagggcaaag tacagtgtgt accttcaggc tgggcacaga     3540
cactctgaaa agccttggca ggaactccct gcaacaaagc agagccctgc aggcaatgcc     3600
```

-continued

```
agctccagag ccctccctga gagcctcatg ggcaaagatg tgcacaacag gtgtttctca   3660
tagccccaaa ctgagaatga agcaaacagc catctgaagg aaaacaggca aataaacgat   3720
ggcaggttca tgaaatgcaa acccagacag ccagaaggac aacagtgagg gttacaggtg   3780
actctgtggt tgagttcatg acaatgctga gtaattggag taacaaagga aagtccaaaa   3840
aatactttca atgtgatttc ttctaaataa aatttacagc cggcaaaatg aactatcttc   3900
ttaagggata aactttccac taggaaaact ataaggaaaa tcaagaaaag gatgatcaca   3960
taaacacagt ggtcgttact tctactgggg aaggaagagg gtatgaactg agacacacag   4020
ggttggcaag tctcctaaca agaacagaac aaatacatta cagtaccttg aaaacagcag   4080
ttaaaattct aaattgcaag aagaggaaaa tgcacacagc tgtgtttaga aaattctcag   4140
tccagcactg ttcataatag caaagacatt aacccaggtt ggataaataa acgatgacac   4200
aggcaattgc acaatgatac agacatacat tcagtatatg agacattgat gatgtatccc   4260
caaagaaatg actttaaaga gaaaggcct gatatgtggt ggcactcacc tccctgggca   4320
tccccggaca ggctgcaggc acactgtgtg gcagggcagg ctggtacctg ctggcagctc   4380
ctggggcctg atgtggagca ggcacagagc cgtatccccc cgaggacata tacccccaag   4440
gacggcacag ttggtacatt ccggagacaa gcaactcagc cacactccca ggccagagcc   4500
cgagagggac gcccatgcac agggaggcag agcccagctc ctccacagcc agcagcaccc   4560
gtgcaggggc cgccatctgg caggcacaga gcatgggctg ggaggagggg cagggacacc   4620
aggcagggtt ggcaccaact gaaaattaca gaagtctcat acatctacct cagccttgcc   4680
tgacctgggc ctcacctgac ctggacctca cctggcctgg acctcacctg cctagacct   4740 cacctctggg cttcacctga gctcggcctc acctgacttg gaccttgcct gtcctgagct   4800
cacatgatct gggcctcacc tgacctgggt ttcacctgac ctgggcttca cctgacctgg   4860
gcctcatctg acctgggcct cactggcctg gacctcacct ggcctgggct tcacctggcc   4920
tcaggcctca tctgcacctg ctccaggtct tgctggaacc tcagtagcac tgaggctgca   4980
ggggctcatc cagggttgca gaatgactct agaacctccc acatctcagc tttctgggtg   5040
gaggcacctg gtggcccagg gaatataaaa agcctgaatg atgcctgcgt gatttggggg   5100
caatttataa acccaaaagg acatggccat gcagcgggta gggacaatac agacagatat   5160
cagcctgaaa tggagcctca gggcacaggt gggcacggac actgtccacc taagccaggg   5220
gcagacccga gtgtccccgc agtagacctg agagcgctgg gcccacagcc tccctcggt   5280 gccctgctac ctcctcaggt cagccctgga catcccgggt ttccccaggc ctggcggtag   5340
gtttggggtg aggtctgtgt cactgtggta tcaccatttt tggagtggtc attataccca   5400
cagtgtcaca gagtccatca aaaacccatc cctgggaacc ttctgccaca gccctccctg   5460
tggggcaccg ccgcgtgcca tgttaggatt ttgactgagg acacagcacc atgggtatgg   5520
tggctaccgc agcagtgcag cccgtgaccc aaacacacag gcagcaggc acaacagaca   5580 agcccacaag tgaccaccct gagctcctgc ctgccagccc tggagaccat gaaacagatg   5640
gccaggatta tcccataggt cagccagacc tcagtccaac aggtctgcat cgctgctgcc   5700
ctccaatacc agtccggatg gggacagggc tgcccacat taccatttgc tgccatccgg   5760
ccaacagtcc cagaagcccc tccctcaagg ctgggccaca tgtgtggacc ctgagagccc   5820
cccatgtctg agtaggggca ccaggaaggt ggggctggcc ctgtgcactg tccctgcccc   5880
tgtggtccct ggcctgcctg gccctgacac ctggcctct cctgggtcat ttccaagaca   5940
gaagacattc ccaggacagc tggagctggg agtccatcat cctgcctggc cgtcctgagt   6000
```

```
cctgcgcctt tccaaacctc acccgggaag ccaacagagg aatcacctcc cacaggcaga    6060
gacaaagacc ttccagaaat ctctgtctct ctcccagtg gcaccctct tccagggcag     6120 tcctcagtga tatcacagtg ggaacccaca tctggatcgg gactgccccc agaacacaag   6180
atggcccaca gggacagccc cacagcccag cccttcccag accctaaaa ggcgtcccac    6240 cccctgcatc tgccccaggg ctcaaactcc aggaggactg actcctgcac accctcctgc   6300
cagacatcac ctcagcccct cctggaaggg acaggagcgc gcaagggtga gtcagaccct   6360
cctgccctcg atggcaggcg gagaagattc agaaaggtct gagatcccca ggacgcagca   6420
ccactgtcaa tggggcccc agacgcctgg accagggcct gcgtgggaaa ggcctctggg    6480
cacactcagg ggcttttgt gaagggtcct cctactgtgt gaccacagtc actaccacag    6540
tgatgaaccc agcagcaaaa actgaccgga ctcccaaggt ttatgcacac ttctccgctc   6600
agagctctcc aggatcagaa gagccgggcc caagggtttc tgcccagacc ctcggcctct   6660
agggacatct tggccatgac agccatggg ctggtgcccc acacatcgtc tgccttcaaa    6720
caagggcttc agagggctct gaggtgacct cactgatgac acaggtgcc ctggccctt     6780 ccccaccagc tgcaccagac cccgtcatga cagatgcccc gattccaaca gccaattcct   6840
ggggccagga atcgctgtag acaccagcct ccttccaaca cctcctgcca attgcctgga   6900
ttcccatccc ggttggaatc aagaggacag catcccccag gctcccaaca ggcaggactc   6960
ccacaccctc ctctgagagg ccgctgtgtt ccgtagggcc aggctgcaga cagtcccct    7020 cacctgccac tagacaaatg cctgctgtag atgtccccac ctggaaaata ccactcatgg   7080
agcccccagc cccaggtaca gctgtagaga gagtctctga ggcccctaag aagtagccat   7140
gcccagttct gccgggaccc tcggccaggc tgacaggagt ggacgctgga gctgggccca   7200
tactgggcca cataggagct caccagtgag ggcaggagag cacatgccgg ggagcaccca   7260
gcctcctgct gaccagaggc ccgtcccaga gcccaggagg ctgcagaggc ctctccaggg   7320
ggacactgtg catgtctggt ccctgagcag ccccccacgt ccccagtcct gggggcccct   7380
ggcacagctg tctggaccct ctctattccc tgggaagctc ctcctgacag ccccgcctcc   7440
agttccaggt gtggttattg tcaggggtg tcagactgtg gtggacacag ccatggttac    7500
cacagtggtg ctgcccatag cagcaaccag gccaagtaga caggcccctg ctgtgcagcc   7560
ccaggcctcc agctcacctg cttctcctgg ggctctcaag gctgctgttt ctgcactct    7620 ccctctgtg gggagggttc cctcagtggg agatctgttc tcaacatccc acggcctcat    7680
tcctgcaagg aaggccaatg gatgggcaac ctcacatgcc gcggctaaga tagggtgggc   7740
agcctggcgg ggacaggaca tcctgctggg gtatctgtca ctgtgcctag tggggcactg   7800
gctcccaaac aacgcagtcc ttgccaaaat cccacggcc tccccgcta ggggctggcc     7860 tgatctcctg cagtcctagg aggctgctga cctccagaat ggctccgtcc ccagttccag   7920
ggcgagagca gatcccaggc cggctgcaga ctggaggcc accccctcct tcccagggtt    7980
cactgcaggt gaccagggca ggaaatggcc tgaacacagg ataaccgggg ccatccccca   8040
acagagtcca cccctcctg ctctgtaccc cgcaccccc aggccagccc atgacatccg     8100
acaaccccac accagagtca ctgccggtgt ctgcctagg gaggacccct cagccccac     8160 cctgtctaga ggactgggga ggacaggaca cgccctctcc ttatggttcc cccacctggc   8220
tctggctggg acccttgggg tgtggacaga aaggacgctt gcctgattgg ccccaggag    8280 cccagaactt ctctccaggg accccagccc gagcacccc ttacccagga cccagccctg    8340
```

| | |
|---|---|
| cccctcctcc cctctgctct cctctcatca ccccatggga atccagaatc cccaggaagc | 8400 |
| catcaggaag ggctgaggga ggaagtgggg ccactgcacc accaggcagg aggctctgtc | 8460 |
| tttgtgaacc cagggaggtg ccagcctcct agagggtatg gtccaccctg cctatggctc | 8520 |
| ccacagtggc aggctgcagg gaaggaccag ggacggtgtg ggggagggct cagggccccg | 8580 |
| cgggtgctcc atcttggatg agcctatctc tctcacccac ggactcgccc acctcctctt | 8640 |
| caccctggcc acacgtcgtc cacaccatcc taagtcccac ctacaccaga gccggcacag | 8700 |
| ccagtgcaga cagaggctgg ggtgcagggg ggccgactgg gcagcttcgg ggagggagga | 8760 |
| atggaggaag gggagttcag tgaagaggcc ccctcccct gggtccagga tcctcctctg | 8820 |
| ggaccccgg atcccatccc ctccaggctc tgggaggaga agcaggatgg gagaatctgt | 8880 |
| gcgggaccct ctcacagtgg aatacctcca cagcggctca ggccagatac aaaagcccct | 8940 |
| cagtgagccc tccactgcag tgctgggcct gggggcagcc gctcccacac aggatgaacc | 9000 |
| cagcaccccg aggatgtcct gccaggggga gctcagagcc atgaaggagc aggatatggg | 9060 |
| accccgata caggcacaga cctcagctcc attcaggact gccacgtcct gccctgggag | 9120 |
| gaacccttt ctctagtccc tgcaggccag gaggcagctg actcctgact tggacgccta | 9180 |
| ttccagacac cagacagagg ggcaggcccc ccagaaccag ggatgaggac gccccgtcaa | 9240 |
| ggccagaaaa gaccaagttg cgctgagccc agcaagggaa ggtccccaaa caaaccagga | 9300 |
| agtttctgaa ggtgtctgtg tcacagtgga gcatagccac tcgtcccaca gtgacactcg | 9360 |
| ccaggccaga aaccccatcc caagtcagcg gaatgcagag agagcaggga ggacatgttt | 9420 |
| aggatctgag gccgcacctg cacccaggc cagcagacgt ctcctgtcca cggcaccctg | 9480 |
| ccatgtcctg catttctgga agaacaaggg caggctgaag ggggtccagg accaggagat | 9540 |
| gggtccgctc tacccagaga aggagccagg caggacacaa gccccc | 9586 |

<210> SEQ ID NO 2
<211> LENGTH: 9268
<212> TYPE: DNA
<213> ORGANISM: Homo sapiens
<220> FEATURE:
<221> NAME/KEY: misc_feature
<222> LOCATION: (1)..(9268)
<223> OTHER INFORMATION: HD 1.7-6.13

<400> SEQUENCE: 2

| | |
|---|---|
| tccccattga ggctgacctg cccagagggt cctgggccca cccaacacac cggggcggaa | 60 |
| tgtgtgcagg cctcggtctc tgtgggtgtt ccgctagctg gggctcacag tgctcacccc | 120 |
| acacctaaaa cgagccacag cctccggagc ccctgaagga gaccccgccc acaagcccag | 180 |
| cccccaccca ggaggcccca gagcacaggg cgccccgtcg gattctgaac agccccgagt | 240 |
| cacagtgggt atcactggca ctaccactgt gagaaaagct tcgtccaaaa cggtctcctg | 300 |
| gccacagtcg gaggcccgc cagagagggg agcagccacc ccaaacccat gttctgccgg | 360 |
| ctcccatgac cccgtgcacc tggagcccca cggtgtcccc actggatggg aggacaaggg | 420 |
| ccgggggctc cggcgggtcg gggcaggggc ttgatggctt ccttctgccg tggccccatt | 480 |
| gcccctggct ggagttgacc cttctgacaa gtgtcctcag agagtcaggg atcagtggca | 540 |
| cctcccaaca tcaaccccac gcagcccagg cacaaacccc acatccaggg ccaactccag | 600 |
| gaacagagac accccaatac cctggggac cccgaccctg atgactcccg tccatctct | 660 |
| gtccctcact tggggcctgc tgcggggcga gcacttggga gcaaactcag gcttagggga | 720 |
| caccactgtg ggcctgacct cgagcaggcc acagacccct ccctcctgcc ctggtgcagc | 780 |

```
acagactttg gggtctgggc agggaggaac ttctggcagg tcaccaagca cagagccccc    840
aggctgaggt ggccccaggg ggaacccag caggtggccc actacccttc ctcccagctg    900
gaccccatgt cttccccaag atagggtgc catccaaggc aggtcctcca tggagccccc    960
ttcaggctcc tctccagacc ccactgggcc tcagtcccca ctctaggaat gcagccacca   1020
cgggcacacc aggcagccca ggcccagcca ccctgcagtg cccaagccca caccctggag   1080
gagagcaggg tgcgtctggg aggggctggg ctccccaccc ccaccccac ctgcacaccc    1140
cacccacccct tgcccgggcc cctgcagga gggtcagagc cccatgggga tatggactta   1200
gggtctcact cacgcacctc ccctcctggg agaaggggtc tcatgcccag atcccccag    1260
cagcgctggt cacaggtaga ggcagtggcc ccagggccac cctgacctgg cccctcaggc   1320
tcctctagcc ctggctgccc tgctgtccct gggaggcctg ggctccacca gaccacaggt   1380
ctagggcacc gcccacactg gggccgccca cacacagctc acaggaagaa gataagctcc   1440
agacccccag gccgggacc tgccttgctg ctacgacttc ctgccccaga cctcgttgcc    1500
ctccccgtc cacttacaca caggccagga agctgttccc acacagacca accccagacg    1560
gggaccacct ggcactcagg tcactgccat ttccttctcc attcacttcc aatgcctctg   1620
tgcttcctcc ctcctccttc cttcggggga gcaccctgtg cagctcctcc ctgcagtcca   1680
cacccctgggg agacccgacc ctgcagccca caccctgggg agacctgacc ctcctccagc  1740
cctttctccc ccgctgctct tgccacccac caagacagcc ctggggtcct gtccctacag   1800
cccccacccca gttctctacc tagaccccgtc ttcctccctc taaacacctc tcccaggcca  1860
accctacacc tgcaggccct cccctccact gccaaagacc ctcagtttct cctgcctgtg   1920
cccacccccg tgctcctcct gcccacagct cgagctcttc ctctcctagg gccctgagg    1980
gatggcattg accgtgccct cgcacccaca cactgcccat gccctcacat tcctcctggc   2040
cactccagcc ccactcccct ctcaggcctg gctctggtat ttctgggaca aagccttacc   2100
caagtctttc ccatgcaggc ctgggccctt accctcactg cccggttaca gggcagcctc   2160
ctgtgcacag aagcagggag ctcagccctt ccacaggcag aaggcactga agaaatcgg    2220
cctccagcgc cttgacacac gtctgcctgt gtctctcact gcccgcacct gcagggaggc   2280
tcggcactcc ctctaaagac gagggatcca ggcagcagca tcacaggaga atgcagggct   2340
accagacatc ccagtcctct cacaggcctc tcctgggaag agacctgaag acgcccagtc   2400
aacggagtct aacaccaaac ctccctggag gccgatgggt agtaacggag tcattgccag   2460
acctggaggc aggggagcag tgagcccgag cccacaccat agggccagag acagccact    2520
gacatcccaa gccactcact ggtggtccca caacacccca tggaaagagg acagacccac   2580
agtcccacct ggaccagggc agagactgct gagacccagc accagaacca accaagaaac   2640
accaggcaac agcatcagag ggggctctgg cagaacagag gagggaggt tccttcacc    2700
agcaggcgct tcccttgacc gaagacagga tccatgcaac tcccccagga caaaggagga   2760
gcccccttgtt cagcactggg ctcagagtcc tctccaagac acccagagtt tcagacaaaa   2820
acccctggga atgcacagtc tcagcaggag agccagccag agccagcaag atggggctca   2880
gtgacacccg cagggacagg aggatttttgt gggggctcgt gtcactgtga ggacattgta   2940
ctcatggtgt atgccatacc cacagtgaca cagcccccatt cccaaagccc tactgcaaac   3000
gcattccact tctggggctg aggggctggg ggagcgtctg ggaaataggg ctcaggggtg   3060
tccatcaatg cccaaaacgc accagactcc cctccataca tcacacccac cagccagcga   3120
```

```
gcagagtaaa cagaaaatga gaagcaagct ggggaagctt gcacaggccc caaggaaaga   3180
gctttggcgg gtgtgtaaga ggggatgcgg cagagcctg agcagggcct tttgctgttt    3240
ctgctttcct gtgcagagag ttccataaac tggtgttcga gatcaatggc tgggagtgag   3300
cccaggagga cagcgtggga agagcacagg aaggaggag cagccgctat cctacactgt    3360
catctttcga aagtttgcct tgtgcccaca ctgctgcatc atgggatgct taacagctga   3420
tgtagacaca gctaaagaga gaatcagtga gatggatttg cagcacagat ctgaataaat   3480
tctccagaat gtggagcagc acagaagcaa gcacacagaa agtgcctgat gcaaggacaa   3540
agttcagtgg gcaccttcag gcattgctgc tgggcacaga cactctgaaa agccctggca   3600
ggaactccct gtgacaaagc agaaccctca ggcaatgcca gccccagagc cctccctgag   3660
agcctcatgg gcaaagatgt gcacaacagg tgtttctcat agcccaaaac tgagagcaaa   3720
gcaaacgtcc atctgaagga gaacaggcaa ataaacgatg gcaggttcat gaaatgcaaa   3780
cccagacagc cacaagcaca aaagtacagg gttataagcg actctggttg agttcatgac   3840
aatgctgagt aattggagta acaaagtaaa ctccaaaaaa tactttcaat gtgatttctt   3900
ctaaataaaa tttacaccct gcaaaatgaa ctgtcttctt aagggataca tttcccagtt   3960
agaaaaccat aaagaaaacc aagaaaagga tgatcacata aacacagtgg tggttacttc   4020
tgctggggaa ggaagagggt atgaactgag atacacaggg tgggcaagtc tcctaacaag   4080
aacagaacga atacattaca gtaccttgaa aacagcagtt aaacttctaa attgcaagaa   4140
gaggaaaatg cacacagttg tgtttagaaa attctcagtc cagcactgtt cataatagca   4200
aagacattaa cccaggtcgg ataaataagc gatgacacag gcaattgcac aatgatacag   4260
acatatattt agtatatgag acatcgatga tgtatcccca aataaacgac tttaaagaga   4320
taaagggctg atgtgtggtg gcattcacct ccctgggatc cccggacagg ttgcaggctc   4380
actgtgcagc agggcaggcg ggtacctgct ggcagttcct ggggcctgat gtggagcaag   4440
cgcagggcca tatatcccgg aggacggcac agtcagtgaa ttccagagag aagcaactca   4500
gccacactcc ccaggcagag cccgagaggg acgcccacgc acagggaggc agagcccagc   4560
acctccgcag ccagcaccac ctgcgcacgg gccaccacct tgcaggcaca gagtgggtgc   4620
tgagaggagg ggcagggaca ccaggcaggg tgagcaccca gagaaaactg cagacgcctc   4680
acacatccac ctcagcctcc cctgacctgg acctcactgg cctgggcctc acttaacctg   4740
ggcttcacct gaccttggcc tcacctgact tggacctcgc ctgtcccaag ctttacctga   4800
cctgggcctc aactcacctg aacgtctcct gacctgggtt taacctgtcc tggaactcac   4860
ctggccttgg cttcccctga cctggacctc atctggcctg gcttcacct ggcctgggcc    4920 tcacctgacc tggacctcat ctggcctgga cctcacctgg cctggacttc acctggcctg   4980
ggcttcacct gacctggacc tcacctggcc tcgggcctca cctgcacctg ctccaggtct   5040
tgctggagcc tgagtagcac tgagggtgca gaagctcatc cagggttggg gaatgactct   5100
agaagtctcc cacatctgac ctttctgggt ggaggcagct ggtggccctg ggaatataaa   5160
aatctccaga atgatgactc tgtgatttgt gggcaactta tgaacccgaa aggacatggc   5220
catggggtgg gtagggacat agggacagat gccagcctga ggtggagcct caggacacag   5280
gtgggcacgg acactatcca cataagcgag ggatagaccc gagtgtcccc acagcagacc   5340
tgagagcgct gggcccacag cctcccctca gagccctgct gcctcctccg gtcagccctg   5400
gacatcccag gtttccccag gcctggcggt aggtttagaa tgaggtctgt gtcactgtgg   5460
tatcaccata ttttgactgg tcattataac cacagtgtca cagagtccat caaaaaccca   5520
```

```
tgcctggaag cttcccgcca cagccctccc catggggccc tgctgcctcc tcaggtcagc    5580
cccggacatc ccgggtttcc ccaggctggg cggtaggttt ggggtgaggt ctgtgtcact    5640
gtggtatcac catggttcgg ggagtcatta taaccacagt gtcacagagt ccatcaaaaa    5700
cccatccctg ggagcctccc gccacagccc tccctgcagg ggaccggtac gtgccatgtt    5760
aggattttga tcgaggagac agcaccatgg gtatggtggc taccacagca gtgcagcctg    5820
tgacccaaac ccgcagggca gcaggcacga tggacaggcc cgtgactgac cacgctgggc    5880
tccagcctgc cagccctgga gatcatgaaa cagatggcca aggtcaccct acaggtcatc    5940
cagatctggc tccaggggt ctgcatcgct gctgccctcc caacgccagt ccaaatggga    6000
cagggacggc ctcacagcac catctgctgc catcaggcca gcgatcccag aagcccctcc    6060
ctcaaggctg ggcacatgtg tggacactga gagccctcat atctgagtag ggcaccagg    6120 agggagggc tggccctgtg cactgtccct gcccctgtgg tccctggcct gcctggccct    6180
gacacctgag cctctcctgg gtcatttcca agacagaaga cattcctggg gacagccgga    6240
gctgggcgtc gctcatcctg cccggccgtc ctgagtcctg ctcatttcca gacctcaccg    6300
gggaagccaa cagaggactc gcctcccaca ttcagagaca aagaaccttc cagaaatccc    6360
tgcctctctc cccagtggac accctcttcc aggacagtcc tcagtggcat cacagcggcc    6420
tgagatcccc aggacgcagc accgctgtca ataggggccc caaatgcctg gaccagggcc    6480
tgcgtgggaa aggcctctgg ccacactcgg gcttttttgtg aagggccctc ctgctgtgtg    6540
accacagtca ctaccatagt gatgaaccca gtggcaaaaa ctggctggaa acccaggggc    6600
tgtgtgcacg cctcagcttg gagctctcca ggagcacaag agccgggccc aaggatttgt    6660
gcccagaccc tcagcctcta gggacacctg ggtcatctca gctgggctg gtgccctgca    6720 caccatcttc ctccaaatag gggcttcaga gggctctgag gtgacctcac tcatgaccac    6780
aggtgacctg gccttccct gccagctata ccagaccctg tcttgacaga tgccccgatt    6840
ccaacagcca attcctggga ccctgaatag ctgtagacac cagcctcatt ccagtacctc    6900
ctgccaattg cctggattcc catcctggct ggaatcaaga aggcagcatc cgccaggctc    6960
ccaacaggca ggactcccgc acaccctcct ctgagaggcc gctgtgttcc gcagggccag    7020
gccctggaca gttcccctca cctgccacta gagaaacacc tgccattgtc gtccccacct    7080
ggaaaagacc actcgtggag cccccagccc caggtacagc tgtagagaca gtcctcgagg    7140
cccctaagaa ggagccatgc ccagttctgc cgggaccctc ggccaggccg acaggagtgg    7200
acgctggagc tgggcccaca ctgggccaca taggagctca ccagtgaggg caggagagca    7260
catgccgggg agcacccagc ctcctgctga ccagaggccc gtcccagagc caggaggct    7320 gcagaggcct ctccagggag acactgtgca tgtctggtac ctaagcagcc ccccacgtcc    7380
ccagtcctgg gggcccctgg ctcagctgtc tgggcccctcc ctgctccctg ggaagctcct    7440
cctgacagcc ccgcctccag ttccaggtgt ggttattgtc aggcgatgtc agactgtggt    7500
ggacatagtg gccaccatta ccacagtggt gccgcccata gcagcaacca ggccaagtag    7560
acaggcccct gctgcgcagc cccaggcatc cacttcacct gcttctcctg gggctctcaa    7620
ggctgctgtc tgtcctctgg ccctctgtgg ggagggttcc ctcagtggga ggtctgtgct    7680
ccagggcagg gatgattgag atagaaatca aaggctggca gggaaaggca gcttcccgcc    7740
ctgagaggtg caggcagcac cacggagcca cggagtcaca gagccacgga gccccattg    7800 tgggcatttg agagtgctgt gccccggca ggccagccc tgatggggaa gcctgtccca    7860
```

```
tcccacagcc cgggtcccac gggcagcggg cacagaagct gccaggttgt cctctatgat    7920
cctcatccct ccagcagcat cccctccaca gtggggaaac tgaggcttgg agcaccaccc    7980 ggcccctgg aaatgaggct gtgagcccag acagtgggcc cagagcactg tgagtacccc     8040
ggcagtacct ggctgcaggg atcagccaga gatgccaaac cctgagtgac cagcctacag    8100
gaggatccgg ccccacccag gccactcgat taatgctcaa ccccctgccc tggagacctc    8160
ttccagtacc accagcagct cagcttctca gggcctcatc cctgcaagga aggtcaaggg    8220
ctgggcctgc agaaacaca gcaccctccc tagccctggc taagacaggg tgggcagacg     8280
gctgtggacg ggacatattg ctggggcatt tctcactgtc acttctgggt ggtagctctg    8340
acaaaaacgc agaccctgcc aaaatcccca ctgcctcccg ctaggggctg gcctggaatc    8400
ctgctgtcct aggaggctgc tgacctccag gatggctccg tccccagttc cagggcgaga    8460
gcagatccca ggcaggctgt aggctgggag gccacccctg cccttgccgg ggttgaatgc    8520
aggtgcccaa gcaggaaat ggcatgagca cagggatgac cgggacatgc cccaccagag     8580
tgcgcccctt cctgctctgc accctgcacc ccccaggcca gccacgacg tccaacaact     8640 gggcctgggt ggcagcccca cccagacagg acagacccag caccctgagg aggtcctgcc    8700 aggggagct aagagccatg aaggagcaag atatggggcc cccgatacag gcacagatgt     8760
cagctccatc caggaccacc cagcccacac cctgagagga acgtctgtct ccagcctctg    8820
caggtcggga ggcagctgac ccctgacttg gaccccatt ccagacacca gacagaggcg     8880
caggcccccc agaaccaggg ttgagggacg ccccgtcaaa gccagacaaa accaaggggt    8940
gttgagccca gcaagggaag gcccccaaac agaccaggag gtttctgaag gtgtctgtgt    9000
cacagtgggg catagccaca gctggtacca cagtgacact cacccagcca gaaaccccat    9060
tccaagtcag cggaagcaga gagagcaggg aggacacgtt taggatctga gactgcacct    9120
gacacccagg ccagcagacg tctcccctcc agggcacccc accctgtcct gcatttctgc    9180
aagatcaggg gcggcctgag ggggggtcta gggtgaggag atgggtcccc tgtacaccaa    9240
ggaggagtta ggcaggtccc gagcactc                                       9268
```

<210> SEQ ID NO 3
<211> LENGTH: 9441
<212> TYPE: DNA
<213> ORGANISM: Homo sapiens
<220> FEATURE:
<221> NAME/KEY: misc_feature
<222> LOCATION: (1)..(9441)
<223> OTHER INFORMATION: HD 1.14-6.19

<400> SEQUENCE: 3

```
tccccattga ggctgacctg cccagagagt cctgggccca ccccacacac cggggcggaa      60
tgtgtgcagg cctcggtctc tgtgggtgtt ccgctagctg gggctcacag tgctcacccc     120
acacctaaaa tgagccacag cctccggagc cccgcagga ccccgccc acaagcccag        180 ccccacccca ggaggcccca gagctcaggg cgccccgtcg gattccgaac agccccgagt     240
cacagcgggt ataaccggaa ccaccactgt cagaatagct acgtcaaaaa ctgtccagtg     300
gccactgccg gaggccccgc cagagagggc agcagccact ctgatcccat gtcctgccgg    360
ctcccatgac ccccagcacg cggagcccca cagtgtcccc actggatggg aggacaagag    420
ctggggattc cggcgggtcg gggcagggc ttgatcgcat ccttctgccg tggctccagt     480
gcccctggct ggagttgacc cttctgacaa gtgtcctcag agacagggc atcaccggcg     540 cctcccaaca tcaaccccag gcagcacagg cacaaacccc acatccagag ccaactccag    600
```

```
gagcagagac accccaatac cctggggac cccgaccctg atgacttccc actggaattc        660
gccgtagagt ccaccaggac caaagaccct gcctctgcct ctgtccctca ctcaggacct        720
gctgccgggc gaggccttgg gagcagactt gggcttaggg gacaccagtg tgaccccgac        780
cttgaccagg acgcagacct ttccttcctt tcctggggca gcacagactt tggggtctgg        840
gccaggagga acttctggca ggtcgccaag cacagaggcc acaggctgag gtggccctgg        900
aaagacctcc aggaggtggc cactcccctt cctcccagct ggaccccatg tcctccccaa        960
gataagggtg ccatccaagg caggtgctcc ttggagcccc attcagactc ctccctggac       1020
cccactgggc ctcagtccca gctctgggga tgaagccacc acaagcacac caggcagccc       1080
aggcccagcc accctgcagt gcccaagcac acactctgga gcagagcagg gtgcctctgg       1140
gaggggctga gctccccacc ccaccccccac ctgcacaccc cacccacccc tgcccagcgg       1200
ctctgcagga gggtcagagc cccacatggg gtatggactt agggtctcac tcacgtggct       1260
cccatcatga gtgaagggc ctcaagccca ggttcccaca gcagcgcctg tcgcaagtgg        1320
aggcagaggc ccgagggcca ccctgacctg gtccctgagg ttcctgcagc ccaggctgcc       1380
ctgctgtccc tgggaggcct gggctccacc agaccacagg tccagggcac cgggtgcagg       1440
agccacccac acacagctca caggaagaag ataagctcca gaccccagg gccagaacct       1500
gccttcctgc tactgcttcc tgccccagac ctgggcgccc tccccgtcc acttacacac       1560
aggccaggaa gctgttccca cacagaacaa ccccaaacca ggaccgcctg gcactcaggt       1620
ggctgccatt tccttctcca tttgctccca gcgcctctgt cctccctggt tcctccttcg       1680
ggggaacagc ctgtgcagcc agtccctgca gcccacaccc tggggagacc caaccctgcc       1740
tggggccctt ccaaccctgc tgctcttact gcccacccag aaaactctgg ggtcctgtcc       1800
ctgcagtccc taccctggtc tccacccaga cccctgtgta tcactccaga caccctccc        1860
aggcaaaccc tgcacctgca ggccctgtcc tcttctgtcg ctagagcctc agtttctccc       1920
ccctgtgccc acccctacc tcctcctgcc cacaactcta actcttcttc tcctggagcc       1980
cctgagccat ggcattgacc ctgccctccc accaccaca gcccatgccc tcaccttcct       2040
cctggccact ccgaccccgc cccctctcag gccaagccct ggtatttcca ggacaaaggc       2100
tcacccaagt cttttcccagg caggcctggg ctcttgccct cacttcccgg ttacacggga       2160
gcctcctgtg cacagaagca gggagctcag cccttccaca gcagaaggc actgaaagaa        2220
atcggcctcc agcaccttga cacacgtccg cccgtgtctc tcactgcccg cacctgcagg       2280
gaggctccgc actccctcta aagacaaggg atccaggcag cagcatcacg ggagaatgca       2340
gggctcccag acatcccagt cctctcacag gcctctcctg gaagagacc tgcagccacc        2400
accaaacagc cacagaggct gctggatagt aactgagtca atgaccgacc tggagggcag       2460
gggagcagtg agccggagcc cataccatag ggacagagac cagccgctga catcccgagc       2520
tcctcaatgg tggccccata acacacctag gaaacataac acaccacag ccccacctgg        2580
aacagggcag agactgctga gcccccagca ccagccccaa gaaacaccag gcaacagtat       2640
cagagggggc tcccgagaaa gagaggaggg gagatctcct tcaccatcaa atgcttccct       2700
tgaccaaaaa cagggtccac gcaactcccc caggacaaag gaggagcccc ctatacagca       2760
ctgggctcag agtcctctct gagacaccct gagtttcaga caacaacccg ctggaatgca       2820
cagtctcagc aggagaacag accaaagcca gcaaaaggga cctcggtgac accagtaggg       2880
acaggaggat tttgtggggg ctcgtgtcac tgtgaggaca ttgtagtcat ggtagctgcc       2940
```

```
actcccacag tgacacagac ccattcccaa agccctactg caaacacacc cactcctggg    3000
gctgaggggc tgggggagcg tctgggaagt agggtccagg ggtgtctatc aatgtccaaa    3060
atgcaccaga ctccccgcca aacaccaccc caccagccag cgagcagggt aaacagaaaa    3120
tgagaggctc tgggaagctt gcacaggccc caaggaaaga gctttggcgg gtgtgcaaga    3180
ggggatgcag gcagagcctg agcagggcct tttgctgttt ctgctttcct gtgcagagag    3240
ttccataaac tggtgttcaa gatcagtggc tgggaatgag cccaggaggg cagtctgtgg    3300
gaagagcaca gggaaggagg agcagccgct atcctacact gtcatctttc aaaagtttgc    3360
cttgtgacca cactattgca tcatgggatg cttaagagct gatgtagaca cagctaaaga    3420
gagaatcagt gagatgaatt tgcagcatag atctgaataa actctccaga atgtggagca    3480
gtacagaagc aaacacacag aaagtgcctg atgcaaggac aaagttcagt gggcaccttc    3540
aggcattgct gctgggcaca gacactctga aaagccttgg caggatctcc ctgcgacaaa    3600
gcagaaccct caggcaatgc cagccccaga gccctccctg agagcgtcat ggggaaagat    3660
gtgcagaaca gctgattatc atagactcaa actgagaaca gagcaaacgt ccatctgaag    3720
aacagtcaaa taagcaatgg taggttcatg caatgcaaac ccagacagcc aggggacaac    3780
agtagagggc tacaggcggc tttgcggttg agttcatgac aatgctgagt aattggagta    3840
acagaggaaa gcccaaaaaa tactttaat gtgatttctt ctaaataaaa tttacaccag    3900
gcaaaatgaa ctgtcttctt aagggataaa ctttcccctg gaaaaactac aaggaaaatt    3960
aagaaaacga tgatcacata aacacagttg tggttacttc tactggggaa ggaagagggt    4020
atgagctgag acacacagag tcggcaagtc tccaagcaag cacagaacga atacattaca    4080
gtaccttgaa tacagcagtt aaacttctaa atcgcaagaa caggaaaatg cacacagctg    4140
tgtttagaaa attctcagtc cagcactatt cataatagca aagacattaa cccaggttgg    4200
ataaataaat gatgacacag gcaattgcac aatgatacag acatacattt agtacatgag    4260
acatcgatga tgtatcccca aagaaatgac tttaaagaga aaaggcctga tgtgtggtgg    4320
cactcacctc cctgggatcc ccggacaggt tgcaggcaca ctgtgtggca gggcaggctg    4380
gtacatgctg gcagctcctg gggcctgatg tggagcaagc gcagggctgt ataccccccaa   4440 ggatggcaca gtcagtgaat tccagagaga agcagctcag ccacactgcc caggcagagc    4500
ccgagaggga cgcccacgta cagggaggca gagcccagct cctccacagc caccaccacc    4560
tgtgcacggg ccaccacctt gcaggcacag agtgggtgct gagaggaggg gcagggacac    4620
caggcagggt gagcacccag agaaaactgc agaagcctca cacatccacc tcagcctccc    4680
ctgacctgga cctcacctgg tctggacctc acctggcctg gcctcacct gacctggacc    4740 tcacctggcc tgggcttcac ctgacctgga cctcacctgg cctccggcct cacctgcacc    4800
tgctccaggt cttgctggaa cctgagtagc actgaggctg cagaagctca tccagggttg    4860
gggaatgact ctggaactct cccacatctg acctttctgg gtggaggcat ctggtggccc    4920
tgggaatata aaagcccca gaatggtgcc tgcgtgattt ggggggcaatt tatgaacccg    4980 aaaggacatg gccatggggt gggtagggac atagggacag atgccagcct gaggtggagc    5040
ctcaggacac agttggacgc ggacactatc cacataagcg agggacagac ccgagtgttc    5100
ctgcagtaga acctgagagcg ctgggcccac agcctcccct cggtgccctg ctgcctcctc    5160
aggtcagccc tggacatccc gggtttcccc aggccagatg gtaggtttga agtgaggtct    5220
gtgtcactgt ggtatcatga tcacgtttgg gggagtcatc gttataccca cagcatcaca    5280
cggtccatca gaaacccatg ccacagccct ccccgcaggg gaccgccgcg tgccatgtta    5340
```

```
cgattttgat cgaggacaca gcgccatggg tatggtggct accacagcag tgcagcccat    5400
gacccaaaca cacagggcag caggcacaat ggacaggcct gtgagtgacc atgctgggct    5460
ccagcccgcc agccccggag accatgaaac agatggccaa ggtcacccca cagttcagcc    5520
agacatggct ccgtggggtc tgcatcgctg ctgccctcta acaccagccc agatggggac    5580
aaggccaacc ccacattacc atctcctgct gtccacccag tggtcccaga agcccctccc    5640
tcatggctga gccacatgtg tgaaccctga gcaccccca tgtcagagta ggggcagcag    5700
aagggcgggg ctggccctgt gcactgtccc tgcacccatg gtccctcgcc tgcctggccc    5760
tgacacctga gcctcttctg agtcatttct aagatagaag acattcccgg ggacagccgg    5820
agctgggcgt cgctcatccc gcccggccgt cctgagtcct gcttgtttcc agacctcacc    5880
agggaagcca acagaggact cacctcacac agtcagagac aaagaacctt ccagaaatcc    5940
ctgtctcact ccccagtggg caccttcttc caggacattc ctcggtcgca tcacagcagg    6000
cacccacatc tggatcagga cggccccag aacacaagat ggccatggg acagccca    6060 caacccaggc cttcccagac ccctaaaagg cgtcccaccc cctgcacctg ccccagggct    6120
aaaaatccag gaggcttgac tcccgcatac ccctccagcca gacatcacct cagccccctc    6180
ctggagggga caggagcccg ggagggtgag tcagacccac ctgccctcga tggcaggcgg    6240
ggaagattca gaaaggcctg agatcccag gacgcagcac cactgtcaat gggggcccca    6300
gacgcctgga ccagggcctg cgtgggaaag gccgctgggc acactcaggg gcttttgtg    6360 aaggcccctc ctactgtgtg accacggtca ctaccacagt gatgaaacta gcagcaaaaa    6420
ctggccggac acccagggac catgcacact tctcagcttg gagctctcca ggaccagaag    6480
agtcaggtct gagggtttgt agccagaccc tcggcctcta gggacaccct ggccatcaca    6540
gcggatgggc tggtgcccca catgccatct gctccaaaca ggggcttcag agggctctga    6600
ggtgacttca ctcatgacca caggtgccct ggccccttcc ccgccagcta caccgaaccc    6660
tgtcccaaca gctgccccag ttccaacagc caattcctgg ggcccagaat tgctgtagac    6720
accagcctcg ttccagcacc tcctgccaat tgcctggatt cacatcctgg ctggaatcaa    6780
gagggcagca tccgccaggc tcccaacagg caggactccc gcacaccctc ctctgagagg    6840
ccgctgtgtt ccgcagggcc aggccctgga cagttcccct cacctgccac tagagaaaca    6900
cctgccattg tcgtccccac ctggaaaaga ccactcgtgg agcccccagc cccaggtaca    6960
gctgtagaga gactccccga gggatctaag aaggagccat gcgcagttct gccgggaccc    7020
tcggccaggc cgacaggagt ggacactgga gctgggccca cactgggcca cataggagct    7080
caccagtgag ggcaggagag cacatgccgg ggagcaccca gcctcctgct gaccagaggc    7140
ccgtcccaga gcccaggagg ctgcagaggc ctctccaggg ggacactgtg catgtctggt    7200
ccctgagcag ccccccacgt ccccagtcct gggggcccct ggcacagctg tctggaccct    7260
ccctgttccc tgggaagctc ctcctgacag ccccgcctcc agttccaggt gtggttattg    7320 tcaggggtg tcagactgtg gtggacacag ccatggttac cacagtggtg ctgcccatag    7380
cagcaaccag gccaagtaga caggcccctg ctgtgcagcc ccaggcctcc acttcacctg    7440
cttctcctgg ggctctcaag gtcactgttg tctgtactct gccctctgtg gggagggttc    7500
cctcagtggg aggtctgttc tcaacatccc agggcctcat gtctgcacgg aaggccaatg    7560
gatgggcaac ctcacatgcc gcggctaaga tagggtgggc agcctggcgg gggacagtac    7620
atactgctgg ggtgtctgtc actgtgccta gtggggcact ggctcccaaa caacgcagtc    7680
```

| | |
|---|---|
| ctcgccaaaa tccccacagc ctcccctgct aggggctggc ctgatctcct gcagtcctag | 7740 |
| gaggctgctg acctccagaa tgtctccgtc cccagttcca gggcgagagc agatcccagg | 7800 |
| ccggctgcag actgggaggc caccccctcc ttcccagggt tcactggagg tgaccaaggt | 7860 |
| aggaaatggc cttaacacag ggatgactgc gccatcccc aacagagtca gcccctcct | 7920 |
| gctctgtacc ccgcaccccc caggccagtc cacgaaaacc agggcccccac atcagagtca | 7980 |
| ctgcctggcc cggccctggg gcggacccct cagcccccac cctgtctaga ggacttgggg | 8040 |
| ggacaggaca caggccctct ccttatggtt cccccacctg cctccggccg ggaccccttgg | 8100 |
| ggtgtggaca gaaaggacac ctgcctaatt ggccccagg aacccagaac ttctctccag | 8160 |
| ggaccccagc ccgagcaccc ccttacccag gacccagccc tgcccctcct cccctctgct | 8220 |
| ctcctctcat cacccatgg gaatccggta tccccaggaa gccatcagga agggctgaag | 8280 |
| gaggaagcgg ggccgtgcac caccgggcag gaggctccgt cttcgtgaac ccaggaagt | 8340 |
| gccagcctcc tagagggtat ggtccaccct gcctggggct cccaccgtgg caggctgcgg | 8400 |
| ggaaggacca gggacggtgt ggggggagggc tcagggccct gcgggtgctc ctccatcttc | 8460 |
| ggtgagcctc ccccttcacc caccgtcccg cccacctcct ctccaccctg gctgcacgtc | 8520 |
| ttccacacca tcctgagtcc tacctacacc agagccagca aagccagtgc agacaaaggc | 8580 |
| tggggtgcag gggggctgcc agggcagctt cggggaggga aggatggagg gaggggaggt | 8640 |
| cagtgaagag gcccccttcc cctgggtcca ggatcctcct ctgggacccc cggatcccat | 8700 |
| cccctcctgg ctctgggagg agaagcagga tgggagaatc tgtgcgggac cctctcacag | 8760 |
| tggaatatcc ccacagcggc tcaggccaga cccaaaagcc cctcagtgag ccctccactg | 8820 |
| cagtcctggg cctgggtagc agcccctccc acagaggaca gacccagcac ccgaagaag | 8880 |
| tcctgccagg gggagctcag agccatgaaa gagcaggata tggggtcccc gatacaggca | 8940 |
| cagacctcag ctccatccag gcccaccggg acccaccatg ggaggaacac ctgtctccgg | 9000 |
| gttgtgaggt agctggcctc tgtctcggac cccactccag acaccagaca gaggggcagg | 9060 |
| ccccccaaaa ccagggttga gggatgatcc gtcaaggcag acaagaccaa ggggcactga | 9120 |
| ccccagcaag ggaaggctcc caaacagacg aggaggtttc tgaagctgtc tgtatcacag | 9180 |
| tggggcatag ccatggctgg taccacagtg acactcgcca ggccagaaac ccgtcccaa | 9240 |
| gtcagcggaa gcagagagag cagggaggac acgtttagga tctgaggccg cacctgacac | 9300 |
| ccagggcagc agacgtctcc cctccagggc accctccacc gtcctgcgtt tcttcaagaa | 9360 |
| taggggcggc ctgaggggggt ccagggccag gcgataggtc ccctctaccc caaggaggag | 9420 |
| ccaggcagga cccgagcacc g | 9441 |

<210> SEQ ID NO 4
<211> LENGTH: 11592
<212> TYPE: DNA
<213> ORGANISM: Homo sapiens
<220> FEATURE:
<221> NAME/KEY: misc_feature
<222> LOCATION: (1)..(11592)
<223> OTHER INFORMATION: HD 1.20-6.25, 1.26

<400> SEQUENCE: 4

| | |
|---|---|
| tccccattga ggctgacctg cccagacggg cctgggccca ccccacacac cggggcggaa | 60 |
| tgtgtgcagg cccagtctc tgtgggtgtt ccgctagctg gggcccccag tgctcacccc | 120 |
| acacctaaag cgagccccag cctccagagc cccctaagca ttcccgcc agcagcccag | 180 |
| cccctgcccc cacccaggag gccccagagc tcagggcgcc tggtcggatt ctgaacagcc | 240 |

```
ccgagtcaca gtgggtatca ctggcacgac caccgtgaga aaaactgtgt ccaaaactga    300
ctcctggcag cagtcggagg ccccgccaga gaggggagca gccggcctga acccatgtcc    360
tgccggttcc catgaccccc agcacccaga gccccacggt gtcccgttg gataatgagg    420 acaagggctg ggggctccgg tggtttgcgg cagggacttg atcacatcct tctgctgtgg    480
ccccattgcc tctggctgga gttgacccct ctgacaagtg tcctcagaaa gacagggatc    540
accggcacct cccaatatca accccaggca gcacagacac aaaccccaca tccagagcca    600
actccaggag cagagacacc ccaacactct ggggacccc aaccgtgata actccccact    660
ggaatccgcc ccagagtcta ccaggaccaa aggccctgcc ctgtctctgt ccctcactca    720
gggcctcctg cagggcgagc gcttgggagc agactcggtc ttaggggaca ccactgtggg    780
ccccaacttt gatgaggcca ctgacccttc cttcctttcc tggggcagca cagactttgg    840
ggtctgggca gggaagaact actggctggt ggccaatcac agagccccca ggccgaggtg    900
gccccaagaa ggccctcagg aggtggccac tccacttcct cccagctgga ccccaggtcc    960
tccccaagat aggggtgcca tccaaggcag gtcctccatg gagccccctt cagactcctc    1020
ccgggacccc actggacctc agtccctgct ctgggaatgc agccaccaca agcacaccag    1080
gaagcccagg cccagccacc ctgcagtggg caagcccaca ctctggagca gagcagggtg    1140
cgtctgggag gggctaacct ccccaccccc caccccccat ctgcacacag ccacctacca    1200
ctgcccagac cctctgcagg agggccaagc caccatgggg tatggactta gggtctcact    1260
cacgtgcctc ccctcctggg agaaggggcc tcatgcccag atccctgcag cactagacac    1320
agctggaggc agtggcccca gggccaccct gacctggcat ctaaggctgc tccagcccag    1380
acagcactgc cgttcctggg aagcctgggc tccaccagac cacaggtcca gggcacagcc    1440
cacaggagcc acccacacac agctcacagg aagaagataa gctccagacc ccagggcggg    1500
acctgccttc ctgccaccac ttacacacag gccaggagc tgttcccaca cagatcaacc    1560
ccaaaccggg actgcctggc actagggtca ctgccatttc cctctccatt ccctcccagt    1620
gcctctgtgc tccctccttc tggggaacac cctgtgcagc ccctcctgc agccacacg    1680 ctggggagac cccaccctgc ctcgggcctt ttctacctgc tgcacttgcc gcccacccaa    1740
acaaccctgg gtacgtgacc ctgcagtcct caccctgatc tgcaaccaga cccctgtccc    1800
tccctctaaa caccctccc aggccaactc tgcacctgca ggccctccgc tcttctgcca    1860
caagagcctc aggttttcct acctgtgccc acccctaac ccctcctgcc cacaacttga    1920
gttcttcctc tcctggagcc cttgagccat ggcactgacc ctacactccc acccacacac    1980
tgcccatgcc atcaccttcc tcctggacac tctgaccccg ctcccctccc tctcagaccc    2040
ggccctggta tttccaggac aaaggctcac ccaagtcttc cccatgcagg cccttgccct    2100
cactgcctgg ttacacggga gcctcctgtg cgcagaagca gggagctcag ctcttccaca    2160
ggcagaaggc actgaaagaa atcagcctcc agtgccttga cacacgtccg cctgtgtctc    2220
tcactgcctg cacctgcagg gaggctccgc actccctcta aagatgaggg atccaggcag    2280
caacatcacg ggagaatgca gggctcccag acagcccagc cctctcgcag gcctctcctg    2340
ggaagagacc tgcagccacc actgaacagc cacggaggtc gctggatagt aaccgagtca    2400
gtgaccgacc tggagggcag gggagcagtg aaccggagcc cataccatag ggacagagac    2460
cagccgctaa catcccgagc ccctcactgg cggcccagac acccccgtg aaagagaac    2520 agacccacag tcccacctgg aacagggcag acactgctga gcccccagca ccagccccaa    2580
```

```
gaaacactag gcaacagcat cagagggggc tcctgagaaa gagaggaggg gaggtctcct    2640
tcaccatcaa atgcttccct tgaccaaaaa cagggtccac gcaactcccc caggacaaag    2700
gaggagcccc ctgtacagca ctgggctcag agtcctctct gagacaggct cagtttcaga    2760
caacaacccg ctggaatgca cagtctcagc aggagagcca ggccagagcc agcaagagga    2820
gactcggtga caccagtctc ctgtagggac aggaggattt tgtgggggtt cgtgtcactg    2880
tgagcacatt gtggtggtca ctgccattcc cacagtgaca caaccccatt cctaaagccc    2940
tactgcaaac gcacccactc ctgggactga ggggctgggg gagcgtctgg gaagtatggc    3000
ctaggggtgt ccatcaatgc ccaaaatgca ccagactctc cccaagacat caccccacca    3060
gccagtgagc agagtaaaca gaaaatgaga agcagctggg aagcttgcac aggccccaag    3120
gaaagagctt tggcaggtgt gcaagagggg atgtgggcag agcctcagca gggccttttg    3180
ctgtttctgc tttcctgtgc agagagttcc ataaactggt attcaagatc aatggctggg    3240
agtgagccca ggaggacagt gtgggaagag cacaggaag gaggagcagc cgctatccta    3300
cactgtcatc ttttgaaagt ttgccctgtg cccacaatgc tgcatcatgg gatgcttaac    3360
agctgatgta gacacagcta aagagagaat cagtgaaatg gatttgcagc acagatctga    3420
ataaatcctc cagaatgtgg agcagcacag aagcaagcac acagaaagtg cctgatgcca    3480
aggcaaagtt cagtgggcac cttcaggcat tgctgctggg cacagacact ctgaaaagca    3540
ctggcaggaa ctgcctgtga caaagcagaa ccctcaggca atgccagccc tagagccctt    3600
cctgagaacc tcatgggcaa agatgtgcag aacagctgtt tgtcatagcc ccaaactatg    3660
gggctggaca aagcaaacgt ccatctgaag gagaacagac aaataaacga tggcaggttc    3720
atgaaatgca aactaggaca gccagaggac aacagtagag agctacaggc ggctttgcgg    3780
ttgagttcat gacaatgctg agtaattgga gtaacagagg aaagcccaaa aaatactttt    3840
aatgtgattt cttctaaata aaatttacac ccggcaaaat gaactatctt cttaagggat    3900
aaactttccc ctggaaaaac tataaggaaa atcaagaaaa cgatgatcac ataaacacag    3960
tggtggttac ttctactggg gaaggaagag ggtatgagct gagacacaca gagtcggcaa    4020
gtctcctaac aagaacagaa caaatacatt acagtacctt gaaaacagca gttaaacttc    4080
taaatcgcaa gaagaggaaa atgcacacac ctgtgtttag aaaattctca gtccagcact    4140
gttcataata gcaaagacat taacccaggt tggataaata agcgatgaca caggcaattg    4200
cacaatgata cagacataca ttcagtatat gagacatcga tgatgtatcc ccaaagaaat    4260
gactttaaag agaaaaggcc tgatgtgtgg tggcaatcac ctccctgggc atccccggac    4320
aggctgcagg ctcactgtgt ggcagggcag gcaggcacct gctggcagct cctggggcct    4380
gatgtggagc aggcacagag ctgtatatcc ccaaggaagg tacagtcagt gcattccaga    4440
gagaagcaac tcagccacac tccctggcca gaacccaaga tgcacaccca tgcacaggga    4500
ggcagagccc agcacctccg cagccaccac cacctgcgca cgggccacca ccttgcaggc    4560
acagagtggg tgctgagagg agggcaggg acaccaggca gggtgagcac ccagagaaaa    4620
ctgcagaagc ctcacacatc cctcacctgg cctgggcttc acctgacctg gacctcacct    4680
ggcctcgggc ctcacctgca cctgctccag gtcttgctgg agcctgagta gcactgaggc    4740
tgtagggact catccagggt tggggaatga ctctgcaact ctcccacatc tgacctttct    4800
gggtggaggc acctggtggc ccagggaata taaaaagccc cagaatgatg cctgtgtgat    4860
ttgggggcaa tttatgaacc cgaaaggaca tggccatggg gtgggtaggg acagtaggga    4920
cagatgtcag cctgaggtga agcctcagga cacaggtggg catggacagt gtccacctaa    4980
```

```
gcgagggaca gacccgagtg tccctgcagt agacctgaga gcgctgggcc cacagcctcc   5040
cctcgggggcc ctgctgcctc ctcaggtcag ccctggacat cccgggtttc cccaggcctg  5100
gcggtaggtt tgaagtgagg tctgtgtcac tgtggtatca ctatcatagt agtggtcatt   5160
actaccacag tgtcacagag tccatcaaaa actcatgcct gggagcctcc caccacagcc   5220
ctccctgcgg gggaccgctg catgccgtgt taggattttg atcgaggaca cggcgccatg   5280
ggtatggtgg ctaccacagc agtgcagccc atgacccaaa cacacggggc agcagaaaca   5340
atggacaggc ccacaagtga ccatgatggg ctccagccca ccagcccag agaccatgaa    5400
acagatggcc aaggtcaccc tacaggtcat ccagatctgg ctccaagggg tctgcatcgc   5460
tgctgccctc ccaacgccaa accagatgga gacagggccg gccccatagc accatctgct   5520
gccgtccacc cagcagtccc ggaagcccct ccctgaacgc tgggccacgt gtgtgaaccc   5580
tgcgagcccc ccatgtcaga gtaggggcag caggagggcg gggctggccc tgtgcactgt   5640
cactgcccct gtggtccctg gcctgcctgg ccctgacacc tgagcctctc ctgggtcatt   5700
tccaagacat tcccagggac agccggagct gggagtcgct catcctgcct ggctgtcctg   5760
agtcctgctc atttccagac ctcaccaggg aagccaacag aggactcacc tcacacagtc   5820
agagacaacg aaccttccag aaatccctgt ttctctcccc agtgagagaa accctcttcc   5880
agggtttctc ttctctcccca ccctcttcca ggacagtcct cagcagcatc acagcgggaa   5940
cgcacatctg gatcaggacg gcccccagaa cacgcgatgg cccatgggga cagcccagcc   6000
cttcccagac ccctaaaagg tatcccacc ttgcacctgc cccagggctc aaactccagg   6060
aggcctgact cctgcacacc ctcctgccag atatcacctc agccccctcc tggaggggac   6120
aggagcccgg gagggtgagt cagacccacc tgccctcaat ggcaggcggg gaagattcag   6180
aaaggcctga atccccagg acgcagcacc actgtcaatg ggggccccag acgcctggac    6240
cagggcctgt gtgggaaagg cctctggcca cactcagggg ctttttgtga agggccctcc   6300
tgctgtgtga ccacggtggt cactcccaca gtgatgaaac cagcagcaaa aactgaccgg   6360
actcgcaggg tttatgcaca cttctcggct cggagctctc caggagcaca agagccaggc   6420
ccgagggttt gtgcccagac cctcggcctc tagggacacc cgggccatct tagccgatgg   6480
gctgatgccc tgcacaccgt gtgctgccaa acaggggctt cagagggctc tgaggtgact   6540
tcactcatga ccacaggtgc cctggtccct tcactgccag ctgcaccaga ccctgttccg   6600
agagatgccc cagttccaaa agccaattcc tggggccggg aattactgta gacaccagcc   6660
tcattccagt acctcctgcc aattgcctgg attcccatcc tggctggaat caagagggca   6720
gcatccgcca ggctcccaac aggcaggact cccacacacc ctcctctgag aggccgctgt   6780
gttccgcagg gccaggccgc agacagttcc cctcacctgc ccatgtagaa acacctgcca   6840
ttgtcgtccc cacctggcaa agaccacttg tggagccccc agccccaggt acagctgtag   6900
agagagtcct cgaggcccct aagaaggagc catgcccagt tctgccggga ccctcggcca   6960
ggccgacagg agtggacgct ggagctgggc ccacactggg ccacatagga gctcaccagt   7020
gagggcagga gagcacatgc cggggagcac ccagcctcct gctgaccaga gacccgtccc   7080
agagcccagg aggctgcaga ggcctctcca gggggacaca gtgcatgtct ggtccctgag   7140
cagcccccag gctctctagc actgggggcc cctggcacag ctgtctggac cctccctgtt   7200
ccctgggaag ctcctcctga cagccccgcc tccagttcca ggtgtggtta ttgtcagggg   7260
gtgccaggcc gtggtagaca tggccaccat taccacagtg gtgccgccca tagcagcaac   7320
```

| | |
|---|---|
| caggccaagt agacagaccc ctgccacgca gccccaggcc tccagctcac ctgcttctcc | 7380 |
| tgggctctc aaggctgctg tctgccctct ggccctctgt ggggaggtt ccctcagtgg | 7440 |
| gaggtctgtg ctccagggca gggatgactg agatagaaat caaaggctgg cagggaaagg | 7500 |
| cagcttcccg ccctgagagg tgcaggcagc accacagagc catggagtca cagagccacg | 7560 |
| gagcccccag tgtgggcgtg tgagggtgct gggctcccgg caggcccagc cctgatgggg | 7620 |
| aagcctgccc cgtcccacag cccaggtccc caggggcagc aggcacagaa gctgccaagc | 7680 |
| tgtgctctac gatcctcatc cctccagcag catccactcc acagtgggga aactgagcct | 7740 |
| tggagaacca cccagccccc tggaaacaag gcggggagcc cagacagtgg gcccagagca | 7800 |
| ctgtgtgtat cctggcacta ggtgcaggga ccacccggag atccccatca ctgagtggcc | 7860 |
| agcctgcaga aggacccaac cccaaccagg ccgcttgatt aagctccatc ccctgtcct | 7920 |
| gggaacctct tcccagcgcc accaacagct cggcttccca ggcctcatc cctccaagga | 7980 |
| aggccaaagg ctgggcctgc caggggcaca gtaccctccc ttgccctggc taagacaggg | 8040 |
| tgggcagacg gctgcagata ggacatattg ctggggcatc ttgctctgtg actactgggt | 8100 |
| actggctctc aacgcagacc ctaccaaaat ccccactgcc tccctgcta ggggctggcc | 8160 |
| tggtctcctc ctgctgtcct aggaggctgc tgacctccag gatggcttct gtccccagtt | 8220 |
| ctagggccag agcagatccc aggcaggctg taggctggga ggccacccct gtccttgccg | 8280 |
| aggttcagtg caggcaccca ggacaggaaa tggcctgaac acaggatga ctgtgccatg | 8340 |
| ccctacctaa gtccgcccct ttctactctg caaccccac tccccaggtc agcccatgac | 8400 |
| gaccaacaac ccaacaccag agtcactgcc tggccctgcc ctggggagga ccctcagcc | 8460 |
| cccaccctgt ctagaggagt tggggggaca ggacacaggc tctctcctta tggttccccc | 8520 |
| acctggctcc tgccgggacc cttggggtgt ggacagaaag gacgcctgcc taattggccc | 8580 |
| ccaggaaccc agaacttctc tccagggacc ccagcccgag cacccccttca cccaggaccc | 8640 |
| agccctgccc ctcctcccct ctgctctcct ctcatcactc catgggaatc cagaatcccc | 8700 |
| aggaagccat caggaagggc tgaaggagga agcggggccg ctgcaccacc gggcaggagg | 8760 |
| ctccgtcttc gtgaacccag ggaagtgcca gcctcctaga gggtatggtc caccctgcct | 8820 |
| ggggctccca ccgtggcagg ctgcggggaa ggaccaggga cggtgtgggg gagggctcag | 8880 |
| ggccctgcag gtgctccatc ttggatgagc ccatccctct cacccaccga cccgcccacc | 8940 |
| tcctctccac cctggccaca cgtcgtccac accatcctga gtcccaccta caccagagcc | 9000 |
| agcagagcca gtgcagacag aggctggggt gcaggggggc cgccagggca gctttgggga | 9060 |
| gggaggaatg gaggaagggg aggtcagtga agaggccccc ctcccctggg tctaggatcc | 9120 |
| acctttggga ccccggatc ccatcccctc caggctctgg gaggagaagc aggatgggag | 9180 |
| attctgtgca ggaccctctc acagtggaat acctccacag cggctcaggc cagatacaaa | 9240 |
| agccctcag tgagccctcc actgcagtgc agggcctggg ggcagcccct cccacagagg | 9300 |
| acagacccag caccccgaag aagtcctgcc aggggagct cagagccatg aaggagcaag | 9360 |
| atatggggac cccaatactg gcacagacct cagctccatc caggcccacc aggacccacc | 9420 |
| atgggtggaa cacctgtctc cggccctgc tggctgtgag gcagctggcc tctgtctcgg | 9480 |
| accccccattc cagacaccag acagagggac aggccccca gaaccagtgt tgagggacac | 9540 |
| ccctgtccag ggcagccaag tccaagaggc gcgctgagcc cagcaaggga aggcccccaa | 9600 |
| acaaaccagg aggtttctga agctgtctgt gtcacagtcg ggcatagcca cggctaccac | 9660 |
| aatgacactg ggcaggacag aaaccccatc ccaagtcagc cgaaggcaga gagagcaggc | 9720 |

```
aggacacatt taggatctga ggccacacct gacactcaag ccaacagatg tctccctcc      9780 agggcgccct gccctgttca gtgttcctga gaaaacaggg gcagcctgag gggatccagg    9840
gccaggagat gggtcccctc taccccgagg aggagccagg cgggaatccc agccccctcc    9900
ccattgaggc catcctgccc agaggggccc ggacccaccc cacacaccca ggcagaatgt    9960
gtgcaggcct caggctctgt gggtgccgct agctggggct gccagtcctc accccacacc    10020
taaggtgagc cacagccgcc agagcctcca caggagaccc cacccagcag cccagccccc    10080
acccaggagg ccccagagct cagggcgcct gggtggattc tgaacagccc cgagtcacgg    10140
tgggtatcat gggagccact accactgtga gaaaagctat gtccaaaact gtctcccggc    10200
cactgctgga ggcccagcca gagaagggac cagccgcccg aacatacgac cttcccagac    10260
ctcatgaccc ccagcacttg gagctccaca gtgtccccat tggatggtga ggatgggggc    10320
cggggccatc tgcacctccc aacatcaccc ccaggcagca caggcacaaa ccccaaatcc    10380
agagccgaca ccaggaacac agacacccca atacccgtggg ggaccctggc cctggtgact    10440
tcccactggg atccaccccc gtgtccacct ggatcaaaga ccccaccgct gtctctgtcc    10500
ctcactcagg gcctgctgag gggcgggtgc tttggagcag actcaggttt aggggccacc    10560
attgtggggc ccaacctcga ccaggacaca gatttttctt tcctgccctg ggcaacaca     10620 gactttgggg tctgtgcagg gaggaccttc tggaaagtca ccaagcacag agccctgact    10680
gaggtggtct caggaagacc cccaggaggg ggcttgtgcc ccttcctctc atgtggaccc    10740 catgccccc aagatagggg catcatgcag ggcaggtcct ccatgcagcc accactaggc    10800
aactccctgg cgccggtccc cactgcgcct ccatcccggc tctggggatg cagccaccat    10860
ggccacacca ggcagcccgg gtccagcaac cctgcagtgc ccaagccctt ggcaggattc    10920
ccagaggctg gagcccaccc ctcctcatcc ccccacacct gcacacacac acctacccc     10980 tgcccagtcc ccctccagga gggttggagc cgcccatagg gtgggggctc caggtctcac    11040
tcactcgctt cccttcctgg gcaaaggagc ctcgtgcccc ggtcccccct gacggcgctg    11100
ggcacaggtg tgggtactgg gccccagggc tcctccagcc ccagctgccc tgctctccct    11160
gggaggcctg ggcaccacca gaccaccagt ccagggcaca gccccaggga gccgcccact    11220
gccagctcac aggaagaaga taagcttcag accctcaggg ccgggagctg ccttcctgcc    11280
acccctccct gccccagacc tccatgccct ccccaaacca cttacacaca agccaggag    11340 ctgtttccac acagttcaac cccaaaccag gacggcctgg cactcgggtc actgccattt    11400
ctgtctgcat tcgctcccag cgcccctgtg ttccctccct cctccctcct tcctttcttc    11460
ctgcattggg ttcatgccgc agagtgccag gtgcaggtca gccctgagct tgggtcacc    11520 tcctcactga aggcagcctc agggtgccca ggggcaggca gggtgggggt gaggcttcca    11580
gctccaaccg ct                                                        11592
```

<210> SEQ ID NO 5
<211> LENGTH: 689
<212> TYPE: DNA
<213> ORGANISM: Mus musculus
<220> FEATURE:
<221> NAME/KEY: misc_feature
<222> LOCATION: (1)..(689)
<223> OTHER INFORMATION: Mouse Ei (an intronic enhancer)

<400> SEQUENCE: 5

```
tctagagagg tctggtggag cctgcaaaag tccagctttc aaaggaacac agaagtatgt      60
```

| | |
|---|---|
| gtatggaata ttagaagatg ttgcttttac tcttaagttg gttcctagga aaaatagtta | 120 |
| aatactgtga ctttaaaatg tgagagggtt ttcaagtact cattttttta aatgtccaaa | 180 |
| attcttgtca atcagtttga ggtcttgttt gtgtagaact gatattactt aaagtttaac | 240 |
| cgaggaatgg gagtgaggct ctctcataac ctattcagaa ctgactttta acaataataa | 300 |
| attaagtttc aaatattttt aaatgaattg agcaatgttg agttggagtc aagatggccg | 360 |
| atcagaacca gaacacctgc agcagctggc aggaagcagg tcatgtggca aggctatttg | 420 |
| gggaagggaa aataaaacca ctaggtaaac ttgtagctgt ggtttgaaga agtggttttg | 480 |
| aaacactctg tccagcccca ccaaaccgaa agtccaggct gagcaaaaca ccacctgggt | 540 |
| aatttgcatt tctaaaataa gttgaggatt cagccgaaac tggagaggtc ctctttttaac | 600 |
| ttattgagtt caacctttta attttagctt gagtagttct agtttcccca aacttaagtt | 660 |
| tatcgacttc taaaatgtat ttagaattc | 689 |

<210> SEQ ID NO 6
<211> LENGTH: 3518
<212> TYPE: DNA
<213> ORGANISM: Mus musculus
<220> FEATURE:
<221> NAME/KEY: misc_feature
<222> LOCATION: (1)..(3518)
<223> OTHER INFORMATION: Mouse Switch Region

<400> SEQUENCE: 6

| | |
|---|---|
| acttatttca gttgaacatg ctggttggtg gttgagagga cactcagtca gtcagtgacg | 60 |
| tgaagggctt ctaagccagt ccacatgctc tgtgtgaact ccctctggcc ctgcttattg | 120 |
| ttgaatgggc caaaggtctg agaccaggct gctgctgggt aggcctggac tttgggtctc | 180 |
| ccacccagac ctgggaatgt atggttgtgg cttctgccac ccatccacct ggctgctcat | 240 |
| ggaccagcca gcctcggtgg cttttgaagga acaattccac acaaagactc tggacctctc | 300 |
| cgaaaccagg caccgcaaat ggtaagccag aggcagccac agctgtggct gctgctctta | 360 |
| aagcttgtaa actgtttctg cttaagaggg actgagtctt cagtcattgc tttagggga | 420 |
| gaaagagaca tttgtgtgtc ttttgagtac cgttgtctgg gtcactcaca tttaactttc | 480 |
| cttgaaaaac tagtaaaaga aaatgttgc ctgttaacca ataatcatag agctcatggt | 540 |
| actttgagga aatcttagaa agcgtgtata caattgtctg gaattatttc agttaagtgt | 600 |
| attagttgag gtactgatgc tgtctctact tcagttatac atgtgggttt gaattttgaa | 660 |
| tctattctgg ctcttcttaa gcagaaaatt tagataaaat ggatacctca gtggttttta | 720 |
| atggtgggtt taatatagaa ggaatttaaa ttggaagcta atttagaatc agtaaggagg | 780 |
| gacccaggct aagaaggcaa tcctgggatt ctggaagaaa agatgttttt agttttata | 840 |
| gaaaacacta ctacattctt gatctacaac tcaatgtggt ttaatgaatt tgaagttgcc | 900 |
| agtaaatgta cttcctggtt gttaaagaat ggtatcaaag gacagtgctt agatccgagg | 960 |
| tgagtgtgag aggacagggg ctgggtatg gatacgcaga aggaaggcca cagctgtaca | 1020 |
| gaattgagaa agaatagaga cctgcagttg aggccagcag gtcggctgga ctaactctcc | 1080 |
| agccacagta atgacccaga cagagaaagc cagactcata aagcttgctg agcaaaatta | 1140 |
| agggaacaag gttgagagcc ctagtaagcg aggctctaaa aagcacagct gagctgagat | 1200 |
| gggtgggctt ctctgagtgc ttctaaaatg cgctaaactg aggtgattac tctgaggtaa | 1260 |
| gcaaagctgg gcttgagcca aaatgaagta gactgtaatg aactgaaatg agctgggcca | 1320 |
| ctaagctaaa ctaggctggc ttaaccgaga tgagccaaac tggaatgaac ttcattaatc | 1380 |

```
taggttgaat agagctaaac tctactgcct acactggact gttctgagct gagatgagct    1440
ggggtgagct cagctatgct acgctgtgtt ggggtgagct gatctgaaat gagatactct    1500
ggagtagctg agatggggtg agatggggtg agctgagctg ggctgagcta gactgagctg    1560
agctagggtg agctgagctg ggtgagctga gctaagctgg ggtgagctga gctgagcttg    1620
gctgagctag ggtgagctgg gctgagctgg ggtgagctga gctgagctgg ggtaagctgg    1680
gatgagctgg ggtgagctga gctgagctgg agtgagctga gctgggctga gctggggtga    1740
gctgggctga gctgggctga gctgggctga gctggggtga gctgagctgg ggtgagctga    1800
gctgagctgg ggtgagctga gctgagctgg ggtgagctgg ggtgagctga gctggggtga    1860
gctgagctga gctggggtga gctgagctga gctgagctgg ggtgagctga gctgagctga    1920
gctgagctga gctgagctga gctggggtga gctgagctga gctgagctgg ggtgagctgg    1980
ggtgagctga gctgagctgg agtgagctga gctgggctga gctggggtga gctgggctga    2040
gctggggtga gctgagctga gctgagctga gctggggtga gctgagctga gctggggtga    2100
gctgagctgg ggtgagctgg gctgagctga gctgagctga gctgagctga gctgagctga    2160
gctgagctga gctgagctga gctgagctga gctgagctga gctgagctgg ggtgagctga    2220
gctgagctgg gctgagctgg ggtgagctgg gctgagctgg gctgagctgg gctgagctgg    2280
ggtgagctga gctggggtga gctgagctga gctgggctga gctgagctga gctggggtga    2340
gctgagctga gctggggtga gctgagctga gctgagctgg ggtgagctga gctgagctgg    2400
gctgagcagg gctgagctgg ggtgagctga gctgagctgg ggtgagctgg gctgagctgg    2460
gctgagctga gctgagctgg gctgagctgg gctgagctgg gctgagctgg gctgagctgg    2520
gctgagctgg ggtgagctga gctggggtga gctggggtga gctgagctgg ggtgagctga    2580
gctggggtga gctgagctga gctggggtga gctgagctgg ggtgagctga gctgagctgg    2640
ggtgagctga gctgagctgg ggtgagctga gctagggtga actgggctgg gtgagctgga    2700
gtgagctgag ctgaggtgaa ctggggtgag ccgggatgtt ttgagttgag ctggggtaag    2760
atgagctgaa ctggggtaaa ctgggatgag ctgtggtgag cggagctgga ttgaactgag    2820
ctgtgtgagc tgagctgggg tcagctgagc aagagtgagt agagctggct ggccagaacc    2880
agaatcaatt aggctaagtg agccagattg tgctgggatc agctgtactc agatgagctg    2940
ggatgaggta ggctgggatg agctgggcta gctgacatgg attatgtgag gctgagctag    3000
catgggctgg cctagctgat gagctaagct tgaatgagcg gggctgagct ggactcagat    3060
gtgctagact gagctgtact ggatgatctg gtgtagggtg atctggactc aactgggctg    3120
gctgatggga tgcgccaggt tgaactaggc tcagataagt taggctgagt agggcctggt    3180
tgagatggtt cgggatgagc tgggaaaaga tggactcgga ccatgaactg gctgagctg     3240 ggttgggaga ccatgaattg agctgaactg agtgcagctg ggataaactg ggttgagcta    3300
agaatagact acctgaattg tgccaaactc ggctgggatc aattggaaat tatcaggatt    3360
tagatgagcc ggactaaact atgctgagct ggactggttg gatgtgttga actggcctgc    3420
tgctgggctg gcatagctga gttgaactta aatgaggaag gctgagcaag gctagcctgc    3480
ttgcatagag ctgaacttta gcctagcctg agctggac                           3518

<210> SEQ ID NO 7
<211> LENGTH: 315
<212> TYPE: DNA
<213> ORGANISM: Mus musculus
<220> FEATURE:
```

<221> NAME/KEY: misc_feature
<222> LOCATION: (1)..(315)
<223> OTHER INFORMATION: mouse IgM exon 1

<400> SEQUENCE: 7

```
agagtcagtc cttcccaaat gtcttccccc tcgtctcctg cgagagcccc ctgtctgata      60
agaatctggt ggccatgggc tgcctggccc gggacttcct gcccagcacc atttccttca     120
cctggaacta ccagaacaac actgaagtca tccagggtat cagaaccttc ccaacactga     180
ggacaggggg caagtaccta gccacctcgc aggtgttgct gtctcccaag agcatccttg     240
aaggttcaga tgaatacctg gtatgcaaaa tccactacgg aggcaaaaac aaagatctgc     300
atgtgcccat tccag                                                     315
```

<210> SEQ ID NO 8
<211> LENGTH: 5
<212> TYPE: PRT
<213> ORGANISM: Homo sapiens

<400> SEQUENCE: 8

Val Gln Leu Glu Arg
1               5

<210> SEQ ID NO 9
<211> LENGTH: 5
<212> TYPE: PRT
<213> ORGANISM: Unknown
<220> FEATURE:
<223> OTHER INFORMATION: Mammal

<400> SEQUENCE: 9

Val Pro Leu Ala Arg
1               5

<210> SEQ ID NO 10
<211> LENGTH: 5
<212> TYPE: PRT
<213> ORGANISM: Unknown
<220> FEATURE:
<223> OTHER INFORMATION: Mammal

<400> SEQUENCE: 10

Val Ser Leu Ala Leu
1               5

<210> SEQ ID NO 11
<211> LENGTH: 5
<212> TYPE: PRT
<213> ORGANISM: Unknown
<220> FEATURE:
<223> OTHER INFORMATION: Mammal

<400> SEQUENCE: 11

Val Ser Leu Ala Arg
1               5

<210> SEQ ID NO 12
<211> LENGTH: 4
<212> TYPE: PRT
<213> ORGANISM: Homo sapiens

<400> SEQUENCE: 12

Trp Glu Leu Leu
1

```
<210> SEQ ID NO 13
<211> LENGTH: 6
<212> TYPE: PRT
<213> ORGANISM: Unknown
<220> FEATURE:
<223> OTHER INFORMATION: Mammal

<400> SEQUENCE: 13

Val Ser Trp Glu Pro Leu
1               5

<210> SEQ ID NO 14
<211> LENGTH: 5
<212> TYPE: PRT
<213> ORGANISM: Homo sapiens

<400> SEQUENCE: 14

Tyr Gln Leu Leu Tyr
1               5

<210> SEQ ID NO 15
<211> LENGTH: 6
<212> TYPE: PRT
<213> ORGANISM: Unknown
<220> FEATURE:
<223> OTHER INFORMATION: Mammal

<400> SEQUENCE: 15

Ser Tyr Gln Leu Pro Tyr
1               5

<210> SEQ ID NO 16
<211> LENGTH: 4
<212> TYPE: PRT
<213> ORGANISM: Homo sapiens

<400> SEQUENCE: 16

Arg Ile Leu Tyr
1

<210> SEQ ID NO 17
<211> LENGTH: 5
<212> TYPE: PRT
<213> ORGANISM: Homo sapiens

<400> SEQUENCE: 17

Trp Cys Met Leu Tyr
1               5

<210> SEQ ID NO 18
<211> LENGTH: 10
<212> TYPE: PRT
<213> ORGANISM: Unknown
<220> FEATURE:
<223> OTHER INFORMATION: Mammal

<400> SEQUENCE: 18

Arg Thr Leu Tyr Ser Trp Cys Met Pro Tyr
1               5                   10

<210> SEQ ID NO 19
<211> LENGTH: 5
<212> TYPE: PRT
<213> ORGANISM: Homo sapiens

<400> SEQUENCE: 19
```

```
Ser Ile Leu Trp Trp
1               5

<210> SEQ ID NO 20
<211> LENGTH: 9
<212> TYPE: PRT
<213> ORGANISM: Unknown
<220> FEATURE:
<223> OTHER INFORMATION: Mammal

<400> SEQUENCE: 20

Ser Thr Leu Trp Trp Ser Leu Pro Phe
1               5

<210> SEQ ID NO 21
<211> LENGTH: 10
<212> TYPE: PRT
<213> ORGANISM: Homo sapiens

<400> SEQUENCE: 21

Val Leu Arg Phe Leu Glu Trp Leu Leu Tyr
1               5                   10

<210> SEQ ID NO 22
<211> LENGTH: 10
<212> TYPE: PRT
<213> ORGANISM: Unknown
<220> FEATURE:
<223> OTHER INFORMATION: Mammal

<400> SEQUENCE: 22

Val Ser Pro Phe Leu Glu Trp Ser Leu Tyr
1               5                   10

<210> SEQ ID NO 23
<211> LENGTH: 9
<212> TYPE: PRT
<213> ORGANISM: Homo sapiens

<400> SEQUENCE: 23

Val Leu Arg Tyr Phe Asp Trp Leu Leu
1               5

<210> SEQ ID NO 24
<211> LENGTH: 9
<212> TYPE: PRT
<213> ORGANISM: Unknown
<220> FEATURE:
<223> OTHER INFORMATION: Mammal

<400> SEQUENCE: 24

Val Ser Pro Tyr Phe Asp Trp Ser Leu
1               5

<210> SEQ ID NO 25
<211> LENGTH: 9
<212> TYPE: PRT
<213> ORGANISM: Homo sapiens

<400> SEQUENCE: 25

Val Leu Leu Trp Phe Gly Glu Leu Leu
1               5

<210> SEQ ID NO 26
<211> LENGTH: 9
```

```
<212> TYPE: PRT
<213> ORGANISM: Unknown
<220> FEATURE:
<223> OTHER INFORMATION: Mammal

<400> SEQUENCE: 26

Val Ser Pro Trp Phe Gly Glu Ser Leu
1               5

<210> SEQ ID NO 27
<211> LENGTH: 9
<212> TYPE: PRT
<213> ORGANISM: Homo sapiens

<400> SEQUENCE: 27

Leu Arg Leu Gly Glu Leu Ser Leu Tyr
1               5

<210> SEQ ID NO 28
<211> LENGTH: 9
<212> TYPE: PRT
<213> ORGANISM: Unknown
<220> FEATURE:
<223> OTHER INFORMATION: Mammal

<400> SEQUENCE: 28

Ser Arg Leu Gly Glu Ser Ser Leu Tyr
1               5

<210> SEQ ID NO 29
<211> LENGTH: 4
<212> TYPE: PRT
<213> ORGANISM: Homo sapiens

<400> SEQUENCE: 29

Trp Leu Leu Leu
1

<210> SEQ ID NO 30
<211> LENGTH: 4
<212> TYPE: PRT
<213> ORGANISM: Unknown
<220> FEATURE:
<223> OTHER INFORMATION: Mammal

<400> SEQUENCE: 30

Val Ser Leu Ser
1

<210> SEQ ID NO 31
<211> LENGTH: 4
<212> TYPE: PRT
<213> ORGANISM: Unknown
<220> FEATURE:
<223> OTHER INFORMATION: Mammal

<400> SEQUENCE: 31

Trp Ser Leu Leu
1

<210> SEQ ID NO 32
<211> LENGTH: 4
<212> TYPE: PRT
<213> ORGANISM: Unknown
<220> FEATURE:
<223> OTHER INFORMATION: Mammal
```

```
<400> SEQUENCE: 32

Pro Gln Ser Leu
1

<210> SEQ ID NO 33
<211> LENGTH: 4
<212> TYPE: PRT
<213> ORGANISM: Unknown
<220> FEATURE:
<223> OTHER INFORMATION: Mammal

<400> SEQUENCE: 33

Pro Arg Ser Leu
1

<210> SEQ ID NO 34
<211> LENGTH: 5
<212> TYPE: PRT
<213> ORGANISM: Unknown
<220> FEATURE:
<223> OTHER INFORMATION: Mammal

<400> SEQUENCE: 34

Pro Arg Trp Ser Leu
1               5

<210> SEQ ID NO 35
<211> LENGTH: 6
<212> TYPE: PRT
<213> ORGANISM: Homo sapiens

<400> SEQUENCE: 35

Trp Ile Gln Leu Trp Leu
1               5

<210> SEQ ID NO 36
<211> LENGTH: 6
<212> TYPE: PRT
<213> ORGANISM: Unknown
<220> FEATURE:
<223> OTHER INFORMATION: Mammal

<400> SEQUENCE: 36

Trp Thr Gln Pro Trp Leu
1               5

<210> SEQ ID NO 37
<211> LENGTH: 4
<212> TYPE: PRT
<213> ORGANISM: Homo sapiens

<400> SEQUENCE: 37

Trp Leu Arg Leu
1

<210> SEQ ID NO 38
<211> LENGTH: 4
<212> TYPE: PRT
<213> ORGANISM: Unknown
<220> FEATURE:
<223> OTHER INFORMATION: Mammal

<400> SEQUENCE: 38

Trp Pro Pro Leu
1
```

```
<210> SEQ ID NO 39
<211> LENGTH: 5
<212> TYPE: PRT
<213> ORGANISM: Homo sapiens

<400> SEQUENCE: 39

Arg Trp Leu Gln Leu
1               5

<210> SEQ ID NO 40
<211> LENGTH: 5
<212> TYPE: PRT
<213> ORGANISM: Unknown
<220> FEATURE:
<223> OTHER INFORMATION: Mammal

<400> SEQUENCE: 40

Thr Trp Pro Pro Leu
1               5

<210> SEQ ID NO 41
<211> LENGTH: 4
<212> TYPE: PRT
<213> ORGANISM: Homo sapiens

<400> SEQUENCE: 41

Gln Gln Leu Val
1

<210> SEQ ID NO 42
<211> LENGTH: 4
<212> TYPE: PRT
<213> ORGANISM: Unknown
<220> FEATURE:
<223> OTHER INFORMATION: Mammal

<400> SEQUENCE: 42

Pro Gln Leu Val
1

<210> SEQ ID NO 43
<211> LENGTH: 4
<212> TYPE: PRT
<213> ORGANISM: Homo sapiens

<400> SEQUENCE: 43

Gln Trp Leu Val
1

<210> SEQ ID NO 44
<211> LENGTH: 4
<212> TYPE: PRT
<213> ORGANISM: Unknown
<220> FEATURE:
<223> OTHER INFORMATION: Mammal

<400> SEQUENCE: 44

Pro Trp Leu Val
1

<210> SEQ ID NO 45
<211> LENGTH: 5
<212> TYPE: PRT
<213> ORGANISM: Homo sapiens

<400> SEQUENCE: 45
```

```
Tyr Asn Trp Asn Asp
1               5

<210> SEQ ID NO 46
<211> LENGTH: 5
<212> TYPE: PRT
<213> ORGANISM: Unknown
<220> FEATURE:
<223> OTHER INFORMATION: Mammal

<400> SEQUENCE: 46

Tyr His Trp His Asp
1               5

<210> SEQ ID NO 47
<211> LENGTH: 5
<212> TYPE: PRT
<213> ORGANISM: Homo sapiens

<400> SEQUENCE: 47

Tyr Asn Trp Asn Tyr
1               5

<210> SEQ ID NO 48
<211> LENGTH: 5
<212> TYPE: PRT
<213> ORGANISM: Unknown
<220> FEATURE:
<223> OTHER INFORMATION: Mammal

<400> SEQUENCE: 48

Tyr His Trp His Tyr
1               5

<210> SEQ ID NO 49
<211> LENGTH: 6
<212> TYPE: PRT
<213> ORGANISM: Homo sapiens

<400> SEQUENCE: 49

Tyr Ser Gly Ser Tyr Tyr
1               5

<210> SEQ ID NO 50
<211> LENGTH: 6
<212> TYPE: PRT
<213> ORGANISM: Unknown
<220> FEATURE:
<223> OTHER INFORMATION: Mammal

<400> SEQUENCE: 50

Tyr His Gly Ser His Tyr
1               5

<210> SEQ ID NO 51
<211> LENGTH: 10
<212> TYPE: PRT
<213> ORGANISM: Homo sapiens

<400> SEQUENCE: 51

Gly Tyr Cys Ser Ser Thr Ser Cys Tyr Thr
1               5                   10

<210> SEQ ID NO 52
<211> LENGTH: 10
```

```
<212> TYPE: PRT
<213> ORGANISM: Unknown
<220> FEATURE:
<223> OTHER INFORMATION: Mammal

<400> SEQUENCE: 52

Gly His Cys Ser His Thr Ser Cys His Thr
1               5                   10

<210> SEQ ID NO 53
<211> LENGTH: 10
<212> TYPE: PRT
<213> ORGANISM: Homo sapiens

<400> SEQUENCE: 53

Gly Tyr Cys Thr Asn Gly Val Cys Tyr Thr
1               5                   10

<210> SEQ ID NO 54
<211> LENGTH: 10
<212> TYPE: PRT
<213> ORGANISM: Unknown
<220> FEATURE:
<223> OTHER INFORMATION: Mammal

<400> SEQUENCE: 54

Gly His Cys Thr His Gly Val Cys His Thr
1               5                   10

<210> SEQ ID NO 55
<211> LENGTH: 10
<212> TYPE: PRT
<213> ORGANISM: Homo sapiens

<400> SEQUENCE: 55

Gly Tyr Cys Ser Gly Gly Ser Cys Tyr Ser
1               5                   10

<210> SEQ ID NO 56
<211> LENGTH: 10
<212> TYPE: PRT
<213> ORGANISM: Unknown
<220> FEATURE:
<223> OTHER INFORMATION: Mammal

<400> SEQUENCE: 56

Gly His Cys Ser His Gly Ser Cys His Ser
1               5                   10

<210> SEQ ID NO 57
<211> LENGTH: 9
<212> TYPE: PRT
<213> ORGANISM: Homo sapiens

<400> SEQUENCE: 57

Ala Tyr Cys Gly Gly Asp Cys Tyr Ser
1               5

<210> SEQ ID NO 58
<211> LENGTH: 9
<212> TYPE: PRT
<213> ORGANISM: Unknown
<220> FEATURE:
<223> OTHER INFORMATION: Mammal

<400> SEQUENCE: 58
```

Ala His Cys Gly Gly His Cys His Ser
1               5

<210> SEQ ID NO 59
<211> LENGTH: 10
<212> TYPE: PRT
<213> ORGANISM: Homo sapiens

<400> SEQUENCE: 59

Tyr Tyr Asp Phe Trp Ser Gly Tyr Tyr Thr
1               5                   10

<210> SEQ ID NO 60
<211> LENGTH: 10
<212> TYPE: PRT
<213> ORGANISM: Unknown
<220> FEATURE:
<223> OTHER INFORMATION: Mammal

<400> SEQUENCE: 60

Tyr His His Phe Trp Ser Gly His Tyr Thr
1               5                   10

<210> SEQ ID NO 61
<211> LENGTH: 10
<212> TYPE: PRT
<213> ORGANISM: Homo sapiens

<400> SEQUENCE: 61

Tyr Tyr Asp Ile Leu Thr Gly Tyr Tyr Asn
1               5                   10

<210> SEQ ID NO 62
<211> LENGTH: 10
<212> TYPE: PRT
<213> ORGANISM: Unknown
<220> FEATURE:
<223> OTHER INFORMATION: Mammal

<400> SEQUENCE: 62

Tyr His His Ile Leu Thr Gly His Tyr Asn
1               5                   10

<210> SEQ ID NO 63
<211> LENGTH: 10
<212> TYPE: PRT
<213> ORGANISM: Homo sapiens

<400> SEQUENCE: 63

Tyr Tyr Tyr Gly Ser Gly Ser Tyr Tyr Asn
1               5                   10

<210> SEQ ID NO 64
<211> LENGTH: 10
<212> TYPE: PRT
<213> ORGANISM: Unknown
<220> FEATURE:
<223> OTHER INFORMATION: Mammal

<400> SEQUENCE: 64

Tyr His His Gly Ser Gly Ser His Tyr Asn
1               5                   10

<210> SEQ ID NO 65
<211> LENGTH: 12
<212> TYPE: PRT

```
<213> ORGANISM: Homo sapiens

<400> SEQUENCE: 65

Tyr Tyr Asp Tyr Val Trp Gly Ser Tyr Arg Tyr Thr
1               5                   10

<210> SEQ ID NO 66
<211> LENGTH: 12
<212> TYPE: PRT
<213> ORGANISM: Unknown
<220> FEATURE:
<223> OTHER INFORMATION: Mammal

<400> SEQUENCE: 66

Tyr His Asp His Val Trp Gly Ser His Arg Tyr Thr
1               5                   10

<210> SEQ ID NO 67
<211> LENGTH: 10
<212> TYPE: PRT
<213> ORGANISM: Homo sapiens

<400> SEQUENCE: 67

Tyr Tyr Tyr Asp Ser Ser Gly Tyr Tyr Tyr
1               5                   10

<210> SEQ ID NO 68
<211> LENGTH: 10
<212> TYPE: PRT
<213> ORGANISM: Unknown
<220> FEATURE:
<223> OTHER INFORMATION: Mammal

<400> SEQUENCE: 68

Tyr His Tyr His Ser Ser Gly His Tyr Tyr
1               5                   10

<210> SEQ ID NO 69
<211> LENGTH: 5
<212> TYPE: PRT
<213> ORGANISM: Homo sapiens

<400> SEQUENCE: 69

Asp Tyr Ser Asn Tyr
1               5

<210> SEQ ID NO 70
<211> LENGTH: 4
<212> TYPE: PRT
<213> ORGANISM: Unknown
<220> FEATURE:
<223> OTHER INFORMATION: Mammal

<400> SEQUENCE: 70

Pro Gln Ser Leu
1

<210> SEQ ID NO 71
<211> LENGTH: 5
<212> TYPE: PRT
<213> ORGANISM: Homo sapiens

<400> SEQUENCE: 71

Asp Tyr Gly Asp Tyr
1               5
```

<210> SEQ ID NO 72
<211> LENGTH: 5
<212> TYPE: PRT
<213> ORGANISM: Unknown
<220> FEATURE:
<223> OTHER INFORMATION: Mammal

<400> SEQUENCE: 72

Asp His Gly His Tyr
1               5

<210> SEQ ID NO 73
<211> LENGTH: 6
<212> TYPE: PRT
<213> ORGANISM: Homo sapiens

<400> SEQUENCE: 73

Asp Tyr Gly Gly Asn Ser
1               5

<210> SEQ ID NO 74
<211> LENGTH: 6
<212> TYPE: PRT
<213> ORGANISM: Unknown
<220> FEATURE:
<223> OTHER INFORMATION: Mammal

<400> SEQUENCE: 74

Asp His Gly Gly His Ser
1               5

<210> SEQ ID NO 75
<211> LENGTH: 6
<212> TYPE: PRT
<213> ORGANISM: Homo sapiens

<400> SEQUENCE: 75

Gly Tyr Ser Tyr Gly Tyr
1               5

<210> SEQ ID NO 76
<211> LENGTH: 6
<212> TYPE: PRT
<213> ORGANISM: Unknown
<220> FEATURE:
<223> OTHER INFORMATION: Mammal

<400> SEQUENCE: 76

Gly His Ser His Gly Tyr
1               5

<210> SEQ ID NO 77
<211> LENGTH: 7
<212> TYPE: PRT
<213> ORGANISM: Homo sapiens

<400> SEQUENCE: 77

Gly Tyr Ser Gly Tyr Asp Tyr
1               5

<210> SEQ ID NO 78
<211> LENGTH: 7
<212> TYPE: PRT
<213> ORGANISM: Unknown
<220> FEATURE:
<223> OTHER INFORMATION: Mammal

```
<400> SEQUENCE: 78

Gly His Ser Gly His His Tyr
1               5

<210> SEQ ID NO 79
<211> LENGTH: 6
<212> TYPE: PRT
<213> ORGANISM: Homo sapiens

<400> SEQUENCE: 79

Arg Asp Gly Tyr Asn Tyr
1               5

<210> SEQ ID NO 80
<211> LENGTH: 6
<212> TYPE: PRT
<213> ORGANISM: Unknown
<220> FEATURE:
<223> OTHER INFORMATION: Mammal

<400> SEQUENCE: 80

Arg His Gly His His Tyr
1               5

<210> SEQ ID NO 81
<211> LENGTH: 6
<212> TYPE: PRT
<213> ORGANISM: Homo sapiens

<400> SEQUENCE: 81

Glu Tyr Ser Ser Ser Ser
1               5

<210> SEQ ID NO 82
<211> LENGTH: 6
<212> TYPE: PRT
<213> ORGANISM: Unknown
<220> FEATURE:
<223> OTHER INFORMATION: Mammal

<400> SEQUENCE: 82

Glu His Ser His Ser Ser
1               5

<210> SEQ ID NO 83
<211> LENGTH: 7
<212> TYPE: PRT
<213> ORGANISM: Homo sapiens

<400> SEQUENCE: 83

Gly Tyr Ser Ser Ser Trp Tyr
1               5

<210> SEQ ID NO 84
<211> LENGTH: 7
<212> TYPE: PRT
<213> ORGANISM: Unknown
<220> FEATURE:
<223> OTHER INFORMATION: Mammal

<400> SEQUENCE: 84

Gly His Ser His Ser Trp Tyr
1               5
```

```
<210> SEQ ID NO 85
<211> LENGTH: 7
<212> TYPE: PRT
<213> ORGANISM: Homo sapiens

<400> SEQUENCE: 85

Gly Tyr Ser Ser Gly Trp Tyr
1               5

<210> SEQ ID NO 86
<211> LENGTH: 7
<212> TYPE: PRT
<213> ORGANISM: Unknown
<220> FEATURE:
<223> OTHER INFORMATION: Mammal

<400> SEQUENCE: 86

Gly His Ser His Gly Trp Tyr
1               5

<210> SEQ ID NO 87
<211> LENGTH: 6
<212> TYPE: PRT
<213> ORGANISM: Homo sapiens

<400> SEQUENCE: 87

Gly Tyr Ser Ser Gly Tyr
1               5

<210> SEQ ID NO 88
<211> LENGTH: 5
<212> TYPE: PRT
<213> ORGANISM: Homo sapiens

<400> SEQUENCE: 88

Gly Thr Thr Gly Thr
1               5

<210> SEQ ID NO 89
<211> LENGTH: 5
<212> TYPE: PRT
<213> ORGANISM: Homo sapiens

<400> SEQUENCE: 89

Gly Ile Thr Gly Thr
1               5

<210> SEQ ID NO 90
<211> LENGTH: 6
<212> TYPE: PRT
<213> ORGANISM: Homo sapiens

<400> SEQUENCE: 90

Gly Ile Val Gly Ala Thr
1               5

<210> SEQ ID NO 91
<211> LENGTH: 6
<212> TYPE: PRT
<213> ORGANISM: Unknown
<220> FEATURE:
<223> OTHER INFORMATION: Mammal

<400> SEQUENCE: 91

Gly Ile Met Gly Ala Thr
1               5
```

```
<210> SEQ ID NO 92
<211> LENGTH: 9
<212> TYPE: PRT
<213> ORGANISM: Homo sapiens

<400> SEQUENCE: 92

Asp Ile Val Val Val Pro Ala Ala Ile
1               5

<210> SEQ ID NO 93
<211> LENGTH: 9
<212> TYPE: PRT
<213> ORGANISM: Unknown
<220> FEATURE:
<223> OTHER INFORMATION: Mammal

<400> SEQUENCE: 93

Asp Ile Val Val Ile Pro Ala Ala Ile
1               5

<210> SEQ ID NO 94
<211> LENGTH: 9
<212> TYPE: PRT
<213> ORGANISM: Homo sapiens

<400> SEQUENCE: 94

Asp Ile Val Leu Met Val Tyr Ala Ile
1               5

<210> SEQ ID NO 95
<211> LENGTH: 9
<212> TYPE: PRT
<213> ORGANISM: Homo sapiens

<400> SEQUENCE: 95

Asp Ile Val Val Val Ala Ala Thr
1               5

<210> SEQ ID NO 96
<211> LENGTH: 9
<212> TYPE: PRT
<213> ORGANISM: Unknown
<220> FEATURE:
<223> OTHER INFORMATION: Mammal

<400> SEQUENCE: 96

Asp Ile Val Val Met Val Ala Ala Thr
1               5

<210> SEQ ID NO 97
<211> LENGTH: 8
<212> TYPE: PRT
<213> ORGANISM: Homo sapiens

<400> SEQUENCE: 97

His Ile Val Val Val Thr Ala Ile
1               5

<210> SEQ ID NO 98
<211> LENGTH: 9
<212> TYPE: PRT
<213> ORGANISM: Homo sapiens

<400> SEQUENCE: 98
```

Ile Thr Ile Phe Gly Val Val Ile Ile
1               5

<210> SEQ ID NO 99
<211> LENGTH: 4
<212> TYPE: PRT
<213> ORGANISM: Homo sapiens

<400> SEQUENCE: 99

Ile Thr Ile Phe
1

<210> SEQ ID NO 100
<211> LENGTH: 4
<212> TYPE: PRT
<213> ORGANISM: Homo sapiens

<400> SEQUENCE: 100

Leu Val Ile Ile
1

<210> SEQ ID NO 101
<211> LENGTH: 9
<212> TYPE: PRT
<213> ORGANISM: Homo sapiens

<400> SEQUENCE: 101

Ile Thr Met Val Arg Gly Val Ile Ile
1               5

<210> SEQ ID NO 102
<211> LENGTH: 11
<212> TYPE: PRT
<213> ORGANISM: Homo sapiens

<400> SEQUENCE: 102

Ile Met Ile Thr Phe Gly Gly Val Ile Val Ile
1               5                   10

<210> SEQ ID NO 103
<211> LENGTH: 9
<212> TYPE: PRT
<213> ORGANISM: Homo sapiens

<400> SEQUENCE: 103

Ile Thr Met Ile Val Val Val Ile Thr
1               5

<210> SEQ ID NO 104
<211> LENGTH: 8
<212> TYPE: PRT
<213> ORGANISM: Unknown
<220> FEATURE:
<223> OTHER INFORMATION: Mammal

<400> SEQUENCE: 104

Ile Thr Ile Val Val Val Ile Thr
1               5

<210> SEQ ID NO 105
<211> LENGTH: 4
<212> TYPE: PRT
<213> ORGANISM: Homo sapiens

<400> SEQUENCE: 105

Thr Thr Val Thr
1

<210> SEQ ID NO 106
<211> LENGTH: 5
<212> TYPE: PRT
<213> ORGANISM: Homo sapiens

<400> SEQUENCE: 106

Thr Thr Val Val Thr
1               5

<210> SEQ ID NO 107
<211> LENGTH: 6
<212> TYPE: PRT
<213> ORGANISM: Homo sapiens

<400> SEQUENCE: 107

Val Asp Thr Ala Met Val
1               5

<210> SEQ ID NO 108
<211> LENGTH: 7
<212> TYPE: PRT
<213> ORGANISM: Homo sapiens

<400> SEQUENCE: 108

Val Asp Ile Val Ala Thr Ile
1               5

<210> SEQ ID NO 109
<211> LENGTH: 6
<212> TYPE: PRT
<213> ORGANISM: Homo sapiens

<400> SEQUENCE: 109

Val Glu Met Ala Thr Ile
1               5

<210> SEQ ID NO 110
<211> LENGTH: 6
<212> TYPE: PRT
<213> ORGANISM: Unknown
<220> FEATURE:
<223> OTHER INFORMATION: Mammal

<400> SEQUENCE: 110

Val Asp Met Ala Thr Ile
1               5

<210> SEQ ID NO 111
<211> LENGTH: 5
<212> TYPE: PRT
<213> ORGANISM: Homo sapiens

<400> SEQUENCE: 111

Ser Ile Ala Ala Arg
1               5

<210> SEQ ID NO 112
<211> LENGTH: 5
<212> TYPE: PRT
<213> ORGANISM: Unknown
<220> FEATURE:
<223> OTHER INFORMATION: Mammal

```
<400> SEQUENCE: 112

Ser Ile Ala Thr Arg
1               5

<210> SEQ ID NO 113
<211> LENGTH: 6
<212> TYPE: PRT
<213> ORGANISM: Homo sapiens

<400> SEQUENCE: 113

Gly Ile Ala Ala Ala Gly
1               5

<210> SEQ ID NO 114
<211> LENGTH: 6
<212> TYPE: PRT
<213> ORGANISM: Unknown
<220> FEATURE:
<223> OTHER INFORMATION: Mammal

<400> SEQUENCE: 114

Gly Ile Ala Thr Ala Gly
1               5

<210> SEQ ID NO 115
<211> LENGTH: 6
<212> TYPE: PRT
<213> ORGANISM: Homo sapiens

<400> SEQUENCE: 115

Gly Ile Ala Val Ala Gly
1               5

<210> SEQ ID NO 116
<211> LENGTH: 6
<212> TYPE: PRT
<213> ORGANISM: Unknown
<220> FEATURE:
<223> OTHER INFORMATION: Mammal

<400> SEQUENCE: 116

Gly Ile Ala Met Ala Gly
1               5

<210> SEQ ID NO 117
<211> LENGTH: 5
<212> TYPE: PRT
<213> ORGANISM: Homo sapiens

<400> SEQUENCE: 117

Gly Ile Ala Ala Ala
1               5

<210> SEQ ID NO 118
<211> LENGTH: 5
<212> TYPE: PRT
<213> ORGANISM: Unknown
<220> FEATURE:
<223> OTHER INFORMATION: Mammal

<400> SEQUENCE: 118

Gly Ile Ala Thr Ala
1               5

<210> SEQ ID NO 119
```

```
<211> LENGTH: 19
<212> TYPE: DNA
<213> ORGANISM: Unknown
<220> FEATURE:
<223> OTHER INFORMATION: Mammal

<400> SEQUENCE: 119
cgggtcactg ccatttctg                                                  19

<210> SEQ ID NO 120
<211> LENGTH: 20
<212> TYPE: DNA
<213> ORGANISM: Unknown
<220> FEATURE:
<223> OTHER INFORMATION: Mammal

<400> SEQUENCE: 120
tctgcattcg ctcccagcgc                                                 20

<210> SEQ ID NO 121
<211> LENGTH: 19
<212> TYPE: DNA
<213> ORGANISM: Unknown
<220> FEATURE:
<223> OTHER INFORMATION: Mammal

<400> SEQUENCE: 121
tctgcggcat gaacccaat                                                  19

<210> SEQ ID NO 122
<211> LENGTH: 19
<212> TYPE: DNA
<213> ORGANISM: Unknown
<220> FEATURE:
<223> OTHER INFORMATION: Mammal

<400> SEQUENCE: 122
gtgcagggag gaccttctg                                                  19

<210> SEQ ID NO 123
<211> LENGTH: 24
<212> TYPE: DNA
<213> ORGANISM: Unknown
<220> FEATURE:
<223> OTHER INFORMATION: Mammal

<400> SEQUENCE: 123
agtcaccaag cacagagccc tgac                                            24

<210> SEQ ID NO 124
<211> LENGTH: 19
<212> TYPE: DNA
<213> ORGANISM: Unknown
<220> FEATURE:
<223> OTHER INFORMATION: Mammal

<400> SEQUENCE: 124
gccagggagt tgcctagtg                                                  19

<210> SEQ ID NO 125
<211> LENGTH: 19
<212> TYPE: DNA
<213> ORGANISM: Unknown
<220> FEATURE:
<223> OTHER INFORMATION: Mammal

<400> SEQUENCE: 125
```
gtggcccact tcccttcct                                          19

<210> SEQ ID NO 126
<211> LENGTH: 22
<212> TYPE: DNA
<213> ORGANISM: Unknown
<220> FEATURE:
<223> OTHER INFORMATION: Mammal

<400> SEQUENCE: 126
cagctggaac ccaccatgac ct                                      22

<210> SEQ ID NO 127
<211> LENGTH: 18
<212> TYPE: DNA
<213> ORGANISM: Unknown
<220> FEATURE:
<223> OTHER INFORMATION: Mammal

<400> SEQUENCE: 127
gacctgcctc ggatgaca                                           18

<210> SEQ ID NO 128
<211> LENGTH: 19
<212> TYPE: DNA
<213> ORGANISM: Unknown
<220> FEATURE:
<223> OTHER INFORMATION: Mammal

<400> SEQUENCE: 128
tggccagaac tgaccctac                                          19

<210> SEQ ID NO 129
<211> LENGTH: 20
<212> TYPE: DNA
<213> ORGANISM: Unknown
<220> FEATURE:
<223> OTHER INFORMATION: Mammal

<400> SEQUENCE: 129
accgacaaga gtccctcagg                                         20

<210> SEQ ID NO 130
<211> LENGTH: 19
<212> TYPE: DNA
<213> ORGANISM: Unknown
<220> FEATURE:
<223> OTHER INFORMATION: Mammal

<400> SEQUENCE: 130
ggagtcggct ctggatgtg                                          19

<210> SEQ ID NO 131
<211> LENGTH: 17
<212> TYPE: DNA
<213> ORGANISM: Unknown
<220> FEATURE:
<223> OTHER INFORMATION: Mammal

<400> SEQUENCE: 131
tgcggccgat cttagcc                                            17

<210> SEQ ID NO 132
<211> LENGTH: 21
<212> TYPE: DNA

```
<213> ORGANISM: Unknown
<220> FEATURE:
<223> OTHER INFORMATION: Mammal

<400> SEQUENCE: 132
acgagcgggt tcggcccatt c                                              21

<210> SEQ ID NO 133
<211> LENGTH: 18
<212> TYPE: DNA
<213> ORGANISM: Unknown
<220> FEATURE:
<223> OTHER INFORMATION: Mammal

<400> SEQUENCE: 133
ttgaccgatt ccttgcgg                                                  18

<210> SEQ ID NO 134
<211> LENGTH: 19
<212> TYPE: DNA
<213> ORGANISM: Unknown
<220> FEATURE:
<223> OTHER INFORMATION: Mammal

<400> SEQUENCE: 134
cagtcccgtt gatccagcc                                                 19

<210> SEQ ID NO 135
<211> LENGTH: 30
<212> TYPE: DNA
<213> ORGANISM: Unknown
<220> FEATURE:
<223> OTHER INFORMATION: Mammal

<400> SEQUENCE: 135
cccatcaggg attttgtatc tctgtggacg                                     30

<210> SEQ ID NO 136
<211> LENGTH: 21
<212> TYPE: DNA
<213> ORGANISM: Unknown
<220> FEATURE:
<223> OTHER INFORMATION: Mammal

<400> SEQUENCE: 136
ggatatgcag cactgtgcca c                                              21

<210> SEQ ID NO 137
<211> LENGTH: 19
<212> TYPE: DNA
<213> ORGANISM: Unknown
<220> FEATURE:
<223> OTHER INFORMATION: Mammal

<400> SEQUENCE: 137
tcctccaacg acaggtccc                                                 19

<210> SEQ ID NO 138
<211> LENGTH: 24
<212> TYPE: DNA
<213> ORGANISM: Unknown
<220> FEATURE:
<223> OTHER INFORMATION: Mammal

<400> SEQUENCE: 138
tccctggaac tctgccccga caca                                           24
```

<210> SEQ ID NO 139
<211> LENGTH: 20
<212> TYPE: DNA
<213> ORGANISM: Unknown
<220> FEATURE:
<223> OTHER INFORMATION: Mammal

<400> SEQUENCE: 139
gatgaactga cgggcacagg                                              20

<210> SEQ ID NO 140
<211> LENGTH: 20
<212> TYPE: DNA
<213> ORGANISM: Unknown
<220> FEATURE:
<223> OTHER INFORMATION: Mammal

<400> SEQUENCE: 140
atcacactca tcccatcccc                                              20

<210> SEQ ID NO 141
<211> LENGTH: 29
<212> TYPE: DNA
<213> ORGANISM: Unknown
<220> FEATURE:
<223> OTHER INFORMATION: Mammal

<400> SEQUENCE: 141
cccttcccta agtaccacag agtgggctc                                    29

<210> SEQ ID NO 142
<211> LENGTH: 20
<212> TYPE: DNA
<213> ORGANISM: Unknown
<220> FEATURE:
<223> OTHER INFORMATION: Mammal

<400> SEQUENCE: 142
cacagggaag caggaactgc                                              20

<210> SEQ ID NO 143
<211> LENGTH: 18
<212> TYPE: DNA
<213> ORGANISM: Unknown
<220> FEATURE:
<223> OTHER INFORMATION: Mammal

<400> SEQUENCE: 143
ggagccaggc aggacaca                                                18

<210> SEQ ID NO 144
<211> LENGTH: 19
<212> TYPE: DNA
<213> ORGANISM: Unknown
<220> FEATURE:
<223> OTHER INFORMATION: Mammal

<400> SEQUENCE: 144
tgggctcgta gtttgacgt                                               19

<210> SEQ ID NO 145
<211> LENGTH: 23
<212> TYPE: DNA
<213> ORGANISM: Unknown
<220> FEATURE:

<223> OTHER INFORMATION: Mammal

<400> SEQUENCE: 145
gggactttct tacccacact tca                                          23

<210> SEQ ID NO 146
<211> LENGTH: 24
<212> TYPE: DNA
<213> ORGANISM: Unknown
<220> FEATURE:
<223> OTHER INFORMATION: Mammal

<400> SEQUENCE: 146
ggtcccgagc actcttaatt aaac                                         24

<210> SEQ ID NO 147
<211> LENGTH: 16
<212> TYPE: DNA
<213> ORGANISM: Unknown
<220> FEATURE:
<223> OTHER INFORMATION: Mammal

<400> SEQUENCE: 147
cctcgaatgg aactac                                                  16

<210> SEQ ID NO 148
<211> LENGTH: 21
<212> TYPE: DNA
<213> ORGANISM: Unknown
<220> FEATURE:
<223> OTHER INFORMATION: Mammal

<400> SEQUENCE: 148
gggagagcaa ccattcgttg t                                            21

<210> SEQ ID NO 149
<211> LENGTH: 19
<212> TYPE: DNA
<213> ORGANISM: Unknown
<220> FEATURE:
<223> OTHER INFORMATION: Mammal

<400> SEQUENCE: 149
ccgagcaccg atgcatcta                                               19

<210> SEQ ID NO 150
<211> LENGTH: 16
<212> TYPE: DNA
<213> ORGANISM: Unknown
<220> FEATURE:
<223> OTHER INFORMATION: Mammal

<400> SEQUENCE: 150
cgcagtcatg taatgc                                                  16

<210> SEQ ID NO 151
<211> LENGTH: 20
<212> TYPE: DNA
<213> ORGANISM: Unknown
<220> FEATURE:
<223> OTHER INFORMATION: Mammal

<400> SEQUENCE: 151
gggaggcgaa ctgactgtca                                              20

-continued

```
<210> SEQ ID NO 152
<211> LENGTH: 19
<212> TYPE: DNA
<213> ORGANISM: Unknown
<220> FEATURE:
<223> OTHER INFORMATION: Mammal

<400> SEQUENCE: 152
ggtggagagg ctattcggc                                                  19

<210> SEQ ID NO 153
<211> LENGTH: 23
<212> TYPE: DNA
<213> ORGANISM: Unknown
<220> FEATURE:
<223> OTHER INFORMATION: Mammal

<400> SEQUENCE: 153
tgggcacaac agacaatcgg ctg                                             23

<210> SEQ ID NO 154
<211> LENGTH: 17
<212> TYPE: DNA
<213> ORGANISM: Unknown
<220> FEATURE:
<223> OTHER INFORMATION: Mammal

<400> SEQUENCE: 154
gaacacggcg gcatcag                                                    17

<210> SEQ ID NO 155
<211> LENGTH: 17
<212> TYPE: DNA
<213> ORGANISM: Homo sapiens

<400> SEQUENCE: 155
ggtacaactg gaacgac                                                    17

<210> SEQ ID NO 156
<211> LENGTH: 17
<212> TYPE: DNA
<213> ORGANISM: Homo sapiens

<400> SEQUENCE: 156
ggtataactg gaactac                                                    17

<210> SEQ ID NO 157
<211> LENGTH: 17
<212> TYPE: DNA
<213> ORGANISM: Homo sapiens

<400> SEQUENCE: 157
ggtataaccg gaaccac                                                    17

<210> SEQ ID NO 158
<211> LENGTH: 5
<212> TYPE: PRT
<213> ORGANISM: Homo sapiens

<400> SEQUENCE: 158

Tyr Asn Arg Asn His
1               5

<210> SEQ ID NO 159
<211> LENGTH: 17
```

<210> SEQ ID NO 159
<211> LENGTH: 17
<212> TYPE: DNA
<213> ORGANISM: Homo sapiens

<400> SEQUENCE: 159
ggtataactg gaacgac                                                  17

<210> SEQ ID NO 160
<211> LENGTH: 20
<212> TYPE: DNA
<213> ORGANISM: Homo sapiens

<400> SEQUENCE: 160
ggtatagtgg gagctactac                                               20

<210> SEQ ID NO 161
<211> LENGTH: 31
<212> TYPE: DNA
<213> ORGANISM: Homo sapiens

<400> SEQUENCE: 161
aggatattgt agtagtacca gctgctatgc c                                  31

<210> SEQ ID NO 162
<211> LENGTH: 5
<212> TYPE: PRT
<213> ORGANISM: Homo sapiens

<400> SEQUENCE: 162

Tyr Gln Leu Leu Cys
1               5

<210> SEQ ID NO 163
<211> LENGTH: 10
<212> TYPE: PRT
<213> ORGANISM: Homo sapiens

<400> SEQUENCE: 163

Gly Tyr Cys Ser Ser Thr Ser Cys Tyr Ala
1               5                   10

<210> SEQ ID NO 164
<211> LENGTH: 9
<212> TYPE: PRT
<213> ORGANISM: Homo sapiens

<400> SEQUENCE: 164

Asp Ile Val Val Val Pro Ala Ala Met
1               5

<210> SEQ ID NO 165
<211> LENGTH: 31
<212> TYPE: DNA
<213> ORGANISM: Homo sapiens

<400> SEQUENCE: 165
aggatattgt agtagtacca gctgctatac c                                  31

<210> SEQ ID NO 166
<211> LENGTH: 31
<212> TYPE: DNA
<213> ORGANISM: Homo sapiens

<400> SEQUENCE: 166
tggatattgt agtagtacca gctgctatgc c                                  31

<210> SEQ ID NO 167
<211> LENGTH: 5
<212> TYPE: PRT
<213> ORGANISM: Homo sapiens

<400> SEQUENCE: 167

Tyr Gln Leu Leu Cys
1               5

<210> SEQ ID NO 168
<211> LENGTH: 10
<212> TYPE: PRT
<213> ORGANISM: Homo sapiens

<400> SEQUENCE: 168

Gly Tyr Cys Ser Ser Thr Ser Cys Tyr Ala
1               5                   10

<210> SEQ ID NO 169
<211> LENGTH: 9
<212> TYPE: PRT
<213> ORGANISM: Homo sapiens

<400> SEQUENCE: 169

Asp Ile Val Val Pro Ala Ala Met
1               5

<210> SEQ ID NO 170
<211> LENGTH: 31
<212> TYPE: DNA
<213> ORGANISM: Homo sapiens

<400> SEQUENCE: 170
aggatattgt actaatggtg tatgctatac c                                31

<210> SEQ ID NO 171
<211> LENGTH: 31
<212> TYPE: DNA
<213> ORGANISM: Homo sapiens

<400> SEQUENCE: 171
aagatattgt actggtggtg tatgctatac c                                31

<210> SEQ ID NO 172
<211> LENGTH: 10
<212> TYPE: PRT
<213> ORGANISM: Homo sapiens

<400> SEQUENCE: 172

Arg Ile Leu Tyr Trp Trp Cys Met Leu Tyr
1               5                   10

<210> SEQ ID NO 173
<211> LENGTH: 10
<212> TYPE: PRT
<213> ORGANISM: Homo sapiens

<400> SEQUENCE: 173

Gly Tyr Cys Thr Gly Gly Val Cys Tyr Thr
1               5                   10

<210> SEQ ID NO 174
<211> LENGTH: 9

```
<212> TYPE: PRT
<213> ORGANISM: Homo sapiens

<400> SEQUENCE: 174

Asp Ile Val Leu Val Val Tyr Ala Ile
1               5

<210> SEQ ID NO 175
<211> LENGTH: 31
<212> TYPE: DNA
<213> ORGANISM: Homo sapiens

<400> SEQUENCE: 175
aggatattgt agtggtggta gctgctactc c                              31

<210> SEQ ID NO 176
<211> LENGTH: 28
<212> TYPE: DNA
<213> ORGANISM: Homo sapiens

<400> SEQUENCE: 176
agcatattgt ggtggtgatt gctattcc                                  28

<210> SEQ ID NO 177
<211> LENGTH: 8
<212> TYPE: PRT
<213> ORGANISM: Homo sapiens

<400> SEQUENCE: 177

His Ile Val Val Val Ile Ala Ile
1               5

<210> SEQ ID NO 178
<211> LENGTH: 28
<212> TYPE: DNA
<213> ORGANISM: Homo sapiens

<400> SEQUENCE: 178
agcatattgt ggtggtgact gctattcc                                  28

<210> SEQ ID NO 179
<211> LENGTH: 31
<212> TYPE: DNA
<213> ORGANISM: Homo sapiens

<400> SEQUENCE: 179
gtattacgat ttttggagtg gttattatac c                              31

<210> SEQ ID NO 180
<211> LENGTH: 31
<212> TYPE: DNA
<213> ORGANISM: Homo sapiens

<400> SEQUENCE: 180
gtattagcat ttttggagtg gttattatac c                              31

<210> SEQ ID NO 181
<211> LENGTH: 10
<212> TYPE: PRT
<213> ORGANISM: Unknown
<220> FEATURE:
<223> OTHER INFORMATION: Mammal

<400> SEQUENCE: 181
```

Val Leu Ala Phe Leu Glu Trp Leu Leu Tyr
1               5                   10

<210> SEQ ID NO 182
<211> LENGTH: 8
<212> TYPE: PRT
<213> ORGANISM: Homo sapiens

<400> SEQUENCE: 182

His Phe Trp Ser Gly Tyr Tyr Thr
1               5

<210> SEQ ID NO 183
<211> LENGTH: 9
<212> TYPE: PRT
<213> ORGANISM: Homo sapiens

<400> SEQUENCE: 183

Ile Ser Ile Phe Gly Val Val Ile Ile
1               5

<210> SEQ ID NO 184
<211> LENGTH: 31
<212> TYPE: DNA
<213> ORGANISM: Homo sapiens

<400> SEQUENCE: 184
gtattacgat attttgactg gttattataa c                            31

<210> SEQ ID NO 185
<211> LENGTH: 31
<212> TYPE: DNA
<213> ORGANISM: Homo sapiens

<400> SEQUENCE: 185
gtattactat ggttcgggga gttattataa c                            31

<210> SEQ ID NO 186
<211> LENGTH: 30
<212> TYPE: DNA
<213> ORGANISM: Homo sapiens

<400> SEQUENCE: 186
gtattactat gttcggggag ttattataac                              30

<210> SEQ ID NO 187
<211> LENGTH: 10
<212> TYPE: PRT
<213> ORGANISM: Homo sapiens

<400> SEQUENCE: 187

Val Leu Leu Cys Ser Gly Ser Tyr Tyr Asn
1               5                   10

<210> SEQ ID NO 188
<211> LENGTH: 9
<212> TYPE: PRT
<213> ORGANISM: Homo sapiens

<400> SEQUENCE: 188

Tyr Tyr Tyr Val Arg Gly Val Ile Ile
1               5

<210> SEQ ID NO 189

```
<211> LENGTH: 8
<212> TYPE: PRT
<213> ORGANISM: Homo sapiens

<400> SEQUENCE: 189

Ile Thr Met Phe Gly Arg Leu Leu
1               5

<210> SEQ ID NO 190
<211> LENGTH: 37
<212> TYPE: DNA
<213> ORGANISM: Homo sapiens

<400> SEQUENCE: 190
gtattatgat tacgtttggg ggagttatgc ttatacc                              37

<210> SEQ ID NO 191
<211> LENGTH: 9
<212> TYPE: PRT
<213> ORGANISM: Homo sapiens

<400> SEQUENCE: 191

Leu Arg Leu Gly Glu Leu Cys Leu Tyr
1               5

<210> SEQ ID NO 192
<211> LENGTH: 12
<212> TYPE: PRT
<213> ORGANISM: Homo sapiens

<400> SEQUENCE: 192

Tyr Tyr Asp Tyr Val Trp Gly Ser Tyr Ala Tyr Thr
1               5                   10

<210> SEQ ID NO 193
<211> LENGTH: 11
<212> TYPE: PRT
<213> ORGANISM: Homo sapiens

<400> SEQUENCE: 193

Ile Met Ile Thr Phe Gly Gly Val Met Leu Ile
1               5                   10

<210> SEQ ID NO 194
<211> LENGTH: 31
<212> TYPE: DNA
<213> ORGANISM: Homo sapiens

<400> SEQUENCE: 194
gtattactat gatagtagtg gttattacta c                                    31

<210> SEQ ID NO 195
<211> LENGTH: 16
<212> TYPE: DNA
<213> ORGANISM: Homo sapiens

<400> SEQUENCE: 195
tgactacagt aactac                                                     16

<210> SEQ ID NO 196
<211> LENGTH: 16
<212> TYPE: DNA
<213> ORGANISM: Homo sapiens

<400> SEQUENCE: 196
```

```
tgactacggt gactac                                                    16

<210> SEQ ID NO 197
<211> LENGTH: 19
<212> TYPE: DNA
<213> ORGANISM: Homo sapiens

<400> SEQUENCE: 197
tgactacggt ggtaactcc                                                 19

<210> SEQ ID NO 198
<211> LENGTH: 20
<212> TYPE: DNA
<213> ORGANISM: Homo sapiens

<400> SEQUENCE: 198
gtggatacag ctatggttac                                                20

<210> SEQ ID NO 199
<211> LENGTH: 23
<212> TYPE: DNA
<213> ORGANISM: Homo sapiens

<400> SEQUENCE: 199
gtggatatag tggctacgat tac                                            23

<210> SEQ ID NO 200
<211> LENGTH: 20
<212> TYPE: DNA
<213> ORGANISM: Homo sapiens

<400> SEQUENCE: 200
gtagagatgg ctacaattac                                                20

<210> SEQ ID NO 201
<211> LENGTH: 18
<212> TYPE: DNA
<213> ORGANISM: Homo sapiens

<400> SEQUENCE: 201
gagtatagca gctcgtcc                                                  18

<210> SEQ ID NO 202
<211> LENGTH: 21
<212> TYPE: DNA
<213> ORGANISM: Homo sapiens

<400> SEQUENCE: 202
gggtatagca gcagctggta c                                              21

<210> SEQ ID NO 203
<211> LENGTH: 21
<212> TYPE: DNA
<213> ORGANISM: Homo sapiens

<400> SEQUENCE: 203
gggtatagca gtggctggta c                                              21

<210> SEQ ID NO 204
<211> LENGTH: 18
<212> TYPE: DNA
<213> ORGANISM: Homo sapiens
```

```
<400> SEQUENCE: 204
gggtatagca gcggctac                                                   18

<210> SEQ ID NO 205
<211> LENGTH: 11
<212> TYPE: DNA
<213> ORGANISM: Homo sapiens

<400> SEQUENCE: 205
ctaactgggg a                                                          11

<210> SEQ ID NO 206
<211> LENGTH: 17
<212> TYPE: DNA
<213> ORGANISM: Unknown
<220> FEATURE:
<223> OTHER INFORMATION: Mammal

<400> SEQUENCE: 206
gtcgttccag ttgtacc                                                    17

<210> SEQ ID NO 207
<211> LENGTH: 5
<212> TYPE: PRT
<213> ORGANISM: Unknown
<220> FEATURE:
<223> OTHER INFORMATION: Mammal

<400> SEQUENCE: 207

Val Val Pro Val Val
1               5

<210> SEQ ID NO 208
<211> LENGTH: 5
<212> TYPE: PRT
<213> ORGANISM: Unknown
<220> FEATURE:
<223> OTHER INFORMATION: Mammal

<400> SEQUENCE: 208

Ser Phe Gln Leu Tyr
1               5

<210> SEQ ID NO 209
<211> LENGTH: 5
<212> TYPE: PRT
<213> ORGANISM: Unknown
<220> FEATURE:
<223> OTHER INFORMATION: Mammal

<400> SEQUENCE: 209

Arg Ser Ser Cys Thr
1               5

<210> SEQ ID NO 210
<211> LENGTH: 17
<212> TYPE: DNA
<213> ORGANISM: Unknown
<220> FEATURE:
<223> OTHER INFORMATION: Mammal

<400> SEQUENCE: 210
gtagttccag ttatacc                                                    17

<210> SEQ ID NO 211
```

```
<211> LENGTH: 5
<212> TYPE: PRT
<213> ORGANISM: Unknown
<220> FEATURE:
<223> OTHER INFORMATION: Mammal

<400> SEQUENCE: 211

Val Val Pro Val Ile
1               5

<210> SEQ ID NO 212
<211> LENGTH: 4
<212> TYPE: PRT
<213> ORGANISM: Unknown
<220> FEATURE:
<223> OTHER INFORMATION: Mammal

<400> SEQUENCE: 212

Phe Gln Leu Tyr
1

<210> SEQ ID NO 213
<211> LENGTH: 5
<212> TYPE: PRT
<213> ORGANISM: Unknown
<220> FEATURE:
<223> OTHER INFORMATION: Mammal

<400> SEQUENCE: 213

Ser Ser Ser Tyr Thr
1               5

<210> SEQ ID NO 214
<211> LENGTH: 17
<212> TYPE: DNA
<213> ORGANISM: Unknown
<220> FEATURE:
<223> OTHER INFORMATION: Mammal

<400> SEQUENCE: 214
gtggttccgg ttatacc                                           17

<210> SEQ ID NO 215
<211> LENGTH: 5
<212> TYPE: PRT
<213> ORGANISM: Unknown
<220> FEATURE:
<223> OTHER INFORMATION: Mammal

<400> SEQUENCE: 215

Trp Phe Arg Leu Tyr
1               5

<210> SEQ ID NO 216
<211> LENGTH: 5
<212> TYPE: PRT
<213> ORGANISM: Unknown
<220> FEATURE:
<223> OTHER INFORMATION: Mammal

<400> SEQUENCE: 216

Gly Ser Gly Tyr Thr
1               5

<210> SEQ ID NO 217
<211> LENGTH: 17
<212> TYPE: DNA
```

```
<213> ORGANISM: Unknown
<220> FEATURE:
<223> OTHER INFORMATION: Mammal

<400> SEQUENCE: 217
gtcgttccag ttatacc                                                  17

<210> SEQ ID NO 218
<211> LENGTH: 5
<212> TYPE: PRT
<213> ORGANISM: Unknown
<220> FEATURE:
<223> OTHER INFORMATION: Mammal

<400> SEQUENCE: 218

Arg Ser Ser Tyr Thr
1               5

<210> SEQ ID NO 219
<211> LENGTH: 20
<212> TYPE: DNA
<213> ORGANISM: Unknown
<220> FEATURE:
<223> OTHER INFORMATION: Mammal

<400> SEQUENCE: 219
gtagtagctc ccactatacc                                               20

<210> SEQ ID NO 220
<211> LENGTH: 6
<212> TYPE: PRT
<213> ORGANISM: Unknown
<220> FEATURE:
<223> OTHER INFORMATION: Mammal

<400> SEQUENCE: 220

Val Val Ala Pro Thr Ile
1               5

<210> SEQ ID NO 221
<211> LENGTH: 4
<212> TYPE: PRT
<213> ORGANISM: Unknown
<220> FEATURE:
<223> OTHER INFORMATION: Mammal

<400> SEQUENCE: 221

Leu Pro Leu Tyr
1

<210> SEQ ID NO 222
<211> LENGTH: 6
<212> TYPE: PRT
<213> ORGANISM: Unknown
<220> FEATURE:
<223> OTHER INFORMATION: Mammal

<400> SEQUENCE: 222

Ser Ser Ser His Tyr Thr
1               5

<210> SEQ ID NO 223
<211> LENGTH: 31
<212> TYPE: DNA
<213> ORGANISM: Unknown
<220> FEATURE:
<223> OTHER INFORMATION: Mammal
```

```
<400> SEQUENCE: 223
ggcatagcag ctggtactac tacaatatcc t                                    31

<210> SEQ ID NO 224
<211> LENGTH: 10
<212> TYPE: PRT
<213> ORGANISM: Unknown
<220> FEATURE:
<223> OTHER INFORMATION: Mammal

<400> SEQUENCE: 224

Gly Ile Ala Ala Gly Thr Thr Thr Ile Ser
1               5                   10

<210> SEQ ID NO 225
<211> LENGTH: 8
<212> TYPE: PRT
<213> ORGANISM: Unknown
<220> FEATURE:
<223> OTHER INFORMATION: Mammal

<400> SEQUENCE: 225

Gln Leu Val Leu Leu Gln Tyr Pro
1               5

<210> SEQ ID NO 226
<211> LENGTH: 9
<212> TYPE: PRT
<213> ORGANISM: Unknown
<220> FEATURE:
<223> OTHER INFORMATION: Mammal

<400> SEQUENCE: 226

His Ser Ser Trp Tyr Tyr Tyr Asn Ile
1               5

<210> SEQ ID NO 227
<211> LENGTH: 31
<212> TYPE: DNA
<213> ORGANISM: Unknown
<220> FEATURE:
<223> OTHER INFORMATION: Mammal

<400> SEQUENCE: 227
ggtatagcag ctggtactac tacaatatcc t                                    31

<210> SEQ ID NO 228
<211> LENGTH: 31
<212> TYPE: DNA
<213> ORGANISM: Unknown
<220> FEATURE:
<223> OTHER INFORMATION: Mammal

<400> SEQUENCE: 228
ggcatagcag ctggtactac tacaatatcc a                                    31

<210> SEQ ID NO 229
<211> LENGTH: 31
<212> TYPE: DNA
<213> ORGANISM: Unknown
<220> FEATURE:
<223> OTHER INFORMATION: Mammal

<400> SEQUENCE: 229
ggtatagcat acaccattag tacaatatcc t                                    31
```

```
<210> SEQ ID NO 230
<211> LENGTH: 10
<212> TYPE: PRT
<213> ORGANISM: Unknown
<220> FEATURE:
<223> OTHER INFORMATION: Mammal

<400> SEQUENCE: 230

Gly Ile Ala Tyr Thr Ile Ser Thr Ile Ser
1               5                   10

<210> SEQ ID NO 231
<211> LENGTH: 8
<212> TYPE: PRT
<213> ORGANISM: Unknown
<220> FEATURE:
<223> OTHER INFORMATION: Mammal

<400> SEQUENCE: 231

His Thr Pro Leu Val Gln Tyr Pro
1               5

<210> SEQ ID NO 232
<211> LENGTH: 5
<212> TYPE: PRT
<213> ORGANISM: Unknown
<220> FEATURE:
<223> OTHER INFORMATION: Mammal

<400> SEQUENCE: 232

Tyr Ser Ile His His
1               5

<210> SEQ ID NO 233
<211> LENGTH: 31
<212> TYPE: DNA
<213> ORGANISM: Unknown
<220> FEATURE:
<223> OTHER INFORMATION: Mammal

<400> SEQUENCE: 233
ggtatagcat acaccaccag tacaatatct t                          31

<210> SEQ ID NO 234
<211> LENGTH: 10
<212> TYPE: PRT
<213> ORGANISM: Unknown
<220> FEATURE:
<223> OTHER INFORMATION: Mammal

<400> SEQUENCE: 234

Gly Ile Ala Tyr Thr Thr Ser Thr Ile Ser
1               5                   10

<210> SEQ ID NO 235
<211> LENGTH: 8
<212> TYPE: PRT
<213> ORGANISM: Unknown
<220> FEATURE:
<223> OTHER INFORMATION: Mammal

<400> SEQUENCE: 235

His Thr Pro Pro Val Gln Tyr Leu
1               5
```

```
<210> SEQ ID NO 236
<211> LENGTH: 9
<212> TYPE: PRT
<213> ORGANISM: Unknown
<220> FEATURE:
<223> OTHER INFORMATION: Mammal

<400> SEQUENCE: 236

Tyr Ser Ile His His Gln Tyr Asn Ile
1               5

<210> SEQ ID NO 237
<211> LENGTH: 31
<212> TYPE: DNA
<213> ORGANISM: Unknown
<220> FEATURE:
<223> OTHER INFORMATION: Mammal

<400> SEQUENCE: 237
ggagtagcag ctaccaccac tacaatatcc t                                   31

<210> SEQ ID NO 238
<211> LENGTH: 10
<212> TYPE: PRT
<213> ORGANISM: Unknown
<220> FEATURE:
<223> OTHER INFORMATION: Mammal

<400> SEQUENCE: 238

Gly Val Ala Ala Thr Thr Thr Thr Ile Ser
1               5                   10

<210> SEQ ID NO 239
<211> LENGTH: 8
<212> TYPE: PRT
<213> ORGANISM: Unknown
<220> FEATURE:
<223> OTHER INFORMATION: Mammal

<400> SEQUENCE: 239

Gln Leu Pro Pro Leu Gln Tyr Pro
1               5

<210> SEQ ID NO 240
<211> LENGTH: 9
<212> TYPE: PRT
<213> ORGANISM: Unknown
<220> FEATURE:
<223> OTHER INFORMATION: Mammal

<400> SEQUENCE: 240

Ser Ser Ser Tyr His His Tyr Asn Ile
1               5

<210> SEQ ID NO 241
<211> LENGTH: 28
<212> TYPE: DNA
<213> ORGANISM: Unknown
<220> FEATURE:
<223> OTHER INFORMATION: Mammal

<400> SEQUENCE: 241
ggaatagcaa tcaccaccac aatatgct                                       28

<210> SEQ ID NO 242
<211> LENGTH: 9
<212> TYPE: PRT
```

```
<213> ORGANISM: Unknown
<220> FEATURE:
<223> OTHER INFORMATION: Mammal

<400> SEQUENCE: 242

Gly Ile Ala Ile Thr Thr Thr Ile Cys
1               5

<210> SEQ ID NO 243
<211> LENGTH: 7
<212> TYPE: PRT
<213> ORGANISM: Unknown
<220> FEATURE:
<223> OTHER INFORMATION: Mammal

<400> SEQUENCE: 243

Gln Ser Pro Pro Gln Tyr Ala
1               5

<210> SEQ ID NO 244
<211> LENGTH: 8
<212> TYPE: PRT
<213> ORGANISM: Unknown
<220> FEATURE:
<223> OTHER INFORMATION: Mammal

<400> SEQUENCE: 244

Asn Ser Asn His His His Asn Met
1               5

<210> SEQ ID NO 245
<211> LENGTH: 28
<212> TYPE: DNA
<213> ORGANISM: Unknown
<220> FEATURE:
<223> OTHER INFORMATION: Mammal

<400> SEQUENCE: 245
ggaatagcag tcaccaccac aatatgct                                        28

<210> SEQ ID NO 246
<211> LENGTH: 9
<212> TYPE: PRT
<213> ORGANISM: Unknown
<220> FEATURE:
<223> OTHER INFORMATION: Mammal

<400> SEQUENCE: 246

Gly Ile Ala Val Thr Thr Thr Ile Cys
1               5

<210> SEQ ID NO 247
<211> LENGTH: 7
<212> TYPE: PRT
<213> ORGANISM: Unknown
<220> FEATURE:
<223> OTHER INFORMATION: Mammal

<400> SEQUENCE: 247

Gln Ser Pro Pro Gln Tyr Ala
1               5

<210> SEQ ID NO 248
<211> LENGTH: 8
<212> TYPE: PRT
<213> ORGANISM: Unknown
<220> FEATURE:
```

```
<223> OTHER INFORMATION: Mammal

<400> SEQUENCE: 248

Asn Ser Ser His His His Asn Met
1               5

<210> SEQ ID NO 249
<211> LENGTH: 31
<212> TYPE: DNA
<213> ORGANISM: Unknown
<220> FEATURE:
<223> OTHER INFORMATION: Mammal

<400> SEQUENCE: 249
ggtataataa ccactccaaa aatcgtaata c                                          31

<210> SEQ ID NO 250
<211> LENGTH: 10
<212> TYPE: PRT
<213> ORGANISM: Unknown
<220> FEATURE:
<223> OTHER INFORMATION: Mammal

<400> SEQUENCE: 250

Gly Ile Ile Thr Thr Pro Lys Ile Val Ile
1               5                   10

<210> SEQ ID NO 251
<211> LENGTH: 5
<212> TYPE: PRT
<213> ORGANISM: Unknown
<220> FEATURE:
<223> OTHER INFORMATION: Mammal

<400> SEQUENCE: 251

Pro Leu Gln Lys Ser
1               5

<210> SEQ ID NO 252
<211> LENGTH: 9
<212> TYPE: PRT
<213> ORGANISM: Unknown
<220> FEATURE:
<223> OTHER INFORMATION: Mammal

<400> SEQUENCE: 252

Tyr Asn Asn His Ser Lys Asn Arg Asn
1               5

<210> SEQ ID NO 253
<211> LENGTH: 31
<212> TYPE: DNA
<213> ORGANISM: Unknown
<220> FEATURE:
<223> OTHER INFORMATION: Mammal

<400> SEQUENCE: 253
ggtataataa ccactccaaa aatgctaata c                                          31

<210> SEQ ID NO 254
<211> LENGTH: 10
<212> TYPE: PRT
<213> ORGANISM: Unknown
<220> FEATURE:
<223> OTHER INFORMATION: Mammal

<400> SEQUENCE: 254
```

```
Gly Ile Ile Thr Thr Pro Lys Met Leu Ile
1               5                   10

<210> SEQ ID NO 255
<211> LENGTH: 5
<212> TYPE: PRT
<213> ORGANISM: Unknown
<220> FEATURE:
<223> OTHER INFORMATION: Mammal

<400> SEQUENCE: 255

Pro Leu Gln Lys Cys
1               5

<210> SEQ ID NO 256
<211> LENGTH: 9
<212> TYPE: PRT
<213> ORGANISM: Unknown
<220> FEATURE:
<223> OTHER INFORMATION: Mammal

<400> SEQUENCE: 256

Tyr Asn Asn His Ser Lys Asn Ala Asn
1               5

<210> SEQ ID NO 257
<211> LENGTH: 31
<212> TYPE: DNA
<213> ORGANISM: Unknown
<220> FEATURE:
<223> OTHER INFORMATION: Mammal

<400> SEQUENCE: 257
gttataataa ccagtcaaaa tatcgtaata c                                    31

<210> SEQ ID NO 258
<211> LENGTH: 10
<212> TYPE: PRT
<213> ORGANISM: Unknown
<220> FEATURE:
<223> OTHER INFORMATION: Mammal

<400> SEQUENCE: 258

Val Ile Ile Thr Ser Gln Asn Ile Val Ile
1               5                   10

<210> SEQ ID NO 259
<211> LENGTH: 5
<212> TYPE: PRT
<213> ORGANISM: Unknown
<220> FEATURE:
<223> OTHER INFORMATION: Mammal

<400> SEQUENCE: 259

Pro Val Lys Ile Ser
1               5

<210> SEQ ID NO 260
<211> LENGTH: 9
<212> TYPE: PRT
<213> ORGANISM: Unknown
<220> FEATURE:
<223> OTHER INFORMATION: Mammal

<400> SEQUENCE: 260

Tyr Asn Asn Gln Ser Lys Tyr Arg Asn
```

```
<210> SEQ ID NO 261
<211> LENGTH: 31
<212> TYPE: DNA
<213> ORGANISM: Unknown
<220> FEATURE:
<223> OTHER INFORMATION: Mammal

<400> SEQUENCE: 261
gttataataa ctcccccgaac catagtaata c                                   31

<210> SEQ ID NO 262
<211> LENGTH: 10
<212> TYPE: PRT
<213> ORGANISM: Unknown
<220> FEATURE:
<223> OTHER INFORMATION: Mammal

<400> SEQUENCE: 262

Val Ile Ile Thr Pro Arg Thr Ile Val Ile
1               5                   10

<210> SEQ ID NO 263
<211> LENGTH: 4
<212> TYPE: PRT
<213> ORGANISM: Unknown
<220> FEATURE:
<223> OTHER INFORMATION: Mammal

<400> SEQUENCE: 263

Leu Pro Glu Pro
1

<210> SEQ ID NO 264
<211> LENGTH: 9
<212> TYPE: PRT
<213> ORGANISM: Unknown
<220> FEATURE:
<223> OTHER INFORMATION: Mammal

<400> SEQUENCE: 264

Tyr Asn Asn Ser Pro Asn His Ser Asn
1               5

<210> SEQ ID NO 265
<211> LENGTH: 30
<212> TYPE: DNA
<213> ORGANISM: Unknown
<220> FEATURE:
<223> OTHER INFORMATION: Mammal

<400> SEQUENCE: 265
gttataataa ctcccccgaac atagtaatac                                     30

<210> SEQ ID NO 266
<211> LENGTH: 7
<212> TYPE: PRT
<213> ORGANISM: Unknown
<220> FEATURE:
<223> OTHER INFORMATION: Mammal

<400> SEQUENCE: 266

Val Ile Ile Thr Pro Arg Thr
1               5
```

```
<210> SEQ ID NO 267
<211> LENGTH: 6
<212> TYPE: PRT
<213> ORGANISM: Unknown
<220> FEATURE:
<223> OTHER INFORMATION: Mammal

<400> SEQUENCE: 267

Leu Pro Glu His Ser Asn
1               5

<210> SEQ ID NO 268
<211> LENGTH: 9
<212> TYPE: PRT
<213> ORGANISM: Unknown
<220> FEATURE:
<223> OTHER INFORMATION: Mammal

<400> SEQUENCE: 268

Tyr Asn Asn Ser Pro Asn Ile Val Ile
1               5

<210> SEQ ID NO 269
<211> LENGTH: 37
<212> TYPE: DNA
<213> ORGANISM: Unknown
<220> FEATURE:
<223> OTHER INFORMATION: Mammal

<400> SEQUENCE: 269
ggtataagca taactccccc aaacgtaatc ataatac                              37

<210> SEQ ID NO 270
<211> LENGTH: 12
<212> TYPE: PRT
<213> ORGANISM: Unknown
<220> FEATURE:
<223> OTHER INFORMATION: Mammal

<400> SEQUENCE: 270

Gly Ile Ser Ile Thr Pro Pro Asn Val Ile Ile Ile
1               5                   10

<210> SEQ ID NO 271
<211> LENGTH: 4
<212> TYPE: PRT
<213> ORGANISM: Unknown
<220> FEATURE:
<223> OTHER INFORMATION: Mammal

<400> SEQUENCE: 271

Leu Pro Gln Thr
1

<210> SEQ ID NO 272
<211> LENGTH: 11
<212> TYPE: PRT
<213> ORGANISM: Unknown
<220> FEATURE:
<223> OTHER INFORMATION: Mammal

<400> SEQUENCE: 272

Tyr Lys His Asn Ser Pro Lys Arg Asn His Asn
1               5                   10

<210> SEQ ID NO 273
<211> LENGTH: 31
```

<212> TYPE: DNA
<213> ORGANISM: Unknown
<220> FEATURE:
<223> OTHER INFORMATION: Mammal

<400> SEQUENCE: 273
gtagtaataa ccactactat catagtaata c                               31

<210> SEQ ID NO 274
<211> LENGTH: 10
<212> TYPE: PRT
<213> ORGANISM: Unknown
<220> FEATURE:
<223> OTHER INFORMATION: Mammal

<400> SEQUENCE: 274

Val Val Ile Thr Thr Thr Ile Ile Val Ile
1               5                   10

<210> SEQ ID NO 275
<211> LENGTH: 4
<212> TYPE: PRT
<213> ORGANISM: Unknown
<220> FEATURE:
<223> OTHER INFORMATION: Mammal

<400> SEQUENCE: 275

Pro Leu Leu Ser
1

<210> SEQ ID NO 276
<211> LENGTH: 9
<212> TYPE: PRT
<213> ORGANISM: Unknown
<220> FEATURE:
<223> OTHER INFORMATION: Mammal

<400> SEQUENCE: 276

Ser Asn Asn His Tyr Tyr His Ser Asn
1               5

<210> SEQ ID NO 277
<211> LENGTH: 16
<212> TYPE: DNA
<213> ORGANISM: Unknown
<220> FEATURE:
<223> OTHER INFORMATION: Mammal

<400> SEQUENCE: 277
gtagttactg tagtca                                                16

<210> SEQ ID NO 278
<211> LENGTH: 5
<212> TYPE: PRT
<213> ORGANISM: Unknown
<220> FEATURE:
<223> OTHER INFORMATION: Mammal

<400> SEQUENCE: 278

Val Val Thr Val Val
1               5

<210> SEQ ID NO 279
<211> LENGTH: 4
<212> TYPE: PRT
<213> ORGANISM: Unknown
<220> FEATURE:

```
<223> OTHER INFORMATION: Mammal

<400> SEQUENCE: 279

Ser Tyr Cys Ser
1

<210> SEQ ID NO 280
<211> LENGTH: 16
<212> TYPE: DNA
<213> ORGANISM: Unknown
<220> FEATURE:
<223> OTHER INFORMATION: Mammal

<400> SEQUENCE: 280
gtagtcaccg tagtca                                                   16

<210> SEQ ID NO 281
<211> LENGTH: 4
<212> TYPE: PRT
<213> ORGANISM: Unknown
<220> FEATURE:
<223> OTHER INFORMATION: Mammal

<400> SEQUENCE: 281

Ser His Arg Ser
1

<210> SEQ ID NO 282
<211> LENGTH: 19
<212> TYPE: DNA
<213> ORGANISM: Unknown
<220> FEATURE:
<223> OTHER INFORMATION: Mammal

<400> SEQUENCE: 282
ggagttacca ccgtagtca                                                19

<210> SEQ ID NO 283
<211> LENGTH: 6
<212> TYPE: PRT
<213> ORGANISM: Unknown
<220> FEATURE:
<223> OTHER INFORMATION: Mammal

<400> SEQUENCE: 283

Gly Val Thr Thr Val Val
1               5

<210> SEQ ID NO 284
<211> LENGTH: 4
<212> TYPE: PRT
<213> ORGANISM: Unknown
<220> FEATURE:
<223> OTHER INFORMATION: Mammal

<400> SEQUENCE: 284

Glu Leu Pro Pro
1

<210> SEQ ID NO 285
<211> LENGTH: 5
<212> TYPE: PRT
<213> ORGANISM: Unknown
<220> FEATURE:
<223> OTHER INFORMATION: Mammal

<400> SEQUENCE: 285
```

Ser Tyr His Arg Ser
1               5

<210> SEQ ID NO 286
<211> LENGTH: 20
<212> TYPE: DNA
<213> ORGANISM: Unknown
<220> FEATURE:
<223> OTHER INFORMATION: Mammal

<400> SEQUENCE: 286
gtaaccatag ctgtatccac                                              20

<210> SEQ ID NO 287
<211> LENGTH: 6
<212> TYPE: PRT
<213> ORGANISM: Unknown
<220> FEATURE:
<223> OTHER INFORMATION: Mammal

<400> SEQUENCE: 287

Val Thr Ile Ala Val Ser
1               5

<210> SEQ ID NO 288
<211> LENGTH: 6
<212> TYPE: PRT
<213> ORGANISM: Unknown
<220> FEATURE:
<223> OTHER INFORMATION: Mammal

<400> SEQUENCE: 288

Asn His Ser Cys Ile His
1               5

<210> SEQ ID NO 289
<211> LENGTH: 23
<212> TYPE: DNA
<213> ORGANISM: Unknown
<220> FEATURE:
<223> OTHER INFORMATION: Mammal

<400> SEQUENCE: 289
gtaatcgtag ccactatatc cac                                          23

<210> SEQ ID NO 290
<211> LENGTH: 7
<212> TYPE: PRT
<213> ORGANISM: Unknown
<220> FEATURE:
<223> OTHER INFORMATION: Mammal

<400> SEQUENCE: 290

Val Ile Val Ala Thr Ile Ser
1               5

<210> SEQ ID NO 291
<211> LENGTH: 4
<212> TYPE: PRT
<213> ORGANISM: Unknown
<220> FEATURE:
<223> OTHER INFORMATION: Mammal

<400> SEQUENCE: 291

Pro Leu Tyr Pro
1

<210> SEQ ID NO 292
<211> LENGTH: 7
<212> TYPE: PRT
<213> ORGANISM: Unknown
<220> FEATURE:
<223> OTHER INFORMATION: Mammal

<400> SEQUENCE: 292

Asn Arg Ser His Tyr Ile His
1               5

<210> SEQ ID NO 293
<211> LENGTH: 20
<212> TYPE: DNA
<213> ORGANISM: Unknown
<220> FEATURE:
<223> OTHER INFORMATION: Mammal

<400> SEQUENCE: 293
gtaattgtag ccatctctac                                              20

<210> SEQ ID NO 294
<211> LENGTH: 6
<212> TYPE: PRT
<213> ORGANISM: Unknown
<220> FEATURE:
<223> OTHER INFORMATION: Mammal

<400> SEQUENCE: 294

Val Ile Val Ala Ile Ser
1               5

<210> SEQ ID NO 295
<211> LENGTH: 6
<212> TYPE: PRT
<213> ORGANISM: Unknown
<220> FEATURE:
<223> OTHER INFORMATION: Mammal

<400> SEQUENCE: 295

Asn Cys Ser His Leu Tyr
1               5

<210> SEQ ID NO 296
<211> LENGTH: 18
<212> TYPE: DNA
<213> ORGANISM: Unknown
<220> FEATURE:
<223> OTHER INFORMATION: Mammal

<400> SEQUENCE: 296
ggacgagctg ctatactc                                                18

<210> SEQ ID NO 297
<211> LENGTH: 6
<212> TYPE: PRT
<213> ORGANISM: Unknown
<220> FEATURE:
<223> OTHER INFORMATION: Mammal

<400> SEQUENCE: 297

Gly Arg Ala Ala Ile Leu
1               5

<210> SEQ ID NO 298

```
<211> LENGTH: 5
<212> TYPE: PRT
<213> ORGANISM: Unknown
<220> FEATURE:
<223> OTHER INFORMATION: Mammal

<400> SEQUENCE: 298

Asp Glu Leu Leu Tyr
1               5

<210> SEQ ID NO 299
<211> LENGTH: 5
<212> TYPE: PRT
<213> ORGANISM: Unknown
<220> FEATURE:
<223> OTHER INFORMATION: Mammal

<400> SEQUENCE: 299

Thr Ser Cys Tyr Thr
1               5

<210> SEQ ID NO 300
<211> LENGTH: 21
<212> TYPE: DNA
<213> ORGANISM: Unknown
<220> FEATURE:
<223> OTHER INFORMATION: Mammal

<400> SEQUENCE: 300
gtaccagctg ctgctatacc c                                       21

<210> SEQ ID NO 301
<211> LENGTH: 7
<212> TYPE: PRT
<213> ORGANISM: Unknown
<220> FEATURE:
<223> OTHER INFORMATION: Mammal

<400> SEQUENCE: 301

Val Pro Ala Ala Ala Ile Pro
1               5

<210> SEQ ID NO 302
<211> LENGTH: 6
<212> TYPE: PRT
<213> ORGANISM: Unknown
<220> FEATURE:
<223> OTHER INFORMATION: Mammal

<400> SEQUENCE: 302

Tyr Gln Leu Leu Leu Tyr
1               5

<210> SEQ ID NO 303
<211> LENGTH: 6
<212> TYPE: PRT
<213> ORGANISM: Unknown
<220> FEATURE:
<223> OTHER INFORMATION: Mammal

<400> SEQUENCE: 303

Thr Ser Cys Cys Tyr Thr
1               5

<210> SEQ ID NO 304
<211> LENGTH: 21
<212> TYPE: DNA
```

```
<213> ORGANISM: Unknown
<220> FEATURE:
<223> OTHER INFORMATION: Mammal

<400> SEQUENCE: 304
gtaccagcca ctgctatacc c                                              21

<210> SEQ ID NO 305
<211> LENGTH: 7
<212> TYPE: PRT
<213> ORGANISM: Unknown
<220> FEATURE:
<223> OTHER INFORMATION: Mammal'

<400> SEQUENCE: 305

Val Pro Ala Thr Ala Ile Pro
1               5

<210> SEQ ID NO 306
<211> LENGTH: 6
<212> TYPE: PRT
<213> ORGANISM: Unknown
<220> FEATURE:
<223> OTHER INFORMATION: Mammal

<400> SEQUENCE: 306

Tyr Gln Pro Leu Leu Tyr
1               5

<210> SEQ ID NO 307
<211> LENGTH: 6
<212> TYPE: PRT
<213> ORGANISM: Unknown
<220> FEATURE:
<223> OTHER INFORMATION: Mammal

<400> SEQUENCE: 307

Thr Ser His Cys Tyr Thr
1               5

<210> SEQ ID NO 308
<211> LENGTH: 18
<212> TYPE: DNA
<213> ORGANISM: Unknown
<220> FEATURE:
<223> OTHER INFORMATION: Mammal

<400> SEQUENCE: 308
gtagccgctg ctataccc                                                  18

<210> SEQ ID NO 309
<211> LENGTH: 6
<212> TYPE: PRT
<213> ORGANISM: Unknown
<220> FEATURE:
<223> OTHER INFORMATION: Mammal

<400> SEQUENCE: 309

Val Ala Ala Ala Ile Pro
1               5

<210> SEQ ID NO 310
<211> LENGTH: 4
<212> TYPE: PRT
<213> ORGANISM: Unknown
<220> FEATURE:
<223> OTHER INFORMATION: Mammal
```

<400> SEQUENCE: 310

Pro Leu Leu Tyr
1

<210> SEQ ID NO 311
<211> LENGTH: 5
<212> TYPE: PRT
<213> ORGANISM: Unknown
<220> FEATURE:
<223> OTHER INFORMATION: Mammal

<400> SEQUENCE: 311

Ser Arg Cys Tyr Thr
1               5

<210> SEQ ID NO 312
<211> LENGTH: 366
<212> TYPE: DNA
<213> ORGANISM: Homo sapiens

<400> SEQUENCE: 312
caggtgcagc tacagcagtg gggcgcagga ctgttgaagc cttcggatac cctgtccctc      60
acctgcgctg tctatggtgg gtccttcagt ggttactact ggagctggat ccgccagccc     120
ccagggaagg ggctggagtg gattggggaa atcaatcata gtggaagcac caactacaac     180
ccgtccctca agagtcgagt caccatatca gtagacacgt ccaagaacca gttctccctg     240
aagctgagct ctgtgaccgc cgcggacacg gctgtgtatt actgtgcggg catagccat      300 ggctggtact actactacta cggtatggac gtctggggcc aagggaccac ggtcaccgtc     360
tcctca                                                                366

<210> SEQ ID NO 313
<211> LENGTH: 122
<212> TYPE: PRT
<213> ORGANISM: Homo sapiens

<400> SEQUENCE: 313

Gln Val Gln Leu Gln Gln Trp Gly Ala Gly Leu Leu Lys Pro Ser Asp
1               5                   10                  15

Thr Leu Ser Leu Thr Cys Ala Val Tyr Gly Gly Ser Phe Ser Gly Tyr
                20                  25                  30

Tyr Trp Ser Trp Ile Arg Gln Pro Pro Gly Lys Gly Leu Glu Trp Ile
            35                  40                  45

Gly Glu Ile Asn His Ser Gly Ser Thr Asn Tyr Asn Pro Ser Leu Lys
        50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Gly His Ser His Gly Trp Tyr Tyr Tyr Tyr Gly Met Asp Val Trp
            100                 105                 110

Gly Gln Gly Thr Thr Val Thr Val Ser Ser
        115                 120

<210> SEQ ID NO 314
<211> LENGTH: 96
<212> TYPE: PRT
<213> ORGANISM: Homo sapiens

<400> SEQUENCE: 314

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

<210> SEQ ID NO 315
<211> LENGTH: 355
<212> TYPE: DNA
<213> ORGANISM: Homo sapiens

<400> SEQUENCE: 315
caggtgcagc tgcaggagtc gggcccagga ctggtgaagc cttcacagac cctgtccctc        60
acctgcactg tctctggtgg ctccatcagc agtggtggtt actactggag ctggatccgc       120
cagcacccag ggaagggcct ggagtggatt gggtacatct attacagtgg gagcacctac       180
tacaacccgt ccctcaagag tcgagttacc atatcagtag acacgtctaa gaaccagttc       240
tccctgaagc tgagctctgt gactgccgcg gacacggccg tgtattactg tgcgaggggg       300
gaccacggtc actacgacta ctggggccag ggaaccctgg tcaccgtctc ctcag            355

<210> SEQ ID NO 316
<211> LENGTH: 118
<212> TYPE: PRT
<213> ORGANISM: Homo sapiens

<400> SEQUENCE: 316

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Asp His Gly His Tyr Asp Tyr Trp Gly Gln Gly Thr
            100                 105                 110

Leu Val Thr Val Ser Ser
        115

<210> SEQ ID NO 317
<211> LENGTH: 98
<212> TYPE: PRT
<213> ORGANISM: Homo sapiens

<400> SEQUENCE: 317

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
            85                  90                  95

Cys Ala
```

<210> SEQ ID NO 318
<211> LENGTH: 370
<212> TYPE: DNA
<213> ORGANISM: Homo sapiens

<400> SEQUENCE: 318

```
cagctgcagc tgcaggagtc gggcccagga ctggtgaagc cttcggagac cctgtccctc      60
acctgcactg tctctggtgg ctccatcagc agtagtagtt actactgggg ctggatccgc     120
cagcccccag ggaaggggct ggagtggatt gggagtatct attatagtgg gagcacctac     180
tacaacccgt ccctcaagag tcgagtcacc atatccgtag acacgtccaa gaaccagttc     240
tccctgaagc tgagctctgt gaccgccgca gacacggctg tgtattactg tgcgagacat     300
gaagggcata gccaccttaa ctggttcgac ccctggggcc agggggggaac cctggtcacc     360
gtctcctcag                                                             370
```

<210> SEQ ID NO 319
<211> LENGTH: 123
<212> TYPE: PRT
<213> ORGANISM: Homo sapiens

<400> SEQUENCE: 319

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
            85                  90                  95

Cys Ala Arg His Glu Gly His Ser His Leu Asn Trp Phe Asp Pro Trp
            100                 105                 110

Gly Gln Gly Gly Thr Leu Val Thr Val Ser Ser
        115                 120
```

<210> SEQ ID NO 320
<211> LENGTH: 99
<212> TYPE: PRT

<213> ORGANISM: Homo sapiens

<400> SEQUENCE: 320

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg
```

<210> SEQ ID NO 321
<211> LENGTH: 22
<212> TYPE: DNA
<213> ORGANISM: Unknown
<220> FEATURE:
<223> OTHER INFORMATION: Mammal

<400> SEQUENCE: 321
tcttatcaga caggggctc tc                                         22

<210> SEQ ID NO 322
<211> LENGTH: 22
<212> TYPE: DNA
<213> ORGANISM: Unknown
<220> FEATURE:
<223> OTHER INFORMATION: Mammal

<400> SEQUENCE: 322
ggaagacatt tgggaaggac tg                                        22

<210> SEQ ID NO 323
<211> LENGTH: 4
<212> TYPE: PRT
<213> ORGANISM: Unknown
<220> FEATURE:
<223> OTHER INFORMATION: Mammal
<220> FEATURE:
<221> NAME/KEY: MISC_FEATURE
<222> LOCATION: (3)..(3)
<223> OTHER INFORMATION: wherin the "Xaa" represents any amino acid

<400> SEQUENCE: 323

Phe Gly Xaa Gly
1

<210> SEQ ID NO 324
<211> LENGTH: 4
<212> TYPE: PRT
<213> ORGANISM: Unknown
<220> FEATURE:

```
<223> OTHER INFORMATION: Mammal
<220> FEATURE:
<221> NAME/KEY: MISC_FEATURE
<222> LOCATION: (3)..(3)
<223> OTHER INFORMATION: wherein the "Xaa" represents any amino acid

<400> SEQUENCE: 324

Trp Gly Xaa Gly
1
```